US007608751B2

(12) United States Patent
Van Der Vossen et al.

(10) Patent No.: US 7,608,751 B2
(45) Date of Patent: Oct. 27, 2009

(54) FUNGUS RESISTANT PLANTS AND THEIR USES

(75) Inventors: Edwin Andries Gerard Van Der Vossen, Utrecht (NL); Josephus Jacoubs Henricus Maria Allefs, Emmeloord (NL); Marina Woutera Maria Muskens, Emmeloord (NL)

(73) Assignee: Kweek-En Researchbedruf Agrico B.V., Emmeloord (NL)

( * ) Notice: Subject to any disclaimer, the term of this patent is extended or adjusted under 35 U.S.C. 154(b) by 0 days.

(21) Appl. No.: 10/567,980

(22) PCT Filed: Aug. 3, 2004

(86) PCT No.: PCT/EP2004/008683

§ 371 (c)(1),
(2), (4) Date: Apr. 24, 2006

(87) PCT Pub. No.: WO2005/014631

PCT Pub. Date: Feb. 17, 2005

(65) Prior Publication Data

US 2006/0248610 A1 Nov. 2, 2006

(30) Foreign Application Priority Data

Aug. 11, 2003 (EP) ................... 03018266

(51) Int. Cl.
*C07H 21/04* (2006.01)
*C12N 15/82* (2006.01)
*C12N 15/87* (2006.01)

(52) U.S. Cl. ................ 800/279; 800/278; 536/23.6
(58) Field of Classification Search ............... None
See application file for complete search history.

(56) References Cited

U.S. PATENT DOCUMENTS

2003/0221215 A1  11/2003  Allefs et al.

FOREIGN PATENT DOCUMENTS

EP  1334979 A1  8/2003
WO  WO-98/06750 A2  2/1998

OTHER PUBLICATIONS

Song et al Aug. 5, 2003 PNAS 100:9128-9133.*
Song et al Jul. 15, 2003 GenBank Accession No. AY303171.*
Falcon-Perez JM et al. 1999, J Biol Chem. 274:23584-90.*
Veronese et al. 2003, Plant Physiology 131:1580-1590.*
Lazar et al. 1988, Mol. Cell. Biol. 8:1247-1252.*
Hill et al 1998, Biochem. Biophys. Res. Comm. 244:573-577.*
Fourgoux-Nicol et al 1999, Plant Molecular Biology 40 :857-872.*
Ballova et al. 2002, The Plant Journal 30:361-371.*
Osusky et al 2000, Nature Biotechnology 18:1162-1166.*
alignment of AF447489 vs SEQ ID No. 2 (p. 1-3).*
Rossi, M., et al., "The nematode resistance gene *Mi* of tomato confers resistance against the potato aphid", Proc. Natl. Acad. Sci. USA (1998), vol. 95, pp. 9750-9754.
Rossi, M., et al., "Lycopersicon esculentum disease resistance gene homolog Mi-copy2 gene, complete cds.", Aug. 19, 1998, Accession No. U81378.
Milligan, S. B., et al., "The Root Knot Nematode Resistance Gene *Mi* from Tomato Is a Member of the Leucine Zipper, Nucleotide Binding, Leucine-Rich Repeat Family of Plant Genes", The Plant Cell (1998), The Plant Cell, vol. 10, pp. 1307-1319.
Zaitsev, V.S., et al., "Solanum nigrum NBS-LRR pseudogene, partial sequence", Nov. 13, 2001, Accession No. AY055116.
Song, J., et al., "Gene *RB* cloned from *Solanum bulbocastanum* confers broad spectrum resistance to potato late blight", PNAS (2003), vol. 100, No. 16, pp. 9128-9133.
Bradeen, J.M., et al., "Concomitant reiterative BAC walking and fine genetic mapping enable physical map development for the broad-spectrum late blight resistance region, *RB*", Mol. Gen. Genomics (2003), vol. 269, pp. 603-611.
Van Der Vossen, E., et al., "An ancient *R* gene from the wild potato species *Solanum bulbocastanum* confers broad-spectrum resistance to *Phytophthora infestans* in cultivated potato and tomato", The Plant Journal (2003), vol. 36, pp. 867-882.

* cited by examiner

*Primary Examiner*—Elizabeth F McElwain
*Assistant Examiner*—Li Zheng
(74) *Attorney, Agent, or Firm*—Connolly Bove Lodge & Hutz LLP

(57) ABSTRACT

The present invention relates to a novel method for increasing the resistance, of a plant, in particular of a Solanaceae, preferably of potato and tomato, to plant pathogens of the phylum Oomyceta comprising increasing the activity of the polypeptid of the present invention. The invention further relates to polynucleotides and vectors comprising these polynucleotides. The invention furthermore relates to corresponding vectors, cells, transgenic plants and transgenic propagation material derived from them, methods to produce them and to their use for the production of foodstuffs, feeding stuffs, seed, pharmaceuticals or fine chemicals.

4 Claims, 62 Drawing Sheets

* ARF 87-507 and ARF 87-601 had identical disease progress curves

Figure 4:

Figure 4 dia 3

Figure 4 dia 4

Figure 4 dia 5

Figure 4 dia 6

Figure 12:
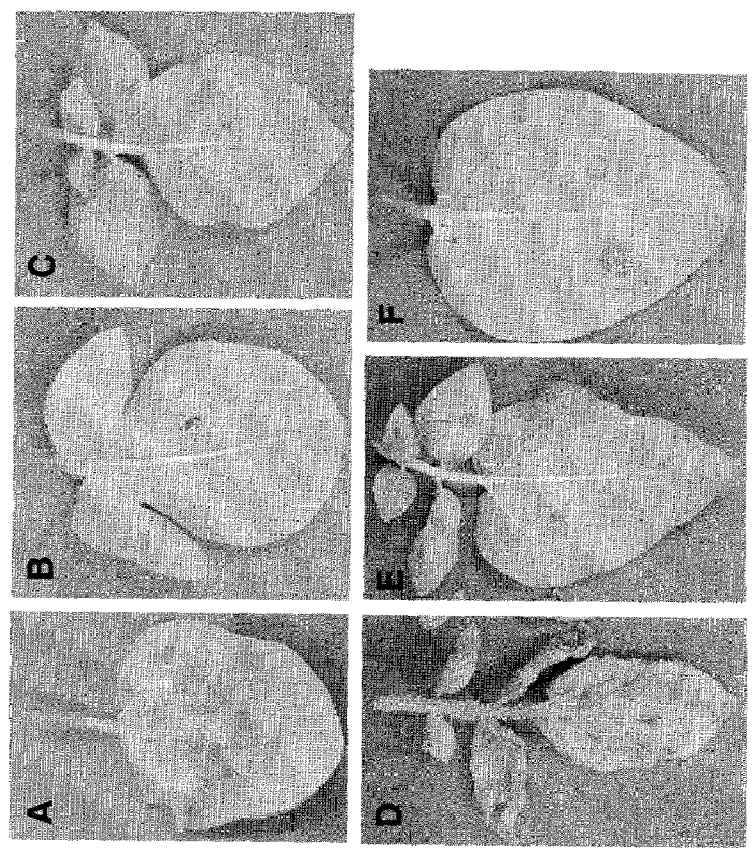

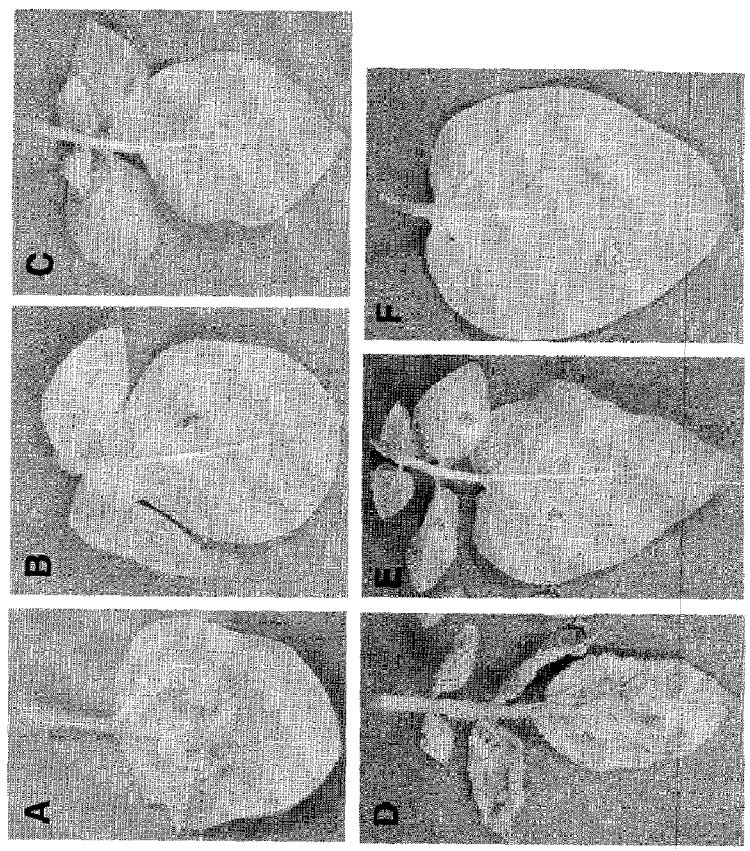
Figure 12 dia2

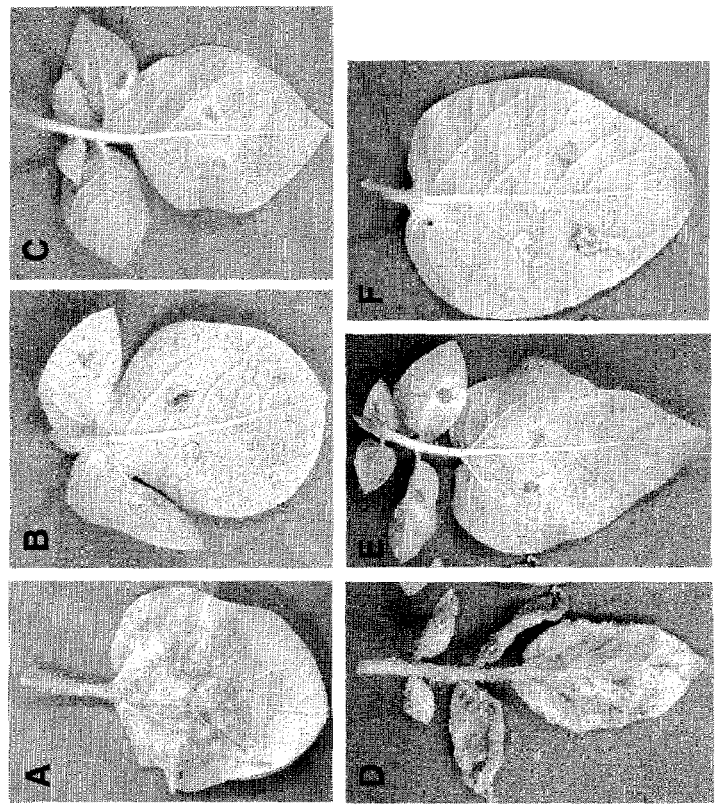
Figure 12 dia 3

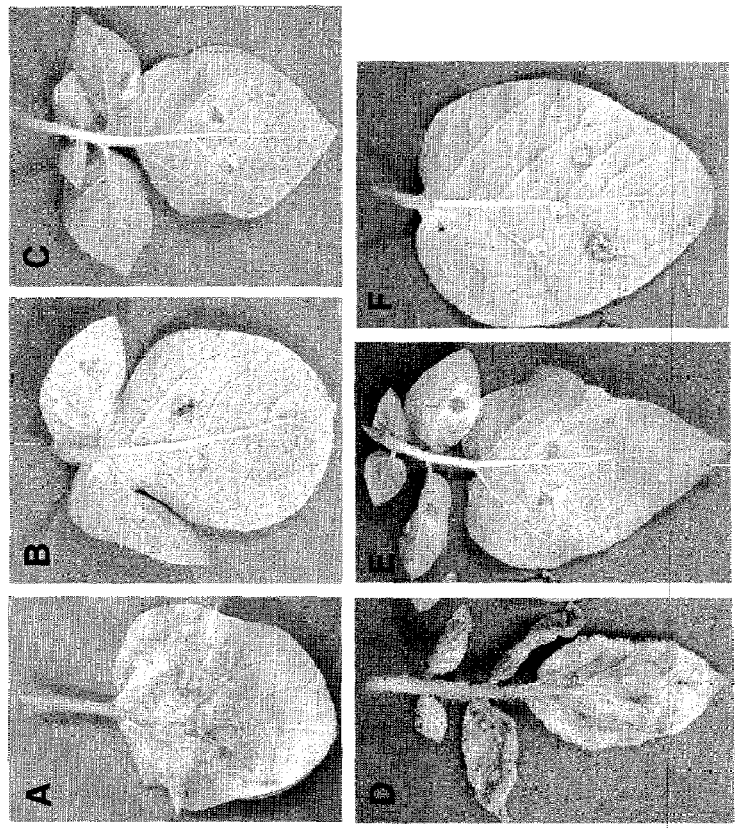
Figure 12 dia 4

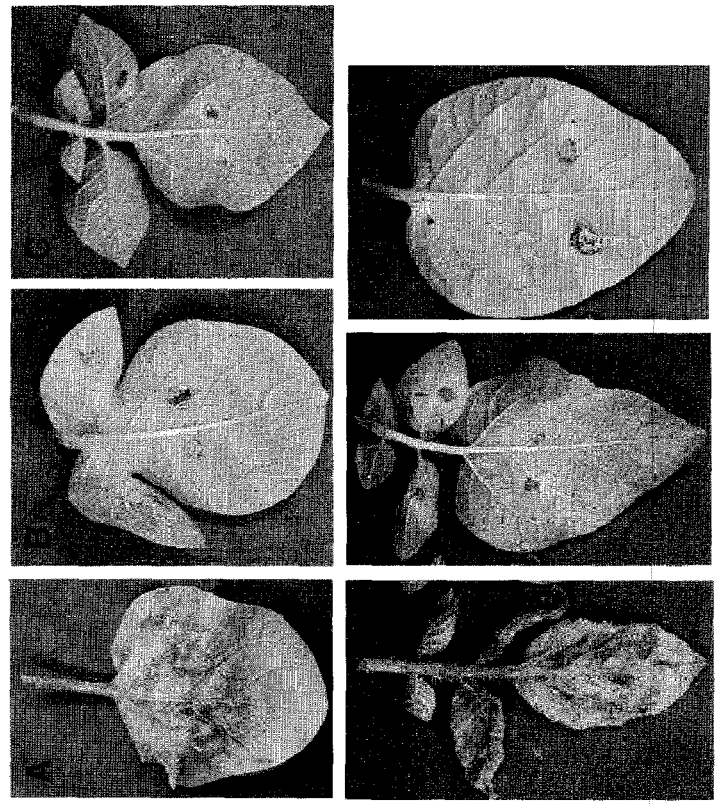
Figure 12 dia 5

Figure 13A

```
ATGGAAAAACGAAAAGATAATGAAGAAGCAAACAACTCATTGGAGTCATT     50
TTCTGCTCTTCGCAAGGATGCTGCCAATGTTCTGGATTTCCTAGAGAGAT    100
TAAAGAATGAAGAAGATCAAAAGGCTGTTGATGTGGATCTGATTGAAAGC    150
CTGAAATTGAAGCTGACATTTATTTGTACATATGTCCAGCTTTCTTATTC    200
CGATTTGGAGAAGTTTGAAGATATAATGACTAGAAAAAGACAAGAGGTTG    250
AGAATCTGCTTCAACCAATTTTGGATGATGATGGCAAAGACGTCGGGTGT    300
AAATATGTCCTTACTAGCCTCGCCGGTAATATGGATGACTGTATAAGCTT    350
GTATCATCGTTCTAAATCAGATGCCACCATGATGGATGAGCAATTGGGCT    400
TCCTCCTCTTGAATCTCTCTCATCTATCCAAGCATCGTGCTGAAAAGATG    450
TTTCCTGGAGTGACTCAATATGAGGTTCTTCAGAATGTATGTGGCAACAT    500
AAGAGATTTCCATGGATTGATAGTGAATTGTTGCATTAAGCATGAGATGG    550
TTGAGAATGTCTTATCTCTGTTTCAACTGATGGCTGAGAGAGTAGGACGC    600
TTCCTTTGGGAGGATCAGGCTGATGAAGACTCTCAACTCTCCGAGCTAGA    650
TGAGGATGATCAGAATGATAAAGACCCTCAACTCTTCAAGCTAGCACATC    700
TACTCTTGAAGATTGTTCCAACTGAATTGGAGGTTATGCACATATGTTAT    750
AAAACTTTGAAAGCTTCAACTTCAACAGAAATTGGACGCTTCATTAAGAA    800
GCTCCTGGAAACCTCTCCGGACATTCTCAGAGAATATCTGATTCATCTAC    850
AAGAGCATATGATAACTGTTATTACCCCTAACACTTCAGGGGCTCGAAAC    900
ATTCATGTCATGATGGAATTCCTATTGATTATTCTTTCTGATATGCCGCC    950
CAAGGACTTTATTCATCATGACAAACTTTTTGATCTCTTGGCTCGTGTTG    100
TAGCACTTACCAGGGAGGTATCAACTCTTGTACGCGACTTGGAAGAGAAA   1050
TTAAGGATTAAAGAGAGTACTGACGAAACAAATTGTGCAACCCTAAAGTT   1100
TCTGGAAAATATTGAACTCCTTAAGGAAGATCTCAAACATGTTTATCTGA   1150
AAGTCCCGGATTCATCTCAATATTGCTTCCCCATGAGTGATGGACCTCTC   1200
TTCATGCATCTGCTACAGAGACACTTAGATGATTTGCTGGATTCCAATGC   1250
TTATTCAATTGCTTTGATAAAGGAACAAATTGGGCTGGTGAAAGAAGACT   1300
TGGAATTCATAAGATCTTTTTTCGCGAATATTGAGCAAGGATTGTATAAA   1350
GATCTCTGGGAACGTGTTCTAGATGTGGCATATGAGGCAAAAGATGTCAT   1400
AGATTCAATTATTGTTCGAGATAATGGTCTCTTACATCTTATTTTCTCAC   1450
TTCCCATTACCAGAAAGAAGATGATGCTTATCAAAGAAGAGGTCTCTGAT   1500
TTACATGAGAACATTTCCAAGAACAGAGGTCTCATCGTTGTGAACTCTCC   1550
CAAGAAACCAGTTGAGAGCAAGTCATTGACAACTGATAAAATAATTGTAG   1600
GTTTTGGTGAGGAGACAAACTTGATACTTAGAAAGCTCACCAGTGGACCG   1650
```

Figure 13A (cont.)

```
GCAGATCTAGATGTCATTTCGATCATTGGTATGCCGGGTTTAGGTAAAAC 1700
TACTTTGGCGTACAAAGTATACAATGATAAATCAGTTTCTAGCCATTTCG 1750
ACCTTCGTGCATGGTGCACGGTCGACCAAGTATATGACGAGAAGAAGTTG 1800
TTGGATAAAATTTTCAATCAAGTTAGTGACTCAAATTCAAAATTGAGTGA 1850
GAATATTGATGTTGCTGATAAACTACGGAAACAATTGTTTGGAAAGAGGT 1900
ATCTTATTGTCTTAGATGACGTGTGGGATACTAATACATGGGATGAGCTA 1950
ACAAGACCTTTTCCTGATGGTATGAAAGGAAGTAGAATTATTTTGACAAC 2000
TCGAGAAAAGAAAGTTGCTTTGCATGGAAAGCTCTACACTGATCCTCTTA 2050
ACCTTCGATTGCTAAGATCAGAAGAAAGTTGGGAGTTATTAGAGAAAAGG 2100
GCATTTGGAAACGAGAGTTGCCCTGATGAACTATTGGATGTTGGTAAAGA 2150
AATAGCCGAAAATTGTAAAGGGCTTCCTTTGGTGGTGGATCTGATTGCTG 2200
GAATCATTGCTGGGAGGGAAAAGAAAAAGAGTGTGTGGCTTGAAGTTGTA 2250
AATAATTTGCATTCCTTTATTTTGAAGAATGAAGTGGAAGTGATGAAAGT 2300
TATAGAAATAAGTTATGACCACTTACCTGATCACCTGAAGCCATGCTTGC 2350
TGTACTTTGCAAGTGCGCCGAAGGACTGGGTAACGACAATCCATGAGTTG 2400
AAACTTATTTGGGGTTTTGAAGGATTTGTGGAAAAGACAGATATGAAGAG 2450
TCTGGAAGAAGTGGTGAAAATTTATTTGGATGATTTAATTTCCAGTAGCT 2500
TGGTAATTTGTTTCAATGAGATAGGTGATTACCCTACTTGCCAACTTCAT 2550
GATCTTGTGCATGACTTTTGTTTGATAAAAGCAAGAAAGGAAAAGTTGTG 2600
TGATCGGATAAGTTCAAGTGCTCCATCAGATTTGTTGCCACGTCAAATTA 2650
GCATTGATTATGATGATGATGAAGAGCACTTTGGGCTTAATTTTGTCCTG 2700
TTCGGTTCAAATAAGAAAAGGCATTCCGGTAAACACCTCTATTCTTTGAC 2750
CATAAATGGAGATGAGCTGGACGACCATCTTTCTGATACATTTCATCTAA 2800
GACACTTGAGGCTTCTTAGAACCTTGCACCTGGAATCCTCTTTTATCATG 2850
GTTAAAGATTCTTTGCTGAATGAAATATGCATGTTGAATCATTTGAGGTA 2900
CTTAAGCATTGGGACAGAAGTTAAATCTCTGCCTTTGTCTTTCTCAAACC 2950
TCTGGAATCTAGAAATCTTGTTTGTGGATAACAAAGAATCAACCTTGATA 3000
CTATTACCGAGAATTTGGGATCTTGTAAAGTTGCAAGTGCTGTTCACGAC 3050
TGCTTGTTCTTTCTTTGATATGGATGCAGATGAATCAATACTGATAGCAG 3100
AGGACACAAAGTTAGAGAACTTGACAGCATTAGGGGAACTCGTGCTTTCC 3150
TATTGGAAAGATACAGAGGATATTTTCAAAAGGCTTCCCAATCTTCAAGT 3200
GCTTCATTTCAAACTCAAGGAGTCATGGGATTATTCAACAGAGCAATATT 3250
GGTTCCCGAAATTGGATTTCCTAACTGAACTAGAAAAACTCACTGTAGAT 3300
TTTGAAAGATCAAACACAAATGACAGTGGGTCCTCTGCAGCCATAAATCG 3350
GCCATGGGATTTTCACTTTCCTTCGAGTTTGAAAAGATTGCAATTGCATG 3400
```

Figure 13A (cont.)

```
AATTTCCTCTGACATCCGATTCACTATCAACAATAGCGAGACTGCTGAAC  3450
CTTGAAGAGTTGTACCTTTATCGTACAATCATCCATGGGGAAGAATGGAA  3500
CATGGGAGAAGAAGACACCTTTGAGAATCTCAAATGTTTGATGTTGAGTC  3550
AAGTGATTCTTTCCAAGTGGGAGGTTGGAGAGGAATCTTTTCCCACGCTT  3600
GAGAAATTAGAACTGTCGGACTGTCATAATCTTGAGGAGATTCCGTCTAG  3650
TTTTGGGGATATTTATTCCTTGAAAATTATCGAACTTGTAAGGAGCCCTC  3700
AACTTGAAAATTCCGCTCTCAAGATTAAGGAATATGCTGAAGATATGAGG  3750
GGAGGGGACGAGCTTCAGATCCTTGGCCAGAAGGATATCCCGTTATTTAA  3800
GTAG                                                3804
```

Figure 13B

```
ATGGAAAAACGAAAAGATAATGAAGAAGCAAACAACTCATTGGTATGTTA   50
TTTGATAGAGTGAACTGTAAAGTATTGAATTGTAGATATCATGTGGCTTT  100
AAAAATTTGATATGTGTTATTTTGGCAGGAGTCATTTTCTGCTCTTCGCA  150
AGGATGCTGCCAATGTTCTGGATTTCCTAGAGAGATTAAAGAATGAAGAA  2001
GATCAAAGGCTGTTGATGTGGATCTGATTGAAAGCCTGAAATTGAAGCT   2501
GACATTTATTTGTACATATGTCCAGCTTTCTTATTCCGATTTGGAGAAGT  3001
TTGAAGATATAATGACTAGAAAAAGACAAGAGGTTGAGAATCTGCTTCAA  3501
CCAATTTTGGATGATGATGGCAAAGACGTCGGGTGTAAATATGTCCTTAC  4001
TAGCCTCGCCGGTAATATGGATGACTGTATAAGCTTGTATCATCGTTCTA  4501
AATCAGATGCCACCATGATGGATGAGCAATTGGGCTTCCTCCTCTTGAAT  5001
CTCTCTCATCTATCCAAGCATCGTGCTGAAAAGATGTTTCCTGGAGTGAC  5501
TCAATATGAGGTTCTTCAGAATGTATGTGGCAACATAAGAGATTTCCATG  6001
GATTGATAGTGAATTGTTGCATTAAGCATGAGATGGTTGAGAATGTCTTA  6501
TCTCTGTTTCAACTGATGGCTGAGAGAGTAGGACGCTTCCTTTGGGAGGA  7001
TCAGGCTGATGAAGACTCTCAACTCTCCGAGCTAGATGAGGATGATCAGA  7501
ATGATAAAGACCCTCAACTCTTCAAGCTAGCACATCTACTCTTGAAGATT  8001
GTTCCAACTGAATTGGAGGTTATGCACATATGTTATAAAACTTTGAAAGC  8501
TTCAACTTCAACAGAAATTGGACGCTTCATTAAGAAGCTCCTGGAAACCT  9010
CTCCGGACATTCTCAGAGAATATCTGATTCATCTACAAGAGCATATGATA  9510
ACTGTTATTACCCCTAACACTTCAGGGGCTCGAAACATTCATGTCATGAT  1000
GGAATTCCTATTGATTATTCTTTCTGATATGCCGCCCAAGGACTTTATTC  1050
ATCATGACAAACTTTTTGATCTCTTGGCTCGTGTTGTAGCACTTACCAGG  1100
GAGGTATCAACTCTTGTACGCGACTTGGAAGAGAAATTAAGGATTAAAGA  1150
GAGTACTGACGAAACAAATTGTGCAACCCTAAAGTTTCTGGAAAATATTG  1200
AACTCCTTAAGGAAGATCTCAAACATGTTTATCTGAAAGTCCCGGATTCA  1250
TCTCAATATTGCTTCCCCATGAGTGATGGACCTCTCTTCATGCATCTGCT  1300
ACAGAGACACTTAGATGATTTGCTGGATTCCAATGCTTATTCAATTGCTT  1350
TGATAAAGGAACAAATTGGGCTGGTGAAAGAAGACTTGGAATTCATAAGA  1400
TCTTTTTTCGCGAATATTGAGCAAGGATTGTATAAAGATCTCTGGAACG   1450
TGTTCTAGATGTGGCATATGAGGCAAAAGATGTCATAGATTCAATTATTG  1500
TTCGAGATAATGGTCTCTTACATCTTATTTTCTCACTTCCCATTACCAGA  1550
AAGAAGATGATGCTTATCAAAGAAGAGGTCTCTGATTTACATGAGAACAT  1600
TTCCAAGAACAGAGGTCTCATCGTTGTGAACTCTCCCAAGAAACCAGTTG  1650
```

Figure 13B (cont.)

```
AGAGCAAGTCATTGACAACTGATAAAATAATTGTAGGTTTTGGTGAGGAG 1700
ACAAACTTGATACTTAGAAAGCTCACCAGTGGACCGGCAGATCTAGATGT 1750
CATTTCGATCATTGGTATGCCGGGTTTAGGTAAAACTACTTTGGCGTACA 1800
AAGTATACAATGATAAATCAGTTTCTAGCCATTTCGACCTTCGTGCATGG 1850
TGCACGGTCGACCAAGTATATGACGAGAAGAAGTTGTTGGATAAAATTTT 1900
CAATCAAGTTAGTGACTCAAATTCAAAATTGAGTGAGAATATTGATGTTG 1950
CTGATAAACTACGGAAACAATTGTTTGGAAAGAGGTATCTTATTGTCTTA 2000
GATGACGTGTGGGATACTAATACATGGGATGAGCTAACAAGACCTTTTCC 2050
TGATGGTATGAAAGGAAGTAGAATTATTTTGACAACTCGAGAAAAGAAAG 2100
TTGCTTTGCATGGAAAGCTCTACACTGATCCTCTTAACCTTCGATTGCTA 2150
AGATCAGAAGAAAGTTGGGAGTTATTAGAGAAAAGGGCATTTGGAAACGA 2200
GAGTTGCCCTGATGAACTATTGGATGTTGGTAAAGAAATAGCCGAAAATT 2250
GTAAAGGGCTTCCTTTGGTGGTGGATCTGATTGCTGGAATCATTGCTGGG 2300
AGGGAAAAGAAAAAGAGTGTGTGGCTTGAAGTTGTAAATAATTTGCATTC 2350
CTTTATTTTGAAGAATGAAGTGGAAGTGATGAAAGTTATAGAAATAAGTT 2400
ATGACCACTTACCTGATCACCTGAAGCCATGCTTGCTGTACTTTGCAAGT 2450
GCGCCGAAGGACTGGGTAACGACAATCCATGAGTTGAAACTTATTTGGGG 2500
TTTTGAAGGATTTGTGGAAAAGACAGATATGAAGAGTCTGGAAGAAGTGG 2550
TGAAAATTTATTTGGATGATTTAATTTCCAGTAGCTTGGTAATTTGTTTC 2600
AATGAGATAGGTGATTACCCTACTTGCCAACTTCATGATCTTGTGCATGA 2650
CTTTTGTTTGATAAAAGCAAGAAAGGAAAAGTTGTGTGATCGGATAAGTT 2700
CAAGTGCTCCATCAGATTTGTTGCCACGTCAAATTAGCATTGATTATGAT 2750
GATGATGAAGAGCACTTTGGGCTTAATTTTGTCCTGTTCGGTTCAAATAA 2800
GAAAAGGCATTCCGGTAAACACCTCTATTCTTTGACCATAAATGGAGATG 2850
AGCTGGACGACCATCTTTCTGATACATTTCATCTAAGACACTTGAGGCTT 2900
CTTAGAACCTTGCACCTGGAATCCTCTTTTATCATGGTTAAAGATTCTTT 2950
GCTGAATGAAATATGCATGTTGAATCATTTGAGGTACTTAAGCATTGGGA 3000
CAGAAGTTAAATCTCTGCCTTTGTCTTTCTCAAACCTCTGGAATCTAGAA 3050
ATCTTGTTTGTGGATAACAAAGAATCAACCTTGATACTATTACCGAGAAT 3100
TTGGGATCTTGTAAAGTTGCAAGTGCTGTTCACGACTGCTTGTTCTTTCT 3150
TTGATATGGATGCAGATGAATCAATACTGATAGCAGAGGACACAAAGTTA 3200
GAGAACTTGACAGCATTAGGGGAACTCGTGCTTTCCTATTGGAAAGATAC 3250
AGAGGATATTTTCAAAAGGCTTCCCAATCTTCAAGTGCTTCATTTCAAAC 3300
TCAAGGAGTCATGGGATTATTCAACAGAGCAATATTGGTTCCCGAAATTG 3350
GATTTCCTAACTGAACTAGAAAAACTCACTGTAGATTTTGAAAGATCAAA 3400
```

Figure 13B (cont.)

```
CACAAATGACAGTGGGTCCTCTGCAGCCATAAATCGGCCATGGGATTTTC  3450
ACTTTCCTTCGAGTTTGAAAAGATTGCAATTGCATGAATTTCCTCTGACA  3500
TCCGATTCACTATCAACAATAGCGAGACTGCTGAACCTTGAAGAGTTGTA  3550
CCTTTATCGTACAATCATCCATGGGGAAGAATGGAACATGGGAGAAGAAG  3600
ACACCTTTGAGAATCTCAAATGTTTGATGTTGAGTCAAGTGATTCTTTCC  3650
AAGTGGGAGGTTGGAGAGGAATCTTTTCCCACGCTTGAGAAATTAGAACT  3700
GTCGGACTGTCATAATCTTGAGGAGATTCCGTCTAGTTTTGGGGATATTT  3750
ATTCCTTGAAAATTATCGAACTTGTAAGGAGCCCTCAACTTGAAAATTCC  3800
GCTCTCAAGATTAAGGAATATGCTGAAGATATGAGGGGAGGGACGAGCT   3850
TCAGATCCTTGGCCAGAAGGATATCCCGTTATTTAAGTAG            3890
```

Figure 13C

```
GATCTAGAATCACCGAACCTCCCCTCGGTACAGCTCCTCCAGTTCTACCA 50
TGAATTTCATCCACTGATTCCTCTTCAATCGCCATTGCAGATTCTCTCGA 100
TCTATGCTCAAAAAATCCCGAGATAAAACCCTAGATCTGCTTCAAATGCT 150
CTGATACCATGTAATTTCAGTGAATTCTAACTAAACAATGGAGAGAATTA 200
ACTATTTTAGAAAGACTGATTGAAGGAGAAGAAGAGAGAAAAATTCTATA 250
TTGAACTCATGAACCAAAATGAATGAAAAAAATAATGAGAAGAACTATAC 300
TATTACAATCTATATATCTCTATTTATATTCTAATCTGAAGCAGTTAATT 350
TAACTGACTCTAACAACTAGACTGATAGGTGTACATTTTCTGTTAGTGCA 400
CTGCAGTGCATTTAACTAACTGCTTAACATAAAGAATGTTGTTCGAACTT 450
CATTCGAATAGCTTCAATGAGAAGCAAACATGTGTACCTGTAAAGACACA 500
CAGTAAAAGTGTTAATAATGAATAAATATGAATAAATCAAATAATAAATT 550
AAAAATAAAAACACATCCAATTAACATTGGAGGTCTTGAAAATCGATGGT 600
AATTAACAAAGACCCTTGTGAAATTTAAGTCTGTAATTGAAAATTTGAGT 650
ATAGGTTAGGGGACATTTGACTATTTTCTCATTTTCTTTATCTTTTTCCT 700
AATTTGTGGCAGACAAGTGAGGAGGCCCCACTGTAATTGATTCATGCTTT 750
TGCTTTCTTGACTTTTTGGAACAATACTATGCATCATATTTGGTCTTAAT 800
TATTCCTCTGTTTATTTCCAGAATTTTGAGCTCTATACATCTAATAACAA 850
AGCAAGCAGAGGATATATAGTTTCATCAACTAAAAAGGTTAGTCAACTCA 900
TCTAATATTTGCTACTCTCATCTCTATTGAAGTACAGTTATGGAAAAGTA 950
GAAGTGATGTAAGAAAAATGAAAGAACTTTAGTAGGTTAGTTGGATCTAA 1000
CAAAGAGAAAGGGAAATAAATTGCAGGAGAAAGAGAGAGGTTAAATACTT 1050
ACTCACACCACCGATTTACAACAAATCACTTAATTGTGGTTAGTTAATGT 1100
ATACTTTCACCTCATTAAATTATTACTTACCCATGATAAGTTGTATTAAT 1150
TTGGTATTAATATCCGGTGCGGGTGAATTCTTACCGGGTGAGAGGGATGG 1200
GGTTGGAGAGTGTGGAGTGAACAGAAGCAGATGTTTTAGATTTTTTCTAA 1250
GATGACGAAAGATTCCCCTCACTAATGAAAATATATTACTATACGCTATT 1300
AGAGATAGAAAGGTTCGGTACCAGTTGGTCTCGTTTCTGGATGAACCCCA 1350
TTTTTACAAGTCATTTTCTTCAATTCAAATCGCAAGTGTACCTTTATCAT 1400
CTTCCACTAATTAAGTCCTCTTAAGTTCGCGTGAAAATAGTGAAATTATT 1450
GATTATTCTTATCATTTCATCTTCTTTCTCCTGATAAAGTTTTATGTACT 1500
TTTTATGCATCAGGTCTTGAGAACTTGGAAAGGAAAAGTAGAATCATGGA 1550
AAAACGAAAAGATAATGAAGAAGCAAACAACTCATTGGTATGTTATTTGA 1600
TAGAGTGAACTGTAAAGTATTGAATTGTAGATATCATGTGGCTTTAAAAA 1650
```

Figure 13C (cont.)

```
TTTGATATGTGTTATTTTGGCAGGAGTCATTTTCTGCTCTTCGCAAGGAT 17001
GCTGCCAATGTTCTGGATTTCCTAGAGAGATTAAAGAATGAAGAAGATCA 1750
AAAGGCTGTTGATGTGGATCTGATTGAAAGCCTGAAATTGAAGCTGACAT 1800
TTATTTGTACATATGTCCAGCTTTCTTATTCCGATTTGGAGAAGTTTGAA 1850
GATATAATGACTAGAAAAAGACAAGAGGTTGAGAATCTGCTTCAACCAAT 1900
TTTGGATGATGATGGCAAAGACGTCGGGTGTAAATATGTCCTTACTAGCC 1950
TCGCCGGTAATATGGATGACTGTATAAGCTTGTATCATCGTTCTAAATCA 2000
GATGCCACCATGATGGATGAGCAATTGGGCTTCCTCCTCTTGAATCTCTC 2050
TCATCTATCCAAGCATCGTGCTGAAAAGATGTTTCCTGGAGTGACTCAAT 2100
ATGAGGTTCTTCAGAATGTATGTGGCAACATAAGAGATTTCCATGGATTG 2150
ATAGTGAATTGTTGCATTAAGCATGAGATGGTTGAGAATGTCTTATCTCT 2200
GTTTCAACTGATGGCTGAGAGAGTAGGACGCTTCCTTTGGGAGGATCAGG 2250
CTGATGAAGACTCTCAACTCTCCGAGCTAGATGAGGATGATCAGAATGAT 2300
AAAGACCCTCAACTCTTCAAGCTAGCACATCTACTCTTGAAGATTGTTCC 2350
AACTGAATTGGAGGTTATGCACATATGTTATAAAACTTTGAAAGCTTCAA 2400
CTTCAACAGAAATTGGACGCTTCATTAAGAAGCTCCTGGAAACCTCTCCG 2450
GACATTCTCAGAGAATATCTGATTCATCTACAAGAGCATATGATAACTGT 2500
TATTACCCCTAACACTTCAGGGGCTCGAAACATTCATGTCATGATGGAAT 2550
TCCTATTGATTATTCTTTCTGATATGCCGCCCAAGGACTTTATTCATCAT 2600
GACAAACTTTTTGATCTCTTGGCTCGTGTTGTAGCACTTACCAGGGAGGT 2650
ATCAACTCTTGTACGCGACTTGGAAGAGAAATTAAGGATTAAAGAGAGTA 2700
CTGACGAAACAAATTGTGCAACCCTAAAGTTTCTGGAAAATATTGAACTC 2750
CTTAAGGAAGATCTCAAACATGTTTATCTGAAAGTCCCGGATTCATCTCA 2800
ATATTGCTTCCCCATGAGTGATGGACCTCTCTTCATGCATCTGCTACAGA 2850
GACACTTAGATGATTTGCTGGATTCCAATGCTTATTCAATTGCTTTGATA 2900
AAGGAACAAATTGGGCTGGTGAAAGAAGACTTGGAATTCATAAGATCTTT 2950
TTTCGCGAATATTGAGCAAGGATTGTATAAAGATCTCTGGGAACGTGTTC 3000
TAGATGTGGCATATGAGGCAAAAGATGTCATAGATTCAATTATTGTTCGA 3050
GATAATGGTCTCTTACATCTTATTTTCTCACTTCCCATTACCAGAAAGAA 3100
GATGATGCTTATCAAAGAAGAGGTCTCTGATTTACATGAGAACATTTCCA 3150
AGAACAGAGGTCTCATCGTTGTGAACTCTCCCAAGAAACCAGTTGAGAGC 3200
AAGTCATTGACAACTGATAAAATAATTGTAGGTTTTGGTGAGGAGACAAA 3250
CTTGATACTTAGAAAGCTCACCAGTGGACCGGCAGATCTAGATGTCATTT 3300
CGATCATTGGTATGCCGGGTTTAGGTAAAACTACTTTGGCGTACAAAGTA 3350
TACAATGATAAATCAGTTTCTAGCCATTTCGACCTTCGTGCATGGTGCAC 3400
```

Figure 13C (cont.)

```
GGTCGACCAAGTATATGACGAGAAGAAGTTGTTGGATAAAATTTTCAATC  3450
AAGTTAGTGACTCAAATTCAAAATTGAGTGAGAATATTGATGTTGCTGAT  3500
AAACTACGGAAACAATTGTTTGGAAAGAGGTATCTTATTGTCTTAGATGA  3550
CGTGTGGGATACTAATACATGGATGAGCTAACAAGACCTTTTCCTGATG   3600
GTATGAAAGGAAGTAGAATTATTTTGACAACTCGAGAAAAGAAAGTTGCT  3650
TTGCATGGAAAGCTCTACACTGATCCTCTTAACCTTCGATTGCTAAGATC  3700
AGAAGAAAGTTGGGAGTTATTAGAGAAAAGGGCATTTGGAAACGAGAGTT  3750
GCCCTGATGAACTATTGGATGTTGGTAAAGAAATAGCCGAAAATTGTAAA  3800
GGGCTTCCTTTGGTGGTGGATCTGATTGCTGGAATCATTGCTGGGAGGGA  3850
AAAGAAAAAGAGTGTGTGGCTTGAAGTTGTAAATAATTTGCATTCCTTTA  3900
TTTTGAAGAATGAAGTGGAAGTGATGAAAGTTATAGAAATAAGTTATGAC  3950
CACTTACCTGATCACCTGAAGCCATGCTTGCTGTACTTTGCAAGTGCGCC  4000
GAAGGACTGGGTAACGACAATCCATGAGTTGAAACTTATTTGGGGTTTTG  4050
AAGGATTTGTGGAAAAGACAGATATGAAGAGTCTGGAAGAAGTGGTGAAA  4100
ATTTATTTGGATGATTTAATTTCCAGTAGCTTGGTAATTTGTTTCAATGA  4150
GATAGGTGATTACCCTACTTGCCAACTTCATGATCTTGTGCATGACTTTT  4200
GTTTGATAAAAGCAAGAAAGGAAAAGTTGTGTGATCGGATAAGTTCAAGT  4250
GCTCCATCAGATTTGTTGCCACGTCAAATTAGCATTGATTATGATGATGA  4300
TGAAGAGCACTTTGGGCTTAATTTTGTCCTGTTCGGTTCAAATAAGAAAA  4350
GGCATTCCGGTAAACACCTCTATTCTTTGACCATAAATGGAGATGAGCTG  4400
GACGACCATCTTTCTGATACATTTCATCTAAGACACTTGAGGCTTCTTAG  4450
AACCTTGCACCTGGAATCCTCTTTTATCATGGTTAAAGATTCTTTGCTGA  4500
ATGAAATATGCATGTTGAATCATTTGAGGTACTTAAGCATTGGGACAGAA  4550
GTTAAATCTCTGCCTTTGTCTTTCTCAAACCTCTGGAATCTAGAAATCTT  4600
GTTTGTGGATAACAAAGAATCAACCTTGATACTATTACCGAGAATTTGGG  4650
ATCTTGTAAAGTTGCAAGTGCTGTTCACGACTGCTTGTTCTTTCTTTGAT  4700
ATGGATGCAGATGAATCAATACTGATAGCAGAGGACACAAAGTTAGAGAA  4750
CTTGACAGCATTAGGGGAACTCGTGCTTTCCTATTGGAAAGATACAGAGG  4800
ATATTTTCAAAAGGCTTCCCAATCTTCAAGTGCTTCATTTCAAACTCAAG  4850
GAGTCATGGGATTATTCAACAGAGCAATATTGGTTCCCGAAATTGGATTT  4900
CCTAACTGAACTAGAAAAACTCACTGTAGATTTTGAAAGATCAAACACAA  4950
ATGACAGTGGGTCCTCTGCAGCCATAAATCGGCCATGGGATTTTCACTTT  5000
CCTTCGAGTTTGAAAAGATTGCAATTGCATGAATTTCCTCTGACATCCGA  5050
TTCACTATCAACAATAGCGAGACTGCTGAACCTTGAAGAGTTGTACCTTT  5100
ATCGTACAATCATCCATGGGGAAGAATGGAACATGGGAGAAGAAGACACC  5150
```

Figure 13C (cont.)

```
TTTGAGAATCTCAAATGTTTGATGTTGAGTCAAGTGATTCTTTCCAAGTG 5200
GGAGGTTGGAGAGGAATCTTTTCCCACGCTTGAGAAATTAGAACTGTCGG 5250
ACTGTCATAATCTTGAGGAGATTCCGTCTAGTTTTGGGGATATTTATTCC 5300
TTGAAAATTATCGAACTTGTAAGGAGCCCTCAACTTGAAAATTCCGCTCT 5350
CAAGATTAAGGAATATGCTGAAGATATGAGGGGAGGGGACGAGCTTCAGA 5400
TCCTTGGCCAGAAGGATATCCCGTTATTTAAGTAGTTTTTGAGCATTATG 5450
GTTGAAAAGTAGATTGCACTTTGCTGGGTAGATTGTATATGGTTAAGAAA 5500
ATTCTGTTACAGTTGTTATGAAACATTTTTATTTGACTTTTCTGAGTTTC 5550
TTTTAGAAAACTCAGAAGTTTTTAACAAAAATTATAGTTTTTATAAATAC 5600
AATGTGGATTTGCCTTTGGCTGTCCAACTTGGTCTGAAGTCTCATATGCT 5650
CAGAGCACTATCGTTCAACCTCAATCAAGGTACTGATTTAAAATGACATC 5700
TATACTACTTTATCACAAACCCAACGAACTTTCATCTCAAAAGCTAGGCC 5750
AGGAAGTGAAGAGGTTGTAGAGAGCTTATAAGCACTCATGACTTCCTTTT 5800
CTCGAACATTCAACCAACGTAGGCTGAAATCCCACTCTGAACGAAAATAA 5850
GTGTTTGTTTATCAAATTAACTCTCGTAGTAGAACACTGAAATACCTTCT 5900
TCTAAACGTTCAACAAATGGGATTTCCAGCACTCAAAGTGAATGAAAGGT 5950
TCACATTAATCTTCAAAAAGAATTACGACAATTCATGACCACAAGTACAT 6000
TGACAGCACCATTTCAACAGAAGAACAAGTCAATGCTGCATCTTCATCAA 6050
TAATCCGAGTGTCGAACCTCCTTCCTGACACTGTCCTGTATATGTAAAGT 6100
TTCTCAACAGGGCAACTTTCTGGTCTCGTATCTGGATGACCCCTCTCGTC 6150
TATAACTTCAACATTAAGCCCTGGCAACTTCTGGACCAACAGCTTACATG 6200
CTTCAAAACTTACTGAACAATTAGACATCCAAAGGGATCGCATTGTCTCC 6250
AGCTTTGCAGCATTAGCCAACAGAGCCTCATCGCCAAAGGGGCAGTCTCT 6300
AATCTCGAATTTGAAAAAATTGTTGTTGTATGACTTTCCTCTGACATCCG 6350
ATGCACTATCAACAATAGCAAGACTGGAGGTTGGAGAGGAATCCTTTATT 6400
ATACAATCATTCAGGGAGAAGAATGGAACATGGGGGAGGAAGACACTTTT 6450
GAGAATCTGAAATGTGTTAGAGCCACAAGCTACAGAAGTATTGAATTTGT 6500
CATGAATATCAACATTCTTCATCCTAGTTAATTCTTTTTCAATTTTTAAT 6550
AGACTCTCATTTTAATCACTAATATTCTTCTATTTGTGACTTCTTTTCTG 6600
CAGGTGGCAACTTTAAATTCATAAAGTATAGGATTGATGACAAACTCGAA 6650
AAATATCTTAATGAGGTGAAGTTTGAGCAGTCAGCAGATGGTGGTTCCAA 6700
CTCTAAGTTGACAAGCACATACTATCCCGGAGGGCGATTTCAAGCCTGAT 6750
GCATATGGTTAGTGTGGCTAGAGCAGACAGGATGTATTACCTGGATATCT 6800
ACCAAGACGAATCCACAATCAGTTTTATGTCAAGCAATACATGAAGTAAC 6850
TCCCGATAGAACAGTAAAAGCAAGATGTGTAGGTGTATCTCGACTCTAAG 6900
```

Figure 13C (cont.)

```
AGATTGTACATTCCTCTTTGAGATTTTTACTGCTAATACAAATTTACACC 6950
TCAGAAGCGAATCTAGAATTTCTAGAGCATGAATGCACCACTAATGAAAG 7000
GAGAAAAAGGAAGTATGAAGTGGGAATTTGATCCTTGTTTCTAGGTATA  7050
TAAAATTTATCATTCAACTATACTTCATTTAGCAAACAACTCTCTTTGCC 7100
ATTATTTCTCAAACAAGGGCTTCTAATATTGCTAAACTAAAGACTGTCAA 7150
AAGGTAAGTTCATCTTCAAACTCTCTTGTTTACTTTATCTAAAGGGGAAC 7200
TATGAAAACAAGAAACATCAGGAATGTCCCGTAAACAAAGCAGCCTCAT  7250
GCACAAAACATCCAACGTTGGTAGGATTAATGGAGGGATCGCATCCCAGG 7300
AGGATACTGTAGAAAAATTAGTGGCTTCTTTCACCGCTCAAACCCATGAT 7350
CTATAGGTTACATGGAGACAACTTTATGGTTGCTCGTAGGCTCCCGTCAA 7400
TTCTCATAAACCACAACACCAAAGTTGCATCAGACATCATCTTCATTCAC 7450
AAGCTGACAATCTCCACAAGTCTTAGTCAACTTGTAATATGAATATTAGC 7500
CAGGTAGACGTACATATTTACAAAATTGAGTTTCCTATATAATATGGTTT 7550
GAAGGAATGAAACATGATGGGGAGGGTAGATAAAATAATATATGAGGCAT 7600
AAAAATAGGAAAGATATTTGTAGTGAGAGGTTTTGACTTTTTATGCTGCT 7650
TTTGATCTTCAGTTTCTTGTATTCTTTTTCTACTGCTTTCCTCTTCTTTC 7700
TCCTGAGTAAAGTTTTATGTAGGTACTTTTTATACGTCCGATCGTGAGAA 7750
CTTGAAAGAAAGCTCTCTATAGCTATGTTAGGTGCCCACATAAAAAAATG 7800
AAATATTACAAAAACCCTGATAATAAAATACACTAATCTAAGATATTCAC 7850
TGCAACATACATGCAAAATATATATATATAAATTTTCATGAAAATTATAA 7900
CAAATAATAGATGTGAACATATAACTTTAAAAATAATATTACATCCATAA 7950
AGCTTAAATTCTAGATC                                  7967
```

Figure 13D

```
GATCTGCTTCAAATGCTCTGATACCATGTAATTTCAGTGAATTCTAACTA 50
AACAATGGAGAGAATTAACTATTTTAGAAAGACTGATTGAAGGAGAAGAA 100
GAGAGAAAAATTCTATATTGAACTCATGAACCAAAATGAATGAAAAAAAT 150
AATGAGAAGAACTATACTATTACAATCTATATATCTCTATTTATATTCTA 200
ATCTGAAGCAGTTAATTTAACTGACTCTAACAACTAGACTGATAGGTGTA 250
CATTTTCTGTTAGTGCACTGCAGTGCATTTAACTAACTGCTTAACATAAA 300
GAATGTTGTTCGAACTTCATTCGAATAGCTTCAATGAGAAGCAAACATGT 350
GTACCTGTAAAGACACACAGTAAAAGTGTTAATAATGAATAAATATGAAT 400
AAATCAAATAATAAATTAAAAATAAAAACACATCCAATTAACATTGGAGG 450
TCTTGAAAATCGATGGTAATTAACAAAGACCCTTGTGAAATTTAAGTCTG 500
TAATTGAAAATTTGAGTATAGGTTAGGGGACATTTGACTATTTTCTCATT 550
TTCTTTATCTTTTTCCTAATTTGTGGCAGACAAGTGAGGAGGCCCCACTG 600
TAATTGATTCATGCTTTTGCTTTCTTGACTTTTTGGAACAATACTATGCA 650
TCATATTTGGTCTTAATTATTCCTCTGTTTATTTCCAGAATTTTGAGCTC 700
TATACATCTAATAACAAAGCAAGCAGAGGATATATAGTTTCATCAACTAA 750
AAAGGTTAGTCAACTCATCTAATATTTGCTACTCTCATCTCTATTGAAGT 800
ACAGTTATGGAAAAGTAGAAGTGATGTAAGAAAAATGAAAGAACTTTAGT 850
AGGTTAGTTGGATCTAACAAAGAGAAAGGGAAATAAATTGCAGGAGAAAG 900
AGAGAGGTTAAATACTTACTCACACCACCGATTTACAACAAATCACTTAA 950
TTGTGGTTAGTTAATGTATACTTTCACCTCATTAAATTATTACTTACCCA 1000
TGATAAGTTGTATTAATTTGGTATTAATATCCGGTGCGGGTGAATTCTTA 1005
CCGGGTGAGAGGGATGGGGTTGGAGAGTGTGGAGTGAACAGAAGCAGATG 1100
TTTTAGATTTTTTCTAAGATGACGAAAGATTCCCCTCACTAATGAAAATA 1150
TATTACTATACGCTATTAGAGATAGAAAGGTTCGGTACCAGTTGGTCTCG 1200
TTTCTGGATGAACCCCATTTTTACAAGTCATTTTCTTCAATTCAAATCGC 1250
AAGTGTACCTTTATCATCTTCCACTAATTAAGTCCTCTTAAGTTCGCGTG 1300
AAAATAGTGAAATTATTGATTATTCTTATCATTTCATCTTCTTTCTCCTG 1350
ATAAAGTTTTATGTACTTTTTATGCATCAGGTCTTGAGAACTTGGAAAGG 1400
AAAAGTAGAATCATGGAAAAACGAAAGATAATGAAGAAGCAAACAACTC 1450
ATTGGTATGTTATTTGATAGAGTGAACTGTAAAGTATTGAATTGTAGATA 1500
TCATGTGGCTTTAAAAATTTGATATGTGTTATTTTGGCAGGAGTCATTTT 1550
CTGCTCTTCGCAAGGATGCTGCCAATGTTCTGGATTTCCTAGAGAGATTA 1600
AAGAATGAAGAAGATCAAAAGGCTGTTGATGTGGATCTGATTGAAAGCCT 1650
```

Figure 13D (cont.)

```
GAAATTGAAGCTGACATTTATTTGTACATATGTCCAGCTTTCTTATTCCG 1700
ATTTGGAGAAGTTTGAAGATATAATGACTAGAAAAAGACAAGAGGTTGAG 1750
AATCTGCTTCAACCAATTTTGGATGATGATGGCAAAGACGTCGGGTGTAA 1800
ATATGTCCTTACTAGCCTCGCCGGTAATATGGATGACTGTATAAGCTTGT 1850
ATCATCGTTCTAAATCAGATGCCACCATGATGGATGAGCAATTGGGCTTC 1900
CTCCTCTTGAATCTCTCTCATCTATCCAAGCATCGTGCTGAAAAGATGTT 1950
TCCTGGAGTGACTCAATATGAGGTTCTTCAGAATGTATGTGGCAACATAA 2000
GAGATTTCCATGGATTGATAGTGAATTGTTGCATTAAGCATGAGATGGTT 2050
GAGAATGTCTTATCTCTGTTTCAACTGATGGCTGAGAGAGTAGGACGCTT 2100
CCTTTGGGAGGATCAGGCTGATGAAGACTCTCAACTCTCCGAGCTAGATG 2150
AGGATGATCAGAATGATAAAGACCCTCAACTCTTCAAGCTAGCACATCTA 2200
CTCTTGAAGATTGTTCCAACTGAATTGGAGGTTATGCACATATGTTATAA 2250
AACTTTGAAAGCTTCAACTTCAACAGAAATTGGACGCTTCATTAAGAAGC 2300
TCCTGGAAACCTCTCCGGACATTCTCAGAGAATATCTGATTCATCTACAA 2350
GAGCATATGATAACTGTTATTACCCCTAACACTTCAGGGGCTCGAAACAT 2400
TCATGTCATGATGGAATTCCTATTGATTATTCTTTCTGATATGCCGCCCA 2450
AGGACTTTATTCATCATGACAAACTTTTTGATCTCTTGGCTCGTGTTGTA 2500
GCACTTACCAGGGAGGTATCAACTCTTGTACGCGACTTGGAAGAGAAATT 2550
AAGGATTAAAGAGAGTACTGACGAAACAAATTGTGCAACCCTAAAGTTTC 2600
TGGAAAATATTGAACTCCTTAAGGAAGATCTCAAACATGTTTATCTGAAA 2650
GTCCCGGATTCATCTCAATATTGCTTCCCCATGAGTGATGGACCTCTCTT 2700
CATGCATCTGCTACAGAGACACTTAGATGATTTGCTGGATTCCAATGCTT 2750
ATTCAATTGCTTTGATAAAGGAACAAATTGGGCTGGTGAAAGAAGACTTG 2800
GAATTCATAAGATCTTTTTTCGCGAATATTGAGCAAGGATTGTATAAAGA 2850
TCTCTGGGAACGTGTTCTAGATGTGGCATATGAGGCAAAAGATGTCATAG 2900
ATTCAATTATTGTTCGAGATAATGGTCTCTTACATCTTATTTTCTCACTT 2950
CCCATTACCAGAAAGAAGATGATGCTTATCAAAGAAGAGGTCTCTGATTT 3000
ACATGAGAACATTTCCAAGAACAGAGGTCTCATCGTTGTGAACTCTCCCA 3050
AGAAACCAGTTGAGAGCAAGTCATTGACAACTGATAAAATAATTGTAGGT 3100
TTTGGTGAGGAGACAAACTTGATACTTAGAAAGCTCACCAGTGGACCGGC 3150
AGATCTAGATGTCATTTCGATCATTGGTATGCCGGGTTTAGGTAAAACTA 3200
CTTTGGCGTACAAAGTATACAATGATAAATCAGTTTCTAGCCATTTCGAC 3250
CTTCGTGCATGGTGCACGGTCGACCAAGTATATGACGAGAAGAAGTTGTT 3300
GGATAAAATTTTCAATCAAGTTAGTGACTCAAATTCAAAATTGAGTGAGA 3350
ATATTGATGTTGCTGATAAACTACGGAAACAATTGTTTGGAAAGAGGTAT 3400
```

Figure 13D (cont.)

```
CTTATTGTCTTAGATGACGTGTGGGATACTAATACATGGGATGAGCTAAC 3450
AAGACCTTTTCCTGATGGTATGAAAGGAAGTAGAATTATTTTGACAACTC 3500
GAGAAAAGAAAGTTGCTTTGCATGGAAAGCTCTACACTGATCCTCTTAAC 3550
CTTCGATTGCTAAGATCAGAAGAAAGTTGGGAGTTATTAGAGAAAAGGGC 3600
ATTTGGAAACGAGAGTTGCCCTGATGAACTATTGGATGTTGGTAAAGAAA 3650
TAGCCGAAAATTGTAAAGGGCTTCCTTTGGTGGTGGATCTGATTGCTGGA 3700
ATCATTGCTGGGAGGGAAAAGAAAAAGAGTGTGTGGCTTGAAGTTGTAAA 3750
TAATTTGCATTCCTTTATTTTGAAGAATGAAGTGGAAGTGATGAAAGTTA 3800
TAGAAATAAGTTATGACCACTTACCTGATCACCTGAAGCCATGCTTGCTG 3850
TACTTTGCAAGTGCGCCGAAGGACTGGGTAACGACAATCCATGAGTTGAA 3900
ACTTATTTGGGGTTTTGAAGGATTTGTGGAAAAGACAGATATGAAGAGTC 3950
TGGAAGAAGTGGTGAAAATTTATTTGGATGATTTAATTTCCAGTAGCTTG 4000
GTAATTTGTTTCAATGAGATAGGTGATTACCCTACTTGCCAACTTCATGA 4050
TCTTGTGCATGACTTTTGTTTGATAAAAGCAAGAAAGGAAAAGTTGTGTG 4100
ATCGGATAAGTTCAAGTGCTCCATCAGATTTGTTGCCACGTCAAATTAGC 4150
ATTGATTATGATGATGATGAAGAGCACTTTGGGCTTAATTTTGTCCTGTT 4200
CGGTTCAAATAAGAAAAGGCATTCCGGTAAACACCTCTATTCTTTGACCA 4250
TAAATGGAGATGAGCTGGACGACCATCTTTCTGATACATTTCATCTAAGA 4300
CACTTGAGGCTTCTTAGAACCTTGCACCTGGAATCCTCTTTTATCATGGT 4350
TAAAGATTCTTTGCTGAATGAAATATGCATGTTGAATCATTTGAGGTACT 4400
TAAGCATTGGGACAGAAGTTAAATCTCTGCCTTTGTCTTTCTCAAACCTC 4450
TGGAATCTAGAAATCTTGTTTGTGGATAACAAAGAATCAACCTTGATACT 4500
ATTACCGAGAATTTGGGATCTTGTAAAGTTGCAAGTGCTGTTCACGACTG 4550
CTTGTTCTTTCTTTGATATGGATGCAGATGAATCAATACTGATAGCAGAG 4600
GACACAAAGTTAGAGAACTTGACAGCATTAGGGGAACTCGTGCTTTCCTA 4650
TTGGAAAGATACAGAGGATATTTTCAAAAGGCTTCCCAATCTTCAAGTGC 4700
TTCATTTCAAACTCAAGGAGTCATGGATTATTCAACAGAGCAATATTGG 4750
TTCCCGAAATTGGATTTCCTAACTGAACTAGAAAAACTCACTGTAGATTT 4800
TGAAAGATCAAACACAAATGACAGTGGGTCCTCTGCAGCCATAAATCGGC 4850
CATGGGATTTTCACTTTCCTTCGAGTTTGAAAAGATTGCAATTGCATGAA 4900
TTTCCTCTGACATCCGATTCACTATCAACAATAGCGAGACTGCTGAACCT 4950
TGAAGAGTTGTACCTTTATCGTACAATCATCCATGGGGAAGAATGGAACA 5000
TGGGAGAAGAAGACACCTTTGAGAATCTCAAATGTTTGATGTTGAGTCAA 5050
GTGATTCTTTCCAAGTGGGAGGTTGGAGAGGAATCTTTTCCCACGCTTGA 5100
GAAATTAGAACTGTCGGACTGTCATAATCTTGAGGAGATTCCGTCTAGTT 5150
```

Figure 13D (cont.)

```
TTGGGGATATTTATTCCTTGAAAATTATCGAACTTGTAAGGAGCCCTCAA 5200
CTTGAAAATTCCGCTCTCAAGATTAAGGAATATGCTGAAGATATGAGGGG 5250
AGGGGACGAGCTTCAGATCCTTGGCCAGAAGGATATCCCGTTATTTAAGT 5300
AGTTTTTGAGCATTATGGTTGAAAAGTAGATTGCACTTTGCTGGGTAGAT 5350
TGTATATGGTTAAGAAAATTCTGTTACAGTTGTTATGAAACATTTTTATT 5400
TGACTTTTCTGAGTTTCTTTTAGAAAACTCAGAAGTTTTTAACAAAAATT 5450
ATAGTTTTTATAAATACAATGTGGATTTGCCTTTGGCTGTCCAACTTGGT 5500
CTGAAGTCTCATATGCTCAGAGCACTATCGTTCAACCTCAATCAAGGTAC 5550
TGATTTAAAATGACATCTATACTACTTTATCACAAACCCAACGAACTTTC 5600
ATCTCAAAAGCTAGGCCAGGAAGTGAAGAGGTTGTAGAGAGCTTATAAGC 5650
ACTCATGACTTCCTTTTCTCGAACATTCAACCAACGTAGGCTGAAATCCC 5700
ACTCTGAACGAAAATAAGTGTTTGTTTATCAAATTAACTCTCGTAGTAGA 5750
ACACTGAAATACCTTCTTCTAAACGTTCAACAAATGGGATTTCCAGCACT 5800
CAAAGTGAATGAAAGGTTCACATTAATCTTCAAAAAGAATTACGACAATT 5850
CATGACCACAAGTACATTGACAGCACCATTTCAACAGAAGAACAAGTCAA 5900
TGCTGCATCTTCATCAATAATCCGAGTGTCGAACCTCCTTCCTGACACTG 5950
TCCTGTATATGTAAAGTTTCTCAACAGGGCAACTTTCTGGTCTCGTATCT 6000
GGATGACCCCTCTCGTCTATAACTTCAACATTAAGCCCTGGCAACTTCTG 6050
GACCAACAGCTTACATGCTTCAAAACTTACTGAACAATTAGACATCCAAA 6100
GGGATCGCATTGTCTCCAGCTTTGCAGCATTAGCCAACAGAGCCTCATCG 6150
CCAAAGGGGCAGTCTCTAATCTCGAATTTGAAAAAATTGTTGTTGTATGA 6200
CTTTCCTCTGACATCCGATGCACTATCAACAATAGCAAGACTGGAGGTTG 6250
GAGAGGAATCCTTTATTATACAATCATTCAGGGAGAAGAATGGAACATGG 6300
GGGAGGAAGACACTTTTGAGAATCTGAAATGTGTTAGAGCCACAAGCTAC 6350
AGAAGTATTGAATTTGTCATGAATATCAACATTCTTCATCCTAGTTAATT 6400
CTTTTTCAATTTTTAATAGACTCTCATTTTAATCACTAATATTCTTCTAT 6450
TTGTGACTTCTTTTCTGCAGGTGGCAACTTTAAATTCATAAAGTATAGGA 6500
TTGATGACAAACTCGAAAAATATCTTAATGAGGTGAAGTTTGAGCAGTCA 6550
GCAGATGGTGGTTCCAACTCTAAGTTGACAAGCACATACTATCCCGGAGG 6600
GCGATTTCAAGCCTGATGCATATGGTTAGTGTGGCTAGAGCAGACAGGAT 6650
GTATTACCTGGATATCTACCAAGACGAATCCACAATCAGTTTTATGTCAA 6700
GCAATACATGAAGTAACTCCCGATAGAACAGTAAAAGCAAGATGTGTAGG 6750
TGTATCTCGACTCTAAGAGATTGTACATTCCTCTTTGAGATTTTTACTGC 6800
TAATACAAATTTACACCTCAGAAGCGAATCTAGAATTTCTAGAGCATGAA 6850
TGCACCACTAATGAAAGGAGAAAAAAGGAAGTATGAAGTGGGAATTTGAT 6900
```

Figure 13D (cont.)

```
CCTTGTTTCTAGGTATATAAAATTTATCATTCAACTATACTTCATTTAGC 6950
AAACAACTCTCTTTGCCATTATTTCTCAAACAAGGGCTTCTAATATTGCT 7000
AAACTAAAGACTGTCAAAAGGTAAGTTCATCTTCAAACTCTCTTGTTTAC 7050
TTTATCTAAAGGGGAACTATGAAAAACAAGAAACATCAGGAATGTCCCGT 7100
AAACAAAGCAGCCTCATGCACAAAACATCCAACGTTGGTAGGATTAATGG 7150
AGGGATCGCATCCCAGGAGGATACTGTAGAAAAATTAGTGGCTTCTTTCA 7200
CCGCTCAAACCCATGATCTATAGGTTACATGGAGACAACTTTATGGTTGC 7250
TCGTAGGCTCCCGTCAATTCTCATAAACCACAACACCAAAGTTGCATCAG 7300
ACATCATCTTCATTCACAAGCTGACAATCTCCACAAGTCTTAGTCAACTT 7350
GTAATATGAATATTAGCCAGGTAGACGTACATATTTACAAAATTGAGTTT 7400
CCTATATAATATGGTTTGAAGGAATGAAACATGATGGGGAGGGTAGATAA 7450
AATAATATATGAGGCATAAAAATAGGAAAGATATTTGTAGTGAGAGGTTT 7500
TGACTTTTTATGCTGCTTTTGATCTTCAGTTTCTTGTATTCTTTTTCTAC 7550
TGCTTTCCTCTTCTTTCTCCTGAGTAAAGTTTTATGTAGGTACTTTTTAT 7600
ACGTCCGATCGTGAGAACTTGAAAGAAAGCTCTCTATAGCTATGTTAGGT 7650
GCCCACATAAAAAAATGAAATATTACAAAAACCCTGATAATAAAATACAC 7700
TAATCTAAGATATTCACTGCAACATACATGCAAAATATATATATATAAAT 7750
TTTCATGAAAATTATAACAAATAATAGATGTGAACATATAACTTTAAAAA 7800
TAATATTACATCCATAAAGCTTAAATTCTAGATCCATCTATGCTTGTATG 7850
ATGCATAGCTCAGAATATCTCCATCAAGTGTTAAACTACATATTTCATTC 7900
AAATTTATATAGAAAACGATAATTAAGGTGAAAACTTTTATAAAGATATC 7950
GTGTGGTTGTGTGAGTGAGGTGACAAAATAAGTTGTGTGATTATTCAAAA 8000
AGTTTTAATAACGAAAATCCACATGCTTGAATTAATTGAAGCATTAATGT 8050
TGTAACGAAAAATATTACATTTATTGAGTTACTGTGATGTTTTAACTGAT 8100
ATATAAAATAATATTGGTATTTCTCTTCATCTGCGACATAATATGTTTTT 8150
TCATCTTTTTTCAATATACAAAATAGAATTATTATTTTGTTGCATCTTTT 8200
TAAGTACAAATTATTCATATGTATATAGTACAAAATAAAATATTTACTGT 8250
GGTAAAGTAAATGGAATAAGAGGTCATATTTGAAATAACAATATACTATA 8300
CTATGTTAAAGTATTTTTTATAGTTAAAATTTCTCTAGAGTACTTGATTC 8350
TACATACAAATACTAATTTCGTAAAAAAATTAATATTGAATTTCTTCATT 8400
GTTTCTTTATTATTAAATTAGTTTATAATAACTAAACTAAGGTAATAAGA 8450
CCTTAGTTTAGTTAATGTGTGTCTCTGTGATTTCGTTCATAGTCTAAGGG 8500
TGTACTTGTGCCTTATCCCAAAAATGAAGGAATATCAAAAGATATATTAA 8550
AATTAAATTAAATATTTGGAGGTTATGAATATAAAAAGTATCAGAGTTCT 8600
ACATATAAAGAGTAACAATTGAAATAATTAATTAAATATGAGATATGAAG 8650
```

Figure 13D (cont.)

```
GCGGACATTTAAAGAAAATAATAAATAAATAAATTAAAGGGTATAAATTT    8700
CATAATACATAATACCAATAAGCCGTAGAATATCTCCGTCATAATGCATA    8750
AACTAATAAATCACAAATGTATAACTCACATACAAATATTTTTTGATAAA    8800
GAATTTGAATGTTGTAATAGAATGGAGAATAACTTGTGTCTTATTCCATT    8850
ATGTAAGACGTATAAATACAAATACAATGAGCTCTAATTAATTAAGGAAA    8900
CTAAATAAGGAAGGAATCAAAAAATATTATGTCATATCCCTACATATCTG    8950
CTAGAGATTCTATCATATCCTTACATATCTGTTAAGCTATGTCTACACCT    9000
AAAGGTGTCTACAATCATTTTGTAACACTCCCCCTCAAGTTAGAGCATAG    9050
ATATTATTCATTCCCAACTTGTTACAAAGATAATCAACTCGAGTTCCATT    9100
CAACGCTTTTGTGAACAAATCAACTAGTTGCTCTCCTGTCTTCACTTAGC    9150
TAGTGGATATCAGGTTTTCATGAATCTTCTCACGAATAAAATGACAGTCA    9200
ACCTCAATATGTTTAGTTCTTTCATGAGACACCGGATTCAAGGCAATATG    9250
GAGCGCAACTTGATTATCATACTAGAGTTTTGATGGTATATGATGCTTCA    9300
ACCCTATTTCTGTTAAAAGATAATGTATCCACATGATCTCACCCATAGAC    9350
TGTAACATAACTCTGTACTTTGATTCTGCACTAGATCAAGATACAACATT    9400
TTGCTTTTTACTCCTCCATGATACCAGGTTTCATCCAACAAAGACACAAT    9450
AACTTGTAGTAGATCTTCTATCAATTTTCGATCCAGCCCAATCGACATCT    9500
GCAAAACACTCAATATGAGTATGGTCGTGATTTTGATACTATATTCCAAG    9550
ACTAGGAGTTTTCTTCAAGTAACATAGAATATGTTCCAAAGCTGCCCAGT    9600
GTTTGACGTAGGTGCAAACATGAACTAGCTAACAACACTTACTGCAAAAG    9650
CAATATCAAGATGAGTCACAATAAGGTAGTTTAACTTTCCAACTAACCTT    9700
TTGTATCTCTATGGATCATTAAAAGGATCGTCGTCATCTTTCATAAGATG    9750
CATATTGGGAACCATTGGAGAACTTCAGGGTTTGGCTGCCATCTTTCAAT    9800
TTTCTGCAAGTAGATCGAGAGAATATATTCTCTAAGACAAAAGAATTCCC    9850
TTTTTGTTTCTATTTACTTCTACTCCCAAAATGTATTTCAATTGACCCAA    9900
GTCCTTCGTATGAAACCAAGTATGCAGGAAAGACTTGAGGGAAGAGATC    9949
```

Figure 14

A 

B

MEKRKDNEEANNSLESFSALRKDAANVLDFLERLKNEEDQKAVDVDLIE
SLKLKLTFICTYVQLSYSDLEKFEDIMTRKRQEVENLLQPILDDDGKDV
GCKYVLTSLAGNMDDCISLYHRSKSDATMMDEQLGFLLLNLSHLSKHRA
EKMFPGVTQYEVLQNVCGNIRDFHGLIVNCCIKHEMVENVLSLFQLMAE
RVGRFLWEDQADEDSQLSELDEDDQNDKDPQLFKLAHLLLKIVPTELEV
MHICYKTLKASTSTEIGRFIKKLLETSPDILREYLIHLQEHMITVITPN
TSGARNIHVMMEFLLIILSDMPPKDFIHHDKLFDLLARVVALTREVSTL
VRDLEEKLRIKESTDETNCATLKFLENIELLKEDLKHVYLKVPDSSQYC
FPMSDGPLFMHLLQRHLDDLLDSNAYSIALIKEQIGLVKEDLEFIRSFF

LZ  ANIEQGLYKDLWERVLDVAYEAKDVIDSIIVRDNGLLHLIFSLPITRKK
MMLIKEEVSDLHENISKNRGLIVVNSPKKPVESKSLTTDKIIVGFGEET

NLILRKLTSGPADLDVISII*gmpglgkttla*YKVYNDKSVSSHFDLRAW
CTVDQVYDEKKLLDKIFNQVSDSNSKLSENIDVADKLRKQLFG*kryliv
lddvw*DTNTWDELTRPFPDGMKG*sriilttr*EKKVALHGKLYTDPLNLR
NBS  LLRSEESWELLEKRAFGNESCPDELLDVGKEIAENCK*glplvvdliag*I
IAGREKKKSVWLEVVNNLHSFILKNEVEVMKVIEISYDHLPDH*lkpcll
yfas*APKDWVTTIHELKLIWGFEGFVEKTDMKSLEEVVKIYLDDLISSS
LVICFNEIGDYPTCQ*lhdlvhd*FCLIKARKEKLCDRISSSAPSDLLPRQ
ISIDYDD

| | |
|---|---|
| DEEHFGLNFVLFGSNKK | |
| RHSGKHLYSLTINGDE.LDDHLSDTFH | 1 |
| LRHLRLLRTLHLESSFIMVKDSLLNE | 2 |
| ICMLNHLRYLSIGTEVKSLPLSF | 3 |
| SNBLWNLEILFVDNKESTLIL | 4 |
| LPRIWDLVKLQVLFTTACS | 5 |
| FFDMDADESILIAEDTK | 6 |
| LRR  LENLTALGELVLSYWKDT | 7 |
| EDIFKRLPNLQVHFK.LKESWDYSTEQYWFPK | 8 |
| LDFLTELEKLTVDFERSNTNDSGSSAAINRPWD | 9 |
| FHFPSSLKRLQLHEFP.LTSDSLST | 10 |
| IARLLNLEELYLYRTI.IHGEEWNMGE | 11 |
| EDTFENLKCLMLSQVI.LSKWEVG | 12 |
| EESFPTLEKLELSDCHNLEEIPSS | 13 |
| FGDIYSLKIIELVRSPQLENSALK | 14 |
| | 15 |

IKEYAEDMRGGDELQILGQKDIPLFK

```
Mi1.1                VL    S  I D  V    ---   N   L K QV KI   MA
57
Mi1.2         I      VL    S  I  I   ---     N   L K QV KL   MA
57
Rpi-blb2  MEKRKDNEEANNSLESPSALRKDAANVLDFLERLKNEEDQKAVDVDLIESLKLKLTFICT
60

Mi1.1           C  F Q              L  --------- P    TS
109
Mi1.2           Y  F Q      N       SL  --------      TS
109
Rpi-blb2  YVQLSYSDLEKFEDIMTRKRQEVENLLQPILDDDGKDVGCKYVLTSLAGNMDDCISLYHR
120

Mi1.1           Y  I    D      Y      H  I            I         G
169
Mi1.2           Y  I    D      Y      H  I                   L  G
169
Rpi-blb2  S-KSDATMMDEQLGFLLLNLSHLSKHRAEKMFPGVTQYEVLQNVCGNIRDFHGLIVNCCI
179

Mi1.1            P      D   H  D  T    R       E     R SR
229
Mi1.2            P          H     T    R       EH    R SR  Q T
229 Rpi-blb2
       KHEMVENVLSLFQLMAERVGRFLWEDQADEDSQLSELDEDDQNDKDPQLFKLAHLLLKIV 239

Mi1.1        V   I    TN      A V L      Q          P      V       S
289
Mi1.2                 TN      A V         I Q       L   P S L
289
Rpi-blb2  PTELEVMHICYKTLKASTSTEIGRFIKKLLETSPDILREYLIHLQEHMITVITPNTSGAR
299

Mi1.1              L    -          D  GV              EP N     GNNQ
348
Mi1.2              L    -             H GT                N    GNNQ
348
Rpi-blb2  NIHVMMEFLLIILSDMPPKDFIHHDKLFDLLARVVALTREVSTLVRDLEEKLRIKESTDE
359

Mi1.1            DL    K       AL    C           HI    N
408
Mi1.2            DL    K       A N   C           HM    N
408
Rpi-blb2  TNCATLKFLENIELLKEDLKHVYLKVPDSSQYCFPMSDGPLFMHLLQRHLDDLLDSNAYS
419

Mi1.1           E E    Q  K      VD-A       A
467
Mi1.2       S   E E    SQE        GDAA     I A
468
Rpi-blb2  IALIKEQIGLVKEDLEFIRSFFAN-IEQGLYKDLWERVLDVAYEAKDVIDSIIVRDNGLL
478                 -------------------

Mi1.1           I   IK    I A D   P D         R        T     E
527
Mi1.2           I   IK    I A D   P D         R        I     E
528
Rpi-blb2  HLIFSLPITRKKMMLIKEEVSDLHENISKNRGLIVVNSPKKPVESKSLTTDKIIVGFGEE
538

Mi1.1              S      T   S              R           GC
587
```

FIGURE.15

```
Mi1.2                    T        S                   R              G D
588
Rpi-blb2  TNLILRKLTSGPADLDVISIIgmpglgkttlaYKVYNDKSVSSHFDLRAWCTVDQVYDEK
598

Mi1.1    NT  S      D                              T          ESK
647
Mi1.2     T  S   G D N                             T L        EAK
648
Rpi-blb2 RLLDKIFNQVSDSNSKLSENIDVADKLRKQLFGKrylivlddvwDTNTWDELTRPFPDGM
658

Mi1.1             E       N      D     PD
707
Mi1.2             E       N      D     PD      D  T
708
Rpi-blb2 KGSRIILTTREKKVALHGKLYTDPLNLRLLRSEESWELLERRAFGNESCPDELLDVGKEI
718

Mi1.1              A      V       R       QSS S     NS        L      H
767
Mi1.2              A      V       R       QSS S     NS        L      H
768
Rpi-blb2 AENCKglplvvdliagIIAGREKKKSVWLEVVKNLHSFILKNEVEVMKVIEISYDHLPDH
778

Mi1.1              F    TSL  Y  NVYF A     G  E N M         M    Y
827
Mi1.2          H   W    TPL  YLFTVYL A        E GI          M
828
Rpi-blb2 lkpcllyfasAPKDWVTTIHELKLIWGFEGFVEKTDMKSLEEVVKIYLDDLISSSLVICF
838

Mi1.1      YALNF I            N F Q R        T  C E  -
886
Mi1.2      ILNF  I            N F   R        T     E
888
Rpi-blb2 NEIGDYPTCQlhdlvhdFCLIKARKEKLCDRISSSAPSDLLPRQISIDYDDEEHFGLNE
898
                                                              → LRR
Mi1.1    M D         R I Q   SV   A        V D HT
946
Mi1.2    M D         R   Q   SV   A      I V D P L     N
948
Rpi-blb2 VLFQSNKKRHSGKHLYSLTINGDELDDHLSDTFHLRHLRLLRTLHLESSFIMVKDSLLNE
958
              1              2                3
Mi1.1         D Q  Y          S   STNR   V       L     R  SVD
1006
Mi1.2       R R Q Y F          S   S G I V       L     R  SVG
1008
Rpi-blb2 ICMLNHLRYLSIGTEVKSLPLSFSNLWNLEILFVDNKESTLILLPRIWDLVKLQVLFTTA
1018
                4                    5                   6
Mi1.1                     RI T  LI   S     KN   F     L S E
1066
Mi1.2              K      RI    LI   S     MN   F       Q E
1068
Rpi-blb2 CSFFDMDADESILIAEDTKLENLTALGELVLSYWKDTEDIFKRLPNLQVLHFKLKESWDY
1078
               7                8               9
Mi1.1    H  SE       T S G KS         V T        N  I W R
1126
Mi1.2    H   C       T C G KS     HC  VVT        N  E L YD
1128
```

FIGURE 15 (cont.)

```
Rpi-blb2    STEQYWFPKLDFLTELEKLTVDFERSNTNDSGSSAAINRPWDFHFPSSLKRLQLHEFPLT
1138
                              10                              11
Mi1.1                 P    S  H              F NFN  SI
1186
Mi1.2                 P  N S  D   Q          F N  RLLT
1188
Rpi-blb2    SDSLSTIARLLNLEELYLYRTIIHGEEWNMGEEDTFENLKCLMLSQVILSKWEVGEESFP
1198
                              12                    13
Mi1.1       N     K RG   K        P       S KI K    D
1246
Mi1.2       N     K QE GK         P       F KI K    D       K        ND
1248
Rpi-blb2    TLEKLELSDCHNLEEIPSSFGDIYSLKIIELVRSPQLENSALKIKEYAEDMRGGDELQIL
1258
                 14                       15
Mi1.1            N        1255
Mi1.2            N        1257
Rpi-blb2    GQKDIPLFK 1267
```

FIGURE 15 (cont.)

Figure 16: Multiple Sequence Alignments of Mi1.1, Mi1.2 and Rpi-blb2 nucleic acids CLUSTAL W (1.82) Multiple Sequence Alignments

```
Sequence format is Pearson
Sequence 1: Mi1.1      3768 bp
Sequence 2: Mi1.2      3774 bp
Sequence 3: Rpi-blb2   3804 bp
Start of Pairwise alignments
Aligning...
Sequences (1:2) Aligned. Score:  95
Sequences (1:3) Aligned. Score:  89
Sequences (2:3) Aligned. Score:  89
Guide tree        file created:    [/ebi/extserv/clustalw-
work/interactive/clustalw-20040503-14435620.dnd]
Start of Multiple Alignment
There are 2 groups
Aligning...
Group 1: Sequences:   2        Score:68908
Group 2: Sequences:   3        Score:65855
Alignment Score 66872
CLUSTAL-Alignment file created   [/ebi/extserv/clustalw-work/interactive/clustalw-
20040503-14435620.aln]

CLUSTAL W (1.82) multiple sequence alignment

Mi1.1      ATGGAAAAACGAAAAGATAATGAAGAAGCAAACAACTCATTGGTGCTATTTTCTGCTCTT 60
Mi1.2      ATGGAAAAACGAAAAGATATTGAAGAAGCAAACAACTCATTGGTGTTATTTTCTGCTCTT 60
Rpi-blb2   ATGGAAAAACGAAAAGATAATGAAGAAGCAAACAACTCATTGGAGTCATTTTCTGCTCTT 60
           ******************* *********************** *  ************
```

Figure 16 (cont.)

```
Mi1.1     AGCAAGGACATTGCCGATGTTCTGGTTTTCCTAGAGA--------------ATGAGGAAAATCAA  111
Mi1.2     AGCAAGGACATTGCCAATGTTCTTAATTTTCCTAGAGA--------------ATGAGGAAAATCAA  111
Rpi-blb2  CGCAAGGATGCTGCCAATGTCTCGGATTTCCTAGAGAGATTAAAGAGATTAAAGAAGAAGATCAA  120
          * ****  ******  *****   ** ** ********              ***  *** *****

Mi1.1     AAAGCTCTTGACAAAGATCAAGTTGAAAAGATAAAATTGAAAAATGGCATTTATTTGTACA      171
Mi1.2     AAAGCTCTTGACAAAGATCAAGTTGAAAAGATCAAGTTGAAAAATGGCATTTATTTGTACA      171
Rpi-blb2  AAGGCTGTTGATGTGGATCTGATTGAAGAGCCTGAAATTGAAGCTGACATTTATTTGTACA      180
          ** *** *****   **** ****       *       *       * *** ***********

Mi1.1     TATGTTCAGCTTTCTTCTTGTTCCGATTTGAGCAGTTTGAAGATATAATGACTAGAAAAAGA      231
Mi1.2     TATGTTCAGCTTTCTTCTTATTCCGATTTGAGCAGTTTGAAGATATAATGACTAGAAAATAGA      231
Rpi-blb2  TATGTCCAGCTTTCTTCTTATTCCGATTTGGAGTTGAAGAAGTTTGAAGATATAATGACTAGAAAAAGA  240
          ***** *************  ******** **   **    **** * * ***************

Mi1.1     CAAGAGGTTGAGAATCTGCTTCAACCACTTTTGGATGATGATG---------------------  274
Mi1.2     CAAGAGGTTGAGAATCTGCTTCAATCACTTTTGGATGATGATG---------------------  274
Rpi-blb2  CAAGAGGTTGAGAATCTGCTTCAACCAATTTTGGATGATGATGATGATGGCAAAGACGTCGGGTGT  300
          ******************** **  ** ** * ************

Mi1.1     ----------TCTTTACTAGCCTCACCAGTAATATGGATGACTGTATCAGCTTGTATCATCGT  327
Mi1.2     ----------TCCTTACTAGCCTCACCAGTAATATGGATGACTGTATCAGCTTGTATCATCGT  327
Rpi-blb2  AAATATGTCCTTACTAGCCTCGCCGGTAATATGGATGATGGATGGATGACTGTATAAGCTTGTATCATCGT  360
          **   **************  **  ********************* ****************

Mi1.1     TCTTATAAATCAGATGCCATCATGATGAGCAATTGGACTTCCTCTTGAATCTC    387
Mi1.2     TCTTATAAATCAGATGCCATCATGATGAGCAATTGGACTTCCTCTTGAATCTG    387
Rpi-blb2  TCT---AAATCAGATGCCACCATGATGATGAGCAATTGGGCTTCCTCTTGAATCTC  417
          ***    ***********  ******** *********  *************
```

Figure 16 (cont.)

```
Mi1.1    TATCATCTATCCAAGCATCACGCTGAAAAGATATTCCTGGAGTGACTCAATATGAAGTT  447
Mi1.2    TATCATCTATCCAAGCATCACGCTGAAAAGATATTCCTGGAGTGACTCAATATGAAGTT  447
Rpi-blb2 TCTCATCTATCCAAGCATCGTGCTGCTGAAAAGATGTTCCTGGAGTGACTCAATATGAAGTT  477
         * * ***************   *************** ***********************

Mi1.1    CTTCAGAATATATGTGGCAACATAAGAGATTTCCATGGTTGATAGTGAATGGTTGCATT  507
Mi1.2    CTTCAGAATGTATGTGGCAACATAAGAGATTTCCATGGTTGATACTGAATGGTTGCATT  507
Rpi-blb2 CTTCAGAATGTATGTGGCAACATAAGAGATTTCCATGGATTGATAGTGAATTGTTGCATT  537
         ********* ***************************** **** ***** *******

Mi1.1    AAGCATGAGAGATGGTTGAGAATGTCTTRCCTCTGTTTCAACTCATGGCTGACAGAGTAGGA  567
Mi1.2    AAGCATGAGAGATGGTTGAGAATGTCTTACCTCTGTTTCAACTCATGGCTGACAGAGTAGGA  567
Rpi-blb2 AAGCATGAGAGATGGTTGAGAATGTCTTATCTCTGTTTCAACTCATGATGGCTGAGAGAGTAGGA  597
         *****************************  ****************    *****  *****

Mi1.1    CACTTCCTTTGGATGATCAGACTGATGAAGACTCTCGACTCTCCGAGCTAGATGAGGAT  627
Mi1.2    CACTTCCTTTGGAGGATCAGACTGATGAAGACTCTCGCGCTCTCCGAGCTAGATGAGGAT  627
Rpi-blb2 CGCTTCCTTTGGAGGATCAGGCTGATGAAGACTCTCAACTCTCCGAGCTAGATGAGGAT  657
         * ***********  ***** ***************  ******************

Mi1.1    GAACAAAATGATAGAGAGACTCTCGACTTTTCAAGCTAGCACATCTACTCTTGAAGATCGTT  687
Mi1.2    GAACACAATGATAGAGAGACTCTCGACTCTCCCAGCTAACAACATCTACTCTTGAAGATTGTT  687
Rpi-blb2 GATCAGAATGATAAAGACTCTCCAACCCTCAAGCTAGCACATCTACTCTTGAAGATTGTT  717
         ** ** ******* *  ****  ***  ** *** ********************** ***

Mi1.1    CCGGTTGAACTGGAGGTTATACACATATGTTATACAACTTGAAAGCTTCAACTTCAGCT  747
Mi1.2    CCAACTGAACTGGAGGTTATGCACATATGTTATACAAATTGAAAGCTTCAACTTCAGCA  747
Rpi-blb2 CCAACTGAATTGGAGGTTATGCACATATGTTATAAAACTTGAAAGCTTCAACTTCAACA  777
         **   **** **********  ***********   *********************

Mi1.1    GAAGTTGGACTCTTCATTAAGCAGCTTCTAGAAACCTCTCCAGATATTCTGAGGAATAT  807
```

Figure 16 (cont.)

```
Mi1.2      GAAGTTGGACGCTTCATTAAGAAGCTCCTCTGGAAACCTCACCGGATATTCTCAGAGAATAT  807
Rpi-blb2   GAAATTGGACGCTTCATTAAGAAGCTCCTCTGGAAACCTCCGGACATTCTCAGAGAATAT   837
           *** ****** ************************ ***** ** ****** ** ******

Mi1.1      CTAATTCCTCTGCAAGAGCACATGGTAACTGTTATTACCCCTAGCACTTCAGGGGCTCGA   867
Mi1.2      ATCATTCAACTACAAGAGCATATGTTAACTGTTATTCCCCCTAGCACTTTAGGGGCTCGA   867
Rpi-blb2   CTGATTCATCTACAAGAGCATATGATAACTGTTATTACCCCTAACACTTCAGGGGCTCGA   897
             * ****  **  ******* ***  *********  **** **** * ***********

Mi1.1      AACATTCATGTCATGATGGAATTCCTATTACTTATTCTTTCTGATATGCC---CAAGGAC   924
Mi1.2      AACATTCATGTCATGATGGAATTCCTATTACTTATTCTTTCTGATATGCC---CAAGGAC   924
Rpi-blb2   AACATTCATGTCATGATGGAATTCCTATTGATTATTCTTTCTGATATGCCGCCCAAGGAC   957
           *****************************  ******************   ********

Mi1.1      TTTATTCATCATGACAAACTTTTTGATCTCTTGGATCGTGTCGGAGTACTTACCAGGGAG   984
Mi1.2      TTTATTCATCATGACAAACTTTTTGATCTCTTGGCTCTCTTGGAACACTTACCAGGGAG   984
Rpi-blb2   TTTATTCATCATGACAAACTTTTTGATCTCTTGGCTCTCGTGTTGTAGCACTTACCAGGGAG  1017
           **********************************  **  ** *  ** **********

Mi1.1      GTATCAACTCTTGTACGTGACTTGGAAGAGGAACCAAGGAATAAAGAGGGTAATAACCAA  1044
Mi1.2      GTATCGACTCTTGTACGTGACTTGGAAGAGAATAAGGAATTAAGGAATAAAGAGGGTAATAACCAA  1044
Rpi-blb2   GTATCAACTCTTGTACGCGACTTGGAAGAGAAAATTAAGGATTAAAGAGAGTACTGACGAA  1077
           ***** ***********  *********** *  *   ***  ******  ** ** **

Mi1.1      ACAAATTGTGCAACCCTAGACTTGCTGGAAAATATTGAACTCCTCAAGAAAAGATCTCAAA  1104
Mi1.2      ACAAATTGTGCAACCCTAGACTTGCTGGAAAATATTGAACTCCTCAAGAAAAGATCTCAAA  1104
Rpi-blb2   ACAAATTGTGCAACCCTAAAGTTTCTGGAAAATATTGAACTCCTTAAGGAAGATCTCAAA   1137
           ****************** *   ******************** *** *** ********

Mi1.1      CATGTTTATCTGAAAGCCCCTGGATTCATCTCAATGTTGCTTCCCCATGATGTGGACCA   1164
Mi1.2      CATGTTTATCTGAAAGCCCCCAAATTCATCTCAATGTTGCTTCCCCATGATGTGGACCA   1164
```

Figure 16 (cont.)

```
Rpi-blb2    CATGTTTATCTGAAAGTCCCGGATTCATCTCAATATTGCTTCCCATGAGTGATGGACCT  1197
            ************** **   *********************************

Mi1.1       CTCTTCATGCATCTTCTACACATACACTTAAATGATTTGTTAGATTCTAATGCTTATTCA  1224
Mi1.2       CTCTTCATGCATCTTCTACACATACACATGCACTTAAATGATTTGCTAGATTCTAATGCTTATTCA  1224
Rpi-blb2    CTCTTCATGCATCTGCTACAGACACTTAGATGATTTGCTGATTCCAATGCTTATTCA  1257
            ************** ****** *  ****** *  ****** ************

Mi1.1       ATTGCTTTGATAAAGGAAGAAATCGAGCTGGTGAAGCAAGACCTGAAATTCATAAGATCA  1284
Mi1.2       ATTTCTTTGATAAAGGAAGAAATCGAGTTGGTGAGTCAAGAACTGAGTTCATAAGATCA  1284
Rpi-blb2    ATTGCTTTGATAAAGAACAAATTGGGCTGGTGAAAGAAGACTTGGAATTCATAAGATCT  1317
            *** *********** **    *  ***** *  *   ****************

Mi1.1       TTCTTTGTGGATGCTG---AGCAAGGATTGTATAAAGATCTCTGGGCACGTGTTCTAGAT  1341
Mi1.2       TTCTTTGGGATGCTGCTGAGCAAGGATTGTATAAAGATCTGGGCACGTGTTCTAGAT  1344
Rpi-blb2    TTTTTCGCGAATATTG---AGCAAGGATTGTATAAAGATCTCTGGGAACGTGTTCTAGAT  1374
            ** ** **   **  **  *********************** ** **************

Mi1.1       GTGGCTTATGAGGCAAAAGATGTCATAGATTCAATTATTGTTCGAGATAATGGTCTCTTA  1401
Mi1.2       GTGGCTTATGAGGCAAAAGATGTCATAGATTCAATTATTGTTCGAGATAATGGTCTCTTA  1404
Rpi-blb2    GTGGCATATGAGGCAAAAGATGTCATAGATTCAATTATTGTTCGAGATAATGGTCTCTTA  1434
            ***** ****************************************************

Mi1.1       CATCTTATTTCTCACTTCCCATTACCATAAAGAAGATCAAACTTATCAAAGAAGAGATC  1461
Mi1.2       CATCTTATTTTCTCACTTCCCATTACCATAAAGAAGATCAAACTTATCAAAGAAGAGATC  1464
Rpi-blb2    CATCTTATTTCTCACTTCCCATTACCAGAAAGAAGATGATGCTTATCAAAGAAGAGAGTC  1494
            ********* *****************  ********    * *********** *

Mi1.1       TCTGCTTTAGATGAGAACATTCCCAAGGACAGAGAGGTCTAATCGTTGTGAACTCTCCCAAG  1521
Mi1.2       TCTGCTTTAGATGAGAACATTCCCAAGGACAGAGAGGTCTAATCGTTGTGAACTCTCCCAAG  1524
Rpi-blb2    TCTGATTTACATGAGAACAGAGAACAGAGAGGTCTCATCGTTGTGAACTCTCCCAAG  1554
            ****  ***  ******* ******** ** ******* *****************
```

Figure 16 (cont.)

```
              ****  ****  ***************  ******  ****************  ***************************
Mi1.1      AAACCAGTTGAGAGAAAGTCATTGACAACTGATAAAATAACTGTAGGTTTTGAGGAGGAA 1581
Mi1.2      AAACCAGTTGAGAGAAAGTCATTGACAACTGATAAAATAATTGTAGGTTTTGAGGAGGAG 1584
Rpi-blb2   AAACCAGTTGAGAGCAAGTCATTGACAACTGATAAAATAATTGTAGGTTTTGGTGAGGAG 1614
              *************************************************  ******

Mi1.1      ACAAACTTGATACTTAGAAAGCTCACCAGTGGACCGCAGATCTAGATGTCATTTCGATC 1641
Mi1.2      ACAAACTTGATACTTAGAAAGCTCACCAGTGGACCCGCAGATTTAGATGTCATTTCGATC 1644
Rpi-blb2   ACAAACTTGATACTTAGAAAGCTCACCAGTGGACCGGCAGATCTAGATGTCATTTCGATC 1674
              ********************************* *  ********************

Mi1.1      ACTGGTATGCCGGGGTTCAGGTAAAACTACTTTGGCATACAAAGTATACAATGATAAGTCA 1701
Mi1.2      ACCGGTATGCCGGGGTTCAGGTAAAACTACTTTGGCATACAAAGTATACAATGATAAGTCA 1704
Rpi-blb2   ATTGGTATGCCGGGTTTAGGTAAAACTACTTTGGCTACAAAGTATACAATGATAAATCA 1734
           *  ***********  ** ****************  ********************** ***

Mi1.1      GTTTCTAGCCGTTTCGACCTTCGTGCATGGTGCACGGTCGACCAAGGATGTGATGAGAAG 1761
Mi1.2      GTTTCTAGACATTTGACCTTCGTGCATGGTGCACGGTCGATCAAGGATATGATGACGACAAG 1764
Rpi-blb2   GTTTCTAGCCATTTCGACCTTCGTGCATGGTGCACGGTCGACCAAGGTATATGACGAGAAG 1794
           ********  *   ** ********************** **    **  **  ** *

Mi1.1      AAGTTGTTGAATACAATTTCAGTCAAGTTAGTGACTCAGATTCAAAATTGAGTGAGAAT 1821
Mi1.2      AAGTTGTTGGATACAATTTCAGTCAAGTCAAGTAGTGGCTCAGATTCAAAATTGAGTGAGAAT 1824
Rpi-blb2   AAGTTGTTGGATAAATTTCAATCAAGTCAGTAGTGACTCAATTCAAATTCAAAATTGAGTGAGAAT 1854
              ******   ***   ** ********         *********************

Mi1.1      ATTGATGTTGCTGATAAATTACGGAAACAACTGTTTGGAAAGAGGTATCTTATTGTCTTA 1881
Mi1.2      ATTGATGTTGCTGATAAATTGCGGAAACAACTGTTTGGAAAGAGGTATCTTATTGTCTTA 1884
Rpi-blb2   ATTGATGTTGCTGATAAACTACGGAAACAATTGTTTGGAAAGAGGTATCTTATTGTCTTA 1914
           ******************  * ********  **************************
```

Figure 16 (cont.)

```
Mi1.1      GATGACGTGTGGGATACTACTACATGGGATGAGTTAACAAGACCTTTTCCTGAATCTAAG  1941
Mi1.2      GATGATGTGTGGGATACTACTACATGGGATGAGTTGACAAGACCTTTTCCTGAAGCTAAG  1944
Rpi-blb2   GATGACGTGTGGGATACTAATACATGGGATGAGTTAACAAGACCTTTCCTGATGGTATG   1974
           *****  **************  ************** ************* *  *

Mi1.1      AAAGGAAGTAGGATTATTTGACAACTCGGAGAAAGGAAGTGGCTTTGCATGGAAAGCTG   2001
Mi1.2      AAAGGAAGTAGGATTATTTTGACAACTCGAGAAAAGGAAGTGGCTTTGCATGGAAAGCTG  2004
Rpi-blb2   AAAGGAAGTAGAATTATTTTGACAACTCGAGAAAAGAAAGTTGCTTTGCATGGAAAGCTC  2034
           *********** ******* *********  **** ***** ***************

Mi1.1      AACACTGATCCTCTTGACCTTCGATTGCTAAGACCAGATGAAAGTTGGGAACTATTAGAG  2061
Mi1.2      AACACTGATCCTCTTGACCTTCGATTGCTAAGACCAGATGAAAGTTGGGAACTTTTAGAT  2064
Rpi-blb2   TACACTGATCCTCTTAACCTTCGATTGCTAAGATCAGAAGAAAGTTGGGAGTTATTAGAG  2094
            ************** *****************  ****  ********* * *****

Mi1.1      AAAGGGCATTTGGGAATGAGAGTTGCCCTGATGAACTATTAGATGTCGGTAAAGAAATA   2121
Mi1.2      AAAGGACATTTGGTAATGAGAGTTGCCCTGATGAGAGTATTAGATGTCGGTAAAGAAATA  2124
Rpi-blb2   AAAGGGCATTTGGAAACGAGAGTTGCCCTGATGAACTATTGGATGTTGGTAAAGAAATA   2154
           ***** ******* **  ****************  **** ***** ************

Mi1.1      GCCGAAAATTGTAAAGGGCTTCCTTTGGTGGCTGATCTGATTGCTGGAGTCATTGCTGGG  2181
Mi1.2      GCCGAAAATTGTAAAGGGCTTCCTTTGGTGGCTGATCTGATTGCTGGAGTCATTGCTGGG  2184
Rpi-blb2   GCCGAAAATTGTAAAGGGCTTCCTTTGGTGGCTGATCTGATTGCTGGAATCATTGCTGGG  2214
           ************************************************ **********

Mi1.1      AGGGAAAAGAAAAGGAGTGTGTGGCTTGAAGTTCAAAGTAGTTCTTTTATTTTG        2241
Mi1.2      AGGGAAAAGAAAAGGAGTGTGTGGCTTGAAGTTCAAAGTAGTTTCTTTTATTTTG       2244
Rpi-blb2   AGGGAAAAGAAAAGAGTGTGTGGCTTGAAGTTGTAAATAATTGCATTCCTTTATTTTG    2274
           **  **  **** ******* *****
```

Figure 16 (cont.)

```
Mi1.1      AACAGTGAAGTGGAAGTGATGAGAAAGTTATAGAATTAAGTTATGACCATTTACCACATCAC  2301
Mi1.2      AACAGTGAAGTGGAAGTGATGAGAAAGTTATAGAATTAAGTTATGACCATTTACCACATCAC  2304
Rpi-blb2   AAGAATGAAGTGGAAGTGATGAAGTGAAAATAAGTTATGACCACTTACCTGATCAC  2334
           ** *  ************************ *****  ********* *****  *****

Mi1.1      CTCAAGCCATGCTTGCTGTATTTGCAAGTTTTCCGAAGGACACTTCATTGACAATCTAT   2361
Mi1.2      CTCAAGCCATGCTTGCTTCACTTTGCAAGTTGCCAAGGACACTCCTTGACAATCTAT   2364
Rpi-blb2   CTGAAGCCATGCTTGCTGTACTTTGCAAGTGCGCCAAGGACTGGGTAACGACAATCCAT   2394
           ** ************** *  ***********        * ********  *

Mi1.1      GAGTTGAATGTTTATTTCGGTGCTGAAGGATTTGTGGGAAAGACGGAGATGAACAGTATG   2421
Mi1.2      TTGTTTACTGTTTATTTGGGTGCTGAAGGATTTGTGGAAAAGACGGAGATGAAGGGTATA   2424
Rpi-blb2   GAGTTGAAACTTATTTGGGGTTTTGAAGGATTTGTGGAAAAGACAGATATGAAGAGTCTG   2454
           *** *  **  ***   *** *** ***********  ** ***** ** ******  *

Mi1.1      GAAGAAGTGGTGAAGATTTATATGGATGATTAATTACAGTAGCTTGGTAATTTGTTTC   2481
Mi1.2      GAAGAAGTGGTGAAGATTTATATGGATGATTAATTTCCAGTAGCTTGGTAATTTGTTTC   2484
Rpi-blb2   GAAGAAGTGGTGAAAATTTATTTGGATGATTAATTTCCAGTAGCTTGGTAATTTGTTTC   2514
           ************** ***** ** ***********  *********************

Mi1.1      AATGAGATAGGTTATGCACTGAATTTCCAAATTCATGATCTTGTGCATGACTTTTGTTTG   2541
Mi1.2      AATGAGATAGGTTGATATACTGAATTTCCAAATTCATGATCTTGTGCATGACTTTTGTTTG   2544
Rpi-blb2   AATGAGATAGGTTGATTACCCTACTTGCCAACTTCATGATCTTGTGCATGACTTTTGTTTG   2574
           *************    *     **  *  ** ****************************

Mi1.1      ATAAAAGCAAGAAAGGAAAATTTGTTTGATCAGATAAGATCAAGTGCTCCATCAGATTTG   2601
Mi1.2      ATAAAAGCAAGAAGGAAAGGAAAATTTGTTTGATCGGATAAGATCAAGTGCTCCATCAGATTTG   2604
Rpi-blb2   ATAAAAGCAAGAAGAAGGAAAAGTTGTGATCGGATAAGTTCAAGTGCTCCATCAGATTTG   2634
           *************  ****** ****  ****  ***** *******************

Mi1.1      TTGCCTCGTCAAATTACCATTGATTGTGATGAGGAGGAG---CACTTTGGGCTTAATTTT   2658
```

Figure 16 (cont.)

```
Mi1.1      TTGCCTCGTCAAATTACCATTGATTATGATGAGGAGGAGGAGCACTTTGGGCTTAATTTT  2664
Mi1.2
Rpi-blb2   TTGCCACGTCAAATTAGCATTGATTATGATGATGATGAAGAGCACTTTGGGCTTAATTTT  2694
           ***** ******** ************ ** ** **   ** ***************

Mi1.1      GTCATGTTCGATTCAAATAAGAAAAGGCATTCTGGTAAACACCTCTATTCTTTGAGGATA  2718
Mi1.2      GTCATGTTCGATTCAAATAAGAAAAGGCATTCTGGTAAACACCTCTATTCTTTGAGGATA  2724
Rpi-blb2   GTCCTGTTCGGTTCAAATAAGAAAAGGCATTCCGGTAAACACCTCTATTCTTTGACCATA  2754
           ***  ***** ********************* ********************** ***

Mi1.1      ATTGGAGACCAGCTGGATGACAGTGTTTCTGATGCATTTCACCTAAGACACTTGAGGCTT  2778
Mi1.2      AATGGAGACCAGCTGGATGACAGTGTTTCTGATGCATTTCACCTAAGACACTTGAGGCTT  2784
Rpi-blb2   AATGGAGATGAGCTGGACGACCATCTTTCTGATACATTTCATCTAAGACACTTGAGGCTT  2814
           * ******  ******* ***  * ********  ****** *****************

Mi1.1      CTTAGAGTGTTGGACCTGCATACGTCTCTTTTATCATGGTGAAAAGATTCTTTGCTGAATGAA  2838
Mi1.2      ATTAGAGTGTTGGACCTGGAACCTGGAACCCTCTTAATCATGGTGAATGATTCTTTGCTGAATGAA  2844
Rpi-blb2   CTTAGAACCTTGCACCTGGAATCCTCTCTTTTATCATGGTTAAAGATTCTTTGCTGAATGAA  2874
            *****   ***  *****          ** ********  * ***************

Mi1.1      ATATGCATGTTGAATCATTGAGTACTTATCCATTGACACACAAGTTAAATATCTGCCT  2898
Mi1.2      ATATGCATGTTGAATCATTGAGTACTTAAGAATTCGGACACAAGTTAAATATCTGCCT  2904
Rpi-blb2   ATATGCATGTTGAATCATTGAGTACTTAAGCACTTGGGACACAGAAGTTAAATCTCTGCCT  2934
           ***********************     ***      ***** *********** ******

Mi1.1      TTGTCTTTCTCAAACCTCTGGAATCTAGAAAGCCTGTTTGTGTCTACCAACAGATCAATC  2958
Mi1.2      TTCTCTTTCTCAAACCTCTGGAATCTAGAAAGTCTGTTTGTGTCTAACAACAAAGGATCAATC  2964
Rpi-blb2   TTGTCTTTCTCAAACCTCTGGAATCTAGAAATCTAGAAATCTTGTTTGTTGGATAACAAAGAATCAACC  2994
           ** *************************** ** * ***  **    ** ****

Mi1.1      TTGGTACTATTACCGAGAATTTGGATCTTGTAAAGTTGCGAGTGCTGTCCGTGGATGCT  3018
Mi1.2      TTGGTACTATTACCGAGAATTTGGATCTTGTAAAGTTGCGAGTTGCGAGTTGCCGTGTCCGTGGGTGCT  3024
```

Figure 16 (cont.)

```
Rpi-blb2    TTGATACTATTACCGAGAATTTGGGATCTTGTAAAGTTGCAAGTGCTGTTCACGACTGCT  3054
            ***  ***************************  ********  *  *     ****

Mi1.1       TGTTCTTTCTTTGATATGGATGCAGATGAATCAATATTGATAGCAGAGGACACAAAGTTA  3078
Mi1.2       TGTTCTTTCTTTGATATGGATGCAGATGAATGAATATTGATAGCAGAGGACACAAAGTTA  3084
Rpi-blb2    TGTTCTTTCTTTGATATGGATGCAGATGAATCAATACTGATAGCAGAGGACACAAAGTTA  3114
            ******************************* **** ***********************

Mi1.1       GAGAACTTGAGAATATTAACGGAACTGTTGATTTCCTATTCGAAAGATACAAAGAATATT  3138
Mi1.2       GAGAACTTGAGAATATTAGGGGAACTGTTGATTTCCTATTCGAAAGATACAATGAATATT  3144
Rpi-blb2    GAGAACTTGACAGCATTAGGGGAACTCGTGCTTTCCTATTGCTGAAAGATACAGAGGATATT  3174
            ********** *  **** * *****  **  ******* *  ********* * *****

Mi1.1       TTCAAAAGGTTTTCCCAATCTTCAGTTGCTTTCATTTGAACTCAAGGAGTCATGGGATTAT  3198
Mi1.2       TTCAAAAGGTTTTCCCAATCTTCAGTTGCTTTCAGTTGAACTCAAGGAGTCATGGGATTAT  3204
Rpi-blb2    TTCAAAAGGCTTCCCCAATCTTCAAGTGCTTCATTTCAAACTCAAGGAGTCATGGGATTAT  3234
            ********* **  **********  ***** *  ** ** *******************

Mi1.1       TCAACAGAGCAACATTGGTTCTCGGAATTGGATTTCCTAACTGAACTAGAAACACTCTCT  3258
Mi1.2       TCAACAGAGCAACATTGGTTCCCCGAAATTGGATTGCCTAACTGAACTAGAAACACTCTGT  3264
Rpi-blb2    TCAACAGAGCAATATTGGTTCCCCGAAATTGGATTTCCTAACTGAACTAGAAAAACTCACT  3294
            ************ ******** ** ********** *************** *****

Mi1.1       GTAGGTTTTAAAAGTTCAAACACAAACGATAGTGGGTCCTCTGTAGCGACAAATCGGCCG  3318
Mi1.2       GTAGGTTTTAAAAGTTCAAACACAACACAAACCACTGTGGGTCCTCTGTTGTGACAAATCGGCCG  3324
Rpi-blb2    GTAGATTTTGAAAGATCAAACACAACACAATGACAGTGGGTCCTCTGCAGCCATAAATCGGCCA  3354
            **** **** ****  ***********  **  *  ************* * *********

Mi1.1       TGGGATTTTCACTTCCCTTCAAATTTGAAAATACTGTTGGTTGCGTGAATTCCGCTGACA  3378
Mi1.2       TGGGATTTTCACTTCCCTTCAAATTTGAAAGAACTGTTGTTGTATGACTTTCCTCTGACA  3384
Rpi-blb2    TGGGATTTTCACTTTCCTTCGAGTTTGAAAAGATTGCAATTGCATGAATTGAATTTCCTCTGACA  3414
            ************** **** ** *******  * *   *   **  *  * ***** ** ******
```

Figure 16 (cont.)

```
Mi1.1     ****************** ****** * ********   *    ***  * ***** ******
Mi1.2     TCCGATTCACTATCAACAATAGCGAGACTGCCCAACCTTGAAGAGTTGTCCCTTTATCAT  3438
Rpi-blb2  TCCGATTCACTATCAACAATAGCGAGACTGCCCAACCTTGAAAATTGTCCCTTTATGAT  3444
          TCCGATTCACTATCAACAATAGCGAGACTGCTGAACCTTGAAGAGTTGTACCTTTATCGT  3474
          ************************* *  ****** *  ***** *   *******  *

Mi1.1     ACAATCATCCATGGAGAAGAATGGAACATGGGGAGGAAGACACCTTTGAGAATCTCAAA   3498
Mi1.2     ACAATCATCCAGGGAGAGAATGGAACATGGGGAGGAAGACACTTTTGAGAATCTCAAA   3504
Rpi-blb2  ACAATCATCCATGGGAAGAATGGAACATGGGGAGAAGAGACACCTTTGAGAATCTCAAA   3534
          ********** *  ** ****************  ** ****  ** *************

Mi1.1     TTTTTGAACTTCAATCAAGTTAGTATTTCCAAGTGGGAGGTTGGAGAGGAATCCTTCCCC  3558
Mi1.2     TTTTTGAACTTGCGTCTACTGACTCTTTCCAAGTGGGAGGTTGGAGAGGAATCCTTCCCC  3564
Rpi-blb2  TGTTTGATGTTGAGTCAAGTGATTCTTTCCAAGTGGGAGGTTGGAGAGGAATCTTTCCC   3594
          * *****  **   **   **  ** * ************************** ****

Mi1.1     AATCTTGAGAAATTAAAACTGCGGGGATGTCATAAGCTAGAGGAGATTCCACCTAGTTTT  3618
Mi1.2     AATCTTGAGAAATTAAAACTGCAGGAATGTGGTAAGCTTGGAGAGATTCCACCTAGTTTT  3624
Rpi-blb2  ACGCTTGAGAATTAGAACTGTCGGACTGTCATAATCTTGAGGAGATTCCGTCTAGTTTT   3654
          *  ********  ** ***   *** *** ***  ** ****** **** ****

Mi1.1     GGAGATATTTATTCATTGAAATCTATCAAAATTGTAAAGAGTCCTCAACTTGAAGATTCT  3678
Mi1.2     GGAGATATTTATTCATTGAAATTTATCAAAATTGTAAAGAGTCCTCAACTTGAAGATTCT  3684
Rpi-blb2  GGGGATATTTATTCCTTGAAATTATCGAACTTGTAAGGAGCCCCTCAACTTGAAAATTCC  3714
          ** ***********  ****** **** **  ***** ** *  **********  ***

Mi1.1     GCTCTCAAAATTAAGGAATACGCTGAAGATATGAGGGGGACGAGCTTCAGATCCTT     3738
Mi1.2     GCTCTCAAGATTAAGAAATACGCTGAAGATATGAGGAGGACGATCTTCAGATCCTT     3744
Rpi-blb2  GCTCTCAAGATTAAGGAATATGCTGAAGATATGAGGGGGACGAGCTTCAGATCCTT     3774
          ******** ****** **** ***************  *****  **********
```

Figure 16 (cont.)

```
Mi1.1    GGCCAAAAGAATATCCCCTTATTTAAGTAG  3768
Mi1.2    GGCCAGAAGAATATCCCCTTATTTAAGTAG  3774
Rpi-blb2 GGCCAGAAGGATATCCCGTTATTTAAGTAG  3804
         *****  ***  ******  **********
```

Figure 17: Multiple Sequence Alignments of Mi1.1, Mi1.2 and Rpi-blb2 proteins

CLUSTAL W (1.82) Multiple Sequence Alignments

```
Sequence format is Pearson
Sequence 1: Mi1.1       1255 aa
Sequence 2: Mi1.2       1257 aa
Sequence 3: Rpi-blb2    1267 aa
Start of Pairwise alignments
Aligning...
Sequences (1:2) Aligned. Score:  91
Sequences (1:3) Aligned. Score:  82
Sequences (2:3) Aligned. Score:  81
Guide tree        file created:   [/ebi/extserv/clustalw-work/interactive/clustalw-20040503-14322840.dnd]
Start of Multiple Alignment
There are 2 groups
Aligning...
Group 1: Sequences:   2      Score:25939
Group 2: Sequences:   3      Score:24668
Alignment Score 19405
CLUSTAL-Alignment file created   [/ebi/extserv/clustalw-work/interactive/clustalw-20040503-14322840.aln]
```

CLUSTAL W (1.82) multiple sequence alignment

Mi1.1        MEKRKDNEEANNSLVLFSALSKDIADVLVFLE---NEENQKALDKDQVEKIKLKMAFICT 57
```

Figure 17 (cont.)

```
Mi1.2       MEKRKDIEEANNSLVLFSALSKDIANVLIFLE---NEENQKALDKDQVEKLKLKMAFICT    57
Rpi-blb2    MEKRKDNEEANNSLESFSALRKDAANVLDFLERLKNEEDQKAVDVDLIESLKLKLTFICT    60
            **** :***:*.**::**: ****:* .*::****:*:****

Mi1.1       YVQLSCSDFEQFEDIMTRKRQEVENLLQPLLDDD------VFTSLTSNMDDCISLYHR   109
Mi1.2       YVQLSYSDFEQFEDIMTRNRQEVENLLQSLLDDD------VLTSLTSNMDDCISLYHR   109
Rpi-blb2    YVQLSYSDLEKFEDIMTRKRQEVENLLQPILDDDGKDVGCKYVLTSLAGNMDDCISLYHR   120
            **   ::****:****.:**      * :*:* .*******

Mi1.1       SYKSDAIMDEQLDFLLLNLYHLSKHHAEKIFPGVTQYEVLQNICGNIRDFHGLIVNGCI   169
Mi1.2       SYKSDAIMDEQLDFLLLNLYHLSKHHAEKIFPGVTQYEVLQNVCGNIRDFHGLILNGCI   169
Rpi-blb2    S-KSDATMDEQLGFLLLNLSHLSKHRAEKMFPGVTQYEVLQNVCGNIRDFHGLIVNCCI   179
            * .** : *  :*:*********:*********:* **

Mi1.1       KHEMVENVLPLFQLMADRVGHFLMDDQTDEDSRLSELDEDEQNDRDSRLFKLAHLLLKIV   229
Mi1.2       KHEMVENVLPLFQLMAERVGHFLMEDQTDEDSRLSELDEDEHNDRDSRLFQLTHLLLKIV   229
Rpi-blb2    KHEMVENVLSLFQLMAERVGRFLMEDQADEDSQLSELDEDDQNDKDPQLFKLAHLLLKIV   239
            *******.**:*:*::**:***.::*. **:*:******

Mi1.1       PVELEVIHICYTNLKASTSAEVGLFIKQLLETSPDILREYLIPLQEHMVTVITPSTSGAR   289
Mi1.2       PTELEVMHICYTNLKASTSAEVGRFIKKLLETSPDILREYIIQLQEHMLTVIPPSTLGAR   289
Rpi-blb2    PTELEVMHICYKTLKASTSTEIGRFIKKLLETSPDILREYLIHLQEHMITVITPNTSGAR   299
            *.**:. ***:* :* *:**********:* **:*.*.* ***

Mi1.1       NIHVMMEFLLLISDMP-KDFIHHDKLFDLLDRVGVLTREVSTLVRDLEEEPRNKEGNNQ   348
Mi1.2       NIHVMMEFLLLILSDMP-KDFIHHDKLFDLLAHVGTLTREVSTLVRDLEEKLRNKEGNNQ   348
Rpi-blb2    NIHVMMEFLLIILSDMPPKDFIHHDKLFDLLARVVALTREVSTLVRDLEEKLRIKESTDE   359
            **********:* ** *********** * .***********:    .::

Mi1.1       TNCATLDLLENIELLKKDLKHVYLKALDSSQCCFPMSDGPLFMHLLHIHLNDLLDSNAYS   408
Mi1.2       TNCATLDLLENIELLKKDLKHVYLKAPNSSQCCFPMSDGPLFMHLLHMHLINDLLDSNAYS   408
```

Figure 17 (cont.)

```
Rpi-blb2   TNCATLKFLENIELLKEDLKHVYLKVPDSSQYCFPMSDGPLFMHLLQRHLDDLLDSNAYS 419
           ****..:*******:*****  .::*.******.:.********

Mi1.1      IALIKEEIELVKQDLKFIRSFFVD-AEQGLYKDLMARVLDVAYEAKDVIDSIIVRDNGLL 467
Mi1.2      ISLIKEEIELVSQELEFIRSFFGDAAEQGLYKDIWARVLDVAYEAKDVIDSIIVRDNGLL 468
Rpi-blb2   IALIKEQIGLVKEDIEFIRSFFAN-IEQGLYKDIWERVIDVAYEAKDVIDSIIVRDNGLL 478
           *:****.:*  ** .::*.:****    :   :**.:*.*************

Mi1.1      HLIFSLPITIKKIKLIKEEISALDENIPKDRGLIVVNSPKKPVERKSLTTDKITVGFEEE 527
Mi1.2      HLIFSLPITIKKIKLIKEEISALDENIPKDRGLIVVNSPKKPVERKSLTTDKIIVGFEEE 528
Rpi-blb2   HLIFSLPITRKKMLIKEEVSDLHENISKNRGLIVVNSPKKPVESKSLTTDKIIVGFGEE 538
           *******.:****:*.*.***: *:.****.*.**** :* **

Mi1.1      TNLILRKLTSGSADLVISITGMPGSGKTTLAYKVYNDKSVSSRFDLRAWCTVDQGCDEK 587
Mi1.2      TNLILRKLTSGPADLVISITGMPGSGKTTLAYKVYNDKSVSRHFDLRAWCTVDQGYDDK 588
Rpi-blb2   TNLILRKLTSGPADLVISIIGMPGLGKTTLAYKVYNDKSVSSHFDLRAWCTVDQVYDEK 598
           *********.***..*******.::***    *   *:.*:*

Mi1.1      KLLINTIFSQVSDSDSKLSENIDVADKLRKQLFGKRYLIVLDDVWDTTTWDELTRPFPESK 647
Mi1.2      KLLDTIFSQVSGSDSNLSENIDVADKLRKQLFGKRYLIVLIDDVWDTTTIDELTRPFPEAK 648
Rpi-blb2   KLLDKIFNQVSDSNSKLSENIDVADKLRKQLFGKRYLIVLIDDVWDTNTWDELTRPFPDGM 658
           *  :.***.*.:*:*****************.:************..*

Mi1.1      KGSRIILTTREKEVALHGKLNTDPLDLRLLRPDESWELLEKRAFGNESCPDELLDVGKEI 707
Mi1.2      KGSRIILTTREKEVALHGKLNTDPLDLRLLRPDESWELLDKRTFGNESCPDELLDVGKEI 708
Rpi-blb2   KGSRIILTTREKKVALHGKLYTDPLNLRLLRSEESWELLEKRAFGNESCPDELLDVGKEI 718
           *.:***:***.:** .:**** *:*************:.*

Mi1.1      AENCKGLPLVADLIAGVIAGREKKRSVWLEVQSSLSSFILNSEVEVMKVIELSYDHLPHH 767
Mi1.2      AENCKGLPLVADLIAGVIAGREKKRSVWLEVQSSLSSFILNSEVEVMKVIELSYDHLPHH 768
Rpi-blb2   AENCKGLPLVVDLIAGIIAGREKKKSVWLEVVNNLHSFILKNEVEVMKVIEISYDHLPDH 778
           ********.*:*:*****.::*.*:.:******:***:*
```

Figure 17 (cont.)

```
Mi1.1    ******** .** .:*** .:*** .:***** .  .* .** .:.:***** .:*****
Mi1.1    LKPCLLYFASFPKDTSLTIYELNVYFGAEGFVGKTEMNSMEEVVKIYMDDLIYSSLVICF  827
Mi1.2    LKPCLLHFASWPKDTPLTIYLFTVYLGAEGFVEKTEMKGIEEVVKIYMDDLISSSLVICF  828
Rpi-blb2 LKPCLLYFASAPKDWVTTIHELKLIWGFEGFVEKTDMKSLEEVVKIYLDDLISSSLVICF  838
         **** :  *  :   :.:  :      :**:* *****

Mi1.1    NEIGYALNFQIHDLIVHDFCLIKARKENLFDQIRSSAPSDLLPRQITIDCDEEE-HFGLNF  886
Mi1.2    NEIGDILNFQIHDLIVHDFCLIKARKENLFDRIRSSAPSDLLPRQITIDYDEEEEHFGLNF  888
Rpi-blb2 NEIGDYPTCQLHDLIVHDFCLIKARKEKLCDRISSSAPSDLLPRQISIDYDDDEEHFGLNF  898
         **   .  :********:***:*:.:  **********:.  : ***

Mi1.1    VMFDSNKKRHSGKHLYSLRIIGDQLDDSVSDAFHLRHLRLLRVLDLHTSFIMVKDSLLNE  946
Mi1.2    VMFDSNKKRHSGKHLYSLRINGDQLDDSVSDAFHLRHLRLHLRIRVLDIEPSLIMVNDSLLNE  948
Rpi-blb2 VLFGSNKKRHSGKHLYSLTINGDELDDHLSDTFHLRHLRLRTLHLESSFIMVKDSLLNE  958
         *:.:*********   .:.:*  .:*.***:*:  .*   :::**

Mi1.1    ICMLNHLRYLSIDTQVKYLPLSFSNIWNLESLFVSTNRSILVLLPRILDLVKLRVLSVDA  1006
Mi1.2    ICMLNHLRYLRIRTQVKYLPFSFSNIWNLESLFVSNKGSILVLLPRILDLVKLRVLSVGA  1008
Rpi-blb2 ICMLNHLRYLSIGTEVKSLPLSFSNIWNLEILFVDNKESTLILLPRIWDLVKLQVLFTTA  1018
         ********* * *: :******* :. .:  : *:**  *: :.  *

Mi1.1    CSFFDMDADESILIAEDTKLENLRIITELLISYSKDTKNIFKRFPNLQLLSFELKESWDY  1066
Mi1.2    CSFFDMDADESILIAKDTKLENLRIIGELLISYSKDTMNIFKRFPNLQVLQFELKESWDY  1068
Rpi-blb2 CSFFDMDADESILIAEDTKLENLTALGELVLSYWKDTEDIFKRLPNLQVLHFKLKLKESWDY  1078
         *************.:*** .:  *  :*** *:***:.  * *******

Mi1.1    STEQHWFSELDFLTELETLSVGFKSSNTNDSGSSVATNRPWDFHFPSNLKIWLREFPLT  1126
Mi1.2    STEQHWFPKLDCLTELETLCVGFKSSNTHCGSSVVTNRPWDFHFPSNLKELLYDFPLT  1128
Rpi-blb2 STEQYWFPKLDFLTELEKLTVDFERSNTNDSGSSAAINRPWDFHFPSSLKRLQLHEFPLT  1138
         **  . :*  .:: *:  *:  .*  **** ****..  :  * ****
```

Figure 17 (cont.)

```
Mi1.1      SDSLSTIARLPNLEELSLYHTIIHGEEWNMGEEDTFENLKFLNFNQVSISKWEVGEESFP 1186
Mi1.2      SDSLSTIARLPNLENLSLYDTIIQGEEWNMGEEDTFENLKFLNLRLLTLSKWEVGEESFP 1188
Rpi-blb2   SDSLSTIARLLNLEELYLYRTIIHGEEWNMGEEDTFENLKCLMLSQVILSKWEVGEESFP 1198
           ********: : *:********** *  :  :***********

Mi1.1      NLEKLKLRGCHKLEEIPPSFGDIYSLKSIKIVKSPQLEDSALKIKEYAEDMRGGDELQIL 1246
Mi1.2      NLEKLKLQECGKLEEIPPSFGDIYSLKFIKIVKSPQLEDSALKIKKYAEDMRGGNDLQIL 1248
Rpi-blb2   TLEKLELSDCHNLEEIPSSFGDIYSLKIIELVRSPQLENSALKIKEYAEDMRGGDELQIL 1258
            :*** :*   :*** ******  *: *.***:**:***::**

Mi1.1      GQKNIPLFK 1255
Mi1.2      GQKNIPLFK 1257
Rpi-blb2   GQKDIPLFK 1267

                       SEQUENCE LISTING

<160> NUMBER OF SEQ ID NOS: 99

<210> SEQ ID NO 1
<211> LENGTH: 3804
<212> TYPE: DNA
<213> ORGANISM: Solanum bulbocastanum
<220> FEATURE:
<221> NAME/KEY: CDS
<222> LOCATION: (1)..(3804)

<400> SEQUENCE: 1 atg gaa aaa cga aaa gat aat gaa gaa gca aac aac tca ttg gag tca        48
Met Glu Lys Arg Lys Asp Asn Glu Glu Ala Asn Asn Ser Leu Glu Ser
1               5                   10                  15 ttt tct gct ctt cgc aag gat gct gcc aat gtt ctg gat ttc cta gag        96
Phe Ser Ala Leu Arg Lys Asp Ala Ala Asn Val Leu Asp Phe Leu Glu
            20                  25                  30 aga tta aag aat gaa gaa gat caa aag gct gtt gat gtg gat ctg att       144
Arg Leu Lys Asn Glu Glu Asp Gln Lys Ala Val Asp Val Asp Leu Ile
        35                  40                  45 gaa agc ctg aaa ttg aag ctg aca ttt att tgt aca tat gtc cag ctt       192
Glu Ser Leu Lys Leu Lys Leu Thr Phe Ile Cys Thr Tyr Val Gln Leu
    50                  55                  60 tct tat tcc gat ttg gag aag ttt gaa gat ata atg act aga aaa aga       240
Ser Tyr Ser Asp Leu Glu Lys Phe Glu Asp Ile Met Thr Arg Lys Arg
65                  70                  75                  80 caa gag gtt gag aat ctg ctt caa cca att ttg gat gat gat ggc aaa       288
Gln Glu Val Glu Asn Leu Leu Gln Pro Ile Leu Asp Asp Asp Gly Lys
                85                  90                  95
```

-continued

| | | |
|---|---|---|
| gac gtc ggg tgt aaa tat gtc ctt act agc ctc gcc ggt aat atg gat<br>Asp Val Gly Cys Lys Tyr Val Leu Thr Ser Leu Ala Gly Asn Met Asp<br>          100                  105                  110 | 336 |
| gac tgt ata agc ttg tat cat cgt tct aaa tca gat gcc acc atg atg<br>Asp Cys Ile Ser Leu Tyr His Arg Ser Lys Ser Asp Ala Thr Met Met<br>          115                  120                  125 | 384 |
| gat gag caa ttg ggc ttc ctc ctc ttg aat ctc tct cat cta tcc aag<br>Asp Glu Gln Leu Gly Phe Leu Leu Leu Asn Leu Ser His Leu Ser Lys<br>130                  135                  140 | 432 |
| cat cgt gct gaa aag atg ttt cct gga gtg act caa tat gag gtt ctt<br>His Arg Ala Glu Lys Met Phe Pro Gly Val Thr Gln Tyr Glu Val Leu<br>145                  150                  155                  160 | 480 |
| cag aat gta tgt ggc aac ata aga gat ttc cat gga ttg ata gtg aat<br>Gln Asn Val Cys Gly Asn Ile Arg Asp Phe His Gly Leu Ile Val Asn<br>                  165                  170                  175 | 528 |
| tgt tgc att aag cat gag atg gtt gag aat gtc tta tct ctg ttt caa<br>Cys Cys Ile Lys His Glu Met Val Glu Asn Val Leu Ser Leu Phe Gln<br>                  180                  185                  190 | 576 |
| ctg atg gct gag aga gta gga cgc ttc ctt tgg gag gat cag gct gat<br>Leu Met Ala Glu Arg Val Gly Arg Phe Leu Trp Glu Asp Gln Ala Asp<br>          195                  200                  205 | 624 |
| gaa gac tct caa ctc tcc gag cta gat gag gat gat cag aat gat aaa<br>Glu Asp Ser Gln Leu Ser Glu Leu Asp Glu Asp Asp Gln Asn Asp Lys<br>210                  215                  220 | 672 |
| gac cct caa ctc ttc aag cta gca cat cta ctc ttg aag att gtt cca<br>Asp Pro Gln Leu Phe Lys Leu Ala His Leu Leu Leu Lys Ile Val Pro<br>225                  230                  235                  240 | 720 |
| act gaa ttg gag gtt atg cac ata tgt tat aaa act ttg aaa gct tca<br>Thr Glu Leu Glu Val Met His Ile Cys Tyr Lys Thr Leu Lys Ala Ser<br>                  245                  250                  255 | 768 |
| act tca aca gaa att gga cgc ttc att aag aag ctc ctg gaa acc tct<br>Thr Ser Thr Glu Ile Gly Arg Phe Ile Lys Lys Leu Leu Glu Thr Ser<br>          260                  265                  270 | 816 |
| ccg gac att ctc aga gaa tat ctg att cat cta caa gag cat atg ata<br>Pro Asp Ile Leu Arg Glu Tyr Leu Ile His Leu Gln Glu His Met Ile<br>275                  280                  285 | 864 |
| act gtt att acc cct aac act tca ggg gct cga aac att cat gtc atg<br>Thr Val Ile Thr Pro Asn Thr Ser Gly Ala Arg Asn Ile His Val Met<br>290                  295                  300 | 912 |
| atg gaa ttc cta ttg att att ctt tct gat atg ccg ccc aag gac ttt<br>Met Glu Phe Leu Leu Ile Ile Leu Ser Asp Met Pro Pro Lys Asp Phe<br>305                  310                  315                  320 | 960 |
| att cat cat gac aaa ctt ttt gat ctc ttg gct cgt gtt gta gca ctt<br>Ile His His Asp Lys Leu Phe Asp Leu Leu Ala Arg Val Val Ala Leu<br>                  325                  330                  335 | 1008 |
| acc agg gag gta tca act ctt gta cgc gac ttg gaa gag aaa tta agg<br>Thr Arg Glu Val Ser Thr Leu Val Arg Asp Leu Glu Glu Lys Leu Arg<br>                  340                  345                  350 | 1056 |
| att aaa gag agt act gac gaa aca aat tgt gca acc cta aag ttt ctg<br>Ile Lys Glu Ser Thr Asp Glu Thr Asn Cys Ala Thr Leu Lys Phe Leu<br>355                  360                  365 | 1104 |
| gaa aat att gaa ctc ctt aag gaa gat ctc aaa cat gtt tat ctg aaa<br>Glu Asn Ile Glu Leu Leu Lys Glu Asp Leu Lys His Val Tyr Leu Lys<br>370                  375                  380 | 1152 |
| gtc ccg gat tca tct caa tat tgc ttc ccc atg agt gat gga cct ctc<br>Val Pro Asp Ser Ser Gln Tyr Cys Phe Pro Met Ser Asp Gly Pro Leu<br>385                  390                  395                  400 | 1200 |
| ttc atg cat ctg cta cag aga cac tta gat gat ttg ctg gat tcc aat<br>Phe Met His Leu Leu Gln Arg His Leu Asp Asp Leu Leu Asp Ser Asn | 1248 |

-continued

```
                405                 410                 415
gct tat tca att gct ttg ata aag gaa caa att ggg ctg gtg aaa gaa        1296
Ala Tyr Ser Ile Ala Leu Ile Lys Glu Gln Ile Gly Leu Val Lys Glu
            420                 425                 430 gac ttg gaa ttc ata aga tct ttt ttc gcg aat att gag caa gga ttg        1344
Asp Leu Glu Phe Ile Arg Ser Phe Phe Ala Asn Ile Glu Gln Gly Leu
        435                 440                 445 tat aaa gat ctc tgg gaa cgt gtt cta gat gtg gca tat gag gca aaa        1392
Tyr Lys Asp Leu Trp Glu Arg Val Leu Asp Val Ala Tyr Glu Ala Lys
    450                 455                 460 gat gtc ata gat tca att att gtt cga gat aat ggt ctc tta cat ctt        1440
Asp Val Ile Asp Ser Ile Ile Val Arg Asp Asn Gly Leu Leu His Leu
465                 470                 475                 480 att ttc tca ctt ccc att acc aga aag aag atg atg ctt atc aaa gaa        1488
Ile Phe Ser Leu Pro Ile Thr Arg Lys Lys Met Met Leu Ile Lys Glu
                485                 490                 495 gag gtc tct gat tta cat gag aac att tcc aag aac aga ggt ctc atc        1536
Glu Val Ser Asp Leu His Glu Asn Ile Ser Lys Asn Arg Gly Leu Ile
            500                 505                 510 gtt gtg aac tct ccc aag aaa cca gtt gag agc aag tca ttg aca act        1584
Val Val Asn Ser Pro Lys Lys Pro Val Glu Ser Lys Ser Leu Thr Thr
        515                 520                 525 gat aaa ata att gta ggt ttt ggt gag gag aca aac ttg ata ctt aga        1632
Asp Lys Ile Ile Val Gly Phe Gly Glu Glu Thr Asn Leu Ile Leu Arg
    530                 535                 540 aag ctc acc agt gga ccg gca gat cta gat gtc att tcg atc att ggt        1680
Lys Leu Thr Ser Gly Pro Ala Asp Leu Asp Val Ile Ser Ile Ile Gly
545                 550                 555                 560 atg ccg ggt tta ggt aaa act act ttg gcg tac aaa gta tac aat gat        1728
Met Pro Gly Leu Gly Lys Thr Thr Leu Ala Tyr Lys Val Tyr Asn Asp
                565                 570                 575 aaa tca gtt tct agc cat ttc gac ctt cgt gca tgg tgc acg gtc gac        1776
Lys Ser Val Ser Ser His Phe Asp Leu Arg Ala Trp Cys Thr Val Asp
            580                 585                 590 caa gta tat gac gag aag aag ttg ttg gat aaa att ttc aat caa gtt        1824
Gln Val Tyr Asp Glu Lys Lys Leu Leu Asp Lys Ile Phe Asn Gln Val
        595                 600                 605 agt gac tca aat tca aaa ttg agt gag aat att gat gtt gct gat aaa        1872
Ser Asp Ser Asn Ser Lys Leu Ser Glu Asn Ile Asp Val Ala Asp Lys
    610                 615                 620 cta cgg aaa caa ttg ttt gga aag agg tat ctt att gtc tta gat gac        1920
Leu Arg Lys Gln Leu Phe Gly Lys Arg Tyr Leu Ile Val Leu Asp Asp
625                 630                 635                 640 gtg tgg gat act aat aca tgg gat gag cta aca aga cct ttt cct gat        1968
Val Trp Asp Thr Asn Thr Trp Asp Glu Leu Thr Arg Pro Phe Pro Asp
                645                 650                 655 ggt atg aaa gga agt aga att att ttg aca act cga gaa aag aaa gtt        2016
Gly Met Lys Gly Ser Arg Ile Ile Leu Thr Thr Arg Glu Lys Lys Val
            660                 665                 670 gct ttg cat gga aag ctc tac act gat cct ctt aac ctt cga ttg cta        2064
Ala Leu His Gly Lys Leu Tyr Thr Asp Pro Leu Asn Leu Arg Leu Leu
        675                 680                 685 aga tca gaa gaa agt tgg gag tta tta gag aaa agg gca ttt gga aac        2112
Arg Ser Glu Glu Ser Trp Glu Leu Leu Glu Lys Arg Ala Phe Gly Asn
    690                 695                 700 gag agt tgc cct gat gaa cta ttg gat gtt ggt aaa gaa ata gcc gaa        2160
Glu Ser Cys Pro Asp Glu Leu Leu Asp Val Gly Lys Glu Ile Ala Glu
705                 710                 715                 720 aat tgt aaa ggg ctt cct ttg gtg gtg gat ctg att gct gga atc att        2208
```

```
                Asn Cys Lys Gly Leu Pro Leu Val Val Asp Leu Ile Ala Gly Ile Ile
                                    725                 730                 735 gct ggg agg gaa aag aaa aag agt gtg tgg ctt gaa gtt gta aat aat             2256
Ala Gly Arg Glu Lys Lys Lys Ser Val Trp Leu Glu Val Val Asn Asn
                    740                 745                 750 ttg cat tcc ttt att ttg aag aat gaa gtg gaa gtg atg aaa gtt ata             2304
Leu His Ser Phe Ile Leu Lys Asn Glu Val Glu Val Met Lys Val Ile
                755                 760                 765 gaa ata agt tat gac cac tta cct gat cac ctg aag cca tgc ttg ctg             2352
Glu Ile Ser Tyr Asp His Leu Pro Asp His Leu Lys Pro Cys Leu Leu
            770                 775                 780 tac ttt gca agt gcg ccg aag gac tgg gta acg aca atc cat gag ttg             2400
Tyr Phe Ala Ser Ala Pro Lys Asp Trp Val Thr Thr Ile His Glu Leu
785                 790                 795                 800 aaa ctt att tgg ggt ttt gaa gga ttt gtg gaa aag aca gat atg aag             2448
Lys Leu Ile Trp Gly Phe Glu Gly Phe Val Glu Lys Thr Asp Met Lys
                    805                 810                 815 agt ctg gaa gaa gtg gtg aaa att tat ttg gat gat tta att tcc agt             2496
Ser Leu Glu Glu Val Val Lys Ile Tyr Leu Asp Asp Leu Ile Ser Ser
                820                 825                 830 agc ttg gta att tgt ttc aat gag ata ggt gat tac cct act tgc caa             2544
Ser Leu Val Ile Cys Phe Asn Glu Ile Gly Asp Tyr Pro Thr Cys Gln
            835                 840                 845 ctt cat gat ctt gtg cat gac ttt tgt ttg ata aaa gca aga aag gaa             2592
Leu His Asp Leu Val His Asp Phe Cys Leu Ile Lys Ala Arg Lys Glu
        850                 855                 860 aag ttg tgt gat cgg ata agt tca agt gct cca tca gat ttg ttg cca             2640
Lys Leu Cys Asp Arg Ile Ser Ser Ser Ala Pro Ser Asp Leu Leu Pro
865                 870                 875                 880 cgt caa att agc att gat tat gat gat gat gaa gag cac ttt ggg ctt             2688
Arg Gln Ile Ser Ile Asp Tyr Asp Asp Asp Glu Glu His Phe Gly Leu
                    885                 890                 895 aat ttt gtc ctg ttc ggt tca aat aag aaa agg cat tcc ggt aaa cac             2736
Asn Phe Val Leu Phe Gly Ser Asn Lys Lys Arg His Ser Gly Lys His
                900                 905                 910 ctc tat tct ttg acc ata aat gga gat gag ctg gac gac cat ctt tct             2784
Leu Tyr Ser Leu Thr Ile Asn Gly Asp Glu Leu Asp Asp His Leu Ser
            915                 920                 925 gat aca ttt cat cta aga cac ttg agg ctt ctt aga acc ttg cac ctg             2832
Asp Thr Phe His Leu Arg His Leu Arg Leu Leu Arg Thr Leu His Leu
        930                 935                 940 gaa tcc tct ttt atc atg gtt aaa gat tct ttg ctg aat gaa ata tgc             2880
Glu Ser Ser Phe Ile Met Val Lys Asp Ser Leu Leu Asn Glu Ile Cys
945                 950                 955                 960 atg ttg aat cat ttg agg tac tta agc att ggg aca gaa gtt aaa tct             2928
Met Leu Asn His Leu Arg Tyr Leu Ser Ile Gly Thr Glu Val Lys Ser
                    965                 970                 975 ctg cct ttg tct ttc tca aac ctc tgg aat cta gaa atc ttg ttt gtg             2976
Leu Pro Leu Ser Phe Ser Asn Leu Trp Asn Leu Glu Ile Leu Phe Val
                980                 985                 990 gat aac aaa gaa tca acc ttg ata cta tta ccg aga att tgg gat ctt             3024
Asp Asn Lys Glu Ser Thr Leu Ile Leu Leu Pro Arg Ile Trp Asp Leu
            995                 1000                1005 gta aag ttg caa gtg ctg ttc acg act gct tgt tct ttc ttt gat             3069
Val Lys Leu Gln Val Leu Phe Thr Thr Ala Cys Ser Phe Phe Asp
        1010                1015                1020 atg gat gca gat gaa tca ata ctg ata gca gag gac aca aag tta             3114
Met Asp Ala Asp Glu Ser Ile Leu Ile Ala Glu Asp Thr Lys Leu
        1025                1030                1035
```

-continued

| | | |
|---|---|---|
| gag aac ttg aca gca tta ggg gaa ctc gtg ctt tcc tat tgg aaa<br>Glu Asn Leu Thr Ala Leu Gly Glu Leu Val Leu Ser Tyr Trp Lys<br>1040                              1045                        1050 | | 3159 |
| gat aca gag gat att ttc aaa agg ctt ccc aat ctt caa gtg ctt<br>Asp Thr Glu Asp Ile Phe Lys Arg Leu Pro Asn Leu Gln Val Leu<br>1055                              1060                        1065 | | 3204 |
| cat ttc aaa ctc aag gag tca tgg gat tat tca aca gag caa tat<br>His Phe Lys Leu Lys Glu Ser Trp Asp Tyr Ser Thr Glu Gln Tyr<br>1070                              1075                        1080 | | 3249 |
| tgg ttc ccg aaa ttg gat ttc cta act gaa cta gaa aaa ctc act<br>Trp Phe Pro Lys Leu Asp Phe Leu Thr Glu Leu Glu Lys Leu Thr<br>1085                              1090                        1095 | | 3294 |
| gta gat ttt gaa aga tca aac aca aat gac agt ggg tcc tct gca<br>Val Asp Phe Glu Arg Ser Asn Thr Asn Asp Ser Gly Ser Ser Ala<br>1100                              1105                        1110 | | 3339 |
| gcc ata aat cgg cca tgg gat ttt cac ttt cct tcg agt ttg aaa<br>Ala Ile Asn Arg Pro Trp Asp Phe His Phe Pro Ser Ser Leu Lys<br>1115                              1120                        1125 | | 3384 |
| aga ttg caa ttg cat gaa ttt cct ctg aca tcc gat tca cta tca<br>Arg Leu Gln Leu His Glu Phe Pro Leu Thr Ser Asp Ser Leu Ser<br>1130                              1135                        1140 | | 3429 |
| aca ata gcg aga ctg ctg aac ctt gaa gag ttg tac ctt tat cgt<br>Thr Ile Ala Arg Leu Leu Asn Leu Glu Glu Leu Tyr Leu Tyr Arg<br>1145                              1150                        1155 | | 3474 |
| aca atc atc cat ggg gaa gaa tgg aac atg gga gaa gaa gac acc<br>Thr Ile Ile His Gly Glu Glu Trp Asn Met Gly Glu Glu Asp Thr<br>1160                              1165                        1170 | | 3519 |
| ttt gag aat ctc aaa tgt ttg atg ttg agt caa gtg att ctt tcc<br>Phe Glu Asn Leu Lys Cys Leu Met Leu Ser Gln Val Ile Leu Ser<br>1175                              1180                        1185 | | 3564 |
| aag tgg gag gtt gga gag gaa tct ttt ccc acg ctt gag aaa tta<br>Lys Trp Glu Val Gly Glu Glu Ser Phe Pro Thr Leu Glu Lys Leu<br>1190                              1195                        1200 | | 3609 |
| gaa ctg tcg gac tgt cat aat ctt gag gag att ccg tct agt ttt<br>Glu Leu Ser Asp Cys His Asn Leu Glu Glu Ile Pro Ser Ser Phe<br>1205                              1210                        1215 | | 3654 |
| ggg gat att tat tcc ttg aaa att atc gaa ctt gta agg agc cct<br>Gly Asp Ile Tyr Ser Leu Lys Ile Ile Glu Leu Val Arg Ser Pro<br>1220                              1225                        1230 | | 3699 |
| caa ctt gaa aat tcc gct ctc aag att aag gaa tat gct gaa gat<br>Gln Leu Glu Asn Ser Ala Leu Lys Ile Lys Glu Tyr Ala Glu Asp<br>1235                              1240                        1245 | | 3744 |
| atg agg gga ggg gac gag ctt cag atc ctt ggc cag aag gat atc<br>Met Arg Gly Gly Asp Glu Leu Gln Ile Leu Gly Gln Lys Asp Ile<br>1250                              1255                        1260 | | 3789 |
| ccg tta ttt aag tag<br>Pro Leu Phe Lys<br>    1265 | | 3804 |

<210> SEQ ID NO 2
<211> LENGTH: 1267
<212> TYPE: PRT
<213> ORGANISM: Solanum bulbocastanum

<400> SEQUENCE: 2

Met Glu Lys Arg Lys Asp Asn Glu Glu Ala Asn Asn Ser Leu Glu Ser
1                 5                   10                 15

Phe Ser Ala Leu Arg Lys Asp Ala Ala Asn Val Leu Asp Phe Leu Glu
                20                  25               30

Arg Leu Lys Asn Glu Glu Asp Gln Lys Ala Val Asp Val Asp Leu Ile

-continued

```
            35                  40                  45
Glu Ser Leu Lys Leu Lys Leu Thr Phe Ile Cys Thr Tyr Val Gln Leu
 50                  55                  60

Ser Tyr Ser Asp Leu Glu Lys Phe Glu Asp Ile Met Thr Arg Lys Arg
 65                  70                  75                  80

Gln Glu Val Glu Asn Leu Leu Gln Pro Ile Leu Asp Asp Gly Lys
                 85                  90                  95

Asp Val Gly Cys Lys Tyr Val Leu Thr Ser Leu Ala Gly Asn Met Asp
                100                 105                 110

Asp Cys Ile Ser Leu Tyr His Arg Ser Lys Ser Asp Ala Thr Met Met
                115                 120                 125

Asp Glu Gln Leu Gly Phe Leu Leu Asn Leu Ser His Leu Ser Lys
130                 135                 140

His Arg Ala Glu Lys Met Phe Pro Gly Val Thr Gln Tyr Glu Val Leu
145                 150                 155                 160

Gln Asn Val Cys Gly Asn Ile Arg Asp Phe His Gly Leu Ile Val Asn
                165                 170                 175

Cys Cys Ile Lys His Glu Met Val Glu Asn Val Leu Ser Leu Phe Gln
                180                 185                 190

Leu Met Ala Glu Arg Val Gly Arg Phe Leu Trp Glu Asp Gln Ala Asp
                195                 200                 205

Glu Asp Ser Gln Leu Ser Glu Leu Asp Glu Asp Gln Asn Asp Lys
210                 215                 220

Asp Pro Gln Leu Phe Lys Leu Ala His Leu Leu Leu Lys Ile Val Pro
225                 230                 235                 240

Thr Glu Leu Glu Val Met His Ile Cys Tyr Lys Thr Leu Lys Ala Ser
                245                 250                 255

Thr Ser Thr Glu Ile Gly Arg Phe Ile Lys Lys Leu Leu Glu Thr Ser
                260                 265                 270

Pro Asp Ile Leu Arg Glu Tyr Leu Ile His Leu Gln Glu His Met Ile
                275                 280                 285

Thr Val Ile Thr Pro Asn Thr Ser Gly Ala Arg Asn Ile His Val Met
290                 295                 300

Met Glu Phe Leu Leu Ile Ile Leu Ser Asp Met Pro Pro Lys Asp Phe
305                 310                 315                 320

Ile His His Asp Lys Leu Phe Asp Leu Leu Ala Arg Val Val Ala Leu
                325                 330                 335

Thr Arg Glu Val Ser Thr Leu Val Arg Asp Leu Glu Glu Lys Leu Arg
                340                 345                 350

Ile Lys Glu Ser Thr Asp Glu Thr Asn Cys Ala Thr Leu Lys Phe Leu
                355                 360                 365

Glu Asn Ile Glu Leu Leu Lys Glu Asp Leu Lys His Val Tyr Leu Lys
370                 375                 380

Val Pro Asp Ser Ser Gln Tyr Cys Phe Pro Met Ser Asp Gly Pro Leu
385                 390                 395                 400

Phe Met His Leu Leu Gln Arg His Leu Asp Asp Leu Leu Asp Ser Asn
                405                 410                 415

Ala Tyr Ser Ile Ala Leu Ile Lys Glu Gln Ile Gly Leu Val Lys Glu
                420                 425                 430

Asp Leu Glu Phe Ile Arg Ser Phe Ala Asn Ile Glu Gln Gly Leu
                435                 440                 445

Tyr Lys Asp Leu Trp Glu Arg Val Leu Asp Val Ala Tyr Glu Ala Lys
450                 455                 460
```

```
Asp Val Ile Asp Ser Ile Ile Val Arg Asp Asn Gly Leu Leu His Leu
465                 470                 475                 480

Ile Phe Ser Leu Pro Ile Thr Arg Lys Lys Met Met Leu Ile Lys Glu
            485                 490                 495

Glu Val Ser Asp Leu His Glu Asn Ile Ser Lys Asn Arg Gly Leu Ile
            500                 505                 510

Val Val Asn Ser Pro Lys Pro Val Glu Ser Lys Ser Leu Thr Thr
            515                 520                 525

Asp Lys Ile Ile Val Gly Phe Gly Glu Thr Asn Leu Ile Leu Arg
530                 535                 540

Lys Leu Thr Ser Gly Pro Ala Asp Leu Asp Val Ile Ser Ile Ile Gly
545                 550                 555                 560

Met Pro Gly Leu Gly Lys Thr Thr Leu Ala Tyr Lys Val Tyr Asn Asp
            565                 570                 575

Lys Ser Val Ser Ser His Phe Asp Leu Arg Ala Trp Cys Thr Val Asp
            580                 585                 590

Gln Val Tyr Asp Glu Lys Lys Leu Leu Asp Lys Ile Phe Asn Gln Val
            595                 600                 605

Ser Asp Ser Asn Ser Lys Leu Ser Glu Asn Ile Asp Val Ala Asp Lys
610                 615                 620

Leu Arg Lys Gln Leu Phe Gly Lys Arg Tyr Leu Ile Val Leu Asp Asp
625                 630                 635                 640

Val Trp Asp Thr Asn Thr Trp Asp Glu Leu Thr Arg Pro Phe Pro Asp
                645                 650                 655

Gly Met Lys Gly Ser Arg Ile Ile Leu Thr Thr Arg Glu Lys Lys Val
            660                 665                 670

Ala Leu His Gly Lys Leu Tyr Thr Asp Pro Leu Asn Leu Arg Leu Leu
            675                 680                 685

Arg Ser Glu Glu Ser Trp Glu Leu Leu Glu Lys Arg Ala Phe Gly Asn
            690                 695                 700

Glu Ser Cys Pro Asp Glu Leu Leu Asp Val Gly Lys Glu Ile Ala Glu
705                 710                 715                 720

Asn Cys Lys Gly Leu Pro Leu Val Val Asp Leu Ile Ala Gly Ile Ile
                725                 730                 735

Ala Gly Arg Glu Lys Lys Ser Val Trp Leu Glu Val Val Asn Asn
                740                 745                 750

Leu His Ser Phe Ile Leu Lys Asn Glu Val Glu Val Met Lys Val Ile
            755                 760                 765

Glu Ile Ser Tyr Asp His Leu Pro Asp His Leu Lys Pro Cys Leu Leu
            770                 775                 780

Tyr Phe Ala Ser Ala Pro Lys Asp Trp Val Thr Thr Ile His Glu Leu
785                 790                 795                 800

Lys Leu Ile Trp Gly Phe Glu Gly Phe Val Lys Thr Asp Met Lys
                805                 810                 815

Ser Leu Glu Glu Val Val Lys Ile Tyr Leu Asp Asp Leu Ile Ser Ser
            820                 825                 830

Ser Leu Val Ile Cys Phe Asn Glu Ile Gly Asp Tyr Pro Thr Cys Gln
            835                 840                 845

Leu His Asp Leu Val His Asp Phe Cys Leu Ile Lys Ala Arg Lys Glu
            850                 855                 860

Lys Leu Cys Asp Arg Ile Ser Ser Ser Ala Pro Ser Asp Leu Leu Pro
865                 870                 875                 880
```

-continued

```
Arg Gln Ile Ser Ile Asp Tyr Asp Asp Glu His Phe Gly Leu
            885             890             895

Asn Phe Val Leu Phe Gly Ser Asn Lys Lys Arg His Ser Gly Lys His
            900             905             910

Leu Tyr Ser Leu Thr Ile Asn Gly Asp Glu Leu Asp His Leu Ser
            915             920             925

Asp Thr Phe His Leu Arg His Leu Arg Leu Leu Arg Thr Leu His Leu
    930             935             940

Glu Ser Ser Phe Ile Met Val Lys Asp Ser Leu Leu Asn Glu Ile Cys
945             950             955             960

Met Leu Asn His Leu Arg Tyr Leu Ser Ile Gly Thr Glu Val Lys Ser
                965             970             975

Leu Pro Leu Ser Phe Ser Asn Leu Trp Asn Leu Glu Ile Leu Phe Val
            980             985             990

Asp Asn Lys Glu Ser Thr Leu Ile Leu Leu Pro Arg Ile Trp Asp Leu
            995             1000            1005

Val Lys Leu Gln Val Leu Phe Thr Thr Ala Cys Ser Phe Phe Asp
    1010            1015            1020

Met Asp Ala Asp Glu Ser Ile Leu Ile Ala Glu Asp Thr Lys Leu
    1025            1030            1035

Glu Asn Leu Thr Ala Leu Gly Glu Leu Val Leu Ser Tyr Trp Lys
    1040            1045            1050

Asp Thr Glu Asp Ile Phe Lys Arg Leu Pro Asn Leu Gln Val Leu
    1055            1060            1065

His Phe Lys Leu Lys Glu Ser Trp Asp Tyr Ser Thr Glu Gln Tyr
    1070            1075            1080

Trp Phe Pro Lys Leu Asp Phe Leu Thr Glu Leu Glu Lys Leu Thr
    1085            1090            1095

Val Asp Phe Glu Arg Ser Asn Thr Asn Asp Ser Gly Ser Ser Ala
    1100            1105            1110

Ala Ile Asn Arg Pro Trp Asp Phe His Phe Pro Ser Ser Leu Lys
    1115            1120            1125

Arg Leu Gln Leu His Glu Phe Pro Leu Thr Ser Asp Ser Leu Ser
    1130            1135            1140

Thr Ile Ala Arg Leu Leu Asn Leu Glu Glu Leu Tyr Leu Tyr Arg
    1145            1150            1155

Thr Ile Ile His Gly Glu Glu Trp Asn Met Gly Glu Glu Asp Thr
    1160            1165            1170

Phe Glu Asn Leu Lys Cys Leu Met Leu Ser Gln Val Ile Leu Ser
    1175            1180            1185

Lys Trp Glu Val Gly Glu Glu Ser Phe Pro Thr Leu Glu Lys Leu
    1190            1195            1200

Glu Leu Ser Asp Cys His Asn Leu Glu Glu Ile Pro Ser Ser Phe
    1205            1210            1215

Gly Asp Ile Tyr Ser Leu Lys Ile Ile Glu Leu Val Arg Ser Pro
    1220            1225            1230

Gln Leu Glu Asn Ser Ala Leu Lys Ile Lys Glu Tyr Ala Glu Asp
    1235            1240            1245

Met Arg Gly Gly Asp Glu Leu Gln Ile Leu Gly Gln Lys Asp Ile
    1250            1255            1260

Pro Leu Phe Lys
    1265
```

```
<210> SEQ ID NO 3
<211> LENGTH: 3890
<212> TYPE: DNA
<213> ORGANISM: Solanum bulbocastanum
<220> FEATURE:
<221> NAME/KEY: gene
<222> LOCATION: (1)..(3890)
<223> OTHER INFORMATION: Coding nucleic acid sequence of the Rpi-blb2
      gene including the intron sequence (position 43-128).
<220> FEATURE:
<221> NAME/KEY: Intron
<222> LOCATION: (43)..(128)
<223> OTHER INFORMATION: Coding nucleic acid sequence of the Rpi-blb2
      gene including the intron sequence (position 43-128).

<400> SEQUENCE: 3
atggaaaaac gaaagataa tgaagaagca aacaactcat tggtatgtta tttgatagag     60
tgaactgtaa agtattgaat tgtagatatc atgtggcttt aaaaatttga tatgtgttat    120
tttggcagga gtcattttct gctcttcgca aggatgctgc caatgttctg gatttcctag    180
agagattaaa gaatgaagaa gatcaaaagg ctgttgatgt ggatctgatt gaaagcctga    240
aattgaagct gacatttatt tgtacatatg tccagctttc ttattccgat ttggagaagt    300
ttgaagatat aatgactaga aaaagacaag aggttgagaa tctgcttcaa ccaattttgg    360
atgatgatgg caaagacgtc gggtgtaaat atgtccttac tagcctcgcc ggtaatatgg    420
atgactgtat aagcttgtat catcgttcta aatcagatgc caccatgatg gatgagcaat    480
tgggcttcct cctcttgaat ctctctcatc tatccaagca tcgtgctgaa aagatgtttc    540
ctggagtgac tcaatatgag gttcttcaga atgtatgtgg caacataaga gatttccatg    600
gattgatagt gaattgttgc attaagcatg agatggttga aatgtcttta tctctgtttc    660
aactgatggc tgagagagta ggacgcttcc tttggggaga tcaggctgat gaagactctc    720
aactctccga gctagatgag gatgatcaga atgataaaga ccctcaactc ttcaagctag    780
cacatctact cttgaagatt gttccaactg aattggaggt tatgcacata tgttataaaa    840
ctttgaaagc ttcaacttca acagaaattg gacgcttcat taagaagctc ctggaaacct    900
ctccggacat tctcagagaa tatctgattc atctacaaga gcatatgata actgttatta    960
cccctaacac ttcaggggct cgaaacattc atgtcatgat ggaattccta ttgattattc   1020
tttctgatat gccgcccaag gactttattc atcatgacaa actttttgat ctcttggctc   1080
gtgttgtagc acttaccagg gaggtatcaa ctcttgtacg cgacttggaa gagaaattaa   1140
ggattaaaga gagtactgac gaaacaaatt gtgcaaccct aaagtttctg aaaatattg    1200 aactccttaa ggaagatctc aaacatgttt atctgaaagt cccggattca tctcaatatt   1260
gcttccccat gagtgatgga cctctcttca tgcatctgct acagagacac ttagatgatt   1320
tgctggattc caatgcttat tcaattgctt tgataaagga acaaattggg ctggtgaaag   1380
aagacttgga attcataaga tctttttttcg cgaatattga gcaaggattg tataaagatc   1440
tctgggaacg tgttctagat gtggcatatg aggcaaaaga tgtcatagat tcaattattg   1500
ttcgagataa tggtctctta catcttattt tctcacttcc cattaccaga agaagatga    1560 tgcttatcaa agaagaggtc tctgatttac atgagaacat ttccaagaac agaggtctca   1620
tcgttgtgaa ctctcccaag aaaccagttg agagcaagtc attgacaact gataaaataa   1680
ttgtaggttt tggtgaggag acaaacttga tacttagaaa gctcaccagt ggaccggcag   1740
atctagatgt catttcgatc attggtatgc cgggtttagg taaaactact ttggcgtaca   1800
aagtatacaa tgataaatca gtttctagcc atttcgacct tcgtgcatgg tgcacggtcg   1860
```

```
accaagtata tgacgagaag aagttgttgg ataaaatttt caatcaagtt agtgactcaa    1920
attcaaaatt gagtgagaat attgatgttg ctgataaact acggaaacaa ttgtttggaa    1980
agaggtatct tattgtctta gatgacgtgt gggatactaa tacatgggat gagctaacaa    2040
gaccttttcc tgatggtatg aaaggaagta gaattatttt gacaactcga gaaaagaaag    2100
ttgctttgca tggaaagctc tacactgatc ctcttaacct tcgattgcta agatcagaag    2160
aaagttggga gttattagag aaaagggcat ttggaaacga gagttgccct gatgaactat    2220
tggatgttgg taaagaaata gccgaaaatt gtaaagggct tcctttggtg gtggatctga    2280
ttgctggaat cattgctggg agggaaaaga aaaagagtgt gtggcttgaa gttgtaaata    2340
atttgcattc ctttattttg aagaatgaag tggaagtgat gaaagttata gaaataagtt    2400
atgaccactt acctgatcac ctgaagccat gcttgctgta ctttgcaagt gcgccgaagg    2460
actgggtaac gacaatccat gagttgaaac ttatttgggg ttttgaagga tttgtggaaa    2520
agacagatat gaagagtctg gaagaagtgg tgaaaattta tttggatgat ttaatttcca    2580
gtagcttggt aatttgtttc aatgagatag gtgattaccc tacttgccaa cttcatgatc    2640
ttgtgcatga cttttgtttg ataaaagcaa gaaggaaaa gttgtgtgat cggataagtt    2700
caagtgctcc atcagatttg ttgccacgtc aaattagcat tgattatgat gatgatgaag    2760
agcactttgg gcttaatttt gtcctgttcg gttcaaataa gaaaaggcat tccggtaaac    2820
acctctattc tttgaccata aatggagatg agctggacga ccatctttct gatacatttc    2880
atctaagaca cttgaggctt cttagaacct tgcacctgga atcctctttt atcatggtta    2940
aagattcttt gctgaatgaa atatgcatgt tgaatcattt gaggtactta agcattggga    3000
cagaagttaa atctctgcct ttgtctttct caaacctctg gaatctagaa atcttgtttg    3060
tggataacaa agaatcaacc ttgatactat taccgagaat ttgggatctt gtaaagttgc    3120
aagtgctgtt cacgactgct tgttctttct ttgatatgga tgcagatgaa tcaatactga    3180
tagcagagga cacaaagtta gagaacttga cagcattagg ggaactcgtg ctttcctatt    3240
ggaaagatac agaggatatt ttcaaaaggc ttcccaatct tcaagtgctt catttcaaac    3300
tcaaggagtc atgggattat tcaacagagc aatattggtt cccgaaattg gatttcctaa    3360
ctgaactaga aaaactcact gtagattttg aaagatcaaa cacaaatgac agtgggtcct    3420
ctgcagccat aaatcggcca tgggattttc actttccttc gagtttgaaa agattgcaat    3480
tgcatgaatt tcctctgaca tccgattcac tatcaacaat agcgagactg ctgaaccttg    3540
aagagttgta cctttatcgt acaatcatcc atggggaaga atggaacatg ggagaagaag    3600
acacctttga gaatctcaaa tgtttgatgt tgagtcaagt gattctttcc aagtgggagg    3660
ttggagagga atcttttccc acgcttgaga aattagaact gtcggactgt cataatcttg    3720
aggagattcc gtctagtttt ggggatattt attccttgaa aattatcgaa cttgtaagga    3780
gccctcaact tgaaaattcc gctctcaaga ttaaggaata tgctgaagat atgaggggag    3840
gggacgagct tcagatcctt ggccagaagg atatcccgtt atttaagtag               3890
```

<210> SEQ ID NO 4
<211> LENGTH: 1267
<212> TYPE: PRT
<213> ORGANISM: Solanum bulbocastanum
<220> FEATURE:
<221> NAME/KEY: MISC_FEATURE
<222> LOCATION: (1)..(1267)
<223> OTHER INFORMATION: Deduced Rpi-blb2 protein sequence

<400> SEQUENCE: 4

```
Met Glu Lys Arg Lys Asp Asn Glu Ala Asn Asn Ser Leu Glu Ser
1               5                   10                  15

Phe Ser Ala Leu Arg Lys Asp Ala Ala Asn Val Leu Asp Phe Leu Glu
            20                  25                  30

Arg Leu Lys Asn Glu Glu Asp Gln Lys Ala Val Asp Val Asp Leu Ile
            35                  40                  45

Glu Ser Leu Lys Leu Lys Leu Thr Phe Ile Cys Thr Tyr Val Gln Leu
    50                  55                  60

Ser Tyr Ser Asp Leu Glu Lys Phe Glu Asp Ile Met Thr Arg Lys Arg
65                  70                  75                  80

Gln Glu Val Glu Asn Leu Leu Gln Pro Ile Leu Asp Asp Gly Lys
                85                  90                  95

Asp Val Gly Cys Lys Tyr Val Leu Thr Ser Leu Ala Gly Asn Met Asp
            100                 105                 110

Asp Cys Ile Ser Leu Tyr His Arg Ser Lys Ser Asp Ala Thr Met Met
            115                 120                 125

Asp Glu Gln Leu Gly Phe Leu Leu Asn Leu Ser His Leu Ser Lys
    130                 135                 140

His Arg Ala Glu Lys Met Phe Pro Gly Val Thr Gln Tyr Glu Val Leu
145                 150                 155                 160

Gln Asn Val Cys Gly Asn Ile Arg Asp Phe His Gly Leu Ile Val Asn
                165                 170                 175

Cys Cys Ile Lys His Glu Met Val Glu Asn Val Leu Ser Leu Phe Gln
            180                 185                 190

Leu Met Ala Glu Arg Val Gly Arg Phe Leu Trp Glu Asp Gln Ala Asp
        195                 200                 205

Glu Asp Ser Gln Leu Ser Glu Leu Asp Glu Asp Gln Asn Asp Lys
    210                 215                 220

Asp Pro Gln Leu Phe Lys Leu Ala His Leu Leu Leu Lys Ile Val Pro
225                 230                 235                 240

Thr Glu Leu Glu Val Met His Ile Cys Tyr Lys Thr Leu Lys Ala Ser
            245                 250                 255

Thr Ser Thr Glu Ile Gly Arg Phe Ile Lys Lys Leu Leu Glu Thr Ser
            260                 265                 270

Pro Asp Ile Leu Arg Glu Tyr Leu Ile His Leu Gln Glu His Met Ile
            275                 280                 285

Thr Val Ile Thr Pro Asn Thr Ser Gly Ala Arg Asn Ile His Val Met
            290                 295                 300

Met Glu Phe Leu Leu Ile Ile Leu Ser Asp Met Pro Pro Lys Asp Phe
305                 310                 315                 320

Ile His His Asp Lys Leu Phe Asp Leu Leu Ala Arg Val Val Ala Leu
            325                 330                 335

Thr Arg Glu Val Ser Thr Leu Val Arg Asp Leu Glu Glu Lys Leu Arg
            340                 345                 350

Ile Lys Glu Ser Thr Asp Glu Thr Asn Cys Ala Thr Leu Lys Phe Leu
            355                 360                 365

Glu Asn Ile Glu Leu Leu Lys Glu Asp Leu Lys His Val Tyr Leu Lys
            370                 375                 380

Val Pro Asp Ser Ser Gln Tyr Cys Phe Pro Met Ser Asp Gly Pro Leu
385                 390                 395                 400

Phe Met His Leu Leu Gln Arg His Leu Asp Asp Leu Leu Asp Ser Asn
            405                 410                 415
```

-continued

```
Ala Tyr Ser Ile Ala Leu Ile Lys Glu Gln Ile Gly Leu Val Lys Glu
            420                 425                 430

Asp Leu Glu Phe Ile Arg Ser Phe Ala Asn Ile Glu Gln Gly Leu
            435                 440                 445

Tyr Lys Asp Leu Trp Glu Arg Val Leu Asp Val Ala Tyr Glu Ala Lys
        450                 455                 460

Asp Val Ile Asp Ser Ile Ile Val Arg Asp Asn Gly Leu Leu His Leu
465                 470                 475                 480

Ile Phe Ser Leu Pro Ile Thr Arg Lys Lys Met Met Leu Ile Lys Glu
                485                 490                 495

Glu Val Ser Asp Leu His Glu Asn Ile Ser Lys Asn Arg Gly Leu Ile
            500                 505                 510

Val Val Asn Ser Pro Lys Lys Pro Val Glu Ser Lys Ser Leu Thr Thr
            515                 520                 525

Asp Lys Ile Ile Val Gly Phe Gly Glu Glu Thr Asn Leu Ile Leu Arg
        530                 535                 540

Lys Leu Thr Ser Gly Pro Ala Asp Leu Asp Val Ile Ser Ile Ile Gly
545                 550                 555                 560

Met Pro Gly Leu Gly Lys Thr Thr Leu Ala Tyr Lys Val Tyr Asn Asp
                565                 570                 575

Lys Ser Val Ser Ser His Phe Asp Leu Arg Ala Trp Cys Thr Val Asp
            580                 585                 590

Gln Val Tyr Asp Glu Lys Lys Leu Leu Asp Lys Ile Phe Asn Gln Val
            595                 600                 605

Ser Asp Ser Asn Ser Lys Leu Ser Glu Asn Ile Asp Val Ala Asp Lys
        610                 615                 620

Leu Arg Lys Gln Leu Phe Gly Lys Arg Tyr Leu Ile Val Leu Asp Asp
625                 630                 635                 640

Val Trp Asp Thr Asn Thr Trp Asp Glu Leu Thr Arg Pro Phe Pro Asp
                645                 650                 655

Gly Met Lys Gly Ser Arg Ile Ile Leu Thr Thr Arg Glu Lys Lys Val
            660                 665                 670

Ala Leu His Gly Lys Leu Tyr Thr Asp Pro Leu Asn Leu Arg Leu Leu
            675                 680                 685

Arg Ser Glu Glu Ser Trp Glu Leu Leu Glu Lys Arg Ala Phe Gly Asn
        690                 695                 700

Glu Ser Cys Pro Asp Glu Leu Leu Asp Val Gly Lys Glu Ile Ala Glu
705                 710                 715                 720

Asn Cys Lys Gly Leu Pro Leu Val Val Asp Leu Ile Ala Gly Ile Ile
                725                 730                 735

Ala Gly Arg Glu Lys Lys Ser Val Trp Leu Glu Val Val Asn Asn
            740                 745                 750

Leu His Ser Phe Ile Leu Lys Asn Glu Val Glu Val Met Lys Val Ile
            755                 760                 765

Glu Ile Ser Tyr Asp His Leu Pro Asp His Leu Lys Pro Cys Leu Leu
        770                 775                 780

Tyr Phe Ala Ser Ala Pro Lys Asp Trp Val Thr Thr Ile His Glu Leu
785                 790                 795                 800

Lys Leu Ile Trp Gly Phe Glu Gly Phe Val Lys Thr Asp Met Lys
                805                 810                 815

Ser Leu Glu Glu Val Val Lys Ile Tyr Leu Asp Asp Leu Ile Ser Ser
            820                 825                 830

Ser Leu Val Ile Cys Phe Asn Glu Ile Gly Asp Tyr Pro Thr Cys Gln
```

-continued

```
              835                 840                 845
Leu His Asp Leu Val His Asp Phe Cys Leu Ile Lys Ala Arg Lys Glu
    850                 855                 860
Lys Leu Cys Asp Arg Ile Ser Ser Ala Pro Ser Asp Leu Leu Pro
865                 870                 875                 880
Arg Gln Ile Ser Ile Asp Tyr Asp Asp Glu His Phe Gly Leu
                885                 890                 895
Asn Phe Val Leu Phe Gly Ser Asn Lys Lys Arg His Ser Gly Lys His
                900                 905                 910
Leu Tyr Ser Leu Thr Ile Asn Gly Asp Glu Leu Asp Asp His Leu Ser
                915                 920                 925
Asp Thr Phe His Leu Arg His Leu Arg Leu Leu Arg Thr Leu His Leu
    930                 935                 940
Glu Ser Ser Phe Ile Met Val Lys Asp Ser Leu Leu Asn Glu Ile Cys
945                 950                 955                 960
Met Leu Asn His Leu Arg Tyr Leu Ser Ile Gly Thr Glu Val Lys Ser
                965                 970                 975
Leu Pro Leu Ser Phe Ser Asn Leu Trp Asn Leu Glu Ile Leu Phe Val
                980                 985                 990
Asp Asn Lys Glu Ser Thr Leu Ile Leu Leu Pro Arg Ile Trp Asp Leu
                995                 1000                1005
Val Lys Leu Gln Val Leu Phe Thr Thr Ala Cys Ser Phe Phe Asp
    1010                1015                1020
Met Asp Ala Asp Glu Ser Ile Leu Ile Ala Glu Asp Thr Lys Leu
    1025                1030                1035
Glu Asn Leu Thr Ala Leu Gly Glu Leu Val Leu Ser Tyr Trp Lys
    1040                1045                1050
Asp Thr Glu Asp Ile Phe Lys Arg Leu Pro Asn Leu Gln Val Leu
    1055                1060                1065
His Phe Lys Leu Lys Glu Ser Trp Asp Tyr Ser Thr Glu Gln Tyr
    1070                1075                1080
Trp Phe Pro Lys Leu Asp Phe Leu Thr Glu Leu Glu Lys Leu Thr
    1085                1090                1095
Val Asp Phe Glu Arg Ser Asn Thr Asn Asp Ser Gly Ser Ser Ala
    1100                1105                1110
Ala Ile Asn Arg Pro Trp Asp Phe His Phe Pro Ser Ser Leu Lys
    1115                1120                1125
Arg Leu Gln Leu His Glu Phe Pro Leu Thr Ser Asp Ser Leu Ser
    1130                1135                1140
Thr Ile Ala Arg Leu Leu Asn Leu Glu Glu Leu Tyr Leu Tyr Arg
    1145                1150                1155
Thr Ile Ile His Gly Glu Glu Trp Asn Met Gly Glu Glu Asp Thr
    1160                1165                1170
Phe Glu Asn Leu Lys Cys Leu Met Leu Ser Gln Val Ile Leu Ser
    1175                1180                1185
Lys Trp Glu Val Gly Glu Glu Ser Phe Pro Thr Leu Glu Lys Leu
    1190                1195                1200
Glu Leu Ser Asp Cys His Asn Leu Glu Glu Ile Pro Ser Ser Phe
    1205                1210                1215
Gly Asp Ile Tyr Ser Leu Lys Ile Ile Glu Leu Val Arg Ser Pro
    1220                1225                1230
Gln Leu Glu Asn Ser Ala Leu Lys Ile Lys Glu Tyr Ala Glu Asp
    1235                1240                1245
```

```
Met Arg Gly Gly Asp Glu Leu Gln Ile Leu Gly Gln Lys Asp Ile
    1250              1255                1260

Pro Leu Phe Lys
    1265

<210> SEQ ID NO 5
<211> LENGTH: 7967
<212> TYPE: DNA
<213> ORGANISM: Solanum bulbocastanum
<220> FEATURE:
<221> NAME/KEY: misc_feature
<222> LOCATION: (1)..(7967)
<223> OTHER INFORMATION: Sequence of the 7967 bp Sau3AI genomic DNA
      fragment of ARD 1197-1 6 BAC 211 present in p211F-C12, Rpi-blb2
      gene including natural regulatory elements necessary for correct
      expression of the gene.
<220> FEATURE:
<221> NAME/KEY: misc_feature
<222> LOCATION: (1546)..(1548)
<223> OTHER INFORMATION: Start codon: The initiation codon (ATG position
      1546-1548) and the termination codon (TAG position 5433-5435)
<220> FEATURE:
<221> NAME/KEY: misc_feature
<222> LOCATION: (5433)..(5435)
<223> OTHER INFORMATION: Stop codon: The initiation codon (ATG position
      1546-1548) and the termination codon (TAG position 5433-5435)

<400> SEQUENCE: 5
gatctagaat caccgaacct cccctcggta cagctcctcc agttctacca tgaatttcat      60
ccactgattc ctcttcaatc gccattgcag attctctcga tctatgctca aaaaatcccg     120
agataaaacc ctagatctgc ttcaaatgct ctgataccat gtaatttcag tgaattctaa     180
ctaaacaatg gagagaatta actattttag aaagactgat tgaaggagaa gaagagagaa     240
aaattctata ttgaactcat gaaccaaaat gaatgaaaaa ataatgaga agaactatac      300 tattacaatc tatatatctc tatttatatt ctaatctgaa gcagttaatt taactgactc     360
taacaactag actgataggt gtacattttc tgttagtgca ctgcagtgca tttaactaac     420
tgcttaacat aaagaatgtt gttcgaactt cattcgaata gcttcaatga gaagcaaaca     480
tgtgtacctg taaagacaca cagtaaaagt gttaataatg aataaatatg aataaatcaa     540
ataataaatt aaaaataaaa acacatccaa ttaacattgg aggtcttgaa atcgatggt      600 aattaacaaa gaccctcgtg aaatttaagt ctgtaattga aaatttgagt ataggttagg     660
ggacatttga ctattttctc attttctttta tcttttttcct aatttgtggc agacaagtga    720
ggaggcccca ctgtaattga ttcatgcttt tgctttcttg acttttgga acaatactat      780 gcatcatatt tggtcttaat tattcctctg tttatttcca gaattttgag ctctatacat     840
ctaataacaa agcaagcaga ggatatatag tttcatcaac taaaaggtt agtcaactca      900 tctaatattt gctactctca tctctattga agtacagtta tggaaaagta gaagtgatgt     960
aagaaaaatg aaagaacttt agtaggttag ttggatctaa caaagagaaa gggaaataaa    1020
ttgcaggaga aagagagagg ttaaatactt actcacacca ccgatttaca acaaatcact    1080
taattgtggt tagttaatgt atactttcac ctcattaaat tattacttac ccatgataag    1140
ttgtattaat ttggtattaa tatccggtgc gggtgaattc ttaccgggtg agagggatgg    1200
ggttggagag tgtggagtga acagaagcag atgttttaga tttttctaa gatgacgaaa     1260 gattccctc actaatgaaa atatattact atacgctatt agagatagaa aggttcggta    1320
ccagttggtc tcgtttctgg atgaacccca tttttacaag tcatttttctt caattcaaat    1380 cgcaagtgta cctttatcat cttccactaa ttaagtcctc ttaagttcgc gtgaaaatag    1440
```

```
tgaaattatt gattattctt atcatttcat cttctttctc ctgataaagt tttatgtact    1500
ttttatgcat caggtcttga gaacttggaa aggaaaagta gaatcatgga aaaacgaaaa    1560
gataatgaag aagcaaacaa ctcattggta tgttatttga tagagtgaac tgtaaagtat    1620
tgaattgtag atatcatgtg gctttaaaaa tttgatatgt gttattttgg caggagtcat    1680
tttctgctct tcgcaaggat gctgccaatg ttctggattt cctagagaga ttaaagaatg    1740
aagaagatca aaaggctgtt gatgtggatc tgattgaaag cctgaaattg aagctgacat    1800
ttatttgtac atatgtccag ctttcttatt ccgatttgga gaagtttgaa gatataatga    1860
ctagaaaaag acaagaggtt gagaatctgc ttcaaccaat tttggatgat gatggcaaag    1920
acgtcgggtg taaatatgtc cttactagcc tcgccggtaa tatggatgac tgtataagct    1980
tgtatcatcg ttctaaatca gatgccacca tgatggatga gcaattgggc ttcctcctct    2040
tgaatctctc tcatctatcc aagcatcgtg ctgaaaagat gtttcctgga gtgactcaat    2100
atgaggttct tcagaatgta tgtggcaaca taagagattt ccatggattg atagtgaatt    2160
gttgcattaa gcatgagatg gttgagaatg tcttatctct gtttcaactg atggctgaga    2220
gagtaggacg cttcctttgg gaggatcagg ctgatgaaga ctctcaactc tccgagctag    2280
atgaggatga tcagaatgat aaagaccctc aactcttcaa gctagcacat ctactcttga    2340
agattgttcc aactgaattg gaggttatgc acatatgtta taaaactttg aaagcttcaa    2400
cttcaacaga aattggacgc ttcattaaga agctcctgga aacctctccg gacattctca    2460
gagaatatct gattcatcta caagagcata tgataactgt tattacccct aacacttcag    2520
gggctcgaaa cattcatgtc atgatggaat tcctattgat tattctttct gatatgccgc    2580
ccaaggactt tattcatcat gacaaacttt ttgatctctt ggctcgtgtt gtagcactta    2640
ccagggaggt atcaactctt gtacgcgact tggaagagaa attaaggatt aaagagagta    2700
ctgacgaaac aaattgtgca accctaaagt ttctggaaaa tattgaactc cttaaggaag    2760
atctcaaaca tgtttatctg aaagtcccgg attcatctca atattgcttc cccatgagtg    2820
atggacctct cttcatgcat ctgctacaga gacacttaga tgatttgctg gattccaatg    2880
cttattcaat tgctttgata aaggaacaaa ttgggctggt gaaagaagac ttggaattca    2940
taagatcttt tttcgcgaat attgagcaag gattgtataa agatctctgg gaacgtgttc    3000
tagatgtggc atatgaggca aaagatgtca tagattcaat tattgttcga gataatggtc    3060
tcttacatct tattttctca cttcccatta ccagaaagaa gatgatgctt atcaaagaag    3120
aggtctctga tttacatgag aacatttcca agaacagagg tctcatcgtt gtgaactctc    3180
ccaagaaacc agttgagagc aagtcattga caactgataa aataattgta ggttttggtg    3240
aggagacaaa cttgatactt agaaagctca ccagtggacc ggcagatcta gatgtcattt    3300
cgatcattgg tatgccgggt ttaggtaaaa ctactttggc gtacaaagta tacaatgata    3360
aatcagtttc tagccatttc gaccttcgtg catggtgcac ggtcgaccaa gtatatgacg    3420
agaagaagtt gttggataaa attttcaatc aagttagtga ctcaaattca aaattgagtg    3480
agaatattga tgttgctgat aaactacgga acaattgtt tggaaagagg tatcttattg    3540
tcttagatga cgtgtgggat actaatacat gggatgagct aacaagacct tttcctgatg    3600
gtatgaaagg aagtagaatt attttgacaa ctcgagaaaa gaaagttgct ttgcatggaa    3660
agctctacac tgatcctctt aaccttcgat tgctaagatc agaagaaagt tgggagttat    3720
tagagaaaag ggcatttgga aacgagagtt gccctgatga actattggat gttggtaaag    3780
```

```
aaatagccga aaattgtaaa gggcttcctt tggtggtgga tctgattgct ggaatcattg    3840
ctgggaggga aagaaaaag agtgtgtggc ttgaagttgt aaataatttg cattccttta     3900
ttttgaagaa tgaagtggaa gtgatgaaag ttatagaaat aagttatgac cacttacctg    3960
atcacctgaa gccatgcttg ctgtactttg caagtgcgcc gaaggactgg gtaacgacaa    4020
tccatgagtt gaaacttatt tggggttttg aaggatttgt ggaaaagaca gatatgaaga    4080
gtctggaaga agtggtgaaa atttatttgg atgatttaat ttccagtagc ttggtaattt    4140
gtttcaatga gataggtgat taccctactt gccaacttca tgatcttgtg catgactttt    4200
gtttgataaa agcaagaaag gaaaagttgt gtgatcggat aagttcaagt gctccatcag    4260
atttgttgcc acgtcaaatt agcattgatt atgatgatga tgaagagcac tttgggctta    4320
attttgtcct gttcggttca aataagaaaa ggcattccgg taaacacctc tattctttga    4380
ccataaatgg agatgagctg gacgaccatc tttctgatac atttcatcta agacacttga    4440
ggcttcttag aaccttgcac ctggaatcct ctttttatcat ggttaaagat tctttgctga    4500
atgaaatatg catgttgaat catttgaggt acttaagcat gggacagaa gttaaatctc      4560 tgcctttgtc tttctcaaac ctctggaatc tagaaatctt gtttgtggat aacaaagaat    4620
caaccttgat actattaccg agaatttggg atcttgtaaa gttgcaagtg ctgttcacga    4680
ctgcttgttc tttctttgat atggatgcag atgaatcaat actgatagca gaggacacaa    4740
agttagagaa cttgacagca ttaggggaac tcgtgctttc ctattggaaa gatacagagg    4800
atattttcaa aaggcttccc aatcttcaag tgcttcattt caaactcaag gagtcatggg    4860
attattcaac agagcaatat tggttcccga aattggattt cctaactgaa ctagaaaaac    4920
tcactgtaga ttttgaaaga tcaaacacaa atgacagtgg gtcctctgca gccataaatc    4980
ggccatggga ttttcacttt ccttcgagtt tgaaaagatt gcaattgcat gaatttcctc    5040
tgacatccga ttcactatca acaatagcga gactgctgaa ccttgaagag ttgtaccttt    5100
atcgtacaat catccatggg gaagaatgga acatgggaga agaagacacc tttgagaatc    5160
tcaaatgttt gatgttgagt caagtgattc tttccaagtg ggaggttgga gaggaatctt    5220
ttcccacgct tgagaaatta gaactgtcgg actgtcataa tcttgaggag attccgtcta    5280
gttttgggga tatttattcc ttgaaaatta tcgaacttgt aaggagccct caacttgaaa    5340
attccgctct caagattaag gaatatgctg aagatatgag ggggagggac gagcttcaga    5400
tccttggcca gaaggatatc ccgttattta agtagttttt gagcattatg gttgaaaagt    5460
agattgcact ttgctgggta gattgtatat ggttaagaaa attctgttac agttgttatg    5520 aaacatttt atttgacttt tctgagtttc ttttagaaaa ctcagaagtt tttaacaaaa    5580
attatagttt ttataaatac aatgtggatt tgcctttggc tgtccaactt ggtctgaagt    5640
ctcatatgct cagagcacta tcgttcaacc tcaatcaagg tactgattta aaatgacatc    5700
tatactactt tatcacaaac ccaacgaact ttcatctcaa aagctaggcc aggaagtgaa    5760
gaggttgtag agagcttata agcactcatg acttcctttt ctcgaacatt caaccaacgt    5820
aggctgaaat cccactctga acgaaaataa gtgtttgttt atcaaattaa ctctcgtagt    5880
agaacactga aataccttct tctaaacgtt caacaaatgg gatttccagc actcaaagtg    5940
aatgaaaggt tcacattaat cttcaaaaag aattacgaca attcatgacc acaagtacat    6000
tgacagcacc atttcaacag aagaacaagt caatgctgca tcttcatcaa taatccgagt    6060
gtcgaacctc cttcctgaca ctgtcctgta tatgtaaagt ttctcaacag gcaactttc    6120 tggtctcgta tctggatgac ccctctcgtc tataacttca acattaagcc ctggcaactt    6180
```

-continued

```
ctggaccaac agcttacatg cttcaaaact tactgaacaa ttagacatcc aaagggatcg    6240
cattgtctcc agctttgcag cattagccaa cagagcctca tcgccaaagg ggcagtctct    6300
aatctcgaat ttgaaaaaat tgttgttgta tgactttcct ctgacatccg atgcactatc    6360
aacaatagca agactggagg ttggagagga atcctttatt atacaatcat tcagggagaa    6420
gaatggaaca tggggagga agacacttt gagaatctga aatgtgttag agccacaagc    6480
tacagaagta ttgaatttgt catgaatatc aacattcttc atcctagtta attcttttc    6540 aatttttaat agactctcat tttaatcact aatattcttc tatttgtgac ttcttttctg    6600
caggtggcaa ctttaaattc ataaagtata ggattgatga caaactcgaa aaatatctta    6660
atgaggtgaa gtttgagcag tcagcagatg gtggttccaa ctctaagttg acaagcacat    6720
actatcccgg agggcgattt caagcctgat gcatatggtt agtgtggcta gagcagacag    6780
gatgtattac ctggatatct accaagacga atccacaatc agttttatgt caagcaatac    6840
atgaagtaac tcccgataga acagtaaaag caagatgtgt aggtgtatct cgactctaag    6900
agattgtaca ttcctctttg agatttttac tgctaataca aatttacacc tcagaagcga    6960
atctagaatt tctagagcat gaatgcacca ctaatgaaag gagaaaaaag gaagtatgaa    7020
gtgggaattt gatccttgtt tctaggtata taaaatttat cattcaacta tacttcattt    7080
agcaaacaac tctctttgcc attatttctc aaacaagggc ttctaatatt gctaaactaa    7140
agactgtcaa aaggtaagtt catcttcaaa ctctcttgtt tactttatct aaaggggaac    7200
tatgaaaaac aagaaacatc aggaatgtcc cgtaaacaaa gcagcctcat gcacaaaaca    7260
tccaacgttg gtaggattaa tggagggatc gcatcccagg aggatactgt agaaaaatta    7320
gtggcttctt tcaccgctca aacccatgat ctataggtta catggagaca actttatggt    7380
tgctcgtagg ctcccgtcaa ttctcataaa ccacaacacc aaagttgcat cagacatcat    7440
cttcattcac aagctgacaa tctccacaag tcttagtcaa cttgtaatat gaatattagc    7500
caggtagacg tacatattta caaaattgag tttcctatat aatatggttt gaaggaatga    7560
aacatgatgg ggagggtaga taaaataata tatgaggcat aaaaatagga aagatatttg    7620
tagtgagagg ttttgacttt ttatgctgct tttgatcttc agtttcttgt attcttttc    7680 tactgctttc ctcttctttc tcctgagtaa agttttatgt aggtacttt tatacgtccg    7740 atcgtgagaa cttgaaagaa agctctctat agctatgtta ggtgcccaca taaaaaaatg    7800
aaatattaca aaaccctga taataaaata cactaatcta agatattcac tgcaacatac    7860
atgcaaaata tatatatata aattttcatg aaaattataa caaataatag atgtgaacat    7920
ataactttaa aaataatatt acatccataa agcttaaatt ctagatc                 7967
```

<210> SEQ ID NO 6
<211> LENGTH: 9949
<212> TYPE: DNA
<213> ORGANISM: Solanum bulbocastanum
<220> FEATURE:
<221> NAME/KEY: misc_feature
<222> LOCATION: (1)..(9949)
<223> OTHER INFORMATION: Sequence of 9949 bp Sau3AI genomic DNA fragment
      of S. bulbocastanum 2002 BAC BlbSP39 present in pSP39-20. The
      genomic fragment harbours the Rpi-blb2 gene including natural
      elements necessary for expression.
<220> FEATURE:
<221> NAME/KEY: misc_feature
<222> LOCATION: (1413)..(1415)
<223> OTHER INFORMATION: Start codon: Iinitiation codon (ATG position
      1413-1415), the termination codon (TAG position 5300-5303)
<220> FEATURE:

<221> NAME/KEY: misc_feature
<222> LOCATION: (5300)..(5303)
<223> OTHER INFORMATION: Stop codon: Iinitiation codon (ATG position
     1413-1415), the termination codon (TAG position 5300-5303)

<400> SEQUENCE: 6

```
gatctgcttc aaatgctctg ataccatgta atttcagtga attctaacta acaatggag      60
agaattaact attttagaaa gactgattga aggagaagaa gagagaaaaa ttctatattg    120
aactcatgaa ccaaaatgaa tgaaaaaaat aatgagaaga actatactat tacaatctat    180
atatctctat ttatattcta atctgaagca gttaatttaa ctgactctaa caactagact    240
gataggtgta cattttctgt tagtgcactg cagtgcattt aactaactgc ttaacataaa    300
gaatgttgtt cgaacttcat tcgaatagct tcaatgagaa gcaaacatgt gtacctgtaa    360
agacacacag taaaagtgtt aataatgaat aaatatgaat aaatcaaata ataaattaaa    420
aataaaaaca catccaatta acattggagg tcttgaaaat cgatggtaat taacaaagac    480
ccttgtgaaa tttaagtctg taattgaaaa tttgagtata ggttagggga catttgacta    540
ttttctcatt ttctttatct ttttcctaat ttgtggcaga caagtgagga ggccccactg    600
taattgattc atgcttttgc tttcttgact ttttggaaca atactatgca tcatatttgg    660
tcttaattat tcctctgttt atttccagaa ttttgagctc tatacatcta ataacaaagc    720
aagcagagga tatatagttt catcaactaa aaaggttagt caactcatct aatatttgct    780
actctcatct ctattgaagt acagttatgg aaaagtagaa gtgatgtaag aaaaatgaaa    840
gaactttagt aggttagttg gatctaacaa agagaaaggg aaataaattg caggagaaag    900
agagaggtta aatacttact cacaccaccg atttacaaca aatcacttaa ttgtggttag    960
ttaatgtata ctttcacctc attaaattat tacttaccca tgataagttg tattaatttg   1020
gtattaatat ccggtgcggg tgaattctta ccgggtgaga gggatggggt tggagagtgt   1080
ggagtgaaca gaagcagatg ttttagattt tttctaagat gacgaaagat tcccctcact   1140
aatgaaaata tattactata cgctattaga gatagaaagg ttcggtacca gttggtctcg   1200
tttctggatg aacccccattt ttacaagtca ttttcttcaa ttcaaatcgc aagtgtacct   1260
ttatcatctt ccactaatta agtcctctta agttcgcgtg aaaatagtga aattattgat   1320
tattcttatc atttcatctt cttttctcctg ataaagtttt atgtacttttt tatgcatcag   1380
gtcttgagaa cttggaaagg aaaagtagaa tcatggaaaa acgaaaagat aatgaagaag   1440
caaacaactc attggtatgt tatttgatag agtgaactgt aaagtattga attgtagata   1500
tcatgtggct ttaaaaattt gatatgtgtt attttggcag gagtcatttt ctgctcttcg   1560
caaggatgct gccaatgttc tggatttcct agagagatta aagaatgaag aagatcaaaa   1620
ggctgttgat gtggatctga ttgaaagcct gaaattgaag ctgacattta tttgtacata   1680
tgtccagctt tcttattccg atttggagaa gtttgaagat ataatgacta gaaaagaca   1740
agaggttgag aatctgcttc aaccaatttt ggatgatgat ggcaaagacg tcgggtgtaa   1800
atatgtcctt actagcctcg ccggtaatat ggatgactgt ataagcttgt atcatcgttc   1860
taaatcagat gccaccatga tggatgagca attgggcttc ctcctcttga atctctctca   1920
tctatccaag catcgtgctg aaaagatgtt tcctggagtg actcaaatatg aggttcttca   1980
gaatgtatgt ggcaacataa agagatttcca tggattgata gtgaattgtt gcattaagca   2040
tgagatggtt gagaatgtct tatctctgtt tcaactgatg gctgagagag taggacgctt   2100
cctttgggag gatcaggctg atgaagactc tcaactctcc gagctagatg aggatgatca   2160
```

```
gaatgataaa gaccctcaac tcttcaagct agcacatcta ctcttgaaga ttgttccaac    2220
tgaattggag gttatgcaca tatgttataa aactttgaaa gcttcaactt caacagaaat    2280
tggacgcttc attaagaagc tcctggaaac ctctccggac attctcagag aatatctgat    2340
tcatctacaa gagcatatga taactgttat taccoctaac acttcagggg ctcgaaacat    2400
tcatgtcatg atggaattcc tattgattat tctttctgat atgccgccca aggactttat    2460
tcatcatgac aaacttttg atctcttggc tcgtgttgta gcacttacca gggaggtatc    2520
aactcttgta cgcgacttgg aagagaaatt aaggattaaa gagagtactg acgaaacaaa    2580
ttgtgcaacc ctaaagtttc tggaaaatat tgaactcctt aaggaagatc tcaaacatgt    2640
ttatctgaaa gtcccggatt catctcaata ttgcttcccc atgagtgatg acctctctt     2700 catgcatctg ctacagagac acttagatga tttgctggat tccaatgctt attcaattgc    2760
tttgataaag gaacaaattg ggctggtgaa agaagacttg gaattcataa gatctttttt    2820
cgcgaatatt gagcaaggat tgtataaaga tctctgggaa cgtgttctag atgtggcata    2880
tgaggcaaaa gatgtcatag attcaattat tgttcgagat aatggtctct acatcttat     2940 tttctcactt cccattacca gaaagaagat gatgcttatc aaagaagagg tctctgattt    3000
acatgagaac atttccaaga acagaggtct catcgttgtg aactctccca agaaaccagt    3060
tgagagcaag tcattgacaa ctgataaaat aattgtaggt tttggtgagg acaaaactt     3120 gatacttaga aagctcacca gtggaccggc agatctagat gtcatttcga tcattggtat    3180
gccgggttta ggtaaaacta cttggcgta caaagtatac aatgataaat cagtttctag    3240
ccatttcgac cttcgtgcat ggtgcacggt cgaccaagta tatgacgaga agaagttgtt    3300
ggataaaatt ttcaatcaag ttagtgactc aaattcaaaa ttgagtgaga atattgatgt    3360
tgctgataaa ctacggaaac aattgtttgg aaagaggtat cttattgtct tagatgacgt    3420
gtgggatact aatacatggg atgagctaac aagaccttt cctgatggta tgaaaggaag      3480
tagaattatt ttgacaactc gagaaaagaa agttgctttg catggaaagc tctacactga    3540
tcctcttaac cttcgattgc taagatcaga agaaagttgg gagttattag agaaaagggc    3600
atttggaaac gagagttgcc ctgatgaact attggatgtt ggtaaagaaa tagccgaaaa    3660
ttgtaaaggg cttcctttgg tggtggatct gattgctgga atcattgctg ggagggaaaa    3720
gaaaaagagt gtgtggcttg aagttgtaaa taatttgcat tccttttattt tgaagaatga    3780 agtggaagtg atgaaagtta tagaaataag ttatgaccac ttacctgatc acctgaagcc    3840
atgcttgctg tactttgcaa gtcgccgaa ggactgggta acgacaatcc atgagttgaa      3900
acttatttgg ggttttgaag gattttgtgga aagacagat atgaagagtc tggaagaagt     3960
ggtgaaaatt tatttggatg atttaatttc cagtagcttg gtaatttgtt tcaatgagat    4020
aggtgattac cctacttgcc aacttcatga tcttgtgcat gactttttgtt tgataaaagc    4080 aagaaaggaa aagttgtgtg atcggataag ttcaagtgct ccatcagatt tgttgccacg    4140
tcaaattagc attgattatg atgatgatga agagcacttt gggcttaatt ttgtcctgtt    4200
cggttcaaat aagaaaaggc attccggtaa acacctctat tctttgacca taaatggaga    4260
tgagctggac gaccatcttt ctgatacatt tcatctaaga cacttgaggc ttcttagaac    4320
cttgcacctg gaatcctctt ttatcatggt taaagattct ttgctgaatg aaatatgcat    4380
gttgaatcat ttgaggtact taagcattgg gacagaagtt aaatctctgc ctttgtcttt    4440
ctcaaacctc tggaatctag aaatcttgtt tgtggataac aaagaatcaa ccttgatact    4500
attaccgaga attttgggatc ttgtaaagtt gcaagtgctg ttcacgactg cttgttcttt     4560
```

```
ctttgatatg gatgcagatg aatcaatact gatagcagag gacacaaagt tagagaactt    4620
gacagcatta ggggaactcg tgctttccta ttggaaagat acagaggata ttttcaaaag    4680
gcttcccaat cttcaagtgc ttcatttcaa actcaaggag tcatgggatt attcaacaga    4740
gcaatattgg ttcccgaaat tggatttcct aactgaacta gaaaaactca ctgtagattt    4800
tgaaagatca aacacaaatg acagtgggtc tctgcagcc ataaatcggc catgggattt     4860
tcactttcct tcgagtttga aaagattgca attgcatgaa tttcctctga catccgattc    4920
actatcaaca atagcgagac tgctgaacct tgaagagttg tacctttatc gtacaatcat    4980
ccatggggaa gaatggaaca tgggagaaga agacaccttt gagaatctca aatgtttgat    5040
gttgagtcaa gtgattcttt ccaagtggga ggttggagag gaatcttttc ccacgcttga    5100
gaaattagaa ctgtcggact gtcataatct tgaggagatt ccgtctagtt ttggggatat    5160
ttattccttg aaaattatcg aacttgtaag gagccctcaa cttgaaaatt ccgctctcaa    5220
gattaaggaa tatgctgaag atatgagggg aggggacgag cttcagatcc ttggccagaa    5280
ggatatcccg ttatttaagt agttttgag cattatggtt gaaaagtaga ttgcactttg     5340
ctgggtagat tgtatatggt taagaaaatt ctgttacagt tgttatgaaa cattttatt    5400
tgacttttct gagtttcttt tagaaaactc agaagttttt aacaaaaatt atagttttta    5460
taaatacaat gtggatttgc ctttggctgt ccaacttggt ctgaagtctc atatgctcag    5520
agcactatcg ttcaacctca atcaaggtac tgatttaaaa tgacatctat actactttat    5580
cacaaaccca acgaactttc atctcaaaag ctaggccagg aagtgaagag gttgtagaga    5640
gcttataagc actcatgact tccttttctc gaacattcaa ccaacgtagg ctgaaatccc    5700
actctgaacg aaaataagtg tttgtttatc aaattaactc tcgtagtaga acactgaaat    5760
accttcttct aaacgttcaa caaatgggat ttccagcact caaagtgaat gaaaggttca    5820
cattaatctt caaaaagaat tacgacaatt catgaccaca agtacattga cagcaccatt    5880
tcaacagaag aacaagtcaa tgctgcatct tcatcaataa tccgagtgtc gaacctcctt    5940
cctgacactg tcctgtatat gtaaagtttc tcaacagggc aactttctgg tctcgtatct    6000
ggatgacccc tctcgtctat aacttcaaca ttaagccctg gcaacttctg gaccaacagc    6060
ttacatgctt caaaacttac tgaacaatta gacatccaaa gggatcgcat tgtctccagc    6120
tttgcagcat tagccaacag agcctcatcg ccaaaggggc agtctctaat ctcgaatttg    6180
aaaaaattgt tgttgtatga ctttcctctg acatccgatg cactatcaac aatagcaaga    6240
ctggaggttg gagaggaatc ctttattata caatcattca gggagaagaa tggaacatgg    6300
gggaggaaga cacttttgag aatctgaaat gtgttagagc cacaagctac agaagtattg    6360
aatttgtcat gaatatcaac attcttcatc ctagttaatt cttttcaat ttttaataga    6420
ctctcatttt aatcactaat attcttctat ttgtgacttc ttttctgcag gtggcaactt    6480
taaattcata agtatagga ttgatgacaa actcgaaaaa tatcttaatg aggtgaagtt    6540
tgagcagtca gcagatggtg gttccaactc taagttgaca agcacatact atcccggagg    6600
gcgatttcaa gcctgatgca tatggttagt gtggctagag cagacaggat gtattacctg    6660
gatatctacc aagacgaatc cacaatcagt tttatgtcaa gcaatacatg aagtaactcc    6720
cgatagaaca gtaaaagcaa gatgtgtagg tgtatctcga ctctaagaga ttgtacattc    6780
ctctttgaga tttttactgc taatacaaat ttacacctca gaagcgaatc tagaatttct    6840
agagcatgaa tgcaccacta atgaaaggag aaaaaaggaa gtatgaagtg ggaatttgat    6900
```

```
ccttgtttct aggtatataa aatttatcat tcaactatac ttcatttagc aaacaactct   6960
ctttgccatt atttctcaaa caagggcttc taatattgct aaactaaaga ctgtcaaaag   7020
gtaagttcat cttcaaactc tcttgtttac tttatctaaa ggggaactat gaaaaacaag   7080
aaacatcagg aatgtcccgt aaacaaagca gcctcatgca caaacatcc aacgttggta    7140 ggattaatgg agggatcgca tcccaggagg atactgtaga aaaattagtg gcttcttttca  7200 ccgctcaaac ccatgatcta taggttacat ggagacaact ttatggttgc tcgtaggctc   7260
ccgtcaattc tcataaacca caacaccaaa gttgcatcag acatcatctt cattcacaag   7320
ctgacaatct ccacaagtct tagtcaactt gtaatatgaa tattagccag gtagacgtac   7380
atatttacaa aattgagttt cctatataat atggtttgaa ggaatgaaac atgatgggga   7440
gggtagataa ataatatat gaggcataaa ataggaaag atatttgtag tgagaggttt     7500 tgactttta tgctgctttt gatcttcagt ttcttgtatt cttttctac tgctttcctc     7560 ttctttctcc tgagtaaagt tttatgtagg tactttttat acgtccgatc gtgagaactt   7620
gaaagaaagc tctctatagc tatgttaggt gcccacataa aaaatgaaa tattacaaaa    7680 accctgataa taaatacac taatctaaga tattcactgc aacatacatg caaaatatat    7740
atatataaat tttcatgaaa attataacaa ataatagatg tgaacatata actttaaaaa   7800
taatattaca tccataaagc ttaaattcta gatccatcta tgcttgtatg atgcatagct   7860
cagaatatct ccatcaagtg ttaaactaca tatttcattc aaatttatat agaaaacgat   7920
aattaaggtg aaaacttta taaagatatc gtgtggttgt gtgagtgagg tgacaaaata   7980
agttgtgtga ttattcaaaa agttttaata acgaaaatcc acatgcttga attaattgaa   8040
gcattaatgt tgtaacgaaa aatattacat ttattgagtt actgtgatgt tttaactgat   8100
atataaaata atattggtat ttctcttcat ctgcgacata atatgttttt tcatctttt    8160 tcaatataca aaatagaatt attattttgt tgcatctttt taagtacaaa ttattcatat   8220
gtatatagta caaaataaaa tatttactgt ggtaaagtaa atggaataag aggtcatatt   8280
tgaaataaca atatactata ctatgttaaa gtattttta tagttaaaat ttctctagag    8340
tacttgattc tacatacaaa tactaatttc gtaaaaaaat taatattgaa tttcttcatt   8400
gtttctttat tattaaatta gtttataata actaaactaa ggtaataaga ccttagttta   8460
gttaatgtgt gtctctgtga tttcgttcat agtctaaggg tgtacttgtg cctcatccca   8520
aaaatgaagg aatatcaaaa gatatattaa aattaaatta aatatttgga ggttatgaat   8580 ataaaagta tcagagttct acatataaag agtaacaatt gaaataatta attaaatatg    8640
agatatgaag gcggacattt aaagaaaata ataaataaat aaattaaagg gtataaattt   8700
cataatacat aataccaata agccgtagaa tatctccgtc ataatgcata aactaataaa   8760
tcacaaatgt ataactcaca tacaaatatt ttttgataaa gaatttgaat gttgtaatag   8820
aatggagaat aacttgtgtc ttattccatt atgtaagacg tataaataca aatacaatga   8880
gctctaatta attaaggaaa ctaaataagg aaggaatcaa aaaatattat gtcatatccc   8940
tacatatctg ctagagattc tatcatatcc ttacatatct gttaagctat gtctacacct   9000
aaaggtgtct acaatcattt tgtaacactc cccctcaagt tagagcatag atattattca   9060
ttcccaactt gttacaaaga taatcaactc gagttccatt caacgctttt gtgaacaaat   9120
caactagttg ctctcctgtc ttcacttagc tagtggatat caggttttca tgaatcttct   9180
cacgaataaa atgacagtca acctcaatat gtttagttct ttcatgagac accggattca   9240
aggcaatatg gagcgcaact tgattatcat actagagttt tgatggtata tgatgcttca   9300
```

```
acctatttc tgttaaaaga taatgtatcc acatgatctc acccatagac tgtaacataa       9360
ctctgtactt tgattctgca ctagatcaag atacaacatt ttgcttttta ctcctccatg      9420
ataccaggtt tcatccaaca aagacacaat aacttgtagt agatcttcta tcaattttcg      9480
atccagccca atcgacatct gcaaaacact caatatgagt atggtcgtga ttttgatact      9540
atattccaag actaggagtt ttcttcaagt aacatagaat atgttccaaa gctgcccagt      9600
gtttgacgta ggtgcaaaca tgaactagct aacaacactt actgcaaaag caatatcaag      9660
atgagtcaca ataaggtagt ttaactttcc aactaacctt ttgtatctct atggatcatt      9720
aaaaggatcg tcgtcatctt tcataagatg catattggga accattggag aacttcaggg      9780
tttggctgcc atctttcaat tttctgcaag tagatcgaga gaatatattc tctaagacaa      9840
aagaattccc tttttgtttc tatttacttc tactcccaaa atgtatttca attgacccaa      9900
gtccttcgta tgaaaccaag tatgcaggaa agacttgagg gaagagatc                  9949

<210> SEQ ID NO 7
<211> LENGTH: 3768
<212> TYPE: DNA
<213> ORGANISM: Lycopersicon lycopersicum
<220> FEATURE:
<221> NAME/KEY: CDS
<222> LOCATION: (1)..(3768)
<223> OTHER INFORMATION: Mi1.1 from tomato

<400> SEQUENCE: 7 atg gaa aaa cga aaa gat aat gaa gaa gca aac aac tca ttg gtg cta       48
Met Glu Lys Arg Lys Asp Asn Glu Glu Ala Asn Asn Ser Leu Val Leu
1               5                   10                  15 ttt tct gct ctt agc aag gac att gcc gat gtt ctg gtt ttc cta gag       96
Phe Ser Ala Leu Ser Lys Asp Ile Ala Asp Val Leu Val Phe Leu Glu
                20                  25                  30 aat gag gaa aat caa aaa gct ctt gac aaa gat caa gtt gaa aag ata      144
Asn Glu Glu Asn Gln Lys Ala Leu Asp Lys Asp Gln Val Glu Lys Ile
            35                  40                  45 aaa ttg aaa atg gca ttt att tgt aca tat gtt cag ctt tct tgt tcc      192
Lys Leu Lys Met Ala Phe Ile Cys Thr Tyr Val Gln Leu Ser Cys Ser
        50                  55                  60 gat ttt gag cag ttt gaa gat ata atg act aga aaa aga caa gag gtt      240
Asp Phe Glu Gln Phe Glu Asp Ile Met Thr Arg Lys Arg Gln Glu Val
65                  70                  75                  80 gag aat ctg ctt caa cca ctt ttg gat gat gat gtc ttt act agc ctc      288
Glu Asn Leu Leu Gln Pro Leu Leu Asp Asp Asp Val Phe Thr Ser Leu
                85                  90                  95 acc agt aat atg gat gac tgt atc agc ttg tat cat cgt tct tat aaa      336
Thr Ser Asn Met Asp Asp Cys Ile Ser Leu Tyr His Arg Ser Tyr Lys
                100                 105                 110 tca gat gcc atc atg atg gat gag caa ttg gac ttc ctc ctc ttg aat      384
Ser Asp Ala Ile Met Met Asp Glu Gln Leu Asp Phe Leu Leu Leu Asn
            115                 120                 125 ctc tat cat cta tcc aag cat cac gct gaa aag ata ttt cct gga gtg      432
Leu Tyr His Leu Ser Lys His His Ala Glu Lys Ile Phe Pro Gly Val
        130                 135                 140 act caa tat gaa gtt ctt cag aat ata tgt ggc aac ata aga gat ttc      480
Thr Gln Tyr Glu Val Leu Gln Asn Ile Cys Gly Asn Ile Arg Asp Phe
145                 150                 155                 160 cat ggg ttg ata gtg aat ggt tgc att aag cat gag atg gtt gag aat      528
His Gly Leu Ile Val Asn Gly Cys Ile Lys His Glu Met Val Glu Asn
                165                 170                 175
```

-continued

| | | |
|---|---|---|
| gtc ttr cct ctg ttt caa ctc atg gct gac aga gta gga cac ttc ctt<br>Val Xaa Pro Leu Phe Gln Leu Met Ala Asp Arg Val Gly His Phe Leu<br>      180                 185                 190 | 576 | |
| tgg gat gat cag act gat gaa gac tct cga ctc tcc gag cta gat gag<br>Trp Asp Asp Gln Thr Asp Glu Asp Ser Arg Leu Ser Glu Leu Asp Glu<br>          195                 200                 205 | 624 | |
| gat gaa caa aat gat aga gac tct cga ctt ttc aag cta gca cat cta<br>Asp Glu Gln Asn Asp Arg Asp Ser Arg Leu Phe Lys Leu Ala His Leu<br>  210                 215                 220 | 672 | |
| ctc ttg aag atc gtt ccg gtt gaa ctg gag gtt ata cac ata tgt tat<br>Leu Leu Lys Ile Val Pro Val Glu Leu Glu Val Ile His Ile Cys Tyr<br>225                 230                 235                 240 | 720 | |
| aca aac ttg aaa gct tca act tca gct gaa gtt gga ctc ttc att aag<br>Thr Asn Leu Lys Ala Ser Thr Ser Ala Glu Val Gly Leu Phe Ile Lys<br>              245                 250                 255 | 768 | |
| cag ctt cta gaa acc tct cca gat att ctg agg gaa tat cta att cct<br>Gln Leu Leu Glu Thr Ser Pro Asp Ile Leu Arg Glu Tyr Leu Ile Pro<br>          260                 265                 270 | 816 | |
| ctg caa gag cac atg gta act gtt att acc cct agc act tca ggg gct<br>Leu Gln Glu His Met Val Thr Val Ile Thr Pro Ser Thr Ser Gly Ala<br>      275                 280                 285 | 864 | |
| cga aac att cat gtc atg atg gaa ttc cta tta ctt att ctt tct gat<br>Arg Asn Ile His Val Met Met Glu Phe Leu Leu Leu Ile Leu Ser Asp<br>  290                 295                 300 | 912 | |
| atg ccc aag gac ttt att cat cat gac aaa ctt ttt gat ctc ttg gat<br>Met Pro Lys Asp Phe Ile His His Asp Lys Leu Phe Asp Leu Leu Asp<br>305                 310                 315                 320 | 960 | |
| cgt gtc gga gta ctt acc agg gag gta tca act ctt gta cgt gac ttg<br>Arg Val Gly Val Leu Thr Arg Glu Val Ser Thr Leu Val Arg Asp Leu<br>              325                 330                 335 | 1008 | |
| gaa gag gaa cca agg aat aaa gag ggt aat aac caa aca aat tgt gca<br>Glu Glu Glu Pro Arg Asn Lys Glu Gly Asn Asn Gln Thr Asn Cys Ala<br>          340                 345                 350 | 1056 | |
| acc cta gac ttg ctg gaa aat att gaa ctc ctc aag aaa gat ctc aaa<br>Thr Leu Asp Leu Leu Glu Asn Ile Glu Leu Leu Lys Lys Asp Leu Lys<br>      355                 360                 365 | 1104 | |
| cat gtt tat ctg aaa gcc ctg gat tca tct caa tgt tgc ttc ccc atg<br>His Val Tyr Leu Lys Ala Leu Asp Ser Ser Gln Cys Cys Phe Pro Met<br>  370                 375                 380 | 1152 | |
| agt gat gga cca ctc ttc atg cat ctt cta cac ata cac tta aat gat<br>Ser Asp Gly Pro Leu Phe Met His Leu Leu His Ile His Leu Asn Asp<br>385                 390                 395                 400 | 1200 | |
| ttg tta gat tct aat gct tat tca att gct ttg ata aag gaa gaa atc<br>Leu Leu Asp Ser Asn Ala Tyr Ser Ile Ala Leu Ile Lys Glu Glu Ile<br>              405                 410                 415 | 1248 | |
| gag ctg gtg aag caa gac ctg aaa ttc ata aga tca ttc ttt gtg gat<br>Glu Leu Val Lys Gln Asp Leu Lys Phe Ile Arg Ser Phe Phe Val Asp<br>          420                 425                 430 | 1296 | |
| gct gag caa gga ttg tat aaa gat ctc tgg gca cgt gtt cta gat gtg<br>Ala Glu Gln Gly Leu Tyr Lys Asp Leu Trp Ala Arg Val Leu Asp Val<br>      435                 440                 445 | 1344 | |
| gct tat gag gca aaa gat gtc ata gat tca att att gtt cga gat aat<br>Ala Tyr Glu Ala Lys Asp Val Ile Asp Ser Ile Ile Val Arg Asp Asn<br>  450                 455                 460 | 1392 | |
| ggt ctc tta cat ctt att ttc tca ctt ccc att acc ata aag aag atc<br>Gly Leu Leu His Leu Ile Phe Ser Leu Pro Ile Thr Ile Lys Lys Ile<br>465                 470                 475                 480 | 1440 | |
| aaa ctt atc aaa gaa gag atc tct gct tta gat gag aac att ccc aag<br>Lys Leu Ile Lys Glu Glu Ile Ser Ala Leu Asp Glu Asn Ile Pro Lys<br>              485                 490                 495 | 1488 | |

```
gac aga ggt cta atc gtt gtg aac tct ccc aag aaa cca gtt gag aga      1536
Asp Arg Gly Leu Ile Val Val Asn Ser Pro Lys Lys Pro Val Glu Arg
        500                 505                 510 aag tca ttg aca act gat aaa ata act gta ggt ttt gag gag gaa aca      1584
Lys Ser Leu Thr Thr Asp Lys Ile Thr Val Gly Phe Glu Glu Glu Thr
        515                 520                 525 aac ttg ata ctt aga aag ctc acc agt gga tcg gca gat cta gat gtc      1632
Asn Leu Ile Leu Arg Lys Leu Thr Ser Gly Ser Ala Asp Leu Asp Val
        530                 535                 540 att tcg atc act ggt atg ccg ggt tca ggt aaa act act ttg gca tac      1680
Ile Ser Ile Thr Gly Met Pro Gly Ser Gly Lys Thr Thr Leu Ala Tyr
545                 550                 555                 560 aaa gta tac aat gat aag tca gtt tct agc cgt ttc gac ctt cgt gca      1728
Lys Val Tyr Asn Asp Lys Ser Val Ser Ser Arg Phe Asp Leu Arg Ala
                565                 570                 575 tgg tgc acg gtc gac caa gga tgt gat gag aag aag ttg ttg aat aca      1776
Trp Cys Thr Val Asp Gln Gly Cys Asp Glu Lys Lys Leu Leu Asn Thr
                580                 585                 590 att ttc agt caa gtt agt gac tca gat tca aaa ttg agt gag aat att      1824
Ile Phe Ser Gln Val Ser Asp Ser Asp Ser Lys Leu Ser Glu Asn Ile
                595                 600                 605 gat gtt gct gat aaa tta cgg aaa caa ctg ttt gga aag agg tat ctt      1872
Asp Val Ala Asp Lys Leu Arg Lys Gln Leu Phe Gly Lys Arg Tyr Leu
                610                 615                 620 att gtc tta gat gac gtg tgg gat act act aca tgg gat gag tta aca      1920
Ile Val Leu Asp Asp Val Trp Asp Thr Thr Thr Trp Asp Glu Leu Thr
625                 630                 635                 640 aga cct ttt cct gaa tct aag aaa gga agt agg att att ttg aca act      1968
Arg Pro Phe Pro Glu Ser Lys Lys Gly Ser Arg Ile Ile Leu Thr Thr
                645                 650                 655 cgg gaa aag gaa gtg gct ttg cat gga aag ctg aac act gat cct ctt      2016
Arg Glu Lys Glu Val Ala Leu His Gly Lys Leu Asn Thr Asp Pro Leu
                660                 665                 670 gac ctt cga ttg cta aga cca gat gaa agt tgg gaa cta tta gag aaa      2064
Asp Leu Arg Leu Leu Arg Pro Asp Glu Ser Trp Glu Leu Leu Glu Lys
                675                 680                 685 agg gca ttt ggg aat gag agt tgc cct gat gaa cta tta gat gtc ggt      2112
Arg Ala Phe Gly Asn Glu Ser Cys Pro Asp Glu Leu Leu Asp Val Gly
                690                 695                 700 aaa gaa ata gcc gaa aat tgt aaa ggg ctt cct ttg gtg gct gat ctg      2160
Lys Glu Ile Ala Glu Asn Cys Lys Gly Leu Pro Leu Val Ala Asp Leu
705                 710                 715                 720 att gct gga gtc att gct ggg agg gaa aag aaa agg agt gtg tgg ctt      2208
Ile Ala Gly Val Ile Ala Gly Arg Glu Lys Lys Arg Ser Val Trp Leu
                725                 730                 735 gaa gtt caa agt agt ttg agt tct ttt att ttg aac agt gaa gtg gaa      2256
Glu Val Gln Ser Ser Leu Ser Ser Phe Ile Leu Asn Ser Glu Val Glu
                740                 745                 750 gtg atg aaa gtt ata gaa tta agt tat gac cat tta cca cat cac ctc      2304
Val Met Lys Val Ile Glu Leu Ser Tyr Asp His Leu Pro His His Leu
                755                 760                 765 aag cca tgc ttg ctg tat ttt gca agt ttt ccg aag gac act tca ttg      2352
Lys Pro Cys Leu Leu Tyr Phe Ala Ser Phe Pro Lys Asp Thr Ser Leu
                770                 775                 780 aca atc tat gag ttg aat gtt tat ttc ggt gct gaa gga ttt gtg gga      2400
Thr Ile Tyr Glu Leu Asn Val Tyr Phe Gly Ala Glu Gly Phe Val Gly
785                 790                 795                 800 aag acg gag atg aac agt atg gaa gaa gtg gtg aag att tat atg gat      2448
Lys Thr Glu Met Asn Ser Met Glu Glu Val Val Lys Ile Tyr Met Asp
```

-continued

```
                805                 810                 815
gat tta att tac agt agc ttg gta att tgt ttc aat gag ata ggt tat     2496
Asp Leu Ile Tyr Ser Ser Leu Val Ile Cys Phe Asn Glu Ile Gly Tyr
            820                 825                 830 gca ctg aat ttc caa att cat gat ctt gtg cat gac ttt tgt ttg ata     2544
Ala Leu Asn Phe Gln Ile His Asp Leu Val His Asp Phe Cys Leu Ile
                835                 840                 845 aaa gca aga aag gaa aat ttg ttt gat cag ata aga tca agt gct cca     2592
Lys Ala Arg Lys Glu Asn Leu Phe Asp Gln Ile Arg Ser Ser Ala Pro
    850                 855                 860 tca gat ttg ttg cct cgt caa att acc att gat tgt gat gag gag gag     2640
Ser Asp Leu Leu Pro Arg Gln Ile Thr Ile Asp Cys Asp Glu Glu Glu
865                 870                 875                 880 cac ttt ggg ctt aat ttt gtc atg ttc gat tca aat aag aaa agg cat     2688
His Phe Gly Leu Asn Phe Val Met Phe Asp Ser Asn Lys Lys Arg His
                885                 890                 895 tct ggt aaa cac ctc tat tct ttg agg ata att gga gac cag ctg gat     2736
Ser Gly Lys His Leu Tyr Ser Leu Arg Ile Ile Gly Asp Gln Leu Asp
            900                 905                 910 gac agt gtt tct gat gca ttt cac cta aga cac ttg agg ctt ctt aga     2784
Asp Ser Val Ser Asp Ala Phe His Leu Arg His Leu Arg Leu Leu Arg
                915                 920                 925 gtg ttg gac ctg cat acg tct ttt atc atg gtg aaa gat tct ttg ctg     2832
Val Leu Asp Leu His Thr Ser Phe Ile Met Val Lys Asp Ser Leu Leu
    930                 935                 940 aat gaa ata tgc atg ttg aat cat ttg agg tac tta tcc att gac aca     2880
Asn Glu Ile Cys Met Leu Asn His Leu Arg Tyr Leu Ser Ile Asp Thr
945                 950                 955                 960 caa gtt aaa tat ctg cct ttg tct ttc tca aac ctc tgg aat cta gaa     2928
Gln Val Lys Tyr Leu Pro Leu Ser Phe Ser Asn Leu Trp Asn Leu Glu
                965                 970                 975 agc ctg ttt gtg tct acc aac aga tca atc ttg gta cta tta ccg aga     2976
Ser Leu Phe Val Ser Thr Asn Arg Ser Ile Leu Val Leu Leu Pro Arg
            980                 985                 990 att ttg gat ctt gta aag ttg cga  gtg ctg tcc gtg gat  gct tgt tct    3024
Ile Leu Asp Leu Val Lys Leu Arg  Val Leu Ser Val Asp  Ala Cys Ser
                995                 1000                1005 ttc ttt  gat atg gat gca gat  gaa tca ata ttg ata  gca gag gac        3069
Phe Phe  Asp Met Asp Ala Asp  Glu Ser Ile Leu Ile  Ala Glu Asp
     1010                1015                1020 aca aag  tta gag aac ttg aga  ata tta acg gaa ctg  ttg att tcc        3114
Thr Lys  Leu Glu Asn Leu Arg  Ile Leu Thr Glu Leu  Leu Ile Ser
     1025                1030                1035 tat tcg  aaa gat aca aag aat  att ttc aaa agg ttt  ccc aat ctt        3159
Tyr Ser  Lys Asp Thr Lys Asn  Ile Phe Lys Arg Phe  Pro Asn Leu
     1040                1045                1050 cag ttg  ctt tca ttt gaa ctc  aag gag tca tgg gat  tat tca aca        3204
Gln Leu  Leu Ser Phe Glu Leu  Lys Glu Ser Trp Asp  Tyr Ser Thr
     1055                1060                1065 gag caa  cat tgg ttc tcg gaa  ttg gat ttc cta act  gaa cta gaa        3249
Glu Gln  His Trp Phe Ser Glu  Leu Asp Phe Leu Thr  Glu Leu Glu
     1070                1075                1080 aca ctc  tct gta ggt ttt aaa  agt tca aac aca aac  gat agt ggg        3294
Thr Leu  Ser Val Gly Phe Lys  Ser Ser Asn Thr Asn  Asp Ser Gly
     1085                1090                1095 tcc tct  gta gcg aca aat cgg  ccg tgg gat ttt cac  ttc cct tca        3339
Ser Ser  Val Ala Thr Asn Arg  Pro Trp Asp Phe His  Phe Pro Ser
     1100                1105                1110 aat ttg  aaa ata ctg tgg ttg  cgt gaa ttt ccg ctg  aca tcc gat        3384
```

```
Asn Leu Lys Ile Leu Trp Leu Arg Glu Phe Pro Leu Thr Ser Asp
    1115                1120                1125 tca cta tca aca ata gcg aga ctg ccc aac ctt gaa gag ttg tcc          3429
Ser Leu Ser Thr Ile Ala Arg Leu Pro Asn Leu Glu Glu Leu Ser
    1130                1135                1140 ctt tat cat aca atc atc cat gga gaa gaa tgg aac atg ggg gag          3474
Leu Tyr His Thr Ile Ile His Gly Glu Glu Trp Asn Met Gly Glu
    1145                1150                1155 gaa gac acc ttt gag aat ctc aaa ttt ttg aac ttc aat caa gtt          3519
Glu Asp Thr Phe Glu Asn Leu Lys Phe Leu Asn Phe Asn Gln Val
    1160                1165                1170 agt att tcc aag tgg gag gtt gga gag gaa tcc ttc ccc aat ctt          3564
Ser Ile Ser Lys Trp Glu Val Gly Glu Glu Ser Phe Pro Asn Leu
    1175                1180                1185 gag aaa tta aaa ctg cgg gga tgt cat aag cta gag gag att cca          3609
Glu Lys Leu Lys Leu Arg Gly Cys His Lys Leu Glu Glu Ile Pro
    1190                1195                1200 cct agt ttt gga gat att tat tca ttg aaa tct atc aaa att gta          3654
Pro Ser Phe Gly Asp Ile Tyr Ser Leu Lys Ser Ile Lys Ile Val
    1205                1210                1215 aag agt cct caa ctt gaa gat tct gct ctc aaa att aag gaa tac          3699
Lys Ser Pro Gln Leu Glu Asp Ser Ala Leu Lys Ile Lys Glu Tyr
    1220                1225                1230 gct gaa gat atg agg gga ggg gac gag ctt cag atc ctt ggc caa          3744
Ala Glu Asp Met Arg Gly Gly Asp Glu Leu Gln Ile Leu Gly Gln
    1235                1240                1245 aag aat atc ccc tta ttt aag tag                                      3768
Lys Asn Ile Pro Leu Phe Lys
    1250                1255

<210> SEQ ID NO 8
<211> LENGTH: 1255
<212> TYPE: PRT
<213> ORGANISM: Lycopersicon lycopersicum
<220> FEATURE:
<221> NAME/KEY: misc_feature
<222> LOCATION: (178)..(178)
<223> OTHER INFORMATION: The 'Xaa' at location 178 stands for Leu.

<400> SEQUENCE: 8

Met Glu Lys Arg Lys Asp Asn Glu Ala Asn Asn Ser Leu Val Leu
1               5                   10                  15

Phe Ser Ala Leu Ser Lys Asp Ile Ala Asp Val Leu Phe Leu Glu
                20                  25                  30

Asn Glu Glu Asn Gln Lys Ala Leu Asp Lys Asp Gln Val Glu Lys Ile
        35                  40                  45

Lys Leu Lys Met Ala Phe Ile Cys Thr Tyr Val Gln Leu Ser Cys Ser
50                  55                  60

Asp Phe Glu Gln Phe Glu Asp Ile Met Thr Arg Lys Arg Gln Glu Val
65                  70                  75                  80

Glu Asn Leu Leu Gln Pro Leu Leu Asp Asp Val Phe Thr Ser Leu
                85                  90                  95

Thr Ser Asn Met Asp Asp Cys Ile Ser Leu Tyr His Arg Ser Tyr Lys
            100                 105                 110

Ser Asp Ala Ile Met Met Asp Glu Gln Leu Asp Phe Leu Leu Asn
        115                 120                 125

Leu Tyr His Leu Ser Lys His His Ala Glu Lys Ile Phe Pro Gly Val
    130                 135                 140

Thr Gln Tyr Glu Val Leu Gln Asn Ile Cys Gly Asn Ile Arg Asp Phe
```

```
            145                 150                 155                 160
        His Gly Leu Ile Val Asn Gly Cys Ile Lys His Glu Met Val Glu Asn
                        165                 170                 175
        Val Xaa Pro Leu Phe Gln Leu Met Ala Asp Arg Val Gly His Phe Leu
                        180                 185                 190
        Trp Asp Asp Gln Thr Asp Glu Asp Ser Arg Leu Ser Glu Leu Asp Glu
                        195                 200                 205
        Asp Glu Gln Asn Asp Arg Asp Ser Arg Leu Phe Lys Leu Ala His Leu
                        210                 215                 220
        Leu Leu Lys Ile Val Pro Val Glu Leu Glu Val Ile His Ile Cys Tyr
        225                 230                 235                 240
        Thr Asn Leu Lys Ala Ser Thr Ser Ala Glu Val Gly Leu Phe Ile Lys
                        245                 250                 255
        Gln Leu Glu Thr Ser Pro Asp Ile Leu Arg Glu Tyr Leu Ile Pro
                        260                 265                 270
        Leu Gln Glu His Met Val Thr Val Ile Thr Pro Ser Thr Ser Gly Ala
                        275                 280                 285
        Arg Asn Ile His Val Met Met Glu Phe Leu Leu Leu Ile Leu Ser Asp
                        290                 295                 300
        Met Pro Lys Asp Phe Ile His His Asp Lys Leu Phe Asp Leu Leu Asp
        305                 310                 315                 320
        Arg Val Gly Val Leu Thr Arg Glu Val Ser Thr Leu Val Arg Asp Leu
                        325                 330                 335
        Glu Glu Glu Pro Arg Asn Lys Gly Asn Asn Gln Thr Asn Cys Ala
                        340                 345                 350
        Thr Leu Asp Leu Leu Glu Asn Ile Glu Leu Leu Lys Lys Asp Leu Lys
                        355                 360                 365
        His Val Tyr Leu Lys Ala Leu Asp Ser Ser Gln Cys Cys Phe Pro Met
                        370                 375                 380
        Ser Asp Gly Pro Leu Phe Met His Leu Leu His Ile His Leu Asn Asp
        385                 390                 395                 400
        Leu Leu Asp Ser Asn Ala Tyr Ser Ile Ala Leu Ile Lys Glu Glu Ile
                        405                 410                 415
        Glu Leu Val Lys Gln Asp Leu Lys Phe Ile Arg Ser Phe Phe Val Asp
                        420                 425                 430
        Ala Glu Gln Gly Leu Tyr Lys Asp Leu Trp Ala Arg Val Leu Asp Val
                        435                 440                 445
        Ala Tyr Glu Ala Lys Asp Val Ile Asp Ser Ile Val Arg Asp Asn
                        450                 455                 460
        Gly Leu Leu His Leu Ile Phe Ser Leu Pro Ile Thr Ile Lys Lys Ile
        465                 470                 475                 480
        Lys Leu Ile Lys Glu Glu Ile Ser Ala Leu Asp Glu Asn Ile Pro Lys
                        485                 490                 495
        Asp Arg Gly Leu Ile Val Val Asn Ser Pro Lys Pro Val Glu Arg
                        500                 505                 510
        Lys Ser Leu Thr Thr Asp Lys Ile Thr Val Gly Phe Glu Glu Thr
                        515                 520                 525
        Asn Leu Ile Leu Arg Lys Leu Thr Ser Gly Ser Ala Asp Leu Asp Val
                        530                 535                 540
        Ile Ser Ile Thr Gly Met Pro Gly Ser Gly Lys Thr Thr Leu Ala Tyr
        545                 550                 555                 560
        Lys Val Tyr Asn Asp Lys Ser Val Ser Ser Arg Phe Asp Leu Arg Ala
                        565                 570                 575
```

-continued

```
Trp Cys Thr Val Asp Gln Gly Cys Asp Glu Lys Lys Leu Leu Asn Thr
        580                 585                 590

Ile Phe Ser Gln Val Ser Asp Ser Asp Ser Lys Leu Ser Glu Asn Ile
        595                 600                 605

Asp Val Ala Asp Lys Leu Arg Lys Gln Leu Phe Gly Lys Arg Tyr Leu
        610                 615                 620

Ile Val Leu Asp Asp Val Trp Asp Thr Thr Thr Trp Asp Glu Leu Thr
625                 630                 635                 640

Arg Pro Phe Pro Glu Ser Lys Lys Gly Ser Arg Ile Ile Leu Thr Thr
                645                 650                 655

Arg Glu Lys Glu Val Ala Leu His Gly Lys Leu Asn Thr Asp Pro Leu
                660                 665                 670

Asp Leu Arg Leu Leu Arg Pro Asp Glu Ser Trp Glu Leu Leu Glu Lys
                675                 680                 685

Arg Ala Phe Gly Asn Glu Ser Cys Pro Asp Glu Leu Leu Asp Val Gly
                690                 695                 700

Lys Glu Ile Ala Glu Asn Cys Lys Gly Leu Pro Leu Val Ala Asp Leu
705                 710                 715                 720

Ile Ala Gly Val Ile Ala Gly Arg Glu Lys Lys Arg Ser Val Trp Leu
                725                 730                 735

Glu Val Gln Ser Ser Leu Ser Ser Phe Ile Leu Asn Ser Glu Val Glu
                740                 745                 750

Val Met Lys Val Ile Glu Leu Ser Tyr Asp His Leu Pro His His Leu
                755                 760                 765

Lys Pro Cys Leu Leu Tyr Phe Ala Ser Phe Pro Lys Asp Thr Ser Leu
                770                 775                 780

Thr Ile Tyr Glu Leu Asn Val Tyr Phe Gly Ala Glu Gly Phe Val Gly
785                 790                 795                 800

Lys Thr Glu Met Asn Ser Met Glu Glu Val Val Lys Ile Tyr Met Asp
                805                 810                 815

Asp Leu Ile Tyr Ser Ser Leu Val Ile Cys Phe Asn Glu Ile Gly Tyr
                820                 825                 830

Ala Leu Asn Phe Gln Ile His Asp Leu Val His Asp Phe Cys Leu Ile
                835                 840                 845

Lys Ala Arg Lys Glu Asn Leu Phe Asp Gln Ile Arg Ser Ser Ala Pro
                850                 855                 860

Ser Asp Leu Leu Pro Arg Gln Ile Thr Ile Asp Cys Asp Glu Glu Glu
865                 870                 875                 880

His Phe Gly Leu Asn Phe Val Met Phe Asp Ser Asn Lys Lys Arg His
                885                 890                 895

Ser Gly Lys His Leu Tyr Ser Leu Arg Ile Ile Gly Asp Gln Leu Asp
                900                 905                 910

Asp Ser Val Ser Asp Ala Phe His Leu Arg His Leu Arg Leu Leu Arg
                915                 920                 925

Val Leu Asp Leu His Thr Ser Phe Ile Met Val Lys Asp Ser Leu Leu
                930                 935                 940

Asn Glu Ile Cys Met Leu Asn His Leu Arg Tyr Leu Ser Ile Asp Thr
945                 950                 955                 960

Gln Val Lys Tyr Leu Pro Leu Ser Phe Ser Asn Leu Trp Asn Leu Glu
                965                 970                 975

Ser Leu Phe Val Ser Thr Asn Arg Ser Ile Leu Val Leu Leu Pro Arg
                980                 985                 990
```

-continued

```
Ile Leu Asp Leu Val Lys Leu Arg   Val Leu Ser Val Asp   Ala Cys Ser
        995                1000                  1005

Phe Phe Asp Met Asp Ala Asp   Glu Ser Ile Leu Ile   Ala Glu Asp
       1010                1015                 1020

Thr Lys Leu Glu Asn Leu Arg   Ile Leu Thr Glu Leu   Leu Ile Ser
       1025                1030                 1035

Tyr Ser Lys Asp Thr Lys Asn   Ile Phe Lys Arg Phe   Pro Asn Leu
       1040                1045                 1050

Gln Leu Leu Ser Phe Glu Leu   Lys Glu Ser Trp Asp   Tyr Ser Thr
       1055                1060                 1065

Glu Gln His Trp Phe Ser Glu   Leu Asp Phe Leu Thr   Glu Leu Glu
       1070                1075                 1080

Thr Leu Ser Val Gly Phe Lys   Ser Ser Asn Thr Asn   Asp Ser Gly
       1085                1090                 1095

Ser Ser Val Ala Thr Asn Arg   Pro Trp Asp Phe His   Phe Pro Ser
       1100                1105                 1110

Asn Leu Lys Ile Leu Trp Leu   Arg Glu Phe Pro Leu   Thr Ser Asp
       1115                1120                 1125

Ser Leu Ser Thr Ile Ala Arg   Leu Pro Asn Leu Glu   Glu Leu Ser
       1130                1135                 1140

Leu Tyr His Thr Ile Ile His   Gly Glu Glu Trp Asn   Met Gly Glu
       1145                1150                 1155

Glu Asp Thr Phe Glu Asn Leu   Lys Phe Leu Asn Phe   Asn Gln Val
       1160                1165                 1170

Ser Ile Ser Lys Trp Glu Val   Gly Glu Glu Ser Phe   Pro Asn Leu
       1175                1180                 1185

Glu Lys Leu Lys Leu Arg Gly   Cys His Lys Leu Glu   Glu Ile Pro
       1190                1195                 1200

Pro Ser Phe Gly Asp Ile Tyr   Ser Leu Lys Ser Ile   Lys Ile Val
       1205                1210                 1215

Lys Ser Pro Gln Leu Glu Asp   Ser Ala Leu Lys Ile   Lys Glu Tyr
       1220                1225                 1230

Ala Glu Asp Met Arg Gly Gly   Asp Glu Leu Gln Ile   Leu Gly Gln
       1235                1240                 1245

Lys Asn Ile Pro Leu Phe Lys
       1250                1255

<210> SEQ ID NO 9
<211> LENGTH: 3774
<212> TYPE: DNA
<213> ORGANISM: Lycopersicon lycopersicum
<220> FEATURE:
<221> NAME/KEY: CDS
<222> LOCATION: (1)..(3774)
<223> OTHER INFORMATION: Mi1.2 from tomato

<400> SEQUENCE: 9 atg gaa aaa cga aaa gat att gaa gaa gca aac aac tca ttg gtg tta      48
Met Glu Lys Arg Lys Asp Ile Glu Glu Ala Asn Asn Ser Leu Val Leu
1               5                  10                  15 ttt tct gct ctt agc aag gac att gcc aat gtt cta att ttc cta gag      96
Phe Ser Ala Leu Ser Lys Asp Ile Ala Asn Val Leu Ile Phe Leu Glu
            20                  25                  30 aat gag gaa aat caa aaa gct ctt gac aaa gat caa gtt gaa aag cta     144
Asn Glu Glu Asn Gln Lys Ala Leu Asp Lys Asp Gln Val Glu Lys Leu
        35                  40                  45 aaa ttg aaa atg gca ttt att tgt aca tat gtt cag ctt tct tat tcc     192
```

```
                Lys Leu Lys Met Ala Phe Ile Cys Thr Tyr Val Gln Leu Ser Tyr Ser
                 50                  55                  60 gat ttt gag cag ttt gaa gat ata atg act aga aat aga caa gag gtt          240
Asp Phe Glu Gln Phe Glu Asp Ile Met Thr Arg Asn Arg Gln Glu Val
 65              70                  75                  80 gag aat ctg ctt caa tca ctt ttg gat gat gat gtc ctt act agc ctc          288
Glu Asn Leu Leu Gln Ser Leu Leu Asp Asp Asp Val Leu Thr Ser Leu
                     85                  90                  95 acc agt aat atg gat gac tgt atc agc ttg tat cat cgt tct tat aaa          336
Thr Ser Asn Met Asp Asp Cys Ile Ser Leu Tyr His Arg Ser Tyr Lys
                 100                 105                 110 tca gat gcc atc atg atg gat gag caa ttg gac ttc ctc ctc ttg aat          384
Ser Asp Ala Ile Met Met Asp Glu Gln Leu Asp Phe Leu Leu Leu Asn
             115                 120                 125 ctg tat cat cta tcc aag cat cac gct gaa aag ata ttt cct gga gtg          432
Leu Tyr His Leu Ser Lys His His Ala Glu Lys Ile Phe Pro Gly Val
         130                 135                 140 act caa tat gaa gtt ctt cag aat gta tgt ggc aac ata aga gat ttc          480
Thr Gln Tyr Glu Val Leu Gln Asn Val Cys Gly Asn Ile Arg Asp Phe
145                 150                 155                 160 cat ggg ttg ata ctg aat ggt tgc att aag cat gag atg gtt gag aat          528
His Gly Leu Ile Leu Asn Gly Cys Ile Lys His Glu Met Val Glu Asn
                 165                 170                 175 gtc tta cct ctg ttt caa ctc atg gct gaa aga gta gga cac ttc ctt          576
Val Leu Pro Leu Phe Gln Leu Met Ala Glu Arg Val Gly His Phe Leu
             180                 185                 190 tgg gag gat cag act gat gaa gac tct cgg ctc tcc gag cta gat gag          624
Trp Glu Asp Gln Thr Asp Glu Asp Ser Arg Leu Ser Glu Leu Asp Glu
         195                 200                 205 gat gaa cac aat gat aga gac tct cga ctc ttc cag cta aca cat cta          672
Asp Glu His Asn Asp Arg Asp Ser Arg Leu Phe Gln Leu Thr His Leu
210                 215                 220 ctc ttg aag att gtt cca act gaa ctg gag gtt atg cac ata tgt tat          720
Leu Leu Lys Ile Val Pro Thr Glu Leu Glu Val Met His Ile Cys Tyr
225                 230                 235                 240 aca aat ttg aaa gct tca act tca gca gaa gtt gga cgc ttc att aag          768
Thr Asn Leu Lys Ala Ser Thr Ser Ala Glu Val Gly Arg Phe Ile Lys
                 245                 250                 255 aag ctc ctg gaa acc tca ccg gat att ctc aga gaa tat atc att caa          816
Lys Leu Leu Glu Thr Ser Pro Asp Ile Leu Arg Glu Tyr Ile Ile Gln
             260                 265                 270 cta caa gag cat atg tta act gtt att ccc cct agc act tta ggg gct          864
Leu Gln Glu His Met Leu Thr Val Ile Pro Pro Ser Thr Leu Gly Ala
         275                 280                 285 cga aac att cat gtc atg atg gaa ttc cta tta ctt att ctt tct gat          912
Arg Asn Ile His Val Met Met Glu Phe Leu Leu Leu Ile Leu Ser Asp
290                 295                 300 atg ccc aag gac ttt att cat cat gac aaa ctt ttt gat ctc ttg gct          960
Met Pro Lys Asp Phe Ile His His Asp Lys Leu Phe Asp Leu Leu Ala
305                 310                 315                 320 cat gtt gga aca ctt acc agg gag gta tcg act ctt gta cgt gac ttg         1008
His Val Gly Thr Leu Thr Arg Glu Val Ser Thr Leu Val Arg Asp Leu
                 325                 330                 335 gaa gag aaa tta agg aat aaa gag ggt aat aac caa aca aat tgt gca         1056
Glu Glu Lys Leu Arg Asn Lys Glu Gly Asn Asn Gln Thr Asn Cys Ala
             340                 345                 350 acc cta gac ttg ctg gaa aat att gaa ctc ctc aag aaa gat ctc aaa         1104
Thr Leu Asp Leu Leu Glu Asn Ile Glu Leu Leu Lys Lys Asp Leu Lys
         355                 360                 365
```

```
cat gtt tat ctg aaa gcc cca aat tca tct caa tgt tgc ttc ccc atg    1152
His Val Tyr Leu Lys Ala Pro Asn Ser Ser Gln Cys Cys Phe Pro Met
    370             375                 380 agt gat gga cca ctc ttc atg cat ctt cta cac atg cac tta aat gat    1200
Ser Asp Gly Pro Leu Phe Met His Leu Leu His Met His Leu Asn Asp
385             390                 395                 400 ttg cta gat tct aat gct tat tca att tct ttg ata aag gaa gaa atc    1248
Leu Leu Asp Ser Asn Ala Tyr Ser Ile Ser Leu Ile Lys Glu Glu Ile
                405                 410                 415 gag ttg gtg agt caa gaa ctg gaa ttc ata aga tca ttc ttt ggg gat    1296
Glu Leu Val Ser Gln Glu Leu Glu Phe Ile Arg Ser Phe Phe Gly Asp
            420                 425                 430 gct gct gag caa gga ttg tat aaa gat atc tgg gca cgt gtt cta gat    1344
Ala Ala Glu Gln Gly Leu Tyr Lys Asp Ile Trp Ala Arg Val Leu Asp
        435                 440                 445 gtg gct tat gag gca aaa gat gtc ata gat tca att att gtt cga gat    1392
Val Ala Tyr Glu Ala Lys Asp Val Ile Asp Ser Ile Ile Val Arg Asp
450                 455                 460 aat ggt ctc tta cat ctt att ttc tca ctt ccc att acc ata aag aag    1440
Asn Gly Leu Leu His Leu Ile Phe Ser Leu Pro Ile Thr Ile Lys Lys
465                 470                 475                 480 atc aaa ctt atc aaa gaa gag atc tct gct tta gat gag aac att ccc    1488
Ile Lys Leu Ile Lys Glu Glu Ile Ser Ala Leu Asp Glu Asn Ile Pro
                485                 490                 495 aag gac aga ggt cta atc gtt gtg aac tct ccc aag aaa cca gtt gag    1536
Lys Asp Arg Gly Leu Ile Val Val Asn Ser Pro Lys Lys Pro Val Glu
            500                 505                 510 aga aag tca ttg aca act gat aaa ata att gta ggt ttt gag gag gag    1584
Arg Lys Ser Leu Thr Thr Asp Lys Ile Ile Val Gly Phe Glu Glu Glu
        515                 520                 525 aca aac ttg ata ctt aga aag ctc acc agt gga ccc gca gat tta gat    1632
Thr Asn Leu Ile Leu Arg Lys Leu Thr Ser Gly Pro Ala Asp Leu Asp
530                 535                 540 gtc att tcg atc acc ggt atg ccg ggt tca ggt aaa act act ttg gca    1680
Val Ile Ser Ile Thr Gly Met Pro Gly Ser Gly Lys Thr Thr Leu Ala
545                 550                 555                 560 tac aaa gta tac aat gat aag tca gtt tct aga cat ttt gac ctt cgt    1728
Tyr Lys Val Tyr Asn Asp Lys Ser Val Ser Arg His Phe Asp Leu Arg
                565                 570                 575 gca tgg tgc acg gtc gat caa gga tat gac gac aag aag ttg ttg gat    1776
Ala Trp Cys Thr Val Asp Gln Gly Tyr Asp Asp Lys Lys Leu Leu Asp
            580                 585                 590 aca att ttc agt caa gtt agt ggc tca gat tca aat ttg agt gag aat    1824
Thr Ile Phe Ser Gln Val Ser Gly Ser Asp Ser Asn Leu Ser Glu Asn
        595                 600                 605 att gat gtt gct gat aaa ttg cgg aaa caa ctg ttt gga aag agg tat    1872
Ile Asp Val Ala Asp Lys Leu Arg Lys Gln Leu Phe Gly Lys Arg Tyr
610                 615                 620 ctt att gtc tta gat gat gtg tgg gat act act aca ttg gat gag ttg    1920
Leu Ile Val Leu Asp Asp Val Trp Asp Thr Thr Thr Leu Asp Glu Leu
625                 630                 635                 640 aca aga cct ttt cct gaa gct aag aaa gga agt agg att att ttg aca    1968
Thr Arg Pro Phe Pro Glu Ala Lys Lys Gly Ser Arg Ile Ile Leu Thr
                645                 650                 655 act cga gaa aag gaa gtg gct ttg cat gga aag ctg aac act gat cct    2016
Thr Arg Glu Lys Glu Val Ala Leu His Gly Lys Leu Asn Thr Asp Pro
            660                 665                 670 ctt gac ctt cga ttg cta aga cca gat gaa agt tgg gaa ctt tta gat    2064
Leu Asp Leu Arg Leu Leu Arg Pro Asp Glu Ser Trp Glu Leu Leu Asp
        675                 680                 685
```

```
aaa agg aca ttt ggt aat gag agt tgc cct gat gaa cta tta gat gtc      2112
Lys Arg Thr Phe Gly Asn Glu Ser Cys Pro Asp Glu Leu Leu Asp Val
690                 695                 700 ggt aaa gaa ata gcc gaa aat tgt aaa ggg ctt cct ttg gtg gct gat      2160
Gly Lys Glu Ile Ala Glu Asn Cys Lys Gly Leu Pro Leu Val Ala Asp
705                 710                 715                 720 ctg att gct gga gtc att gct ggg agg gaa aag aaa agg agt gtg tgg      2208
Leu Ile Ala Gly Val Ile Ala Gly Arg Glu Lys Lys Arg Ser Val Trp
                725                 730                 735 ctt gaa gtt caa agt agt ttg agt tct ttt att ttg aac agt gaa gtg      2256
Leu Glu Val Gln Ser Ser Leu Ser Ser Phe Ile Leu Asn Ser Glu Val
            740                 745                 750 gaa gtg atg aaa gtt ata gaa tta agt tat gac cat tta cca cat cac      2304
Glu Val Met Lys Val Ile Glu Leu Ser Tyr Asp His Leu Pro His His
            755                 760                 765 ctc aag cca tgc ttg ctt cac ttt gca agt tgg ccg aag gac act cct      2352
Leu Lys Pro Cys Leu Leu His Phe Ala Ser Trp Pro Lys Asp Thr Pro
770                 775                 780 ttg aca atc tat ttg ttt act gtt tat ttg ggt gct gaa gga ttt gtg      2400
Leu Thr Ile Tyr Leu Phe Thr Val Tyr Leu Gly Ala Glu Gly Phe Val
785                 790                 795                 800 gaa aag acg gag atg aag ggt ata gaa gaa gtg gtg aag att tat atg      2448
Glu Lys Thr Glu Met Lys Gly Ile Glu Glu Val Val Lys Ile Tyr Met
                805                 810                 815 gat gat tta att tcc agt agc ttg gta att tgt ttc aat gag ata ggt      2496
Asp Asp Leu Ile Ser Ser Ser Leu Val Ile Cys Phe Asn Glu Ile Gly
            820                 825                 830 gat ata ctg aat ttc caa att cat gat ctt gtg cat gac ttt tgt ttg      2544
Asp Ile Leu Asn Phe Gln Ile His Asp Leu Val His Asp Phe Cys Leu
            835                 840                 845 ata aaa gca aga aag gaa aat ttg ttt gat cgg ata aga tca agt gct      2592
Ile Lys Ala Arg Lys Glu Asn Leu Phe Asp Arg Ile Arg Ser Ser Ala
850                 855                 860 cca tca gat ttg ttg cct cgt caa att acc att gat tat gat gag gag      2640
Pro Ser Asp Leu Leu Pro Arg Gln Ile Thr Ile Asp Tyr Asp Glu Glu
865                 870                 875                 880 gag gag cac ttt ggg ctt aat ttt gtc atg ttc gat tca aat aag aaa      2688
Glu Glu His Phe Gly Leu Asn Phe Val Met Phe Asp Ser Asn Lys Lys
                885                 890                 895 agg cat tct ggt aaa cac ctc tat tct ttg agg ata aat gga gac cag      2736
Arg His Ser Gly Lys His Leu Tyr Ser Leu Arg Ile Asn Gly Asp Gln
            900                 905                 910 ctg gat gac agt gtt tct gat gca ttt cac cta aga cac ttg agg ctt      2784
Leu Asp Asp Ser Val Ser Asp Ala Phe His Leu Arg His Leu Arg Leu
            915                 920                 925 att aga gtg ttg gac ctg gaa ccc tct tta atc atg gtg aat gat tct      2832
Ile Arg Val Leu Asp Leu Glu Pro Ser Leu Ile Met Val Asn Asp Ser
930                 935                 940 ttg ctg aat gaa ata tgc atg ttg aat cat ttg agg tac tta aga att      2880
Leu Leu Asn Glu Ile Cys Met Leu Asn His Leu Arg Tyr Leu Arg Ile
945                 950                 955                 960 cgg aca caa gtt aaa tat ctg cct ttc tct ttc tca aac ctc tgg aat      2928
Arg Thr Gln Val Lys Tyr Leu Pro Phe Ser Phe Ser Asn Leu Trp Asn
                965                 970                 975 cta gaa agt ctg ttt gtg tct aac aaa gga tca atc ttg gta cta tta      2976
Leu Glu Ser Leu Phe Val Ser Asn Lys Gly Ser Ile Leu Val Leu Leu
            980                 985                 990 ccg aga att ttg gat ctt gta aag    ttg cga gtg ctg tcc    gtg ggt gct  3024
Pro Arg Ile Leu Asp Leu Val Lys    Leu Arg Val Leu Ser    Val Gly Ala
```

|  |  |  |  |  |  |  |  |  |  |  |  |  |  |  |
|---|---|---|---|---|---|---|---|---|---|---|---|---|---|---|
|  | 995 |  |  |  | 1000 |  |  |  |  | 1005 |  |  |  |  |

```
tgt tct ttc ttt gat atg gat gca gat gaa tca ata ttg ata gca      3069
Cys Ser Phe Phe Asp Met Asp Ala Asp Glu Ser Ile Leu Ile Ala
    1010                1015                    1020 aag gac aca aag tta gag aac ttg aga ata tta ggg gaa ctg ttg      3114
Lys Asp Thr Lys Leu Glu Asn Leu Arg Ile Leu Gly Glu Leu Leu
1025                    1030                    1035 att tcc tat tcg aaa gat aca atg aat att ttc aaa agg ttt ccc      3159
Ile Ser Tyr Ser Lys Asp Thr Met Asn Ile Phe Lys Arg Phe Pro
    1040                1045                    1050 aat ctt cag gtg ctt cag ttt gaa ctc aag gag tca tgg gat tat      3204
Asn Leu Gln Val Leu Gln Phe Glu Leu Lys Glu Ser Trp Asp Tyr
1055                    1060                    1065 tca aca gag caa cat tgg ttc ccg aaa ttg gat tgc cta act gaa      3249
Ser Thr Glu Gln His Trp Phe Pro Lys Leu Asp Cys Leu Thr Glu
    1070                1075                    1080 cta gaa aca ctc tgt gta ggt ttt aaa agt tca aac aca aac cac      3294
Leu Glu Thr Leu Cys Val Gly Phe Lys Ser Ser Asn Thr Asn His
1085                    1090                    1095 tgt ggg tcc tct gtt gtg aca aat cgg ccg tgg gat ttt cac ttc      3339
Cys Gly Ser Ser Val Val Thr Asn Arg Pro Trp Asp Phe His Phe
    1100                1105                    1110 cct tca aat ttg aaa gaa ctg ttg ttg tat gac ttt cct ctg aca      3384
Pro Ser Asn Leu Lys Glu Leu Leu Leu Tyr Asp Phe Pro Leu Thr
1115                    1120                    1125 tcc gat tca cta tca aca ata gcg aga ctg ccc aac ctt gaa aat      3429
Ser Asp Ser Leu Ser Thr Ile Ala Arg Leu Pro Asn Leu Glu Asn
    1130                1135                    1140 ttg tcc ctt tat gat aca atc atc cag gga gaa gaa tgg aac atg      3474
Leu Ser Leu Tyr Asp Thr Ile Ile Gln Gly Glu Glu Trp Asn Met
1145                    1150                    1155 ggg gag gaa gac act ttt gag aat ctc aaa ttt ttg aac ttg cgt      3519
Gly Glu Glu Asp Thr Phe Glu Asn Leu Lys Phe Leu Asn Leu Arg
    1160                1165                    1170 cta ctg act ctt tcc aag tgg gag gtt gga gag gaa tcc ttc ccc      3564
Leu Leu Thr Leu Ser Lys Trp Glu Val Gly Glu Glu Ser Phe Pro
1175                    1180                    1185 aat ctt gag aaa tta aaa ctg cag gaa tgt ggt aag ctt gag gag      3609
Asn Leu Glu Lys Leu Lys Leu Gln Glu Cys Gly Lys Leu Glu Glu
    1190                1195                    1200 att cca cct agt ttt gga gat att tat tca ttg aaa ttt atc aaa      3654
Ile Pro Pro Ser Phe Gly Asp Ile Tyr Ser Leu Lys Phe Ile Lys
1205                    1210                    1215 att gta aag agt cct caa ctt gaa gat tct gct ctc aag att aag      3699
Ile Val Lys Ser Pro Gln Leu Glu Asp Ser Ala Leu Lys Ile Lys
    1220                1225                    1230 aaa tac gct gaa gat atg aga gga ggg aac gat ctt cag atc ctt      3744
Lys Tyr Ala Glu Asp Met Arg Gly Gly Asn Asp Leu Gln Ile Leu
1235                    1240                    1245 ggc cag aag aat atc ccc tta ttt aag tag                          3774
Gly Gln Lys Asn Ile Pro Leu Phe Lys
    1250                1255
```

<210> SEQ ID NO 10
<211> LENGTH: 1257
<212> TYPE: PRT
<213> ORGANISM: Lycopersicon lycopersicum

<400> SEQUENCE: 10

Met Glu Lys Arg Lys Asp Ile Glu Glu Ala Asn Asn Ser Leu Val Leu

-continued

```
1               5                   10                  15

Phe Ser Ala Leu Ser Lys Asp Ile Ala Asn Val Leu Ile Phe Leu Glu
                20                  25                  30

Asn Glu Glu Asn Gln Lys Ala Leu Asp Lys Asp Gln Val Glu Lys Leu
                35                  40              45

Lys Leu Lys Met Ala Phe Ile Cys Thr Tyr Val Gln Leu Ser Tyr Ser
            50                  55              60

Asp Phe Glu Gln Phe Glu Asp Ile Met Thr Arg Asn Arg Gln Glu Val
65                      70                  75                  80

Glu Asn Leu Leu Gln Ser Leu Leu Asp Asp Val Leu Thr Ser Leu
                85                  90                  95

Thr Ser Asn Met Asp Asp Cys Ile Ser Leu Tyr His Arg Ser Tyr Lys
                100                 105                 110

Ser Asp Ala Ile Met Met Asp Glu Gln Leu Asp Phe Leu Leu Leu Asn
                115                 120                 125

Leu Tyr His Leu Ser Lys His His Ala Glu Lys Ile Phe Pro Gly Val
            130                 135                 140

Thr Gln Tyr Glu Val Leu Gln Asn Val Cys Gly Asn Ile Arg Asp Phe
145                 150                 155                 160

His Gly Leu Ile Leu Asn Gly Cys Ile Lys His Glu Met Val Glu Asn
                165                 170                 175

Val Leu Pro Leu Phe Gln Leu Met Ala Glu Arg Val Gly His Phe Leu
                180                 185                 190

Trp Glu Asp Gln Thr Asp Glu Asp Ser Arg Leu Ser Glu Leu Asp Glu
            195                 200                 205

Asp Glu His Asn Asp Arg Asp Ser Arg Leu Phe Gln Leu Thr His Leu
            210                 215                 220

Leu Leu Lys Ile Val Pro Thr Glu Leu Glu Val Met His Ile Cys Tyr
225                 230                 235                 240

Thr Asn Leu Lys Ala Ser Thr Ser Ala Glu Val Gly Arg Phe Ile Lys
                245                 250                 255

Lys Leu Leu Glu Thr Ser Pro Asp Ile Leu Arg Glu Tyr Ile Ile Gln
                260                 265                 270

Leu Gln Glu His Met Leu Thr Val Ile Pro Pro Ser Thr Leu Gly Ala
            275                 280                 285

Arg Asn Ile His Val Met Met Glu Phe Leu Leu Ile Leu Ser Asp
            290                 295                 300

Met Pro Lys Asp Phe Ile His His Asp Lys Leu Phe Asp Leu Leu Ala
305                 310                 315                 320

His Val Gly Thr Leu Thr Arg Glu Val Ser Thr Leu Val Arg Asp Leu
                325                 330                 335

Glu Glu Lys Leu Arg Asn Lys Glu Gly Asn Asn Gln Thr Asn Cys Ala
                340                 345                 350

Thr Leu Asp Leu Leu Glu Asn Ile Glu Leu Leu Lys Lys Asp Leu Lys
            355                 360                 365

His Val Tyr Leu Lys Ala Pro Asn Ser Ser Gln Cys Cys Phe Pro Met
            370                 375                 380

Ser Asp Gly Pro Leu Phe Met His Leu His Met His Leu Asn Asp
385                 390                 395                 400

Leu Leu Asp Ser Asn Ala Tyr Ser Ile Ser Leu Ile Lys Glu Glu Ile
                405                 410                 415

Glu Leu Val Ser Gln Glu Leu Glu Phe Ile Arg Ser Phe Phe Gly Asp
            420                 425                 430
```

```
Ala Ala Glu Gln Gly Leu Tyr Lys Asp Ile Trp Ala Arg Val Leu Asp
        435                 440                 445

Val Ala Tyr Glu Ala Lys Asp Val Ile Asp Ser Ile Ile Val Arg Asp
    450                 455                 460

Asn Gly Leu Leu His Leu Ile Phe Ser Leu Pro Ile Thr Ile Lys Lys
465                 470                 475                 480

Ile Lys Leu Ile Lys Glu Glu Ile Ser Ala Leu Asp Glu Asn Ile Pro
                485                 490                 495

Lys Asp Arg Gly Leu Ile Val Val Asn Ser Lys Lys Pro Val Glu
            500                 505                 510

Arg Lys Ser Leu Thr Thr Asp Lys Ile Ile Val Gly Phe Glu Glu Glu
        515                 520                 525

Thr Asn Leu Ile Leu Arg Lys Leu Thr Ser Gly Pro Ala Asp Leu Asp
        530                 535                 540

Val Ile Ser Ile Thr Gly Met Pro Gly Ser Gly Lys Thr Thr Leu Ala
545                 550                 555                 560

Tyr Lys Val Tyr Asn Asp Lys Ser Val Ser Arg His Phe Asp Leu Arg
                565                 570                 575

Ala Trp Cys Thr Val Asp Gln Gly Tyr Asp Asp Lys Lys Leu Leu Asp
            580                 585                 590

Thr Ile Phe Ser Gln Val Ser Gly Ser Asp Ser Asn Leu Ser Glu Asn
        595                 600                 605

Ile Asp Val Ala Asp Lys Leu Arg Lys Gln Leu Phe Gly Lys Arg Tyr
        610                 615                 620

Leu Ile Val Leu Asp Asp Val Trp Asp Thr Thr Thr Leu Asp Glu Leu
625                 630                 635                 640

Thr Arg Pro Phe Pro Glu Ala Lys Lys Gly Ser Arg Ile Ile Leu Thr
                645                 650                 655

Thr Arg Glu Lys Glu Val Ala Leu His Gly Lys Leu Asn Thr Asp Pro
            660                 665                 670

Leu Asp Leu Arg Leu Leu Arg Pro Asp Glu Ser Trp Glu Leu Leu Asp
        675                 680                 685

Lys Arg Thr Phe Gly Asn Glu Ser Cys Pro Asp Glu Leu Leu Asp Val
        690                 695                 700

Gly Lys Glu Ile Ala Glu Asn Cys Lys Gly Leu Pro Leu Val Ala Asp
705                 710                 715                 720

Leu Ile Ala Gly Val Ile Ala Gly Arg Glu Lys Lys Arg Ser Val Trp
                725                 730                 735

Leu Glu Val Gln Ser Ser Leu Ser Ser Phe Ile Leu Asn Ser Glu Val
            740                 745                 750

Glu Val Met Lys Val Ile Glu Leu Ser Tyr Asp His Leu Pro His His
        755                 760                 765

Leu Lys Pro Cys Leu Leu His Phe Ala Ser Trp Pro Lys Asp Thr Pro
        770                 775                 780

Leu Thr Ile Tyr Leu Phe Thr Val Tyr Leu Gly Ala Glu Gly Phe Val
785                 790                 795                 800

Glu Lys Thr Glu Met Lys Gly Ile Glu Glu Val Lys Ile Tyr Met
                805                 810                 815

Asp Asp Leu Ile Ser Ser Ser Leu Val Ile Cys Phe Asn Glu Ile Gly
            820                 825                 830

Asp Ile Leu Asn Phe Gln Ile His Asp Leu Val His Asp Phe Cys Leu
        835                 840                 845
```

```
Ile Lys Ala Arg Lys Glu Asn Leu Phe Asp Arg Ile Arg Ser Ser Ala
850                 855                 860

Pro Ser Asp Leu Leu Pro Arg Gln Ile Thr Ile Asp Tyr Asp Glu Glu
865                 870                 875                 880

Glu Glu His Phe Gly Leu Asn Phe Val Met Phe Asp Ser Asn Lys Lys
                885                 890                 895

Arg His Ser Gly Lys His Leu Tyr Ser Leu Arg Ile Asn Gly Asp Gln
                900                 905                 910

Leu Asp Asp Ser Val Ser Asp Ala Phe His Leu Arg His Leu Arg Leu
            915                 920                 925

Ile Arg Val Leu Asp Leu Glu Pro Ser Leu Ile Met Val Asn Asp Ser
930                 935                 940

Leu Leu Asn Glu Ile Cys Met Leu Asn His Leu Arg Tyr Leu Arg Ile
945                 950                 955                 960

Arg Thr Gln Val Lys Tyr Leu Pro Phe Ser Phe Ser Asn Leu Trp Asn
                965                 970                 975

Leu Glu Ser Leu Phe Val Ser Asn Lys Gly Ser Ile Leu Val Leu Leu
                980                 985                 990

Pro Arg Ile Leu Asp Leu Val Lys  Leu Arg Val Leu Ser  Val Gly Ala
            995                 1000                1005

Cys Ser  Phe Phe Asp Met Asp  Ala Asp Glu Ser  Ile Leu Ile Ala
1010                1015                1020

Lys Asp  Thr Lys Leu Glu Asn  Leu Arg Ile Leu Gly  Glu Leu Leu
1025                1030                1035

Ile Ser  Tyr Ser Lys Asp Thr  Met Asn Ile Phe Lys  Arg Phe Pro
1040                1045                1050

Asn Leu  Gln Val Leu Gln Phe  Glu Leu Lys Glu Ser  Trp Asp Tyr
1055                1060                1065

Ser Thr  Glu Gln His Trp Phe  Pro Lys Leu Asp Cys  Leu Thr Glu
1070                1075                1080

Leu Glu  Thr Leu Cys Val Gly  Phe Lys Ser Ser Asn  Thr Asn His
1085                1090                1095

Cys Gly  Ser Ser Val Val Thr  Asn Arg Pro Trp Asp  Phe His Phe
1100                1105                1110

Pro Ser  Asn Leu Lys Glu Leu  Leu Leu Tyr Asp Phe  Pro Leu Thr
1115                1120                1125

Ser Asp  Ser Leu Ser Thr Ile  Ala Arg Leu Pro Asn  Leu Glu Asn
1130                1135                1140

Leu Ser  Leu Tyr Asp Thr Ile  Ile Gln Gly Glu Glu  Trp Asn Met
1145                1150                1155

Gly Glu  Glu Asp Thr Phe Glu  Asn Leu Lys Phe Leu  Asn Leu Arg
1160                1165                1170

Leu Leu  Thr Leu Ser Lys Trp  Glu Val Gly Glu Glu  Ser Phe Pro
1175                1180                1185

Asn Leu  Glu Lys Leu Lys Leu  Gln Glu Cys Gly Lys  Leu Glu Glu
1190                1195                1200

Ile Pro  Pro Ser Phe Gly Asp  Ile Tyr Ser Leu Lys  Phe Ile Lys
1205                1210                1215

Ile Val  Lys Ser Pro Gln Leu  Glu Asp Ser Ala Leu  Lys Ile Lys
1220                1225                1230

Lys Tyr  Ala Glu Asp Met Arg  Gly Gly Asn Asp Leu  Gln Ile Leu
1235                1240                1245

Gly Gln  Lys Asn Ile Pro Leu  Phe Lys
```

```
      1250            1255
```

<210> SEQ ID NO 11
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: mapping marker

<400> SEQUENCE: 11
ttgtggttat cgatgagaat                                               20

<210> SEQ ID NO 12
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 12
gaaacaacag caggatagtg ag                                            22

<210> SEQ ID NO 13
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 13
ttgtggttat cgatgagaat                                               20

<210> SEQ ID NO 14
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 14
gaaacaacag caggatagtg ag                                            22

<210> SEQ ID NO 15
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 15
gaattcagca caaataccaa                                               20

<210> SEQ ID NO 16
<211> LENGTH: 20
<212> TYPE: DNA
<213> ORGANISM: Solanum bulbocastanum
<220> FEATURE:
<221> NAME/KEY: Misc_feature

```
<222> LOCATION: (1)..(20)
<223> OTHER INFORMATION: Mapping marker

<400> SEQUENCE: 16
ttaacgttta ctatcacgag                                                    20

<210> SEQ ID NO 17
<211> LENGTH: 23
<212> TYPE: DNA
<213> ORGANISM: Solanum bulbocastanum
<220> FEATURE:
<221> NAME/KEY: Misc_feature
<222> LOCATION: (1)..(23)
<223> OTHER INFORMATION: Mapping marker

<400> SEQUENCE: 17
gtagaaacag cagcctcata agc                                                23

<210> SEQ ID NO 18
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 18
ttctgcctaa ttgccctgtg                                                    20

<210> SEQ ID NO 19
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 19
ggggttggga agacaacgac ac                                                 22

<210> SEQ ID NO 20
<211> LENGTH: 23
<212> TYPE: DNA
<213> ORGANISM: Solanum bulbocastanum
<220> FEATURE:
<221> NAME/KEY: Misc_feature
<222> LOCATION: (1)..(23)
<223> OTHER INFORMATION: Mapping marker

<400> SEQUENCE: 20
aattccaaga tacagtcaaa tac                                                23

<210> SEQ ID NO 21
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 21
aggcaggatt aacagtagaa g                                                  21

<210> SEQ ID NO 22
```

```
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 22 catgcttta ggaagaagct c                                                21

<210> SEQ ID NO 23
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 23
ttgagacaaa gcagctccac                                                 20

<210> SEQ ID NO 24
<211> LENGTH: 20
<212> TYPE: DNA
<213> ORGANISM: Solanum bulbocastanum

<400> SEQUENCE: 24
acgtttctca cacctacagg                                                 20

<210> SEQ ID NO 25
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 25
tgatggcacg tttgatcgtg                                                 20

<210> SEQ ID NO 26
<211> LENGTH: 20
<212> TYPE: DNA
<213> ORGANISM: Solanum bulbocastanum

<400> SEQUENCE: 26
taagatccaa accagccacc                                                 20

<210> SEQ ID NO 27
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 27
ccttatcaca catgtggcta c                                               21

<210> SEQ ID NO 28
<211> LENGTH: 22
<212> TYPE: DNA
<213> ORGANISM: Solanum bulbocastanum
```

```
<220> FEATURE:
<221> NAME/KEY: Misc_feature
<222> LOCATION: (1)..(22)
<223> OTHER INFORMATION: Mapping marker

<400> SEQUENCE: 28
attgaaacgg aggaagtaca ac                                              22

<210> SEQ ID NO 29
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 29
ttcttcatat ggcagaccaa c                                               21

<210> SEQ ID NO 30
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 30
ctactctgct gacatgcagg                                                 20

<210> SEQ ID NO 31
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 31
gagattctca aggtgtctt cc                                               22

<210> SEQ ID NO 32
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 32
aacctgtgct ttcccattcg                                                 20

<210> SEQ ID NO 33
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 33
ctttcacaag cgtcactttg g                                               21
```

```
<210> SEQ ID NO 34
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 34
taaaaagaat caacagggca ac                                              22

<210> SEQ ID NO 35
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 35
acgactgctc aaagttggcc                                                 20

<210> SEQ ID NO 36
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 36
ccaagaagcc agttgagagc                                                 20

<210> SEQ ID NO 37
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 37
gtagattaca ctatggatat gg                                              22

<210> SEQ ID NO 38
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 38
cagttagcag caatgtcagc                                                 20

<210> SEQ ID NO 39
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker
```

```
<400> SEQUENCE: 39
cattcaacta ggccaaaagt gg                                              22

<210> SEQ ID NO 40
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 40
ccaggtaggt gttttcttcc                                                 20

<210> SEQ ID NO 41
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 41
gttctaagtc agatgccacc                                                 20

<210> SEQ ID NO 42
<211> LENGTH: 19
<212> TYPE: DNA
<213> ORGANISM: Solanum bulbocastanum
<220> FEATURE:
<221> NAME/KEY: Misc_feature
<222> LOCATION: (1)..(19)
<223> OTHER INFORMATION: Mapping marker

<400> SEQUENCE: 42
aagtgctcca acacgagcc                                                  19

<210> SEQ ID NO 43
<211> LENGTH: 19
<212> TYPE: DNA
<213> ORGANISM: Solanum bulbocastanum
<220> FEATURE:
<221> NAME/KEY: Misc_feature
<222> LOCATION: (1)..(19)
<223> OTHER INFORMATION: Mapping marker

<400> SEQUENCE: 43
tgagttctct taccctgcg                                                  19

<210> SEQ ID NO 44
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 44
ggatatccag catcaatgcc                                                 20

<210> SEQ ID NO 45
<211> LENGTH: 20
<212> TYPE: DNA
```

```
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 45
ggtgagcctc cttgcattcc                                                    20

<210> SEQ ID NO 46
<211> LENGTH: 19
<212> TYPE: DNA
<213> ORGANISM: Solanum bulbocastanum
<220> FEATURE:
<221> NAME/KEY: Misc_feature
<222> LOCATION: (1)..(19)
<223> OTHER INFORMATION: Mapping marker

<400> SEQUENCE: 46
cctgagggaa gatgtcacg                                                     19

<210> SEQ ID NO 47
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 47
cctagtttag agtgagtaga c                                                  21

<210> SEQ ID NO 48
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 48
gtgatatatt gctcaaggat cc                                                 22

<210> SEQ ID NO 49
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 49
gttgctggct gtcactgatc                                                    20

<210> SEQ ID NO 50
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 50
gtgatgtgca gggttcaagg                                                    20
```

<210> SEQ ID NO 51
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 51
gattagtgta gatcttagct tg                                        22

<210> SEQ ID NO 52
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 52
aaatctctct cacaattatc cc                                        22

<210> SEQ ID NO 53
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 53
ctattgactg aacctgctga g                                         21

<210> SEQ ID NO 54
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 54
tgaagtcatt tagtccacag c                                         21

<210> SEQ ID NO 55
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 55
agatcggagt gtgaacatgg                                           20

<210> SEQ ID NO 56
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)

<223> OTHER INFORMATION: Mapping marker

<400> SEQUENCE: 56
cttctacttc tagtcgactg c                                        21

<210> SEQ ID NO 57
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 57
cgtagtccat ctgaagctcc                                          20

<210> SEQ ID NO 58
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 58
tcttcttctg ctagtcgtcg                                          20

<210> SEQ ID NO 59
<211> LENGTH: 23
<212> TYPE: DNA
<213> ORGANISM: Solanum bulbocastanum
<220> FEATURE:
<221> NAME/KEY: Misc_feature
<222> LOCATION: (1)..(23)
<223> OTHER INFORMATION: Mapping marker

<400> SEQUENCE: 59
actattctca cgtaagggga cac                                      23

<210> SEQ ID NO 60
<211> LENGTH: 23
<212> TYPE: DNA
<213> ORGANISM: Solanum bulbocastanum
<220> FEATURE:
<221> NAME/KEY: Misc_feature
<222> LOCATION: (1)..(23)
<223> OTHER INFORMATION: Mapping marker

<400> SEQUENCE: 60
gtgtacatgt atgaaactct agc                                      23

<210> SEQ ID NO 61
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 61
gttcctttca atcagaaagt ag                                       22

<210> SEQ ID NO 62
<211> LENGTH: 21

```
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Mapping marker

<400> SEQUENCE: 62
ctttggatga gtcaaaaggc t                                              21

<210> SEQ ID NO 63
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 63
caagttacgg caaccaagag                                                20

<210> SEQ ID NO 64
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Mapping marker

<400> SEQUENCE: 64
ctttgacaca gtgttagaat gc                                             22

<210> SEQ ID NO 65
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 65
cgtgatctag gagttacgac                                                20

<210> SEQ ID NO 66
<211> LENGTH: 25
<212> TYPE: DNA
<213> ORGANISM: Solanum bulbocastanum
<220> FEATURE:
<221> NAME/KEY: Misc_feature
<222> LOCATION: (1)..(25)
<223> OTHER INFORMATION: Mapping marker

<400> SEQUENCE: 66
cttattttaa atacaagaca tctgg                                          25

<210> SEQ ID NO 67
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 67
```

-continued cagaggaaag tcaaccaacg                                               20

<210> SEQ ID NO 68
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Mapping marker

<400> SEQUENCE: 68
cagaggaaag tcaaccaacg                                               20

<210> SEQ ID NO 69
<211> LENGTH: 24
<212> TYPE: DNA
<213> ORGANISM: Solanum bulbocastanum
<220> FEATURE:
<221> NAME/KEY: Misc_feature
<222> LOCATION: (1)..(24)
<223> OTHER INFORMATION: Mapping marker

<400> SEQUENCE: 69
tcggctatga ctgggcacaa caga                                          24

<210> SEQ ID NO 70
<211> LENGTH: 24
<212> TYPE: DNA
<213> ORGANISM: Solanum bulbocastanum
<220> FEATURE:
<221> NAME/KEY: Misc_feature
<222> LOCATION: (1)..(24)
<223> OTHER INFORMATION: Mapping marker

<400> SEQUENCE: 70
aagaaggcga tagaaggcga tgcg                                          24

<210> SEQ ID NO 71
<211> LENGTH: 18
<212> TYPE: DNA
<213> ORGANISM: Solanum bulbocastanum
<220> FEATURE:
<221> NAME/KEY: Misc_feature
<222> LOCATION: (1)..(18)
<223> OTHER INFORMATION: Mapping marker

<400> SEQUENCE: 71
tgtaaaacga cggccagt                                                 18

<210> SEQ ID NO 72
<211> LENGTH: 19
<212> TYPE: DNA
<213> ORGANISM: Solanum bulbocastanum
<220> FEATURE:
<221> NAME/KEY: Misc_feature
<222> LOCATION: (1)..(19)
<223> OTHER INFORMATION: Mapping marker

<400> SEQUENCE: 72
ggaaacagct atgaccatg                                                19

<210> SEQ ID NO 73
<211> LENGTH: 18
<212> TYPE: DNA
<213> ORGANISM: Solanum bulbocastanum
<220> FEATURE:
<221> NAME/KEY: Misc_feature

```
<222> LOCATION: (1)..(18)
<223> OTHER INFORMATION: Primer

<400> SEQUENCE: 73
ttcagcacaa ataccaat                                                 18

<210> SEQ ID NO 74
<211> LENGTH: 18
<212> TYPE: DNA
<213> ORGANISM: Solanum bulbocastanum
<220> FEATURE:
<221> NAME/KEY: Misc_feature
<222> LOCATION: (1)..(18)
<223> OTHER INFORMATION: Primer

<400> SEQUENCE: 74
gatgttcccc ttctttta                                                 18

<210> SEQ ID NO 75
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Primer

<400> SEQUENCE: 75
ttgtggttat cgatgagaat                                               20

<210> SEQ ID NO 76
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Primer

<400> SEQUENCE: 76
acctggcgtt ccttattttt                                               20

<210> SEQ ID NO 77
<211> LENGTH: 15
<212> TYPE: DNA
<213> ORGANISM: Solanum bulbocastanum
<220> FEATURE:
<221> NAME/KEY: misc_feature
<222> LOCATION: (1)..(1)
<223> OTHER INFORMATION: N= A+T+G+C
<220> FEATURE:
<221> NAME/KEY: Misc_feature
<222> LOCATION: (1)..(15)
<223> OTHER INFORMATION: Primer
<220> FEATURE:
<221> NAME/KEY: misc_feature
<222> LOCATION: (7)..(7)
<223> OTHER INFORMATION: W=A+T
<220> FEATURE:
<221> NAME/KEY: misc_feature
<222> LOCATION: (6)..(6)
<223> OTHER INFORMATION: S=G+C
<220> FEATURE:
<221> NAME/KEY: misc_feature
<222> LOCATION: (10)..(10)
<223> OTHER INFORMATION: N=A+T+G+C
<220> FEATURE:
<221> NAME/KEY: misc_feature
<222> LOCATION: (12)..(12)
<223> OTHER INFORMATION: W=A+T
```

```
<400> SEQUENCE: 77
ngtcaswgan awgaa                                                    15

<210> SEQ ID NO 78
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Primer

<400> SEQUENCE: 78
gatggagcgg aaaagccggt g                                             21

<210> SEQ ID NO 79
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Primer

<400> SEQUENCE: 79
ggtgttttgt agcatctcca g                                             21

<210> SEQ ID NO 80
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Primer

<400> SEQUENCE: 80
ccatgattac gccaagctgg                                               20

<210> SEQ ID NO 81
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Primer

<400> SEQUENCE: 81
ggttttccca gtcacgacgt                                               20

<210> SEQ ID NO 82
<211> LENGTH: 20
<212> TYPE: DNA
<213> ORGANISM: Solanum bulbocastanum
<220> FEATURE:
<221> NAME/KEY: Misc_feature
<222> LOCATION: (1)..(20)
<223> OTHER INFORMATION: Primer

<400> SEQUENCE: 82
agaaagctca ccagtggacc                                               20

<210> SEQ ID NO 83
<211> LENGTH: 20
<212> TYPE: DNA
<213> ORGANISM: Solanum bulbocastanum
```

```
<220> FEATURE:
<221> NAME/KEY: Misc_feature
<222> LOCATION: (1)..(20)
<223> OTHER INFORMATION: Primer

<400> SEQUENCE: 83
atttatggct gcagaggacc                                               20

<210> SEQ ID NO 84
<211> LENGTH: 21
<212> TYPE: DNA
<213> ORGANISM: Solanum bulbocastanum

<400> SEQUENCE: 84
aagtccaatt gctcatccat c                                             21

<210> SEQ ID NO 85
<211> LENGTH: 19
<212> TYPE: DNA
<213> ORGANISM: Solanum bulbocastanum
<220> FEATURE:
<221> NAME/KEY: Misc_feature
<222> LOCATION: (1)..(19)
<223> OTHER INFORMATION: Primer

<400> SEQUENCE: 85
tgcaccatgc acgaaggtc                                                19

<210> SEQ ID NO 86
<211> LENGTH: 22
<212> TYPE: DNA
<213> ORGANISM: Solanum bulbocastanum
<220> FEATURE:
<221> NAME/KEY: Misc_feature
<222> LOCATION: (1)..(22)
<223> OTHER INFORMATION: Primer

<400> SEQUENCE: 86
caatwttggt tcccgaaatt gg                                            22

<210> SEQ ID NO 87
<211> LENGTH: 25
<212> TYPE: DNA
<213> ORGANISM: Solanum bulbocastanum
<220> FEATURE:
<221> NAME/KEY: Misc_feature
<222> LOCATION: (1)..(25)
<223> OTHER INFORMATION: Primer

<400> SEQUENCE: 87
atggaaaaac gaaaagataa tgaag                                         25

<210> SEQ ID NO 88
<211> LENGTH: 25
<212> TYPE: DNA
<213> ORGANISM: Solanum bulbocastanum
<220> FEATURE:
<221> NAME/KEY: Misc_feature
<222> LOCATION: (1)..(25)
<223> OTHER INFORMATION: Primer

<400> SEQUENCE: 88
ctacttaaat aacgggatat ccttc                                         25

<210> SEQ ID NO 89
<211> LENGTH: 20
<212> TYPE: DNA
```

<213> ORGANISM: Solanum bulbocastanum
<220> FEATURE:
<221> NAME/KEY: Misc_feature
<222> LOCATION: (1)..(20)
<223> OTHER INFORMATION: Primer

<400> SEQUENCE: 89
cccatgactc cttgagtttg                                               20

<210> SEQ ID NO 90
<211> LENGTH: 21
<212> TYPE: DNA
<213> ORGANISM: Solanum bulbocastanum
<220> FEATURE:
<221> NAME/KEY: Misc_feature
<222> LOCATION: (1)..(21)
<223> OTHER INFORMATION: Primer

<400> SEQUENCE: 90
ggtggggttg ggaagacaac g                                             21

<210> SEQ ID NO 91
<211> LENGTH: 19
<212> TYPE: DNA
<213> ORGANISM: Solanum bulbocastanum
<220> FEATURE:
<221> NAME/KEY: Misc_feature
<222> LOCATION: (1)..(19)
<223> OTHER INFORMATION: Primer

<400> SEQUENCE: 91
gtagactgcg taccaattc                                                19

<210> SEQ ID NO 92
<211> LENGTH: 16
<212> TYPE: DNA
<213> ORGANISM: Solanum bulbocastanum
<220> FEATURE:
<221> NAME/KEY: Misc_feature
<222> LOCATION: (1)..(16)
<223> OTHER INFORMATION: Primer

<400> SEQUENCE: 92
gatgagtcct gagtaa                                                   16

<210> SEQ ID NO 93
<211> LENGTH: 2913
<212> TYPE: DNA
<213> ORGANISM: Solanum bulbocastanum
<220> FEATURE:
<221> NAME/KEY: CDS
<222> LOCATION: (1)..(2913)
<223> OTHER INFORMATION: Rpi-blb or RB (Song, PNAS, 2003, 9128-9133)

<400> SEQUENCE: 93

```
atg gct gaa gct ttc att caa gtt ctg cta gac aat ctc act tct ttc      48
Met Ala Glu Ala Phe Ile Gln Val Leu Leu Asp Asn Leu Thr Ser Phe
1               5                   10                  15 ctc aaa ggg gaa ctt gta ttg ctt ttc ggt ttt caa gat gag ttc caa      96
Leu Lys Gly Glu Leu Val Leu Leu Phe Gly Phe Gln Asp Glu Phe Gln
            20                  25                  30 agg ctt tca agc atg ttt tct aca att caa gcc gtc ctt gaa gat gct     144
Arg Leu Ser Ser Met Phe Ser Thr Ile Gln Ala Val Leu Glu Asp Ala
        35                  40                  45 cag gag aag caa ctc aac aac aag cct cta gaa aat tgg ttg caa aaa     192
Gln Glu Lys Gln Leu Asn Asn Lys Pro Leu Glu Asn Trp Leu Gln Lys
    50                  55                  60
```

```
ctc aat gct gct aca tat gaa gtc gat gac atc ttg gat gaa tat aaa         240
Leu Asn Ala Ala Thr Tyr Glu Val Asp Asp Ile Leu Asp Glu Tyr Lys
 65              70                  75                  80 acc aag gcc aca aga ttc tcc cag tct gaa tat ggc cgt tat cat cca         288
Thr Lys Ala Thr Arg Phe Ser Gln Ser Glu Tyr Gly Arg Tyr His Pro
                 85                  90                  95 aag gtt atc cct ttc cgt cac aag gtc ggg aaa agg atg gac caa gtg         336
Lys Val Ile Pro Phe Arg His Lys Val Gly Lys Arg Met Asp Gln Val
                100                 105                 110 atg aaa aaa cta aag gca att gct gag gaa aga aag aat ttt cat ttg         384
Met Lys Lys Leu Lys Ala Ile Ala Glu Glu Arg Lys Asn Phe His Leu
                115                 120                 125 cac gaa aaa att gta gag aga caa gct gtt aga cgg gaa aca ggt tct         432
His Glu Lys Ile Val Glu Arg Gln Ala Val Arg Arg Glu Thr Gly Ser
130                 135                 140 gta tta acc gaa ccg cag gtt tat gga aga gac aaa gag aaa gat gag         480
Val Leu Thr Glu Pro Gln Val Tyr Gly Arg Asp Lys Glu Lys Asp Glu
145                 150                 155                 160 ata gtg aaa atc cta ata aac aat gtt agt gat gcc caa cac ctt tca         528
Ile Val Lys Ile Leu Ile Asn Asn Val Ser Asp Ala Gln His Leu Ser
                165                 170                 175 gtc ctc cca ata ctt ggt atg ggg gga tta gga aaa acg act ctt gcc         576
Val Leu Pro Ile Leu Gly Met Gly Gly Leu Gly Lys Thr Thr Leu Ala
                180                 185                 190 caa atg gtc ttc aat gac cag aga gtt act gag cat ttc cat tcc aaa         624
Gln Met Val Phe Asn Asp Gln Arg Val Thr Glu His Phe His Ser Lys
                195                 200                 205 ata tgg att tgt gtc tcg gaa gat ttt gat gag aag agg tta ata aag         672
Ile Trp Ile Cys Val Ser Glu Asp Phe Asp Glu Lys Arg Leu Ile Lys
210                 215                 220 gca att gta gaa tct att gaa gga agg cca cta ctt ggt gag atg gac         720
Ala Ile Val Glu Ser Ile Glu Gly Arg Pro Leu Leu Gly Glu Met Asp
225                 230                 235                 240 ttg gct cca ctt caa aag aag ctt cag gag ttg ctg aat gga aaa aga         768
Leu Ala Pro Leu Gln Lys Lys Leu Gln Glu Leu Leu Asn Gly Lys Arg
                245                 250                 255 tac ttg ctt gtc tta gat gat gtt tgg aat gaa gat caa cag aag tgg         816
Tyr Leu Leu Val Leu Asp Asp Val Trp Asn Glu Asp Gln Gln Lys Trp
                260                 265                 270 gct aat tta aga gca gtc ttg aag gtt gga gca agt ggt gct tct gtt         864
Ala Asn Leu Arg Ala Val Leu Lys Val Gly Ala Ser Gly Ala Ser Val
                275                 280                 285 cta acc act act cgt ctt gaa aag gtt gga tca att atg gga aca ttg         912
Leu Thr Thr Thr Arg Leu Glu Lys Val Gly Ser Ile Met Gly Thr Leu
290                 295                 300 caa cca tat gaa ctg tca aat ctg tct caa gaa gat tgt tgg ttg ttg         960
Gln Pro Tyr Glu Leu Ser Asn Leu Ser Gln Glu Asp Cys Trp Leu Leu
305                 310                 315                 320 ttc atg caa cgt gca ttt gga cac caa gaa gaa ata aat cca aac ctt        1008
Phe Met Gln Arg Ala Phe Gly His Gln Glu Glu Ile Asn Pro Asn Leu
                325                 330                 335 gtg gca atc gga aag gag att gtg aaa aaa agt ggt ggt gtg cct cta        1056
Val Ala Ile Gly Lys Glu Ile Val Lys Lys Ser Gly Gly Val Pro Leu
                340                 345                 350 gca gcc aaa act ctt gga ggt att ttg tgc ttc aag aga gaa gaa aga        1104
Ala Ala Lys Thr Leu Gly Gly Ile Leu Cys Phe Lys Arg Glu Glu Arg
                355                 360                 365 gca tgg gaa cat gtg aga gac agt ccg att tgg aat ttg cct caa gat        1152
Ala Trp Glu His Val Arg Asp Ser Pro Ile Trp Asn Leu Pro Gln Asp
```

-continued

```
        370                 375                 380
gaa agt tct att ctg cct gcc ctg agg ctt agt tac cat caa ctt cca   1200
Glu Ser Ser Ile Leu Pro Ala Leu Arg Leu Ser Tyr His Gln Leu Pro
385                 390                 395                 400 ctt gat ttg aaa caa tgc ttt gcg tat tgt gcg gtg ttc cca aag gat   1248
Leu Asp Leu Lys Gln Cys Phe Ala Tyr Cys Ala Val Phe Pro Lys Asp
                405                 410                 415 gcc aaa atg gaa aaa gaa aag cta atc tct ctc tgg atg gcg cat ggt   1296
Ala Lys Met Glu Lys Glu Lys Leu Ile Ser Leu Trp Met Ala His Gly
            420                 425                 430 ttt ctt tta tca aaa gga aac atg gag cta gag gat gtg ggc gat gaa   1344
Phe Leu Leu Ser Lys Gly Asn Met Glu Leu Glu Asp Val Gly Asp Glu
        435                 440                 445 gta tgg aaa gaa tta tac ttg agg tct ttt ttc caa gag att gaa gtt   1392
Val Trp Lys Glu Leu Tyr Leu Arg Ser Phe Phe Gln Glu Ile Glu Val
    450                 455                 460 aaa gat ggt aaa act tat ttc aag atg cat gat ctc atc cat gat ttg   1440
Lys Asp Gly Lys Thr Tyr Phe Lys Met His Asp Leu Ile His Asp Leu
465                 470                 475                 480 gca aca tct ctg ttt tca gca aac aca tca agc agc aat atc cgt gaa   1488
Ala Thr Ser Leu Phe Ser Ala Asn Thr Ser Ser Ser Asn Ile Arg Glu
                485                 490                 495 ata aat aaa cac agt tac aca cat atg atg tcc att ggt ttc gcc gaa   1536
Ile Asn Lys His Ser Tyr Thr His Met Met Ser Ile Gly Phe Ala Glu
            500                 505                 510 gtg gtg ttt ttt tac act ctt ccc ccc ttg gaa aag ttt atc tcg tta   1584
Val Val Phe Phe Tyr Thr Leu Pro Pro Leu Glu Lys Phe Ile Ser Leu
        515                 520                 525 aga gtg ctt aat cta ggt gat tcg aca ttt aat aag tta cca tct tcc   1632
Arg Val Leu Asn Leu Gly Asp Ser Thr Phe Asn Lys Leu Pro Ser Ser
    530                 535                 540 att gga gat cta gta cat tta aga tac ttg aac ctg tat ggc agt ggc   1680
Ile Gly Asp Leu Val His Leu Arg Tyr Leu Asn Leu Tyr Gly Ser Gly
545                 550                 555                 560 atg cgt agt ctt cca aag cag tta tgc aag ctt caa aat ctg caa act   1728
Met Arg Ser Leu Pro Lys Gln Leu Cys Lys Leu Gln Asn Leu Gln Thr
                565                 570                 575 ctt gat cta caa tat tgc acc aag ctt tgt tgt ttg cca aaa gaa aca   1776
Leu Asp Leu Gln Tyr Cys Thr Lys Leu Cys Cys Leu Pro Lys Glu Thr
            580                 585                 590 agt aaa ctt ggt agt ctc cga aat ctt tta ctt gat ggt agc cag tca   1824
Ser Lys Leu Gly Ser Leu Arg Asn Leu Leu Leu Asp Gly Ser Gln Ser
        595                 600                 605 ttg act tgt atg cca cca agg ata gga tca ttg aca tgc ctt aag act   1872
Leu Thr Cys Met Pro Pro Arg Ile Gly Ser Leu Thr Cys Leu Lys Thr
    610                 615                 620 cta ggt caa ttt gtt gtt gga agg aag aaa ggt tat caa ctt ggt gaa   1920
Leu Gly Gln Phe Val Val Gly Arg Lys Lys Gly Tyr Gln Leu Gly Glu
625                 630                 635                 640 cta gga aac cta aat ctc tat ggc tca att aaa atc tcg cat ctt gag   1968
Leu Gly Asn Leu Asn Leu Tyr Gly Ser Ile Lys Ile Ser His Leu Glu
                645                 650                 655 aga gtg aag aat gat aag gac gca aaa gaa gcc aat tta tct gca aaa   2016
Arg Val Lys Asn Asp Lys Asp Ala Lys Glu Ala Asn Leu Ser Ala Lys
            660                 665                 670 ggg aat ctg cat tct tta agc atg agt tgg aat aac ttt gga cca cat   2064
Gly Asn Leu His Ser Leu Ser Met Ser Trp Asn Asn Phe Gly Pro His
        675                 680                 685 ata tat gaa tca gaa gaa gtt aaa gtg ctt gaa gcc ctc aaa cca cac   2112
```

| | | |
|---|---|---|
| Ile Tyr Glu Ser Glu Val Lys Val Leu Glu Ala Leu Lys Pro His<br>     690                    695                    700 | | |
| tcc aat ctg act tct tta aaa atc tat ggc ttc aga gga atc cat ctc<br>Ser Asn Leu Thr Ser Leu Lys Ile Tyr Gly Phe Arg Gly Ile His Leu<br>705                   710                    715               720 | 2160 | |
| cca gag tgg atg aat cac tca gta ttg aaa aat att gtc tct att cta<br>Pro Glu Trp Met Asn His Ser Val Leu Lys Asn Ile Val Ser Ile Leu<br>                   725                   730               735 | 2208 | |
| att agc aac ttc aga aac tgc tca tgc tta cca ccc ttt ggt gat ctg<br>Ile Ser Asn Phe Arg Asn Cys Ser Cys Leu Pro Pro Phe Gly Asp Leu<br>         740                    745                750 | 2256 | |
| cct tgt cta gaa agt cta gag tta cac tgg ggg tct gcg gat gtg gag<br>Pro Cys Leu Glu Ser Leu Glu Leu His Trp Gly Ser Ala Asp Val Glu<br>             755                   760             765 | 2304 | |
| tat gtt gaa gaa gtg gat att gat gtt cat tct gga ttc ccc aca aga<br>Tyr Val Glu Glu Val Asp Ile Asp Val His Ser Gly Phe Pro Thr Arg<br>    770                    775                780 | 2352 | |
| ata agg ttt cca tcc ttg agg aaa ctt gat ata tgg gac ttt ggt agt<br>Ile Arg Phe Pro Ser Leu Arg Lys Leu Asp Ile Trp Asp Phe Gly Ser<br>785                   790                    795               800 | 2400 | |
| ctg aaa gga ttg ctg aaa aag gaa gga gaa gag caa ttc cct gtg ctt<br>Leu Lys Gly Leu Leu Lys Lys Glu Gly Glu Glu Gln Phe Pro Val Leu<br>                   805                   810               815 | 2448 | |
| gaa gag atg ata att cac gag tgc cct ttt ctg acc ctt tct tct aat<br>Glu Glu Met Ile Ile His Glu Cys Pro Phe Leu Thr Leu Ser Ser Asn<br>         820                    825                830 | 2496 | |
| ctt agg gct ctt act tcc ctc aga att tgc tat aat aaa gta gct act<br>Leu Arg Ala Leu Thr Ser Leu Arg Ile Cys Tyr Asn Lys Val Ala Thr<br>             835                   840             845 | 2544 | |
| tca ttc cca gaa gag atg ttc aaa aac ctt gca aat ctc aaa tac ttg<br>Ser Phe Pro Glu Glu Met Phe Lys Asn Leu Ala Asn Leu Lys Tyr Leu<br>850                   855                    860 | 2592 | |
| aca atc tct cgg tgc aat aat ctc aaa gag ctg cct acc agc ttg gct<br>Thr Ile Ser Arg Cys Asn Asn Leu Lys Glu Leu Pro Thr Ser Leu Ala<br>865                   870                    875               880 | 2640 | |
| agt ctg aat gct ttg aaa agt cta aaa att caa ttg tgt tgc gca cta<br>Ser Leu Asn Ala Leu Lys Ser Leu Lys Ile Gln Leu Cys Cys Ala Leu<br>                   885                   890               895 | 2688 | |
| gag agt ctc cct gag gaa ggg ctg gaa ggt tta tct tca ctc aca gag<br>Glu Ser Leu Pro Glu Glu Gly Leu Glu Gly Leu Ser Ser Leu Thr Glu<br>         900                    905                910 | 2736 | |
| tta ttt gtt gaa cac tgt aac atg cta aaa tgt tta cca gag gga ttg<br>Leu Phe Val Glu His Cys Asn Met Leu Lys Cys Leu Pro Glu Gly Leu<br>             915                   920             925 | 2784 | |
| cag cac cta aca acc ctc aca agt tta aaa att cgg gga tgt cca caa<br>Gln His Leu Thr Thr Leu Thr Ser Leu Lys Ile Arg Gly Cys Pro Gln<br>    930                    935                940 | 2832 | |
| ctg atc aag cgg tgt gag aag gga ata gga gaa gac tgg cac aaa att<br>Leu Ile Lys Arg Cys Glu Lys Gly Ile Gly Glu Asp Trp His Lys Ile<br>945                   950                    955               960 | 2880 | |
| tct cac att cct aat gtg aat ata tat att taa<br>Ser His Ile Pro Asn Val Asn Ile Tyr Ile<br>         965                    970 | 2913 | |

<210> SEQ ID NO 94
<211> LENGTH: 970
<212> TYPE: PRT
<213> ORGANISM: Solanum bulbocastanum

<400> SEQUENCE: 94

```
Met Ala Glu Ala Phe Ile Gln Val Leu Leu Asp Asn Leu Thr Ser Phe
1               5                   10                  15

Leu Lys Gly Glu Leu Val Leu Leu Phe Gly Phe Gln Asp Glu Phe Gln
            20                  25                  30

Arg Leu Ser Ser Met Phe Ser Thr Ile Gln Ala Val Leu Glu Asp Ala
                35                  40                  45

Gln Glu Lys Gln Leu Asn Asn Lys Pro Leu Glu Asn Trp Leu Gln Lys
    50                  55                  60

Leu Asn Ala Ala Thr Tyr Glu Val Asp Asp Ile Leu Asp Glu Tyr Lys
65                  70                  75                  80

Thr Lys Ala Thr Arg Phe Ser Gln Ser Glu Tyr Gly Arg Tyr His Pro
                85                  90                  95

Lys Val Ile Pro Phe Arg His Lys Val Gly Lys Arg Met Asp Gln Val
                100                 105                 110

Met Lys Lys Leu Lys Ala Ile Ala Glu Glu Arg Lys Asn Phe His Leu
            115                 120                 125

His Glu Lys Ile Val Glu Arg Gln Ala Val Arg Arg Glu Thr Gly Ser
    130                 135                 140

Val Leu Thr Glu Pro Gln Val Tyr Gly Arg Asp Lys Glu Lys Asp Glu
145                 150                 155                 160

Ile Val Lys Ile Leu Ile Asn Asn Val Ser Asp Ala Gln His Leu Ser
                165                 170                 175

Val Leu Pro Ile Leu Gly Met Gly Gly Leu Gly Lys Thr Thr Leu Ala
                180                 185                 190

Gln Met Val Phe Asn Asp Gln Arg Val Thr Glu His Phe His Ser Lys
            195                 200                 205

Ile Trp Ile Cys Val Ser Glu Asp Phe Asp Glu Lys Arg Leu Ile Lys
    210                 215                 220

Ala Ile Val Glu Ser Ile Glu Gly Arg Pro Leu Leu Gly Glu Met Asp
225                 230                 235                 240

Leu Ala Pro Leu Gln Lys Lys Leu Gln Glu Leu Leu Asn Gly Lys Arg
                245                 250                 255

Tyr Leu Leu Val Leu Asp Asp Val Trp Asn Glu Asp Gln Gln Lys Trp
                260                 265                 270

Ala Asn Leu Arg Ala Val Leu Lys Val Gly Ala Ser Gly Ala Ser Val
            275                 280                 285

Leu Thr Thr Thr Arg Leu Glu Lys Val Gly Ser Ile Met Gly Thr Leu
290                 295                 300

Gln Pro Tyr Glu Leu Ser Asn Leu Ser Gln Glu Asp Cys Trp Leu Leu
305                 310                 315                 320

Phe Met Gln Arg Ala Phe Gly His Gln Glu Ile Asn Pro Asn Leu
                325                 330                 335

Val Ala Ile Gly Lys Glu Ile Val Lys Lys Ser Gly Gly Val Pro Leu
            340                 345                 350

Ala Ala Lys Thr Leu Gly Gly Ile Leu Cys Phe Lys Arg Glu Glu Arg
            355                 360                 365

Ala Trp Glu His Val Arg Asp Ser Pro Ile Trp Asn Leu Pro Gln Asp
        370                 375                 380

Glu Ser Ser Ile Leu Pro Ala Leu Arg Leu Ser Tyr His Gln Leu Pro
385                 390                 395                 400

Leu Asp Leu Lys Gln Cys Phe Ala Tyr Cys Ala Val Phe Pro Lys Asp
                405                 410                 415

Ala Lys Met Glu Lys Glu Lys Leu Ile Ser Leu Trp Met Ala His Gly
```

-continued

```
                420                 425                 430
Phe Leu Leu Ser Lys Gly Asn Met Glu Leu Glu Asp Val Gly Asp Glu
            435                 440                 445
Val Trp Lys Glu Leu Tyr Leu Arg Ser Phe Gln Glu Ile Glu Val
        450                 455                 460
Lys Asp Gly Lys Thr Tyr Phe Lys Met His Asp Leu Ile His Asp Leu
465                 470                 475                 480
Ala Thr Ser Leu Phe Ser Ala Asn Thr Ser Ser Asn Ile Arg Glu
                485                 490                 495
Ile Asn Lys His Ser Tyr Thr His Met Met Ser Ile Gly Phe Ala Glu
            500                 505                 510
Val Val Phe Phe Tyr Thr Leu Pro Pro Leu Glu Lys Phe Ile Ser Leu
        515                 520                 525
Arg Val Leu Asn Leu Gly Asp Ser Thr Phe Asn Lys Leu Pro Ser Ser
        530                 535                 540
Ile Gly Asp Leu Val His Leu Arg Tyr Leu Asn Leu Tyr Gly Ser Gly
545                 550                 555                 560
Met Arg Ser Leu Pro Lys Gln Leu Cys Lys Leu Gln Asn Leu Gln Thr
                565                 570                 575
Leu Asp Leu Gln Tyr Cys Thr Lys Leu Cys Cys Leu Pro Lys Glu Thr
            580                 585                 590
Ser Lys Leu Gly Ser Leu Arg Asn Leu Leu Asp Gly Ser Gln Ser
        595                 600                 605
Leu Thr Cys Met Pro Pro Arg Ile Gly Ser Leu Thr Cys Leu Lys Thr
        610                 615                 620
Leu Gly Gln Phe Val Val Gly Arg Lys Lys Gly Tyr Gln Leu Gly Glu
625                 630                 635                 640
Leu Gly Asn Leu Asn Leu Tyr Gly Ser Ile Lys Ile Ser His Leu Glu
                645                 650                 655
Arg Val Lys Asn Asp Lys Asp Ala Lys Glu Ala Asn Leu Ser Ala Lys
            660                 665                 670
Gly Asn Leu His Ser Leu Ser Met Ser Trp Asn Asn Phe Gly Pro His
        675                 680                 685
Ile Tyr Glu Ser Glu Glu Val Lys Val Leu Glu Ala Leu Lys Pro His
        690                 695                 700
Ser Asn Leu Thr Ser Leu Lys Ile Tyr Gly Phe Arg Gly Ile His Leu
705                 710                 715                 720
Pro Glu Trp Met Asn His Ser Val Leu Lys Asn Ile Val Ser Ile Leu
                725                 730                 735
Ile Ser Asn Phe Arg Asn Cys Ser Cys Leu Pro Pro Phe Gly Asp Leu
            740                 745                 750
Pro Cys Leu Glu Ser Leu Glu Leu His Trp Gly Ser Ala Asp Val Glu
        755                 760                 765
Tyr Val Glu Glu Val Asp Ile Asp Val His Ser Gly Phe Pro Thr Arg
        770                 775                 780
Ile Arg Phe Pro Ser Leu Arg Lys Leu Asp Ile Trp Asp Phe Gly Ser
785                 790                 795                 800
Leu Lys Gly Leu Leu Lys Lys Glu Gly Glu Glu Gln Phe Pro Val Leu
                805                 810                 815
Glu Glu Met Ile Ile His Glu Cys Pro Phe Leu Thr Leu Ser Ser Asn
            820                 825                 830
Leu Arg Ala Leu Thr Ser Leu Arg Ile Cys Tyr Asn Lys Val Ala Thr
        835                 840                 845
```

```
Ser Phe Pro Glu Glu Met Phe Lys Asn Leu Ala Asn Leu Lys Tyr Leu
    850                 855                 860

Thr Ile Ser Arg Cys Asn Asn Leu Lys Glu Leu Pro Thr Ser Leu Ala
865                 870                 875                 880

Ser Leu Asn Ala Leu Lys Ser Leu Lys Ile Gln Leu Cys Cys Ala Leu
                885                 890                 895

Glu Ser Leu Pro Glu Glu Gly Leu Glu Gly Leu Ser Ser Leu Thr Glu
                900                 905                 910

Leu Phe Val Glu His Cys Asn Met Leu Lys Cys Leu Pro Glu Gly Leu
            915                 920                 925

Gln His Leu Thr Thr Leu Thr Ser Leu Lys Ile Arg Gly Cys Pro Gln
    930                 935                 940

Leu Ile Lys Arg Cys Glu Lys Gly Ile Gly Glu Asp Trp His Lys Ile
945                 950                 955                 960

Ser His Ile Pro Asn Val Asn Ile Tyr Ile
                965                 970

<210> SEQ ID NO 95
<211> LENGTH: 23
<212> TYPE: DNA
<213> ORGANISM: Solanum bulbocastanum
<220> FEATURE:
<221> NAME/KEY: misc_feature
<222> LOCATION: (1)..(23)
<223> OTHER INFORMATION: Primer

<400> SEQUENCE: 95
gtgcttcatt caaactcaag gag                                              23

<210> SEQ ID NO 96
<211> LENGTH: 25
<212> TYPE: DNA
<213> ORGANISM: Solanum bulbocastanum
<220> FEATURE:
<221> NAME/KEY: misc_feature
<222> LOCATION: (1)..(25)
<223> OTHER INFORMATION: Primer

<400> SEQUENCE: 96
ctgaactaga aaaactcact gtaga                                            25

<210> SEQ ID NO 97
<211> LENGTH: 24
<212> TYPE: DNA
<213> ORGANISM: Solanum bulbocastanum
<220> FEATURE:
<221> NAME/KEY: misc_feature
<222> LOCATION: (1)..(24)
<223> OTHER INFORMATION: Primer

<400> SEQUENCE: 97
gtttgaaaag attgcaattg catg                                             24

<210> SEQ ID NO 98
<211> LENGTH: 24
<212> TYPE: DNA
<213> ORGANISM: Solanum bulbocastanum
<220> FEATURE:
<221> NAME/KEY: misc_feature
<222> LOCATION: (1)..(24)
<223> OTHER INFORMATION: Primer

<400> SEQUENCE: 98
```

```
                                    -continued
ctcagccatc agttgaaaca gaga                                              24

<210> SEQ ID NO 99
<211> LENGTH: 24
<212> TYPE: DNA
<213> ORGANISM: Solanum bulbocastanum
<220> FEATURE:
<221> NAME/KEY: misc_feature
<222> LOCATION: (1)..(24)
<223> OTHER INFORMATION: Primer

<400> SEQUENCE: 99
gagagagatt caagaggagg aagc                                              24
```

           *:***
```

FUNGUS RESISTANT PLANTS AND THEIR USES

RELATED APPLICATIONS

This application is a national stage application (under 35 U.S.C. 371) of PCT/EP2004/008683 filed Aug. 3, 2004 which claims benefit of European patent application 03018266.1 filed Aug. 11, 2003.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence List-13477-00002-US, date recorded: Oct. 24, 2007, size: 168 KB.

The present invention relates to a novel method for increasing the resistance of a plant, in particular of a Solanaceae, preferably of potato and tomato, to plant pathogens of the phylum Oomycetes comprising increasing the activity of the polypeptide of the present invention. The invention further relates to polynucleotides and vectors comprising these polynucleotides. The invention furthermore relates to corresponding vectors, cells, transgenic plants and transgenic propagation material derived from them, methods to produce them and to their use for the production of foodstuffs, feeding stuffs, seed, pharmaceuticals or fine chemicals.

The aim of plant biotechnology work is the generation of plants with advantageous novel properties, for example for increasing agricultural productivity, increasing the quality in the case of foodstuffs, or for producing specific chemicals or pharmaceuticals (Dunwell J M (2000) J Exp Bot 51 Spec No:487-96). The plant's natural defence mechanisms against pathogens are frequently insufficient. Fungal diseases alone result in annual yield losses of many billions of US$. The introduction of foreign genes from plants, animals or microbial sources can increase the defences. Examples are the protection of tobacco against feeding damage by insects by expressing *Bacillus thuringiensis* endotoxins under the control of the 35S CaMV promoter (Vaeck et al. (1987) Nature 328:33-37) or the protection of tobacco against fungal infection by expressing a bean chitinase under the control of the CaMV promoter (Broglie et al. (1991) Science 254:1194-1197). However, most of the approaches described only offer resistance to a single pathogen or a narrow spectrum of pathogens.

Despite the notorious Irish potato famine of the mid-19$^{th}$ century, late blight still continues to be one of the most devastating of all diseases in crop plants. Late blight is caused by the oomycete fungus *Phytophthora infestans*, a specialised pathogen, primarily causing disease on the foliage and fruits of a range of Solanaceae species, especially potato and tomato. The fungus was first observed in Mexico and for several reasons Mexico is believed to be the centre of origin of the fungus. Both of the mating types A1 and A2 are permanently present in for example the Toluca area. Also, *P. infestans* is reported on native *Solanum* species in remote areas of Mexico. Furthermore, many species of tuber bearing *Solanum* with a high level of resistance to late blight are found in Mexico. Prevailing measures to prevent crop failures or reduced yields imply the application of fungicides that prevent or cure an infection by *P. infestans*. Instead of the massive use of chemical pesticides an alternative approach for controlling late blight could be advantageous: the use of cultivars, which harbour partial or complete resistance to late blight. To obtain late blight resistance, breeders have in the past focussed on the introgression of dominant R genes from *Solanum demissum*, a wild potato species indigenous to Mexico. Eleven such R genes have been identified, several of which have been mapped to specific loci on the genetic map of potato (reviewed in Gebhardt and Valkonen, 2001) and recently the R1 gene has been cloned. R1 and R2 are located on chromosomes 5 and 4, respectively. R3, R6 and R7 are located on chromosome 11. Unknown R genes conferring race specific resistance to late blight have also been described in *S. tuberosum* ssp. *andigena* and *S. berthaultii* and *S. pinnatisectum*. The resistance induced by these R-genes was (nearly) complete but appeared not to be durable in any case. Because of the high level of resistance and ease of transfer, many cultivars contain *S. demissum* derived resistance. Unfortunately, *S. demissum* derived race specific resistance, although nearly complete, is not durable. Once newly bred potato cultivars were grown on larger scale in commercial fields, new virulences emerged in *P. infestans*, which rendered the pathogen able to overcome the introgressed resistance. More durable field resistance to late blight, often quantitative in nature and presumed to be race non-specific, can be found in several Mexican and Central and South American *Solanum* species. However this type of resistance is difficult to transfer into potato cultivars through crossing and phenotypic selection.

Diploid *S. bulbocastanum* from Mexico and Guatemala is one of the tuber bearing species that is long known for its high levels of resistance to late blight. Unfortunately, classic transfer of resistance from wild *Solanum* species to cultivated potato is frequently prevented due to differences in ploidy and Endosperm Balance Number (EBN). Despite these problems, introgression of the *S. bulbocastanum* resistance trait has been successful. Recently, somatic hybrids of *S. bulbocastanum* and *S. tuberosum* and backcrossed germplasm were found to be highly resistant to late blight, even under extreme disease pressure (Helgeson et al., 1998). Despite reports of suppression of recombination, resistance in the backcrossed material appeared to be on chromosome 8 within an approximately 6 cM interval between the RFLP markers CP53 and CT64. A CAPS marker derived from the tomato RFLP probe CT88 cosegregated with resistance.

Accordingly, in the recent years the development of plants resistant to pathogens of the phylum Oomyceta forged ahead. However, 40 years of intense and continuous research and breeding efforts with available germplasm has still not resulted in market introduction of resistant cultivars. The prevailing number of genes identified in the recent years confers merely race specific resistance. Further, the achieved resistance was not durable. In addition, the application of crop protectants is widely considered to be a burden for the environment. Thus, in several Western countries, legislation becomes more restrictive and partly prohibitive to the application of specific fungicides, making chemical control of the disease more difficult. Further, chemical control is expensive. Finally, another restriction is the development of resistance by the fungus to specific fungicides such as metalaxyl, which has been reported from many countries in the world.

Accordingly, the problem underlying the present invention is to provide novel means and methods for an efficient protection of plants against late blight and related diseases.

The solution of the technical problem is achieved by providing the embodiments characterized in the claims.

Accordingly, the present invention relates to a method for generating or increasing the resistance of a plant to plant pathogen of the phylum Oomycetes comprising increasing the activity of Rpi-blb2 protein in the plant or a tissue, organ or cell of the plant or a part thereof.

Rpi-blb2 is a LZ-NBS-LRR type of R gene and shows sequence homology to the tomato gene Mi-1, that confers resistance to three species of root knot nematodes (*Meloidogyne* spp.) as well as to the potato aphid *Macrosiphum euphorbiae* (Vos et al., 1998; Rossi et al., 1998; Milligan et al., 1998) and to both B- and Q-biotypes of whitefly *Bemisia tabaci* (Nombela et al., 2003). As was found for Rpi-blb, Rpi-blb2 also confers full resistance to a range of *P. infestans* isolates carrying multiple virulence factors and race-specificity has not yet been demonstrated.

The term "Rpi-blb2" refers to a polynucleotide encoding a polypeptide having the herein mentioned Rpi-blb2 protein activity or a polypeptide having said Rpi-blb2 protein activity. Whether in the following the term "Rpi-blb2" relates to a polypeptide or a polynucleotide is clear from the context of its usage.

By the term "generating" or "increasing" or "stimulating" "the resistance of a plant" is meant that the resistance of a plant or a part thereof is increased or generated or stimulated in comparison to a reference.

"Conferring", "existing", "generating", "stimulating" or "increasing" a pathogen resistance means that the defence mechanisms of a specific plant species or variety is increasingly resistant to one or more pathogens due to the use of the method according to the invention in comparison with the wild type of the plant, to which the method according to the invention has not been applied, under otherwise identical conditions (such as, for example, climatic conditions, growing conditions, pathogen species and the like). The increased resistance manifests itself preferably in a reduced manifestation of the disease symptoms, disease symptoms comprising—in addition to the abovementioned adverse effects—for example also the penetration efficiency of a pathogen into the plant or plant cells or the proliferation efficiency in or on the same. In this context, the disease symptoms are preferably reduced by at least 10% or at least 20%, especially preferably by at least 40% or 60%, very especially preferably by at least 70% or 80% and most preferably by at least 90% or 95%.

By the term "increased" it is hereby meant that an activity of a gene product is higher than in a reference. Thus, the term "increased" includes that an activity, e.g. the activity of Rpi-blb2 gene product or of an other gene product, is generated de novo, if that activity, e.g the herein described Rpi-blb2 activity, was not found in the reference. The term "increased" also relates to the stimulation of the activity of a gene product. An increased expression of a gene, i.e. its activation can be stimulated on several ways, e.g. by applying chemicals or by biotic stress to an organism. For example, a resistance to infecting parasites mediating gene may be activated by infection with a parasite, e.g. with *P. infestans* and confers than an increased resistance to the same and/or other pathogens.

Thus, in the following, the term "increasing" also comprises the terms "stimulating" and "generating".

"Pathogen resistance" denotes the reduction or weakening of disease symptoms of a plant following infection by a pathogen. The symptoms can be manifold, but preferably encompass those which directly or indirectly have an adverse effect on the quality of the plant, the quantity of the yield, the suitability for use as feeding stuff or foodstuff, or else which make sowing, planting, harvesting or processing of the crop difficult.

"Pathogen" within the scope of the invention means by way of example but not by limitation viruses or viroids, bacteria, fungi, animal pests such as, for example, insects or nematodes.

The term "Rpi-blb2 protein" relates to a protein or polypeptide which expression in a plant or a part confers resistance of the plant or a part of the plant to one of the pathogens described herein in comparison to a non-resistant strain.

The plant or a tissue, organ or cell of the plant or a part thereof comprising increased activity of Rpi-blb2 protein is less susceptible to an infection by a pathogen, in particular to pathogen of the phylum Oomycetes, preferably to *P. infestans*, than a plant or a part thereof which has the identical genetic background but not the genetic elements necessary to allow an expression of Rpi-blb2 (herein named as "wild type" or "reference"). Assays for the testing of the resistance of a plant or a part thereof are well known to a person skilled in the art. The resistance to *P. infestans* can be defined as sporulation index according to Flier, 2001. Flier describes the sporulation index as a level of sporulation per 1 $cm^2$. Thus, a reduction of sporulation per 1 $cm^2$ of 20% compared to a wild type is herein defined as resistance. In the examples illustrating the present invention, the sporulation index was defined as level of sporulation per lesion. Thus, by the term "resistance" can be alternatively meant a reduction of sporulation per lesion of 20% compared to a wild type. The later definition is preferred.

In preferred embodiments the sporulation in an assay is reduced by 30%, more preferred is a reduction of 50%, even more preferred are 70%, even more preferred are more than 80%, more preferred are 85% and 90%. Most preferred is a reduction of 95% or more.

Figure 18:
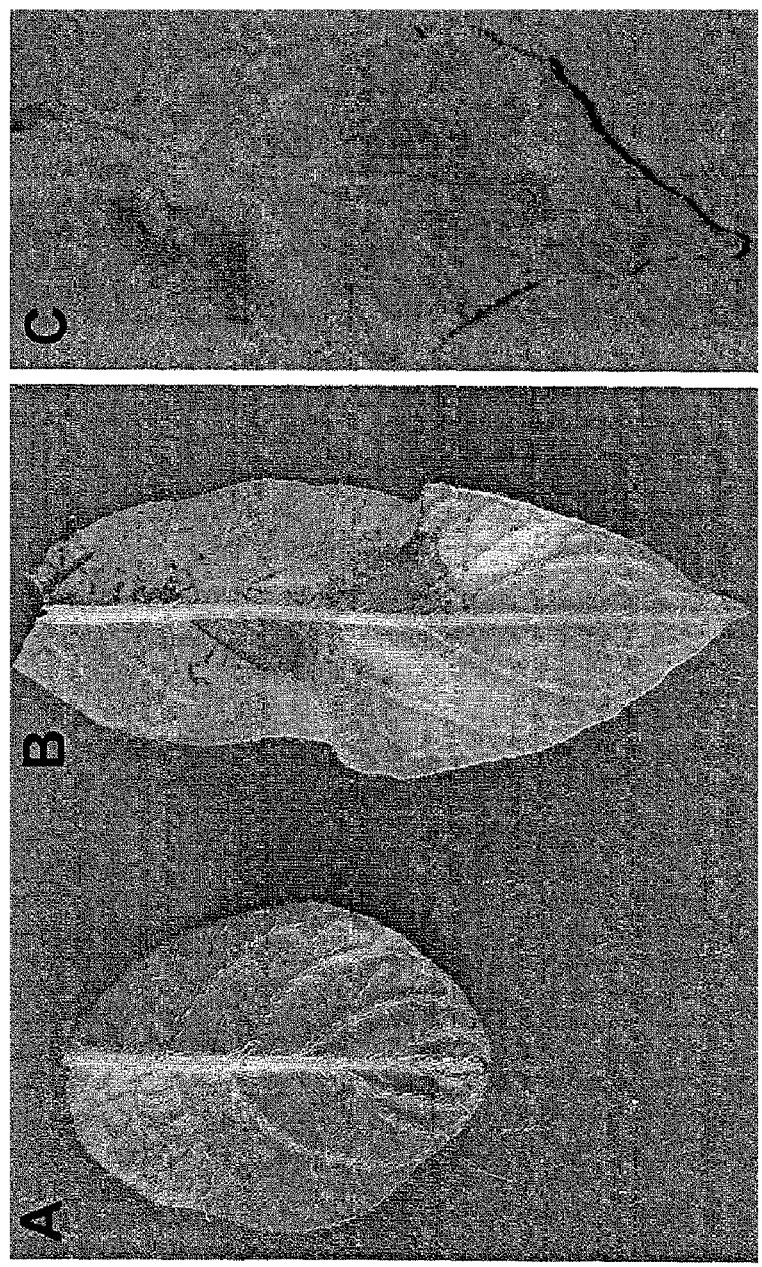

Accordingly, in the present invention by "activity" of a Rpi-blb2 protein is meant, that the protein expression confers said reduction in the sporulation index. Further, it was observed, that a typical response for plants containing Rpi-blb2 to a *P. infestans* infection is the presence of small lesions, without any clear sporulation, at the end of the growing season. Thus, in one embodiment, the activity of Rpi-blb2 is defined as the presence of small lesions without any clear sporulation in experiments as described. Rpi-blb2 resistance shows necrotic regions that contain a low level of sporulation. An experiment performed with detached leaves exemplifies the activity of Rpi-blb2. The experiment is described in example 17 and FIG. 18. The difference between Rpi-blb2 and other *P. infestans* resistance genes is that Rpi-blb2 allows a low level of sporulation (FIG. 18). A detached leaf assay in which the lesions present on Rpi-blb2 genotype (ARD 92-1197-16) shows a low level of sporangia in relation to complete absence of sporangia on a genotype containing the *S. demissum* gene R2. The sporulation index is only 1.1% of a susceptible phenotype (cv. Bintje) (Table 7 and FIG. 18).

Field experiments have also shown that Rpi-blb2 allows a low level of infection. Late blight symptoms developed at a low level during the growing season (FIG. 3, ARF87-801) or at the end of the growing season (FIG. 2, ARF87-601; FIG. 3, ARF87-507 and ARF87-601).

Thus, in one embodiment, the activity of Rpi-blb2 is further defined as resulting after expression in a plant in necrotic regions that contain a low level of sporulation in experiments as described.

Thus, in one embodiment, the method of the present invention produces plants showing necrotic regions that contain a low level of sporulation or less.

The term "reference" relates to an organism or a part thereof, e.g. a cell, which is essentially as identical as possible in genome, proteome, and/or metabolome to the relevant organism or part thereof, e.g. a cell, for example to the plant of the present invention.

Thus, the term "reference" relates for example to an orgamsm or a part thereof, e.g. a cell, which is essentially genetically, proteomically, and/or metabolically identical to the organism of the present invention or a part thereof but an activity of a specific gene product, e.g. Rpi-blb2, cannot be observed as there is a relevant difference in the reference's genome, proteome or metabolome. Thus, the reference can be a plant or a part thereof which does not express or expresses too little of a relevant active gene product, e.g. it does not encode a Rpi-blb2 or does not transcribe a Rpi-blb2 encoding gene or does not translate an active Rpi-blb2 mRNA. Thus, the reference does not provide the modification creating an active gene product in a sufficient quantity to result in an phenotype as described. Whether two plants are essentially genetically identical can be tested with assays known to a person skilled in the art, e.g. via fingerprint analysis, e.g. as described in Roldan-Ruiz, Theor. Appl. Genet., 2001, 1138-1150. The expression pattern of proteins can be tested as described in the art e.g. via gel electrophoresis (1D, 2D, 3D), mass spectrometric analysis and other methods. The metabolome can be analysed by the skilled as described in the art, e.g. via HLPLC, GC, OPLC, LC-MS, GC-MS, LC-MS-MS, and other methods as described e.g. in Fiehn et al., Nature Biotech, 18 (2000), 1157, Raamsdonk et al., Nature Biotech, 19 (2991), 45-50, Buchholz, Anal. Biochem, 295 (2001) 129-137, Soga et al., Anal Chem. 74 (2002) 2233-2239.

In order to increase the resistance to a pathogen the reference organism or the part thereof is susceptible to the infection with the pathogen, e.g. a plant pathogen, e.g. *P. infestans*.

Preferably, the reference is a clone of that organism in which for example a relevant polynucleotide, e.g. the polynucleotide of the invention, or an activator, e.g. an activator of a relevant gene product mediating the activity, e.g. an activator increasing the expression of a relevant polynucleotide or a derivate of said polynucleotide, or an activator of a relevant polypeptide, e.g. of the polypeptide of the present invention, and/or a corresponding the relevant gene product encoding vector has been introduced. For example, a preferred reference in the method of the present invention is an organism or a part thereof, which is a clone of the organism or part thereof, e.g. a cell which has been transfected or transformed with the polynucleotide or vector of the invention.

If the clone as described can not be identified it is state of the art to cleave out, to knock out or to switch off those elements which essentially mediate the relevant activity, e.g. mediating an increased Rpi-blb2 activity, e.g. mediating an increased expression, in the organism, e.g. in the plant. It is well known to skilled person, how to reduce or inhibit the activity of a relevant gene product, e.g. by reducing or inhibiting the expression of e.g. Rpi-blb2. Such a clone can than be compared with an organism produced according to the method of the present invention, e.g. a *P. infestans* resistant, Rpi-blb2 expressing genotype.

The term "plant" as used herein refers to all genera and species of higher and lower plants of the Plant Kingdom. The term includes the mature plants, seed, shoots and seedlings and their derived parts, propagation material, plant organs, tissue, protoplasts, callus and other cultures, for example cell cultures, and any other type of plant cell grouping to give functional or structural units. "Mature plant" refers to a plant at any desired developmental stage beyond that of the seedling. Seedling refers to a young immature plant at an early developmental stage. "Plant" encompasses all annual and perennial monocotyledonous and dicotyledonous plants. Preferred within the scope of the invention are those plants which are employed as foodstuffs or feeding stuffs, for example monocotyledonous or dicotyledonous genera, in particular species, like the above-described ones, e.g. cereal species or members of the Solanaceae family, respectively, most preferably potato and tomato.

As known to a person skilled in the art, the method of the present invention comprises further selecting those plants in which, as opposed or as compared to the reference plant, the resistance to at least one said pathogen exists or is increased.

"Selection" with regard to plants in which—as opposed or as compared to the reference plant—resistance to at least one pathogen exists or is increased means all those methods which are suitable for recognizing an existing or increased resistance to pathogens. These may be symptoms of pathogen infection but may also comprise the herein described symptoms which relate to the quality of the plant, the quantity of the yield, the suitability for use as feeding stuff or foodstuff and the like.

Accordingly, in one embodiment of the method of present invention the Rpi-blb2 protein is encoded by a polynucleotide comprising a nucleic acid molecule selected from the group consisting of:

a) nucleic acid molecules encoding at least the mature form of the polypeptide depicted in SEQ ID NO: 2 or 4;
b) nucleic acid molecules comprising the coding sequence as depicted in SEQ ID NO: 1 or 3, or 5 or 6 encoding at least the mature form of the polypeptide;
c) nucleic acid molecules the nucleotide sequence of which is degenerate as a result of the genetic code to a nucleotide sequence of (a) or (b);
d) nucleic acid molecules encoding a polypeptide derived from the polypeptide encoded by a polynucleotide of (a) to (c) by way of substitution, deletion and/or addition of one or several amino acids of the amino acid sequence of the polypeptide encoded by a polynucleotide of (a) to (c);
e) nucleic acid molecules encoding a polypeptide the sequence of which has an identity of 70% or more to the amino acid sequence of the polypeptide encoded by a nucleic acid molecule of (a) or (b);
f) nucleic acid molecules comprising a fragment or a epitope-bearing portion of a polypeptide encoded by a nucleic acid molecule of any one of (a) to (e);
g) nucleic acid molecules comprising a polynucleotide having a sequence of a nucleic acid molecule amplified from a nucleic acid library using the primers as listed in Tab 3b, in particular ARF1F and ARF1R;
h) nucleic acid molecules encoding a fragment beginning with amino acid: 1, 30, 50, 100, 200, 300, 500, or 1000 and stopping with amino acid 1276, 1000, 500, 300, 200, 50, 30, or 1 of a polypeptide encoded by any one of (a) to (g);
i) nucleic acid molecules comprising at least 20 nucleotides of a polynucleotide of any one of (a) or (d);
j) nucleic acid molecules encoding a polypeptide being recognized by a monoclonal antibody that have been raised against a polypeptide encoded by a nucleic acid molecule of any one of (a) to (h);
k) nucleic acid molecules obtainable by screening an appropriate library under stringent conditions with a probe having the sequence of the nucleic acid molecule of any one of (a) to (j) or of a fragment thereof of at least 15, preferable 30, 60, 100 or more nucleotides; and
l) nucleic acid molecules the complementary strand of which hybridises under stringent conditions with a nucleic acid molecule of any one of (a) or (k);

or the complementary strand of any one of (a) to (l);

or expressing a polypeptide encoded by a segment or linkage group 6 of *Solanum bulbocastanum* which co-segregates with a marker selected from table 3A and which mediates resistance to pathogens, in particular to pathogens selected from the group consisting of phylum Oomycetes;

In one embodiment, the polynucleotide of the method of the invention does not consist of the sequence depicted in Seq. ID NO.: 7 and/or 9 and/or does not consist of the sequence of a nucleic acid molecule encoding a protein depicted in Seq. ID NO.: 8 and/or 10.

In one embodiment, the polynucleotide of the method of the invention does not consist of the sequence of a nucleic acid molecule of Mi1.1 or Mi1.2 and/or of a nucleic acid molecule encoding a Mi1.1 or Mi1.2 protein.

Thus, in one embodiment, the polynucleotide of method of the present invention may not consist of the sequences shown in Rossi et al. 1998, PNAS USA 95:9750-9754, Milligan et al., 1998. Plant Cell 10:1307-1319; and/or WO 9806750. A comparison of the sequences of Rpi-blb2, Mi1.1 and Mi1.2 is shown in FIGS. 15 to 17.

The term "linkage group" as used herein relates to two or more traits and/or loci and/or genes and/or markers that tend to be inherited together as a consequence of an association between said traits and/or loci and/or genes and/or markers. The closer together the traits and/or loci and/or genes and/or markers are, the lower the probability that they will be separated during DNA repair or replication processes such as mitosis or meiosis in eukaryotes, and hence the greater the probability that they will be inherited together. There are as many linkage groups as there are homologous pairs of chromosomes.

The term "linkage group 6" relates to a linkage group of potato or tomato which is affiliated to chromosome 6, such affiliation established by identifying markers of known chromosomal position based on work published by Bernatzky and Tanksley (1986) and Tanksley et al. (1992). Linkage groups bear the same numbers as their respective chromosomes. In tomato, the chromosomes are numbered according to their length measured in pachytene. Such numbers have been applied by Barton (1950); chromosome 1 is the longest, chromosome 12, the shortest. In addition to length, such features as positions of centromere and amount and distribution of heterochromatin serve to identify each chromosome. Short arms are symbolized by "S", long ones by "L"; thus "1S" designates the short arm of chromosome 1; as e.g. in Barton, D. W. (1950) American Journal of Botany. 37,639-643, Bernatzky, R. and Tanksley, S. D. (1986) Genetics 112, 887-898, Tanksley, S. D., et al., (1992) Genetics 132, 1141-1160.

The term "co-segregation" as used herein relates to the tendency for two or more closely linked traits and/or loci and/or genes and/or markers to be inherited together.

For example, the more concrete region of chromosome 6 that co-segregates with Rpi-blb2 is the short arm that, in tomato, bears the morphological marker Mi.

Accordingly, in one embodiment the present invention relates to the method of the present invention, wherein the Rpi-blb2 protein is encoded by the polynucleotide of the present invention, e.g. encoded by a polynucleotide shown in Seq. ID. 1 or 3 or 5 or 6 or a fragment thereof.

On basis of a BLASTX search the genes with the highest homology identified to the identified Rpi-blb2 sequences were the Mi1.1- and Mi1.2-genes and proteins; see FIGS. 15 to 17. Both genes have a high identity to the sequence depicted in Seq. ID NO.: 1 or 3 or 5 or 6 but do not confer resistance to the plant pathogen of the phylum Oomycetes. Therefore the activity of Mi1.1 and Mi1.2 is an other activity as the activity of the polypeptid of the present invention. The sequence of Mi1.1 and Mi1.2 ORF and encoded proteins is herein shown in Seq. ID NO.: 7 to 10. Further, the application EP 401764.4 relates to the Mi-genes. The sequence of prior art Mi1.1- and Mi1.2-genes is excluded from the polynucleotide of the present invention, in particular Seq. ID NO.: 7 and 9 are excluded. Also included may be polynucleotide sequences encoding the polypeptide of Seq. ID NO.: 8 or 10, Thus, in an embodiment also sequences encoding the Mi1.1 and Mi1.2 protein are excluded. Proteins with a lower homology to the polypeptide encoded by the polynucleotide of the present invention are Hero Resistance proteins 1 and 2 (Genbank AccNo.: gi26190252 and gi26190254), Tospovirus resistance proteins A, B, C, D and E [Genbank AccNos.: gi15418709, gi15418710, gi15418712, gi15418713, gi15418714]; R1 [GenbankAccNo.: gi17432423] and Prf [Genbank AccNo.: gi8547237] which sequences or encoded sequences are as well excluded from the sequences of the present invention.

The terms "gene(s)", "polynucleotide", "nucleic acid sequence", "nucleotide sequence", or "nucleic acid molecule(s)" as used herein refer to a polymeric form of nucleotides of any length, either ribonucleotides or deoxyribonucleotides. This term refers only to the primary structure of the molecule.

Thus, this term includes double- and single-stranded DNA, and RNA. It also includes known types of modifications, for example, methylation, "caps" substitution of one or more of the naturally occurring nucleotides with an analogue. Preferably, the DNA sequence of the invention comprises a coding sequence encoding the herein defined polypeptide.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

By "hybridising" it is meant that such nucleic acid molecules hybridise under conventional hybridisation conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)). An example of one such stringent hybridisation condition is hybridisation at 4×SSC at 65° C., followed by a washing in 0.1×SSC at 65° C. for one hour. Alternatively, an exemplary stringent hybridisation condition is in 50% formamide, 4×SSC at 42° C. Further, the conditions during the wash step can be selected from the range of conditions delimited by low-stringency conditions (approximately 2×SSC at 50° C.) and high-stringency conditions (approximately 0.2×SSC at 50° C., preferably at 65° C.) (20×SSC: 0.3M sodium citrate, 3M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridisation. In the presence of 50% form amide, hybridisation is preferably effected at 42° C. Some further examples of conditions for hybridisation and wash step are shown herein below:

(1) Hybridisation conditions can be selected, for example, from the following conditions:

a) 4×SSC at 65° C., b) 6×SSC at 45° C., c) 6×SSC, 100 mg/ml denatured fragmented fish sperm DNA at 68° C.,
d) 6×SSC, 0.5% SDS, 100 mg/ml denatured salmon sperm DNA at 68° C.,
e) 6×SSC, 0.5% SDS, 100 mg/ml denatured fragmented salmon sperm DNA, 50% formamide at 42° C.,
f) 50% formamide, 4×SSC at 42° C.,
g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
h) 2× or 4×SSC at 50° C. (low-stringency condition), or
i) 30 to 40% formamide, 2× or 4×SSC at 42° C. (low-stringency condition).
(2) Wash steps can be selected, for example, from the following conditions:
a) 0.015 M NaCl/0.0015 M sodium citrate/0.1% SDS at 50° C.
b) 0.1×SSC at 65° C.
c) 0.1×SSC, 0.5% SDS at 68° C.
d) 0.1×SSC, 0.5% SDS, 50% formamide at 42° C.
e) 0.2×SSC, 0.1% SDS at 42° C.
f) 2×SSC at 65° C. (low-stringency condition).

In one embodiment of the present invention, the polynucleotide of the invention comprises a polynucleotide which hybridises to a nucleic acid molecule comprising or consisting of a nucleic acid molecule having the sequence shown in Seq ID No. 1 or 3 or 5 or 6 or a fragment thereof. The fragment comprises or consists preferably of 15, 20, 30, 40, 70, 100, 300, 500, 700, 1000 or more residues of Seq ID No. 1 or 3 or 5 or 6.

In a preferred embodiment, the polynucleotide of the invention comprises a polynucleotide which hybridises under "stringent" hybridisation conditions with a nucleic acid molecule comprising or consisting of a nucleic acid molecule having the sequence shown in Seq ID No. 1 or 3 or 5 or 6 or a fragment thereof.

The term "under stringent hybridisation conditions" as used herein refers to any of the herein mentioned stringent hybridisation conditions. In a further embodiment, the term "under stringent hybridisation conditions" refers to the hybridisation conditions mentioned in the examples or used in Sambrook (Molecular Cloning; A Laboratory Manual, 2nd Edition, Cold Spring Harbor Laboratory Press, Cold Spring Harbor, N.Y. (1989).

In one preferred embodiment, the term "under stringent hybridisation conditions" as used herein refers to all of the herein mentioned stringent hybridisation conditions, meaning that a polynucleotide hybridises under all mentioned stringent conditions.

Rpi-blb2 derived from other organisms, may be encoded by other DNA sequences which hybridise to the sequences shown in Seq ID No. 1 or 3 or 5 or 6 under relaxed hybridisation conditions and which code on expression for peptides having the activity of Rpi-blb2. Further, some applications have to be performed at low stringency hybridisation conditions, without any consequences for the specificity of the hybridisation. For example, a Southern blot analysis of total DNA could be probed with a polynucleotide of the present invention and washed at low stringency (55° C. in 2×SSPE, 0.1% SDS). The hybridisation analysis could reveal a simple pattern of only genes encoding Rpi-blb2. A further example of such low-stringent hybridisation conditions are 4×SSC at 50° C. or hybridisation with 30 to 40% formamide at 42° C. Such molecules comprise those which are fragments, analogues or derivatives of Rpi-blb2 of the invention and differ, for example, by way of amino acid and/or nucleotide deletion(s), insertion(s), substitution (s), addition(s) and/or recombination (s) or any other modification(s) known in the art either alone or in combination from the above-described amino acid sequences or their underlying nucleotide sequence(s). However, it is preferred to use high stringency hybridisation conditions.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structurally equivalents can, for example, identified by testing the binding of said polypeptide to antibodies. Structurally equivalent have the similar immunological characteristic, e.g. comprise similar epitopes.

The terms "fragment", "fragment of a sequence" or "part of a sequence" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence.

Typically, the truncated amino acid sequence will range from about 5 to about 1260 amino acids in length. More typically, however, the sequence will be a maximum of about 1000 amino acids in length, preferably a maximum of about 500 or 100 amino acids. It is usually desirable to select sequences of at least about 10, 12 or 15 amino acids, up to a maximum of about 20 or 25 amino acids.

The term "epitope" relates to specific immunoreactive sites within an antigen, also known as antigenic determinates. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive. In one embodiment the present invention relates to a epitope of Rpi-blb2.

The term "one or several amino acids" relates to at least one amino acid but not more than that number of amino acids which would result in a homology of below 70% identity. Preferably, the identity is more than 75% or 80%, more preferred are 85%, 90% or 95%, even more preferred are 96%, 97%, 98%, or 99% identity.

The terms "polynucleotide" and "nucleic acid molecule" also relate to "isolated" polynucleotides or nucleic acids molecules. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the polynucleotide of the present invention can contain less than about 5 kb, 4 kb, 3 kb, 2 kb, 1 kb, 0.5 kb or 0.1 kb or less of nucleotide sequences which naturally flank the nucleic acid molecule in genomic DNA of the cell from which the nucleic acid is derived. Moreover, the polynucleotides of the present invention, in particular an "isolated" nucleic acid molecule, such as a cDNA molecule, can be substantially free of other cellular material, or culture medium when produced by recombinant techniques, or chemical precursors or other chemicals when chemically synthesized.

Further, the polynucleotide of the invention comprises a nucleic acid molecule which is a complement of one of the nucleotide sequences of above mentioned polynucleotides or a portion thereof. A nucleic acid molecule which is complementary to one of the nucleotide sequences shown in SEQ ID No:1 or 3 or 5 or 6 is one which is sufficiently complementary to one of the nucleotide sequences shown in SEQ ID No: 1 or 3 or 5 or 6 such that it can hybridise to one of the nucleotide sequences shown in SEQ ID No: 1 or 3 or 5 or 6, thereby forming a stable duplex.

The polynucleotide of the invention comprises a nucleotide sequence which is at least about 70%, preferably at least about 75%, more preferably at least about 80%, 90%, or 95%, and even more preferably at least about 96%, 97%, 98%, 99% or more homologous to a nucleotide sequence shown in SEQ ID No: 1 or 3 or 5 or 6, or a portion thereof. The polynucleotide of the invention comprises a nucleotide sequence which hybridises, preferably hybridises under stringent conditions as defined herein, to one of the nucleotide sequences shown in SEQ ID No: 1 or 3 or 5 or 6, or a portion thereof.

Moreover, the polynucleotide of the invention can comprise only a portion of the coding region of one of the sequences in SEQ ID No: 1 or 3 or 5 or 6, for example a fragment which can be used as a probe or primer or a fragment encoding a biologically active portion of the Rpi-blb2 protein coding gene. The nucleotide sequences determined from the cloning of the present Rpi-blb2 protein encoding gene allows for the generation of probes and primers designed for use in identifying and/or cloning its homologues in other cell types and organisms. The probe/primer typically comprises substantially purified oligonucleotides. The oligonucleotide typically comprises a region of nucleotide sequence that hybridises under stringent conditions to at least about 12, 15 preferably about 20 or 25, more preferably about 40, 50 or 75 consecutive nucleotides of a sense strand of one of the sequences set forth, e.g., in SEQ ID No. No: 1 or 3 or 5 or 6, an anti-sense sequence of one of the sequences, e.g., set forth in SEQ ID No.: 1 or 3 or 5 or 6, or naturally occurring mutants thereof. Primers based on a nucleotide of invention can be used in PCR reactions to clone Rpi-blb2 homologues, e.g. as the primers described in the examples of the present invention, e.g. as shown in tab 3a or 3b, preferably the primers ARF1F and ARF1R are used. A PCR with the primers univ24R and univ14L will result in a fragment of Rpi-blb2 which can be used as described herein. Said primer sets are interchangeable. The person skilled in the art knows to combine said primers to result in the desired product, e.g. in a full length clone or a partial sequence. Probes based on the Rpi-blb2 nucleotide sequences can be used to detect transcripts or genomic sequences encoding the same or homologous proteins. The probe can further comprise a label group attached thereto, e.g. the label group can be a radioisotope, a fluorescent compound, an enzyme, or an enzyme cofactor. Such probes can be used as a part of a genomic marker test kit for identifying cells which express a Rpi-blb2, such as by measuring a level of a Rpi-blb2-encoding nucleic acid molecule in a sample of cells, e.g., detecting Rpi-blb2 mRNA levels or determining whether a genomic Rpi-blb2 gene has been mutated or deleted.

The polynucleotide of the invention encodes a polypeptide or portion thereof which includes an amino acid sequence which is sufficiently homologous to the amino acid sequence of SEQ ID No: 2 or 4 such that the protein or portion thereof maintains the ability to participate in resistance to pathogens, in particular a Rpi-blb2 protein activity as described in the examples in plants. As used herein, the language "sufficiently homologous" refers to proteins or portions thereof which have amino acid sequences which include a minimum number of identical or equivalent (e.g., an amino acid residue which has a similar side chain as an amino acid residue in one of the sequences of the polypeptide of the present invention), amino acid residues to an amino acid sequence of Seq. ID No.: 2 or 4 such that the protein or portion thereof is able to participate in the resistance of plants to said pathogens. Examples of a Rpi-blb2 protein activity are described herein. Thus, the function of a Rpi-blb2 protein contributes either directly or indirectly to the resistance to plant pathogens, preferably to the pathogens mentioned herein, more preferred to *P. infestans*.

The protein is at least about 70%, preferably at least about 75%, and more preferably at least about 80%, 90%, 95%, and most preferably at least about 96%, 97%, 98%, 99% or more homologous to an entire amino acid sequence of SEQ ID No: 2 or 4.

Portions of proteins encoded by the polynucleotide of the invention are preferably biologically active.

As mentioned herein, the term "biologically active portion" is intended to include a portion, e.g., a domain/motif, that confers resistance to an oomycete plant pathogen and/or *Bemisia tabaci* and/or aphids or has an immunological activity such that it binds to an antibody binding specifically to Rpi-blb2 protein or it has an activity as set forth in the Examples or as described herein.

Additional nucleic acid fragments encoding biologically active portions of the polypeptide of the present invention can be prepared by isolating a portion of one of the sequences in SEQ ID No: 1 or 3 or 5 or 6, expressing the encoded portion of the Rpi-blb2 protein or peptide (e.g., by recombinant expression in vitro) and assessing the activity of the encoded portion of the protein.

The invention further encompasses polynucleotides that differ from one of the nucleotide sequences shown in SEQ ID No: 1 or 3 or 5 or 6 (and portions thereof due to degeneracy of the genetic code and thus encode a Rpi-blb2 polypeptide as that encoded by the sequences shown in SEQ ID No: 2 or 4. Further the polynucleotide of the invention has a nucleotide sequence encoding a protein having an amino acid sequence shown in SEQ ID No: 2 or 4. In a still further embodiment, the polynucleotide of the invention encodes a full length protein which is substantially homologous to an amino acid sequence of SEQ ID No: 2 or 4.

In addition, it will be appreciated by those skilled in the art that DNA sequence polymorphisms that lead to changes in the amino acid sequences may exist within a population (e.g., the *S. bulbocastanum* population). Such genetic polymorphism in the Rpi-blb2 gene may exist among individuals within a population due to natural variation.

As used herein, the terms "gene" and "recombinant gene" refer to nucleic acid molecules comprising an open reading frame encoding a Rpi-blb2, preferably a *S. bulbocastanum*

Rpi-blb2. Such natural variations can typically result in 1-5% variance in the nucleotide sequence of the Rpi-blb2 gene. Any and all such nucleotide variations and resulting amino acid polymorphisms in Rpi-blb2 that are the result of natural variation and that do not alter the functional activity of Rpi-blb2 are intended to be within the scope of the invention.

Polynucleotides corresponding to natural variants and non-*S. bulbocastanum* homologues of the Rpi-blb2 cDNA of the invention can be isolated based on their homology to *S. bulbocastanum* Rpi-blb2 polynucleotides disclosed herein using the polynucleotide of the invention, or a portion thereof, as a hybridisation probe according to standard hybridisation techniques under stringent hybridisation conditions. Accordingly, in another embodiment, a polynucleotide of the invention is at least 20 nucleotides in length. Preferably it hybridises under stringent conditions to the nucleic acid molecule comprising a nucleotide sequence of the polynucleotide of the present invention, e.g. SEQ ID No: 1 or 3 or 5 or 6. In other embodiments, the nucleic acid is at least 20, 30, 50, 100, 250 or more nucleotides in length. The term "hybridises under stringent conditions" is defined above and is intended to describe conditions for hybridisation and washing under which nucleotide sequences at least 65% identical to each other typically remain hybridised to each other. Preferably, the conditions are such that sequences at least about 70%, more preferably at least about 75% or 80%, and even more preferably at least about 85%, 90% or 95% or more identical to each other typically remain hybridised to each other. Preferably, polynucleotide of the invention that hybridises under stringent conditions to a sequence of SEQ ID No: 1 or 3 or 5 or 6 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). Preferably, the polynucleotide encodes a natural *S. bulbocastanum* Rpi-blb2.

In addition to naturally-occurring variants of the Rpi-blb2 sequence that may exist in the population, the skilled artisan will further appreciate that changes can be introduced by mutation into a nucleotide sequence of the polynucleotide encoding Rpi-blb2, thereby leading to changes in the amino acid sequence of the encoded Rpi-blb2, without altering the functional ability of the Rpi-blb2. For example, nucleotide substitutions leading to amino acid substitutions at "non-essential" amino acid residues can be made in a sequence of the polynucleotide encoding Rpi-blb2, e.g. SEQ ID No: 1 or 3 or 5 or 6. A "non-essential" amino acid residue is a residue that can be altered from the wild-type sequence of the Rpi-blb2 protein without altering the activity of said Rpi-blb2 protein, hereas an "essential" amino acid residue is required for Rpi-blb2 protein activity. Other amino acid residues, however, (e.g., those that are not conserved or only semi-conserved in the domain having Rpi-blb2 activity) may not be essential for activity and thus are likely to be amenable to alteration without altering Rpi-blb2 activity.

Accordingly, a person skilled in the art knows that the codon usage between organisms can differ. Therefore he will adapt the codon usage in the polynucleotide of the present invention to the usage of the organism in which the polynucleotide or polypeptide is expressed.

Accordingly, the invention relates to polynucleotides encoding Rpi-blb2 that contain changes in amino acid residues that are not essential for Rpi-blb2 activity. Such Rpi-blb2s differ in amino acid sequence from a sequence contained in SEQ ID No: 2 or 4 yet retain the Rpi-blb2 activity described herein. The polynucleotide can comprise a nucleotide sequence encoding a polypeptide, wherein the polypeptide comprises an amino acid sequence at least about 70% identical to an amino acid sequence of SEQ ID No: 2 or 4 and is capable of participation in the resistance to a plant pathogen. Preferably, the protein encoded by the nucleic acid molecule is at least about 70% identical to the sequence in SEQ ID No: 2 or 4, more preferably at least about 75% identical to one of the sequences in SEQ ID No: 2 or 4, even more preferably at least about 80%, 90%, 95% homologous to the sequence in SEQ ID No: 2 or 4, and most preferably at least about 96%, 97%, 98%, or 99% identical to the sequence in SEQ ID No: 2 or 4.

To determine the percent homology of two amino acid sequences (e.g., one of the sequences of Seq. ID No.: 2 or 4 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID No: 2 or 4) is occupied by the same amino acid residue or nucleotide as the corresponding position in the other sequence (e.g., a mutant form of the sequence selected), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

Homology can be calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389 et seq.), setting the following parameters:

| Gap weight: | 50 | Length weight: | 3 |
| Average match: | 10 | Average mismatch: | 0 |

For example a sequence which has at least 80% homology with sequence SEQ ID NO: 1 at the nucleic acid level is understood as meaning a sequence which, upon comparison with the sequence SEQ ID NO: 1 by the above program algorithm with the above parameter set, has at least 80% homology.

Homology between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| Gap weight: | 8 | Length weight: | 2 |
| Average match: | 2,912 | Average mismatch: | −2,003 |

For example a sequence which has at least 80% homology with sequence SEQ ID NO: 2 at the protein level is understood as meaning a sequence which, upon comparison with the sequence SEQ ID NO: 2 by the above program algorithm with the above parameter set, has at least 80% homology.

In the present application, the homology was determined with the program clustalW, choose sequence analyses and choose option clustalW (multiple sequence alignments). All options were performed under standard conditions, as follows:

alignment: full; output format: aln w/numbers; output order: aligned; color alignment: no; ktup (word size): def; window length: def; score type: percent; topdiag: def; pairgap: def; matrix: def; gap open: def; end gaps: def; gap extension: def; gap distances: def; cpu mode: single; tree graph/type: cladogram; tree graph/distances: hide; phylogenetic tree/tree type: none; phylogenetic tree/correct dist.: off; phylogenetic tree/ignore gaps: off. Therefore a Homology calculation according to clustalW is preferred.

Functional equivalents derived from one of the polypeptides as shown in SEQ ID NO: 2 or 4 according to the invention by substitution, insertion or deletion have at least 70%, preferably at least 80%, by preference at least 90%, especially preferably at least 95%, very especially preferably at least 98%, homology with one of the polypeptides as shown in SEQ ID NO: 2 or 4 according to the invention and are distinguished by essentially the same properties as the polypeptide as shown in SEQ ID NO: 2 or 4.

Functional equivalents derived from the nucleic acid sequence as shown in SEQ ID NO: 1 or 3 or 5 or 6 according to the invention by substitution, insertion or deletion have at least 70%, preferably at least 80%, by preference at least 90%, especially preferably at least 95%, very especially preferably at least 98%, homology with one of the polypeptides as shown in SEQ ID NO: 2 or 4 according to the invention and encode polypeptides having essentially the same properties as the polypeptide as shown in SEQ ID NO: 2 or 4.

"Essentially the same properties" of a functional equivalent is above all understood as meaning conferring a pathogen-resistant phenotype or conferring or increasing the resistance to at least one pathogen while increasing the amount of protein, activity or function of said functional Rpi-blb2 equivalent in a plant or in a tissue, part or cells of the same. The sporulation and lesion phenotype after infection in combination with said increase of the amount of protein, activity or function of the functional equivalent is furthermore understood as an essential property.

A nucleic acid molecule encoding a Rpi-blb2 homologous to a protein sequence of SEQ ID No: 2 or 4 can be created by introducing one or more nucleotide substitutions, additions or deletions into a nucleotide sequence of the polynucleotide of the present invention, in particular of SEQ ID No: 1 or 3 or 5 or 6 such that one or more amino acid substitutions, additions or deletions are introduced into the encoded protein. Mutations can be introduced into the sequences of, e.g., SEQ ID No: 1 or 3 or 5 or 6 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a Rpi-blb2 is preferably replaced with another amino acid residue from the same family. Alternatively, in another embodiment, mutations can be introduced randomly along all or part of a Rpi-blb2 coding sequence, such as by saturation mutagenesis, and the resultant mutants can be screened for a Rpi-blb2 activity described herein to identify mutants that retain Rpi-blb2 activity. Following mutagenesis of one of the sequences of SEQ ID No: 1 or 3 or 5 or 6, the encoded protein can be expressed recombinantly and the activity of the protein can be determined using, for example, assays described herein (see Examples).

In one embodiment, in the method of present invention the activity of Rpi-blb2 protein and of a further resistance protein is increased.

It is expected, that under field conditions the presence of more than one resistance gene is beneficial, in particular genes conferring resistance to the same pathogen. In case a pathogen isolate, e.g. a *P. infestans* race, is present that is able to overcome resistance of one of the R-genes, the other one or more R-gene(s) is/are still functional making it impossible to infect the plant. The present of two undefeated R-genes strongly reduces the chance that a pathogen, in particular a *P. infestans* race, is able to mutate into a race that can overcome two or more R-genes.

In the following "resistance polypeptide" or "resistance protein" relates to a polypeptide which (increased) activity will confer resistance to a susceptible genotype ("wild type" or "reference"). Accordingly, Rpi-blb2 is a resistance protein as well as e.g. Rpi-blb (or RB or Sbu1). A "further resistance protein" relates to an other resistance protein than the protein of the present invention, whereas the term "resistance protein" comprises the polypeptid of the present invention as well as one or more further resistance protein(s). It is further understood, that the term "and a further resistance protein" relates to one or more further resistance proteins. Thus, the activity of one or more resistance proteins can be increased. Further resistance proteins are described below. However, generally any other known resistance protein can be co-expressed with the polypeptid of the present invention or its activity can be increased by any of the methods described herein for Rpi-blb2.

In a preferred embodiment, the further resistance protein comprises a LRR domain and a P-loop.

The cloning and molecular characterisation of over 30 plant disease resistance (R) genes conferring resistance to bacteria, fungi, oomycetes, viruses, nematodes, or insects has allowed their classification in structural classes regardless of pathogen specificity (reviewed in Dangl and Jones, 2001). The most abundant class of characterised R genes, comprising about 0.5 percent of the genes predicted in the *Arabidopsis* genome, is predicted to encode intracellular proteins that carry leucine-rich repeat (LRR) and nucleotide-binding site (NBS) domains, motifs also found in other receptor and signal transduction proteins. NBS-LRR R proteins differ primarily at the N-terminus that either exhibits sequence similarity to the *Drosophila* Toll protein and the mammalian interleukin-1 receptor domain (TIR-NBS-LRR), or code for a coiled-coils structure (CC-NBS-LRR), sometimes in the form of a leucine zipper (LZ-NBS-LRR). Although maybe membrane associated, NBS-LRR proteins are predicted to be cytoplasmic. In contrast, two other classes of R proteins that carry LRRs are predicted to span the cell membrane, with an extracellular LRR domain: the LRR-transmembrane (LRR-TM) Cf proteins and the LRR-TM-kinase Xa21 protein. Characterised R proteins that lack LRRs are the Pto gene from tomato, the Hs1$^{pro-1}$ gene from beet, the mlo gene from barley, the Rpw8 genes from *Arabidopsis* and the Rpg1 gene from barley.

According to the gene-for-gene hypothesis, disease resistance follows perception by plant R proteins of pathogen effector molecules with avirulence (Avr) function, thereby initiating through some kind of elicitor recognition complex, signal transduction pathways leading to a hypersensitive response (HR). In common with other receptors it is generally considered that NBS-LRR R proteins have a modular structure with separate recognition and signalling domains, whereby the LRR is the candidate recognition domain and the N-terminal region including the NBS, the major signalling domain. Functional analysis of recombinant R proteins indicates that recognition specificity indeed resides in the LRR. Moreover, the LRR is the most variable region in closely related NBS-LRR proteins and is under selection to diverge. However, evidence is accumulating that LRRs also contribute to signalling through negative regulation involving putative intramolecular interactions. Currently, five R genes have been cloned from potato, including two R genes conferring resistance to late blight, and all belong to the CC/LZ-NBS-LRR class of plant R genes. While the *S. demissum* derived R1 gene confers race specific resistance to late blight, the recently cloned *S. bulbocastanum* derived gene Rpi-blb (or RB or Sbu1) confers full resistance to a range of *P. infestans* isolates carrying multiple virulence factors and race-specificity has not yet been demonstrated. Furthermore, as described before, progeny plants of somatic hybrids containing Rpi-blb were unaffected by late blight on field experiments in Mexico, where nearly every race of the fungus is found. Through complementation of the susceptible phenotype in cultivated potato and tomato the potential of interspecific transfer of broad-spectrum late blight resistance to cultivated Solanaceae from sexually incompatible host species by transformation with single cloned R genes was demonstrated. U.S. Pat. No. 6,127,607 describes resistance proteins with LRR domains and P-loops. The content of U.S. Pat. No. 6,127,607 is herewith incorporated by reference. In particular columns 6 to 8 and col. 11 describe LRR domains and P-loops. Furthermore Song, 2003, PNAS 100 (16), 9128-9133 shows a comparison of Rpi-blb LRR motifs in FIG. 4 and gives on pages 9132 an over-view about LRR domains. The domains of the polypeptid of the present invention are shown in FIG. 14 as well as in FIG. 15.

Preferably the activity of one or more resistance protein(s) selected from the group consisting of Rpi-blb (synonym RB or Sbu1), Rpi-ABPT1, Rpi-blb3, Rpi-mcd, R1, R-ber (synonym R12), Rpi1, R2, R3a, R3b, R4, R5, R6, R7, R8, R9, R10, R11, Ph-1, Ph-2 and Ph-3 is increased. Preferred is that in addition to Rpi-blb2 at least also the Rpi-blb activity is increased.

In one embodiment of the present invention, the expression of an, e.g. transgenic, Rpi-blb2 protein is increased and further a transgenic resistance gene's expression is increased. The resistance protein coexpressed with the Rpi-blb2 (or RB or Sbu1) is preferably one of the resistance proteins mentioned herein, in particular Rpi-blb, Rpi-ABPT1, Rpi-blb3, R1, Rpi1, R-ber, Rpi-mcd, R2, R3a, R3b, R6, R7, Ph-1, Ph-2 or Ph-3 but can also be one of the others resistance to plant pathogens conferring proteins known to a person skilled in the art.

As mentioned, the term "increased expression" according to this invention also includes a de novo-Expression of a polynucleotide or polypeptide.

Most preferred is an increase of resistance via coexpression of the polypeptid of the present invention together with Rpi-blb. Rpi-blb and Rpi-blb2 provide both full resistance in detached leaf assays to *P. infestans* isolates as described in the examples, and in Song 2003, PNAS 100 (16), 9128.

Said resistance conferring genes are for example described in

RB or Sbu1 (synonym of Rpi-blb): AY336128 [gi: 32693280], (Song et al., 2003). BAC clones 177 013 and CB3A14 comprising the Rpi-blb gene have been deposited in GenBank with accession nos AY303171 and AY303170.

R1: AF447489 [gi: 9117432422], (Ballvora et al., 2002)

Rpi1: Kuhl, J. C., Hanneman, R. E., and Havey, M. J., (2201) Characterization and mapping of Rpi1, a late blight resistance locus from diploid (1EBN) Mexican *Solanum pinnatisectum*. Molecular genet. Genomics 265: 977-985.

R-ber: Ewing, E. E., Simko, I., Smart, C. D., Bonierbale, M. W., Mizubuti, E. S. G., May, G. D., and Fry, W. E., (2000) Genetic mapping from field tests of qualitative and quantitative resistance to *Phytophthora infestans* in a population derived from *Solanum tuberosum* and *Solanum berthaultii*. Molecular breeding 6:25-36.

R2: Li, X., vanEck, H. J., vanderVoort, J. N. A. M., Huigen, D. J., Stam, P., and Jacobsen, E. (1998) Autotetraploids and genetic mapping using common AFLP markers: the R2 allele conferring resistance to *Phytophthora infestans* mapped on potato chromosome 4. Theoretical and Applied Genetics 96 (8): 1121-112.

R3, R6, R7: Elkharbotly, A., Palominosanchez, C., Salamini, F., Jacobsen, E., and Gebhardt, C. (1996) R6 and R7 alleles of potato conferring race-specific resistance to *Phytophthora infestans* (Mont) de Bary identified genetic loci clustering with the R3 locus on chromosome XI. Theoretical and Applied. Genetics 92 (7): 880-884.

Ph-1: Bonde and Murphy (1952) Main Agric. Exp. Stn. Bull. No 497

Ph-2: Moreau, P., Thoquet, P., Olivier, J., Laterrot, H., and Grimsley, N. H. (1998) Genetic mapping of Ph-2, a single locus controlling partial resistance to *Phytophthora infestans* in tomato. Molecular Plant Microbe Interactions 11 (4): 259-269.

Ph-3: Chunwongse, J., Chunwongse, C., Black, L., and Hanson, P. (2002) Molecular mapping of the Ph-3 gene for late blight resistance in tomato. Journal of Horticultural Science & Biotechnology 77 (3): 281-286.

Rpi-blb3, Rpi-ABPT1 and Rpi-mcd: Park, T. H., Van der Vossen, E., Vleeshouwers, V. G. A. A., Tan, A., Visser, R. G. F. and Van Eck, H. J. 2004. Major resistance genes for tuber and leaf resistance to *Phytophthora infestans* in potato: An outline of a PhD project. Crop Functional Genomics 2004, July 2004, Jeju, Korea, page 93.

R3a and R3b: Huang, S., Vleeshouwers, V. G. A. A., Werij, J. S., Hutten, R. C. B., Van Eck, H. J., Visser, R. G. F, and Jacobsen, E. (2004). The R3 resistance to *Phytophthora infestans* in potato is conferred by two closely linked R genes with distinct specificities. MPMI 17 (4), 428-435.

In one embodiment, the activity of the Rpi-blb2 is increased according to the present invention, e.g. the polynucleotide of the invention's expression is increased and the expression of at least one nucleic acid molecule is increased encoding Rpi-blb, Rpi-ABPT1, Rpi-blb3, Rpi-mcd R1, R-ber, Rpi1, R2, R3a, R3b, R6, R7, Ph-1, Ph-2 and/or Ph-3 whereby the nucleic acid molecule is selected from the group consisting of:

a) nucleic acid molecule encoding at least a mature form of at least
   a Rpi-blb (or RB- or Sbu1-) polypeptide, preferably as encoded by the sequence shown in GenBank Accession no.: AY336128 [gi: 32693280];

a R1 polypeptide, preferably as encoded by the sequence shown in GenBank Accession no.: AF447489 [gi 9117432422];

a Rpi-blb3, Rpi-ABPT1 and/or Rpi-mcd polypeptide, preferably encoded by the sequence shown in or derivable by the information given in Park, T. H., Van der Vossen, E., Vleeshouwers, V. G. A. A., Tan, A., Visser, R. G. F. and Van Eck, H. J. 2004. Major resistance genes for tuber and leaf resistance to *Phytophthora infestans* in potato: An outline of a PhD project. Crop Functional Genomics 2004, July 2004, Jeju, Korea, page 93;

a R3a and/or R3b polypeptide, preferably encoded by the sequence shown in or derivable by the information given in Huang, S., Vleeshouwers, V. G. A. A., Werij, J. S., Hutten, R. C. B., Van Eck, H. J., Visser, R. G. F, and Jacobsen, E. (2004). The R3 resistance to *Phytophthora infestans* in potato is conferred by two closely linked R genes with distinct specificities. MPMI 17 (4), 428-435 and/or a pathogen, preferably *P. infestans*, resistance conferring protein mapped and characterized as described, e.g. as for for Rpi1 in Kuhl, J. C., Hanneman, R. E., and Havey, M. J., (2001) Characterization and mapping of Rpi1, a late blight resistance locus from diploid (1EBN) Mexican *Solanum pinnatisectum*. Molecular genet. Genomics 265: 977-985;

for R-ber in Ewing, E. E., Simko, I., Smart, C. D., Bonierbale, M. W., Mizubuti, E. S. G., May, G. D., and Fry, W. E., (2000) Genetic mapping from field tests of qualitative and quantitative resistance to *Phytophthora infestans* in a population derived from *Solanum tuberosum* and *Solanum berthaultii*. Molecular breeding 6:25-36;

for R2 in L1, X., vanEck, H. J., vanderVoort, J. N. A. M., Huigen, D. J., Stam, P., and Jacobsen, E. (1998) Autotetraploids and genetic mapping using common AFLP markers: the R2 allele conferring resistance to *Phytophthora infestans* mapped on potato chromosome 4. Theoretical and Applied Genetics 96 (8): 1121-1128;

for R3, R6, R7 in Elkharbotly, A., Palominosanchez, C., Salamini, F., Jacobsen, E., and Gebhardt, C. (1996) R6 and R7 alleles of potato conferring race-specific resistance to *Phytophthora infestans* (Mont) de Bary identified genetic loci clustering with the R3 locus on chromosome XI. Theoretical and Applied. Genetics 92 (7): 880-884;

for Ph-1 in Bonde and Murphy (1952) Main Agric. Exp. Stn. Bull. No 497; or for Ph-2 in Moreau, P., Thoquet, P., Olivier, J., Laterrot, H., and Grimsley, N. H. (1998) Genetic mapping of Ph-2, a single locus controlling partial resistance to *Phytophthora infestans* in tomato. Molecular Plant Microbe Interactions 11 (4): 259-269; and/or for Ph-3 in Chunwongse, J., Chunwongse, C., Black, L., and Hanson, P. (2002) Molecular mapping of the Ph-3 gene for late blight resistance in tomato. Journal of Horticultural Science & Biotechnology 77 (3): 281-286;

or a pathogen resistance conferring polypeptide, preferably *P. infestans* resistance conferring polypeptide derivable from said publications;

b) nucleic acid molecule the nucleotide sequence of which is degenerate as a result of the genetic code to a nucleotide sequence of (a);

c) nucleic acid molecule encoding a polypeptide derived from the polypeptide encoded by a polynucleotide of (a) or (b) by way of substitution, deletion and/or addition of one or several amino acids of the amino acid sequence of the polypeptide encoded by a polynucleotide of (a) or (b);

d) nucleic acid molecule encoding a polypeptide the sequence of which has an identity of 70% or more to the amino acid sequence of the polypeptide encoded by a nucleic acid molecule of (a);

e) nucleic acid molecules comprising a fragment or a epitopebearing portion of a polypeptide encoded by a nucleic acid molecule of any one of (a) to (d);

f) nucleic acid molecule encoding a fragment beginning with amino acid: 1, 30, 50, 100, 200, 500 or 1000, and stopping with amino acid 1267, 1000, 500, 300, 200, 50, 30, or 1 of a polypeptide encoded by any one of (a) to (e) and with one of said activities;

g) nucleic acid molecule comprising at least 20 nucleotides of a polynucleotide of any one of (a) or (b);

h) nucleic acid molecule encoding a polypeptide being recognized by a monoclonal antibody that have been raised against a polypeptide encoded by a nucleic acid molecule of any one of (a) to (f);

i) nucleic acid molecule obtainable by screening an appropriate library under stringent conditions with a probe having the sequence of the nucleic acid molecule of any one of (a) to (h) or of a fragment thereof of at least 20, preferable 30 or more nucleotides; and j) nucleic acid molecule the complementary strand of which hybridises under stringent conditions with a nucleic acid molecule of any one of (a) or (i);

or the complementary strand of any one of (a) to (j).

Accordingly, the method of present invention confers resistance of one of said plants, plant tissue or plant cell of the present invention to a plant pathogen of a phylum Oomycetes, preferably to a pathogen of the order Pythiales or Peronosperales, more preferred to the family Pythiaceae or Peronosporaceae, more preferred of the genus *Phytophthora* or *Bremia* or *Peronospera* or *Plasmopara*, most preferred wherein the pathogen is of the species *Phytophthora parasitica* var. *nicotianae* (causing, amongst others, black shank in tobacco), *Phytophthora sojae* (causing *Phytophthora* root rot in soybean), *Phytophthora capsici* (causing rots in pepper and cucurbits and tomato), *Phytophthora erythroseptica* (causing Pink rot in potato), *Plasmopara viticola* (causing grapevine downy mildew), *Bremia lactuca* (causing downy mildew in lettuce) or *Peronospora tabaci* (causing blue mould in tobacco).

The activity of Rpi-blb2 in a plant, a plant cell, a plant tissue, a plant organ or part thereof according to the present invention can be increased, generated or stimulated via methods which are well known to a person skilled in the art and e.g. are described in Sambrook et al., Cold Spring Harbor Laboratory Press, NY, 1989.

Thus, in a preferred embodiment, the present invention relates to the method of the invention, wherein the expression is a de novo expression.

The term "de novo-Expression" in a cell, a tissue or in an organism or in a part thereof as understood herein relates to the expression of a gene product after a previous non-detectability of said gene product or an activity of said gene product, in particular of a corresponding polypeptide or polynucleotide in a cell, a tissue or in an organism or in a part thereof. Preferred is that the gene encoding a polypeptide or a polynucleotide in a cell, a tissue or in an organism or in parts thereof and which should be de novo-expressed is not present in the genome in a cell, a tissue or in an organism or in parts thereof. If the expression of a gene product can not be detected in a cell, a tissue or in an organism or in parts thereof, it is generally assumed that no expression occurs in a cell, a tissue or in an organism or in parts thereof. Accordingly, if the activity can not be detected, it is generally assumed that no corresponding activity exists. A person skilled in the art, however, knows that the detection methods and means develop to higher sensitivity. Thus, in a preferred embodiment, the term "de novo-Expression" relates to a novel or additional expression in systems, where the level of activity, e.g. due to a low expression level or the expression of an (nearly) inactive gene product is too low to confer any resistance to a plant pathogen, in particular to *P. infestans*. A comparison of a knock out strain and a low and/or high-expression strain-phenotype can show, whether any difference in resistance to any of the herein mentioned pathogens is observable.

Accordingly, in another embodiment of the present invention, the endogenous activity of a Rpi-blb2 and/or a further resistance protein is increased.

The level of expression in a cell can be increased by methods known to a person skilled in the art. Several techniques are described herein, e.g. the transgenic expression of the polynucleotide or polypeptide of the present invention. The polynucleotide or polypeptide can be of foreign origin. Preferred is that a polynucleotide of the same genetic origin as the host cell, plant cell, plant tissue, or plant is introduced.

The activity, in particular an endogenous activity but also the activity of a transgenic expressed Rpi-blb2 can be increased by several methods. Accordingly, in a preferred embodiment, the activity of the resistance proteins described herein is increased by one or more of the following steps
a) stabilizing the resistance protein;
b) stabilizing the resistance protein encoding mRNA;
c) increasing the specific activity of the resistance protein;
d) expressing or increasing the expression of a homologous or artificial transcription factor for resistance expression;
e) stimulate resistance protein activity through exogenous inducing factors;
f) expressing a transgenic resistance gene; and/or
g) increasing the copy number of the resistance-encoding gene.

In general an activity in an organism, in particular in a plant cell, a plant, or a plant tissue can be increased by increasing the amount of the specific protein, i.e. of the resistance protein, in said organism. "Amount of protein" is understood as meaning the amount of a polypeptide, preferably Rpi-blb2, in an organism, a tissue, a cell or a cell compartment. "Increase" of the amount of protein means the quantitative increase of the amount of a protein in an organism, a tissue, a cell or a cell compartment—for example by one of the methods described herein below—in comparison with the wild type of the same genus and species, to which this method had not been applied, under otherwise identical conditions (such as, for example, culture conditions, plant age and the like). The increase amounts to at least 10%, preferably at least 20% or at least 50%, especially preferably at least 70% or 90%, very especially preferably at least 100%, most preferably at least 200% or more.

"Increase" of the activity is understood as meaning the increase of the total activity of a protein in an organism, a tissue, a cell or a cell compartment in comparison with the wild type of the same genus and species, to which this method had not been applied, under otherwise identical conditions (such as, for example, culture conditions, plant age and the like). The increase amounts to at least 10%, preferably at least 20% or at least 50%, especially preferably at least 70% or 90%, very especially preferably at least 100%, most preferably at least 200% or more.

In this context, the efficacy of the pathogen resistance can deviate both downward or upward in comparison with a value obtained when increasing one of the Rpi-blb2 proteins as shown in SEQ ID NO: 2 or 4. Preferred functional equivalents are those in which the efficacy of the pathogen resistance—measured, for example, by the penetration efficacy of a pathogen or as described herein—differs by not more than 50%, preferably 25%, especially preferably 10% from a comparative value obtained by reducing a Rpi-blb2 protein as shown in SEQ ID NO: 2 or 4. Especially preferred are those sequences where the increase increases the efficacy of pathogen resistance quantitatively by more than 50%, preferably 100%, especially preferably 500%, very especially preferably 1000% based on a comparative value obtained by reducing one of the Rpi-blb2 proteins as shown in SEQ ID NO: 2 or 4.

Any comparison is preferably carried out under analogous conditions. "Analogous conditions" means that all conditions such as, for example, culture or growing conditions, assay conditions (such as buffer, temperature, substrates, pathogen concentration and the like) are kept identical between the experiments to be compared and that the set-ups differ only by the sequence of the Rpi-blb2 polypeptides to be compared, their organism of origin and, if appropriate, the pathogen. When choosing the pathogen, each comparison requires that the pathogen be chosen which is most similar to the other equivalent, taking into consideration the species specificity.

Due to the increased Rpi-blb2 activity, the resistance of a plant or a part thereof is increased. In a preferred embodiment, the method of the present invention results in reduction in the sporulation index of at least 30% after infection with *P. infestans* compared to a wild type, more preferred is a reduction of 50%, even more preferred are 70%, even more preferred are more than 80%, more preferred are 85% and 90%. Most preferred is 95% or more.

Accordingly, the present invention also relates to said polynucleotide of the invention, as defined above encoding a Rpi-blb2 protein comprising a nucleic acid molecule selected from the group consisting of:
a) nucleic acid molecules encoding at least the mature form of the polypeptide depicted in SEQ ID NO: 2 or 4;
b) nucleic acid molecules comprising the coding sequence as depicted in SEQ ID NO: 1 or 3 or 5 or 6 or encoding at least the mature form of the polypeptide;
c) nucleic acid molecules the nucleotide sequence of which is degenerate as a result of the genetic code to a nucleotide sequence of (a) or (b);
d) nucleic acid molecules encoding a polypeptide derived from the polypeptide encoded by a polynucleotide of (a) to (c) by way of substitution, deletion and/or addition of one or several amino acids of the amino acid sequence of the polypeptide encoded by a polynucleotide of (a) to (c);
e) nucleic acid molecules encoding a polypeptide the sequence of which has an identity of 70% or more to the amino acid sequence of the polypeptide encoded by a nucleic acid molecule of (a) or (b);
f) nucleic acid molecules comprising a fragment or a epitope-bearing portion of a polypeptide encoded by a nucleic acid molecule of any one of (a) to (e);
g) nucleic acid molecules comprising a polynucleotide having a sequence of a nucleic acid molecule amplified from a nucleic acid library using the primers as listed in Tab. 3b, preferably ARF1F or ARF1R;
h) nucleic acid molecules encoding polypeptide fragment beginning with amino acid: 1, 30, 50, 100, 200, 300, 500, or 1000 and stopping with, amino acid 1267, 1000, 500, 300, 200, 50, 30, or 1 of a polypeptide encoded by any one of (a) to (g);

i) nucleic acid molecules comprising at least 20 nucleotides of a polynucleotide of any one of (a) or (d);

j) nucleic acid molecules encoding a polypeptide being recognized by a monoclonal antibodies that have been raised against a polypeptide encoded by a nucleic acid molecule of any one of (a) to (h);

k) nucleic acid molecules obtainable by screening an appropriate library under stringent conditions with a probe having the sequence of the nucleic acid molecule of any one of (a) to (j) or of a fragment thereof of at least 15, preferable 30, 60, 90 or more nucleotides; and l) nucleic acid molecules the complementary strand of which hybridises under stringent conditions with a nucleic acid molecule of any one of (a) or (k);

or the complementary strand of any one of (a) to (l);

or encoding a polypeptide encoded by a segment of chromosome 6 or of linkage group 6 of *Solanum bulbocastanum* which co-segregates with a marker selected from table 3a or 3b and which mediates resistance to plant pathogens, preferably of the phylum Oomycetes;

In one embodiment, the polynucleotide of the invention does not consist of the sequence depicted in Seq. ID NO.: 7 and/or 9 and/or does not consist of the sequence of a nucleic acid molecule encoding a protein depicted in Seq. ID NO.: 8 and/or 10.

In one embodiment, the polynucleotide of the present invention does not consist of the sequence of a nucleic acid molecule of Mi1.1 or Mi1.2 and/or of a nucleic acid molecule encoding a Mi1.1 or Mi1.2 protein.

Thus, in one embodiment, the polynucleotide of the present invention may not consist of the sequences shown in Rossi et al. 1998, PNAS USA 95:9750-9754, Milligan et al., 1998. Plant Cell 10:1307-1319; and/or WO 9806750.

In an further embodiment, the polynucleotide of the present invention is derived or isolated from the genome of a organism selected from the group consisting of Menyanthaceae, Solanaceae, Sclerophylacaceae, Duckeodendraceae, Goetzeaceae, Convolvulaceae, Cuscutaceae, Polemoniaceae, and Hydrophyllaceae according to the Systema Naturae 2000, Brands, S. J., Amsterdam or has its origin thereof, more preferably it is selected from the group consisting of *Atropa, Browallia, Brunfelsia, Capsicum, Cestrum, Cyphomandra, Datura, Fabiana, Frariciscea, Hyoscyamus, Lycium, Mandragora, Nicandra, Nicotiana, Petunia, Physalis, Schizanthus* and *Solanum* according to the Systema Naturae 2000, Brands, S. J., Amsterdam or has its origin thereof, even more preferred is a selection out of the group consisting of Solanaceae family, preferably *S. bulbocastanum*, potato (*S. tuberosum*), tomato (*S. lycopersicum*), *petunia*, tree tomato (*S. betaceum*), pear melon (*S. muricatum*) and eggplant (*S. melongena*). Even more preferred are tomato or potato or *S. bulbocastanum* as source for the polynucleotide of the present invention. Most preferred is *S. bulbocastanum* as source.

Rpi-blb2 has been isolated from *S. tuberosum* material derived form ABPT. Thus, from taxonomic perspective the Rpi-blb2 described is also *S. tuberosum-derived*. However, the gene was present on an introgression fragment presumably derived from *S. bulbocastanum*. A lot of *S. tuberosum* varieties contain introgression fragments of related *Solanum* species, but still are *S. tuberosum*. Therefore, *S. tuberosum* can according to the taxonomical system also be a source for the polynucleotide of the present invention, in particular ABPT-derived *S. tuberosum*, as well as other varieties of other *Solanum* species varieties derived in a similar way.

Accordingly, in another embodiment the polynucleotide of the present invention is derived from *S. tuberosum*.

A polynucleotide of the present invention, e.g., a nucleic acid molecule having a nucleotide sequence of Seq ID NO: 1 or 3 or 5 or 6, or a portion thereof, can be isolated using standard molecular biology techniques and the sequence information provided herein. For example, Rpi-blb2 cDNA can be isolated from a library using all or portion of one of the sequences of the polynucleotide of the present invention as a hybridisation probe and standard hybridisation techniques (e.g., as described in Sambrook et al., Molecular Cloning: A Laboratory Manual. $2^{nd}$, ed., Cold Spring Harbor Laboratory, Cold Spring Harbor Laboratory Press, Cold Spring Harbor, N.Y., 1989). Moreover, a polynucleotide encompassing all or a portion of one of the sequences of the polynucleotide of the present invention can be isolated by the polymerase chain reaction using oligonucleotide primers designed based upon this sequence (e.g., a nucleic acid molecule encompassing all or a portion of one of the sequences of polynucleotide of the present invention). For example, mRNA can be isolated from cells, e.g. *S. bulbocastanum* or another plant (e.g., by the guanidinium-thiocyanate extraction procedure of Chirgwin et al. (1979) Biochemistry 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID No: 1 or 3 or 5 or 6. A polynucleotide of the invention can be amplified using cDNA or, alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to a Rpi-blb2 nucleotide sequence can be prepared by standard synthetic techniques, e.g., using an automated DNA synthesizer.

In an embodiment of the present invention the Rpi-blb 2 protein is encoded by a segment of chromosome 6 or linkage group 6 of *Solanum bulbocastanum* or *S. tuberosum*.

Further the present invention comprises a segment of chromosome 6 or linkage group 6 of *S. bulbocastanum* or *S. tuberosum*. In one preferred embodiment in the method of the present invention the Rpi-blb2 protein expressed is encoded by a polynucleotide comprising a segment of chromosome 6 or linkage group 6 of *S. bulbocastanum*. Preferably said segment a group comprises further cis acting element, e.g. promoters, enhancers, binding sites etc. or trans acting elements, like cofactors, activators or other resistance proteins, which confer an increased resistance. Genomic fragments comprising the Rpi-blb2 gene and further regulatory elements are depicted in Seq. ID NO.: 5 and 6.

A person skilled in the art knows how to obtain a chromosome segment, e.g. by cloning chromosome fragments into BACs, as for example Song, 2003, PNAS 100 (16), 9128 or as described herein and in the references cited herein.

Accordingly, in a further embodiment, the polynucleotide of the present invention or a polynucleotide encoding the Rpi-blb2 protein co-segregates with a marker selected from table 3a or comprises a replication site or hybridisation site for said marker. As described in detail in the examples, the resistance to *P. infestans* could be mapped with the markers depicted in table 3a or 3b. As closer a marker is localized to a gene, as higher is the percentage of lines, i.e. offspring clones, in which the gene co-segregates with said marker. Therefore in a preferred embodiment, the polynucleotide of the present invention co-segregates with the Marker E40M58, CT119 and/or CT216.

In a further embodiment, the present invention relates to a method for making a recombinant vector comprising inserting the polynucleotide of the present invention into a vector or inserting said polynucleotide and a further resistance protein into a vector.

Accordingly, in one further embodiment, the present invention relates to a vector containing the polynucleotide of the present invention or said polynucleotide and a further resistance gene produced by the method of the present invention.

As used herein, the term "vector" refers to a nucleic acid molecule capable of transporting a polynucleotide to which it has been linked. One type of vector is a "plasmid", which refers to a circular double stranded DNA loop into which additional DNA segments can be ligated. Another type of vector is a viral vector, wherein additional DNA or RNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The present invention also relates to cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the nucleic acid molecules and vectors of the invention can be reconstituted into liposomes for delivery to target cells.

In another embodiment, the vector of the present invention or the method of the present invention is characterized therein, that the polynucleotide encoding Rpi-blb2 protein or a further resistance protein is operatively linked to expression control sequences and/or a linked to a nucleic acid sequence encoding a transgenic expression regulating signal allowing expression in prokaryotic or eukaryotic host cells.

In a preferred embodiment, the present invention relates to a vector of the present invention or the method of the present invention in which the polynucleotide encoding Rpi-blb2 protein and/or the further resistance protein is operatively linked to expression control sequences of the same species origin as the polynucleotide encoding Rpi-blb2 protein and/or the further resistance protein.

In the case that a nucleic acid molecule according to the invention is expressed in a cell it is in principle possible to modify the coding sequence in such a way that the protein is located in any desired compartment of the plant cell. These include the nucleus, endoplasmatic reticulum, the vacuole, the mitochondria, the plastids like amyloplasts, chloroplasts, chromoplasts, the apoplast, the cytoplasm, extracellular space, oil bodies, peroxisomes and other compartments of plant cells (for review see Kermode, Crit. Rev. Plant Sci. 15, 4 (1996), 285-423 and references cited therein). The polynucleotide can then operatively be fused to an appropriate polynucleotide, e.g., a vector, encoding a signal for the transport into the desirable compartment.

In another preferred embodiment of the present invention relates to a vector in which the polynucleotide of the present invention is operatively linked to expression control sequences allowing expression in prokaryotic or eukaryotic host cells. The nature of such control sequences differs depending upon the host organism. In prokaryotes, control sequences generally include promoter, ribosomal binding site, and terminators. In eukaryotes, generally control sequences include promoters, terminators and, in some instances, enhancers, transactivators; or transcription factors.

The term "control sequence" is intended to include, at a minimum, components the presence of which are necessary for expression, and may also include additional advantageous components.

The term "operatively linked" refers to a juxtaposition wherein the components so described are in a relationship permitting them to function in their intended manner. A control sequence "operatively linked" to a coding sequence is ligated in such a way that expression of the coding sequence is achieved under conditions compatible with the control sequences. In case the control sequence is a promoter, it is obvious for a skilled person that double-stranded nucleic acid is used.

Operable linkage is to be understood as meaning, for example, the sequential arrangement of a promoter with the nucleic acid sequence to be expressed and, if appropriate, further regulatory elements such as, for example, a terminator in such a way that each of the regulatory elements can fulfil its function when the nucleic acid sequence is expressed recombinantly, depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs.

Operable linkage, and an expression cassette, can be generated by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (N.Y.), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or as a signal peptide, may also be positioned between the two sequences. The insertion of sequences may also lead to the expression of fusion proteins. Preferably, the expression cassette, consisting of a linkage of promoter and nucleic acid sequence to be expressed, can exist in a vector-integrated form and be inserted into a plant genome, for example by transformation.

Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick and Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by polynucleotides as described herein.

The recombinant expression vectors of the invention can be designed for expression of said resistance proteins, preferably Rpi-blb2, in prokaryotic or eukaryotic cells. For example, genes encoding the polynucleotide of the invention can be expressed in bacterial cells such as *E. coli, C. glutamicum, Agrobacterium tumefaciens*, insect cells (using baculovirus expression vectors), yeast and other fungal cells (see Romanos, (1992), Yeast 8: 423-488; van den Hondel, (1991) J. W. Bennet & L. L. Lasure, eds., p. 396-428: Academic Press: San Diego; and van den Hondel, (1991) in: Applied Molecular Genetics of Fungi, Peberdy, eds., p. 1-28, Cambridge University Press: Cambridge), algae (Falciatore et al., 1999, Marine Biotechnology. 1, 3:239-251), and multicellular plant cells (see Schmidt, R. (1988), Plant Cell Rep.: 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds.: Kung und R. Wu, Academic Press (1993), 128-43; Potrykus, Annu. Rev. Plant Physiol. Plant Molec. Biol. 42 (1991), 205-225 (and references cited therein) or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Further, the fusion vector can also encode for additional proteins, which expression supports an increase of the activity of Rpi-blb2 or of the resistance of a plant against plant pathogens, e.g. other resistance proteins. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.).

Examples of suitable inducible non-fusion *E. coli* expression vectors include pTrc (Amann (1988) Gene 69:301-315) and pET 11d (Studier et al., Gene Expression Technology: Methods in Enzymology 185, Academic Press, San Diego, Calif. (1990) 60-89.

One strategy to maximize recombinant protein expression is to express the protein in a host bacterium with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *E. coli* or *C. glutamicum* (Wada et al. (1992) Nucleic Acids Res. 20:2111-2118). Such alteration of nucleic acid sequences of the invention can be carried out by standard DNA synthesis techniques.

Further, the vector can be a yeast expression vector. Examples of vectors for expression in yeast *S. cerivisae* include pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.).

Preferably, the polynucleotide of the present invention or described herein is operatively linked to a plant expression control sequence, e.g. an expression cassettes. A plant expression cassette preferably contains regulatory sequences capable to drive gene expression in plants cells and which are operatively linked so that each sequence can fulfil its function such as termination of transcription such as polyadenylation signals. Preferred polyadenylation signals are those originating from *Agrobacterium tumefaciens* t-DNA such as the gene 3 known as octopine synthase of the Ti-plasmid pTiACH5 (Gielen et al., EMBO J. 3 (1984), 835 ff) or functional equivalents thereof but also all other terminators functionally active in plants are suitable.

As plant gene expression is very often not limited on transcriptional levels as plant expression cassette preferably contains other operatively linked sequences like translational enhancers such as the overdrive-sequence containing the 5'-untranslated leader sequence from tobacco mosaic virus enhancing the protein per RNA ratio (Gallie et al 1987, Nucl. Acids Research 15:8693-8711).

Accordingly, the polynucleotide described herein can be operatively linked to an appropriate promoter conferring gene expression in a timely, cell or tissue specific manner. Preferred are promoters driving constitutitive expression (Benfey et al., EMBO J. 8 (1989) 2195-2202) like those derived from plant viruses like the 35S CAMV (Franck et al., Cell 21(1980) 285-294), the 19S CaMV (see also U.S. Pat. No. 5,352,605 and WO8402913) or plant promoters like those from Rubisco small subunit described in U.S. Pat. No. 4,962,028.

The term plant-specific promoters is understood as meaning, in principle, any promoter which is capable of governing the expression of genes, in particular foreign genes, in plants or plant parts, plant cells, plant tissues or plant cultures. In this context, expression can be, for example, constitutive, inducible, or development-dependent.

The following are preferred:

a) Constitutive Promoters

Preferred vectors are those which make possible constitutive expression in plants (Benfey et al. (1989) EMBO J. 8:2195-2202). "Constitutive" promoter is understood as meaning those promoters which ensure expression in a large number of, preferably all, tissues over a substantial period of plant development, preferably at all stages of plant development. In particular a plant promoter or a promoter derived from a plant virus are preferably used. Particularly preferred is the promoter of the CaMV cauliflower mosaic virus 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J. 8:2195-2202). Another suitable constitutive promoter is the "Rubisco small subunit (SSU)" promoter (U.S. Pat. No. 4,962,028), the leguminB promoter (GenBank Acc. No. X03677), the *Agrobacterium nopaline* synthase promoter, the TR dual promoter, the *Agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), and further promoters of genes whose constitutive expression in plants is known to the skilled worker.

b) Tissue-specific Promoters

Preferred are furthermore promoters with specificity for the anthers, ovaries, flowers, leaves, stems, roots, and seeds.

Seed-specific Promoters such as, for example, the phaseolin promoter (U.S. Pat. No. 5,504,200; Bustos M M et al. (1989) Plant Cell 1(9):839-53), the 2S albumin gene promoter (Joseffson L G et al. (1987) J Biol Chem 262:12196-12201), the legumin promoter (Shirsat A et al. (1989) Mol Gen Genet 215(2): 326-331), the USP (unknown seed protein) promoter (Bäumlein H et al. (1991) Mol Gen Genet 225(3):459-67), the napin gene promoter (U.S. Pat. No. 5,608,152; Stalberg K et al. (1996) L Planta 199:515-519), the sucrose binding protein promoter (WO 00/26388) or the legumin B4 promoter (LeB4; Bäumlein H et al. (1991) Mol Gen Genet 225: 121-128; Baeumlein et al. (1992) Plant Journal 2(2):233-9; Fiedler U et al. (1995) Biotechnology (NY) 13(10):1090f), the *Arabidopsis* oleosin promoter (WO 98/45461), the *Brassica* Bce4 promoter (WO 91/13980). Further suitable seed-specific promoters are those of the genes encoding the high-molecular-weight glutenin (HMWG), gliadin, branching enzyme, ADP glucose pyrophosphatase (AGPase) or starch synthase. Furthermore preferred are promoters which permit seed-specific expression in monocots such as maize, barley, wheat, rye, rice and the like. The following can be employed advantageously: the promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the kasirin gene or the secalin gene).

Tuber-, storage-root-, or root-specific promoters such as, for example, the patatin promoter class I (B33), the potato cathepsin D inhibitor promoter.

Leaf-specific Promoters such as the potato cytosolic FBPase promoter (WO 97/05900), the Rubisco (ribulose-1,5-bisphosphate carboxylase) SSU (small subunit) promoter or the ST-LSI promoter from potato (Stockhaus et al. (1989) EMBO J. 8:2445-2451). Very especially preferred are epidermis-specific promoters such as, for example, the OXLP gene (oxalate-oxidase-like protein) promoter (Wei et al. (1998) Plant Mol. Biol. 36:101-112).

Flower-specific Promoters such as, for example, the phytoene synthase promoter (WO 92/16635) or the promoter of the P-rr gene (WO 98/22593).

Anther-specific Promoters such as the 5126 promoter (U.S. Pat. No. 5,689,049, U.S. Pat. No. 5,689,051), the glob-I promoter and the γ-zein promoter.

c) Chemically Inducible Promoters

The expression cassettes can also comprise a chemically inducible promoter (review article: Gatz et al. (1997) Annu Rev Plant Physiol Plant Mol Biol 48:89-108), by which the expression of the exogenous gene in the plant at a particular point in time can be controlled. Such promoters such as, for example, the PRP1 promoter (Ward et al. (1993) Plant Mol Biol 22:361-366), a salicylic-acid-inducible promoter (WO 95/19443), a benzenesulfonamide-inducible promoter (EP 0 388 186), a tetracycline-inducible promoter (Gatz et al. (1992) Plant J 2:397-404), an abscisic-acid-inducible promoter (EP 0 335 528) or an ethanol- or cyclohexanone-inducible promoter (WO 93/21334) can likewise be used.

d) Stress- or Pathogen-inducible Promoters

Further preferred promoters are those which are induced by biotic or abiotic stress such as, for example, the pathogen-inducible promoter of the PRP1 gene (Ward et al. (1993) Plant Mol Biol 22:361-366), the tomato high-temperature-inducible hsp70 or hsp80 promoter (U.S. Pat. No. 5,187,267), the potato low-temperature-inducible alpha-amylase promoter (WO 96/12814), the light-inducible PPDK promoter, or the wounding-induced pinII promoter (EP375091).

Pathogen-inducible promoters encompass those of genes which are induced as a consequence of infection by pathogens, such as, for example, genes of PR proteins, SAR proteins, β-1,3-glucanase, chitinase and the like (for example Redolfi et al. (1983) Neth J Plant Pathol 89:245-254; Uknes, et al. (1992) The Plant Cell 4:645-656; Van Loon (1985) Plant Mol Virol 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968(1989).

Also encompassed are wounding-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of systemin (McGurl et al. (1992) Science 225:1570-1573), of the WIP1 gene (Rohmeier et al. (1993) Plant Mol Biol 22:783-792; Eckelkamp et al. (1993) FEBS Letters 323:73-76), of the MPI gene (Corderok et al. (1994) The Plant J 6(2):141-150) and the like.

e) Development-dependent Promoters

Further suitable promoters are, for example, fruit-maturation-specific promoters such as, for example, the tomato fruit-maturation-specific promoter (WO 94/21794, EP 409 625). Development-dependent promoters comprise partly the tissue-specific promoters, since individual tissues develop by nature in a development-dependent fashion.

It can be advantageously that the polypeptide of the present invention is only active or has only an increased activity in the tissue which is transfected or penetrated by the pathogen mentioned herein. Especially preferred are constitutive promoters and leaf- and/or stem-specific, pathogen-inducible and epidermis-specific promoters, with pathogen-inducible and epidermis-specific promoters being most preferred. Also preferred is the natural promoter, which is e.g. comprised in the genomic fragment depicted in Seq. ID NO.: 5 and 6.

Furthermore, further promoters may be linked operatively to the nucleic acid sequence to be expressed, which promoters make possible the expression in further plant tissues or in other organisms, such as, for example, E. coli bacteria. Suitable plant promoters are, in principle, all of the above-described promoters.

The term "genetic control sequences" is to be understood in the broad sense and refers to also all those sequences which have an effect on the materialization or the function of the expression cassette according to the invention. For example, genetic control sequences modify the transcription and translation in prokaryotic or eukaryotic organisms. Preferably, the expression cassettes according to the invention encompass the promoter with specificity for the embryonic epidermis and/or the flower 5'-upstream of the nucleic acid sequence in question to be expressed recombinantly, and 3'-downstream a terminator sequence as additional genetic control sequence and, if appropriate, further customary regulatory elements, in each case linked operatively to the nucleic acid sequence to be expressed recombinantly.

Genetic control sequences also encompass further promoters, promoter elements, or minimal promoters, all of which can modify the expression-governing properties. Thus, for example, the tissue-specific expression may additionally depend on certain stressors, owing to genetic control sequences. Such elements have been described, for example, for water stress, abscisic acid (Lam E and Chua N H, J Biol Chem 1991; 266(26): 17131-17135) and heat stress (Schoffl F et al., Molecular & General Genetics 217(2-3):246-53, 1989).

Further advantageous control sequences are, for example, the Gram-positive promoters amy and SPO2, and the yeast or fungal promoters ADC1, MFa, AC, P-60, CYC1, GAPDH, TEF, rp28, ADH.

In principle, all natural promoters with their regulatory sequences like those mentioned above may be used for the method according to the invention. In addition, synthetic promoters may also be used advantageously.

Genetic control sequences furthermore also encompass the 5'-untranslated regions, introns or noncoding 3'-region of genes, such as, for example, the actin-1 intron, or the Adh1-S introns 1, 2, and 6 (general reference: The Maize Handbook, Chapter 116, Freeling and Walbot, Eds., Springer, N.Y. (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5' leader sequence (Gallie et al. (1987) Nucl Acids Res 15:8693-8711) and the like. Furthermore, they may promote tissue specificity (Rouster J et al. (1998) Plant J 15:435-440).

The expression cassette may advantageously comprise one or more of what are known as enhancer sequences, linked operatively to the promoter, which make possible an increased recombinant expression of the nucleic acid sequence. Additional advantageous sequences, such as further regulatory elements or terminators, may also be inserted at the 3' end of the nucleic acid sequences to be expressed recombinantly. One or more copies of the nucleic acid sequences to be expressed recombinantly may be present in the gene construct.

In one embodiment the natural terminator sequence comprised in the genomic fragment depicted in Seq ID No.: 5 and/or 6 is used.

Polyadenylation signals which are suitable as control sequences are plant polyadenylation signals, preferably those which essentially correspond to T-DNA polyadenylation signals from *Agrobacterium tumefaciens*, in particular gene 3' of the T-DNA (octopin synthase) of the Ti plasmid pTiACHS (Gielen et al. (1984) EMBO J 3:835 et seq.) or functional equivalents thereof. Examples of terminator sequences which are especially suitable are the OCS (octopin synthase) terminator and the NOS (nopalin synthase) terminator.

Control sequences are furthermore to be understood as those which make possible homologous recombination or insertion into the genome of a host organism or which permit removal from the genome. In the case of homologous recombination, for example the natural promoter of a particular gene may be exchanged for a promoter with specificity for the embryonic epidermis and/or the flower. Methods such as the cre/lox technology permit a tissue-specific, if appropriate inducible, removal of the expression cassette from the genome of the host organism (Sauer B (1998) Methods. 14(4):381-92). In this method, specific flanking sequences (lox sequences), which later allow removal by means of cre recombinase, are attached to the target gene.

An expression cassette and the vectors derived from it may comprise further functional elements. The term functional element is to be understood in the broad sense and refers to all those elements which have an effect on the generation, amplification, or function of the expression cassettes, vectors, or transgenic organisms according to the invention. The following may be mentioned by way of example, but not by limitation:

a) Selection markers which confer a resistance to a metabolism inhibitor such as 2-deoxyglucose-6-phosphate (WO 98/45456), antibiotics or biocides, preferably herbicides, such as, for example, kanamycin, G 418, bleomycin or hygromycin, or else phosphinothricin and the like. Especially preferred selection markers are those which confer resistance to herbicides. Examples which may be mentioned are: DNA sequences which encode phosphinothricin acetyl transferases (PAT) and which inactivate glutamine synthase inhibitors (bar and pat genes), 5-enolpyruvylshikimate-3-phosphate synthase genes (EPSP synthase genes), which confer resistance to Glyphosater (N-(phosphonomethyl)glycine), the gox gene, which encodes Glyphosater-degrading enzymes (Glyphosate oxidoreductase), the deh gene (encoding a dehalogenase which inactivates dalapon), sulfonylurea- and imidazolinone-inactivating acetolactate synthases, and bxn genes, which encode bromoxynil-degrading nitrilase enzymes, the aasa gene, which confers resistance to the antibiotic apectinomycin, the streptomycin phosphotransferase (SPT) gene, which allows resistance to streptomycin, the neomycin phosphotransferase (NPTII) gene, which confers resistance to kanamycin or geneticidin, the hygromycin phosphotransferase (HPT) gene, which mediates resistance to hygromycin, the acetolactate synthase gene (ALS), which confers resistance to sulfonylurea herbicides (for example mutated ALS variants with, for example, the S4 and/or Hra mutation).

b) Reporter genes which encode readily quantifiable proteins and, via their color or enzyme activity, make possible an assessment of the transformation efficacy, the site of expression or the time of expression. Very especially preferred in this context are genes encoding reporter proteins (Schenborn E, Groskreutz D. Mol Biotechnol. 1999; 13(1): 29-44) such as the green fluorescent protein (GFP) (Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui W L et al. (1996) Curr Biol 6:325-330; Leffel S M et al. (1997) Biotechniques. 23(5):912-8), chloramphenicol transferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates; Dellaporta et al., In: Chromosome Structure and Function: Impact of New Concepts, 18th Stadler Genetics Symposium, 11:263-282, 1988), with β-glucuronidase being very especially preferred (Jefferson et al., EMBO J. 1987, 6, 3901-3907).

c) Origins of replication, which ensure amplification of the expression cassettes or vectors according to the invention in, for example, E. coli. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

d) Elements which are necessary for *Agrobacterium*-mediated plant transformation, such as, for example, the right or left border of the T-DNA or the vir region.

To select cells which have successfully undergone homologous recombination, or else to select transformed cells, it is, as a rule, necessary additionally to introduce a selectable marker, which confers resistance to a biocide (for example herbicide), a metabolism inhibitor such as 2-deoxyglucose-6-phosphate (WO 98/45456) or an antibiotic to the cells which have successfully undergone recombination. The selection marker permits the selection of the transformed cells from untransformed ones (McCormick et al. (1986) Plant Cell Reports 5:81-84).

The introduction of an expression cassette according to the invention into an organism or cells, tissues, organs, parts or seeds thereof (preferably into plants or plant cells, tissue, organs, parts or seeds) can be effected advantageously using vectors which comprise the expression cassettes. The expression cassette can be introduced into the vector (for example a plasmid) via a suitable restriction cleavage site. The plasmid formed is first introduced into E. coli. Correctly transformed E. coli are selected, grown, and the recombinant plasmid is obtained by the methods familiar to the skilled worker. Restriction analysis and sequencing may serve to verify the cloning step.

Further promoters for expression in specific plant parts are e.g. the napin-gene promoter from rapeseed (U.S. Pat. No. 5,608,152), the USP-promoter from *Vicia faba* (Baeumlein et al., Mol Gen Genet, 1991, 225 (3):459-67), the oleosin-promoter from *Arabidopsis* (WO9845461), the phaseolin-promoter from *Phaseolus vulgaris* (U.S. Pat. No. 5,504,200), the Bce4-promoter from *Brassica* (WO9113980) or the legumin B4 promoter (LeB4; Baeumlein et al., 1992, Plant Journal, 2 (2):233-9) as well as promoters conferring seed specific expression in monocot plants like maize, barley, wheat, rye, rice etc. Suitable promoters to note are the lpt2 or lpt1-gene promoter from barley (WO9515389 and WO9523230) or those described in WO9916890 (promoters from the barley hordein-gene, the rice glutelin gene, the rice oryzin gene, the rice prolamin gene, the wheat gliadin gene, wheat glutelin gene, the maize zein gene, the oat glutelin gene, the Sorghum kasirin-gene, the rye secalin gene).

Further, the polynucleotide of the invention can be cloned into the expression vector in an antisense orientation. That is, the DNA molecule is operatively linked to a regulatory sequence in a manner which allows for expression (by transcription of the DNA molecule) of an RNA molecule which is antisense to the mRNA encoded by the polynucleotide of the present invention. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acid molecules are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990, FEBS Letters 268:427-430.

In one embodiment the present invention relates to a method of making a recombinant host cell comprising introducing the vector or the polynucleotide of the present invention or said vector or said polynucleotide and a vector for expressing a further resistance protein into a host cell.

Vector DNA can be introduced into prokaryotic or eukaryotic cells via conventional transformation or transfection techniques. As used herein, the terms "transformation" and "transfection", conjugation and transduction are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J.

For stable transfection of eukaryotic cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, and methotrexate or in plants that confer resistance towards a herbicide such as glyphosate or glufosinate. Nucleic acid encoding a selectable marker can be introduced into a host cell on the same vector as that encoding the polypeptide of the present invention or can be introduced on a separate vector. Cells stably transfected with the introduced nucleic acid can be identified by, for example, drug selection (e.g., cells that have incorporated the selectable marker gene will survive, while the other cells die).

Further host cells can be produced which contain selection systems which allow for regulated expression of the introduced gene. For example, inclusion of the polynucleotide of the invention on a vector placing it under control of the lac operon permits expression of the polynucleotide only in the presence of IPTG. Such regulatory systems are well known in the art.

Preferably, the introduced nucleic acid molecule is foreign to the host cell.

By "foreign" it is meant that the nucleic acid molecule is either heterologous with, respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination (Paszkowski (ed.), Homologous Recombination and Gene Silencing in Plants. Kluwer Academic Publishers (1994)).

Accordingly, in another embodiment the present invention relates to a host cell genetically engineered with the polynucleotide of the invention or the vector of the invention, or said vector or said polynucleotide and a vector or a polynucleotide for expressing a further resistance protein.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

For example, a polynucleotide of the present invention can be introduced in bacterial cells, insect cells, fungal cells or mammalian cells (such as Chinese hamster ovary cells (CHO) or COS cells), algae, ciliates, plant cells or fungi. Suitable host cells are known to those skilled in the art. Preferred are *E. coli*, baculovirus, *Agrobacterium*, or plant cells.

Further, the host cell can also be transformed such that further enzymes and proteins are (over)expressed which expression supports an increase of resistance of a plant to pathogens. Preferably, a further resistance gene is also expressed, preferably one or more resistance genes, preferably the genes as mentioned herein, is/are also expressed. Most preferred is a coexpression of Rpi-blb2 and Rpi-blb.

Further preferred are cells of one of herein mentioned plants, in particular, of one of the above-mentioned Solanaceae, most preferred are potato, tomato, *petunia*, tree tomato, pear melon, or eggplant.

In another embodiment, the present invention relates to a process for the production of the polypeptide of the present invention, in particular of a protein having Rpi-blb2 activity comprising culturing the host cell of the invention and recovering the polypeptide encoded by said polynucleotide and expressed by the host cell from the culture or the cells.

The term "expression" means the production of a protein or nucleotide sequence in the cell. However, said term also includes expression of the protein in a cell-free system. It includes transcription into an RNA product, post-transcriptional modification and/or translation to a protein product or polypeptide from an DNA encoding that product, as well as possible post-translational modifications.

Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the protein into the culture medium, etc. Furthermore, such a protein and fragments thereof can be chemically synthesized and/or modified according to standard methods described, for example herein below.

A host cell of the invention, such as a prokaryotic or eukaryotic host cell in culture, can be used to produce (i.e., express) the polypeptide encoded by the polynucleotide of the invention, preferably a polypeptid having Rpi-blb2 activity. An alternate method can be applied in addition in plants by the direct transfer of DNA into developing flowers via electroporation or *Agrobacterium* mediated gene transfer. Accordingly, the invention further provides methods for producing Rpi-blb2 using the host cells of the invention. In one embodiment, the method comprises culturing the host cell of invention in a suitable medium such that the polypeptid of the present invention is produced. Further, the method comprises isolating and/or recovering said polypeptid from the medium or the host cell.

The polypeptide of the present invention is preferably produced by recombinant DNA techniques. For example, a nucleic acid molecule encoding the protein is cloned into an expression vector (as described above), the expression vector is introduced into a host cell (as described above) and said polypeptide is expressed in the host cell. Said polypeptide can then be isolated from the cells by an appropriate purification scheme using standard protein purification techniques. Alternative to recombinant expression, the polypeptide or peptide of the present invention can be synthesized chemically using standard peptide synthesis techniques. Moreover, native Rpi-blb2 can be isolated from cells (e.g., endothelial cells), for example using the antibody of the present invention as described below, in particular, an anti-Rpi-blb2 antibody, which can be produced by standard techniques utilizing the polypeptid of the present invention or fragment thereof, i.e., the polypeptide of this invention.

In one embodiment, the present invention relates to a Rpi-blb2 protein or a protein having Rpi-blb2 activity.

In one embodiment, the present invention relates to a polypeptide having the amino acid sequence encoded by a polynucleotide of the invention or obtainable by a process of the invention.

In one embodiment the polypeptide of the does not consist of the sequence depicted in Seq. ID NO.: 8 and/or 10 and/or does not consist of the sequence encoded by a nucleic acid molecule depicted in Seq. ID NO.: 7 and/or 9.

In one embodiment, the polypeptide of the present invention does not consist of the sequence of Mi1.1 or Mi.1.2 protein and/or of a protein encoded by a nucleic acid molecule encoding a Mi1.1 or Mi1.2 protein.

Thus, in one embodiment, the polypeptide of the present invention may not consist of the sequences shown in Rossi et al. 1998, PNAS USA 95:9750-9754, Milligan et al., 1998. Plant Cell 10:1307-1319; and/or WO 9806750.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

Preferably, the polypeptide is isolated. An "isolated" or "purified" protein or biologically active portion thereof is substantially free of cellular material when produced by recombinant DNA techniques, or chemical precursors or other chemicals when chemically synthesized.

The language "substantially free of cellular material" includes preparations of the polypeptide of the invention in which the protein is separated from cellular components of the cells in which it is naturally or recombinantly produced. In one embodiment, the language "substantially free of cellular material" includes preparations having less than about 30% (by dry weight) of "contaminating protein", more preferably less than about 20% of "contaminating protein", still more preferably less than about 10% of "contaminating protein", and most preferably less than about 5% "contaminating protein". The term "Contaminating protein" relates to polypeptides which are not polypeptides of the present invention. When the polypeptide of the present invention or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations in which subject of the present invention, e.g. the polypeptide of the present invention, is separated from chemical precursors or other chemicals which are involved in the synthesis of the protein. The language "substantially free of chemical precursors or other chemicals" includes preparations having less than about 30% (by dry weight) of chemical precursors or non-Rpi-blb2 chemicals, more preferably less than about 20% chemical precursors or non-Rpi-blb2 chemicals, still more preferably less than about 10% chemical precursors or non-Rpi-blb2 chemicals, and most preferably less than about 5% chemical precursors or non-Rpi-blb2 chemicals. In preferred embodiments, isolated proteins or biologically active portions thereof lack contaminating proteins from the same organism from which the polypeptide of the present invention is derived. Typically, such proteins are produced by recombinant DNA techniques.

A polypeptide of the invention can participate in the polypeptide or portion thereof comprises preferably an amino acid sequence which is sufficiently homologous to an amino acid sequence of SEQ ID No: 2 or 4 such that the protein or portion thereof maintains the ability to confer the resistance of the present invention. The portion of the protein is preferably a biologically active portion as described herein. Preferably, the polypeptide of the invention has an amino acid sequence identical as shown in SEQ ID No: 2 or 4. Further, the polypeptide can have an amino acid sequence which is encoded by a nucleotide sequence which hybridises, preferably hybridises under stringent conditions as described above, to a nucleotide sequence of the polynucleotide of the present invention. Accordingly, the polypeptide has an amino acid sequence which is encoded by a nucleotide sequence that is at least about 70%, preferably at least about 75%, more preferably at least about 80%, 90%, 95%, and even more preferably at least about 96%, 97%, 98%, 99% or more homologous to one of the amino acid sequences of SEQ ID No: 2 or 4. The preferred polypeptide of the present invention preferably possess at least one of the Rpi-blb2 protein activities described herein, e.g. its resistance or immunological activities. A preferred polypeptide of the present invention includes an amino acid sequence encoded by a nucleotide sequence which hybridises, preferably hybridises under stringent conditions, to a nucleotide sequence of SEQ ID No: 1 or 3 or 5 or 6 or which is homologous thereto, as defined above.

Accordingly the polypeptide of the present invention can vary from SEQ ID No: 2, or 4 in amino acid sequence due to natural variation or mutagenesis, as described in detail herein. Accordingly, the polypeptide comprise an amino acid sequence which is at least about 70%, preferably at least about 75%, and more preferably at least about 80, 90, 95%, and most preferably at least about 96%, 97%, 98%, 99% or more homologous to an entire amino acid sequence of SEQ ID No:1 or 3 or 5 or 6.

Biologically active portions of an polypeptide of the present invention include peptides comprising amino acid sequences derived from the amino acid sequence of a Rpi-blb2 protein, e.g., the amino acid sequence shown in SEQ ID No: 2 or 4 or the amino acid sequence of a protein homologous thereto, which include fewer amino acids than a full length Rpi-blb2 protein or the full length protein which is homologous to a Rpi-blb2 protein depicted herein, and exhibit at least one activity of Rpi-blb2 protein. Typically, biologically (or immunological) active portions i.e. peptides, e.g., peptides which are, for example, 5, 10, 15, 20, 30, 35, 36, 37, 38, 39, 40, 50, 100 or more amino acids in length comprise a domain or motif with at least one activity or epitope of a Rpi-blb2 protein. Moreover, other biologically active portions, in which other regions of the polypeptide are deleted, can be prepared by recombinant techniques and evaluated for one or more of the activities described herein.

Manipulation of the Rpi-blb2 polynucleotide of the invention may result in the production of Rpi-blb2 having functional differences from the wild-type Rpi-blb2 protein. These proteins may be improved in efficiency or activity, may be present in greater numbers in the cell than is usual, or may be decreased in efficiency or activity.

Any mutagenesis strategies for Rpi-blb2 to result in increased said resistance or a resistance to another plant pathogen species or an other strain of a plant pathogen species aforementioned, of said compound are not meant to be limiting; variations on these strategies will be readily apparent to one skilled in the art. Using such strategies, and incorporating the mechanisms disclosed herein, the polynucleotide and polypeptide of the invention may be utilized to generate plants or parts thereof; expressing wild type Rpi-blb2 or mutated Rpi-blb2 polynucleotide and protein molecules such that the yield, production, and/or efficiency of production of a desired compound is improved. This desired compound may be any natural product of plants, which includes the final products of biosynthesis pathways and intermediates of naturally-occurring metabolic pathways, as well as molecules which do not naturally occur in the metabolism of said cells, but which are produced by a said cells of the invention.

The invention also provides chimeric or fusion proteins.

As used herein, a "chimeric protein" or "fusion protein" comprises an polypeptide operatively linked to a non-Rpi-blb2 polypeptide.

An "Rpi-blb2 polypeptide" refers to a polypeptide having an amino acid sequence corresponding to polypeptide having a Rpi-blb2 activity, whereas a "non-Rpi-blb2 polypeptide" refers to a polypeptide having an amino acid sequence corresponding to a protein which is not substantially homologous to the Rpi-blb2, e.g., a protein which does not confer the resistance described herein, in particular does not confer resistance to *P. infestans* and which is derived from the same or a different organism. Within the fusion protein, the term "operatively linked" is intended to indicate that the Rpi-blb2 polypeptide and the non-Rpi-blb2 polypeptide are fused to each other so that both sequences fulfil the proposed function addicted to the sequence used. The non-Rpi-blb2 polypeptide can be fused to the N-terminus or C-terminus of the Rpi-blb2 polypeptide. For example, in one embodiment the fusion protein is a GST-LMRP fusion protein in which the Rpi-blb2 sequences are fused to the C-terminus of the GST sequences. Such fusion proteins can facilitate the purification of recombinant Rpi-blb2. In another embodiment, the fusion protein is a Rpi-blb2 containing a heterologous signal sequence at its N-terminus. In certain host cells (e.g., mammalian host cells), expression and/or secretion of a Rpi-blb2 can be increased through use of a heterologous signal sequence.

Preferably, a Rpi-blb2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). The polynucleotide of the invention can be cloned into such an expression vector such that the fusion moiety is linked in-frame to the encoded protein.

Furthermore, folding simulations and computer redesign of structural motifs of the protein of the invention can be performed using appropriate computer programs (Olszewski, Proteins 25 (1996), 286-299; Hoffman, Comput. Appl. Biosci. 11 (1995), 675-679). Computer modelling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of mitogenic cyplin and its receptor, its ligand or other interacting proteins by computer assistant searches for complementary peptide sequences (Fassina, Immunomethods (1994), 114-120. Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used for, e.g., the preparation of peptidomimetics of the protein of the invention or fragments thereof. Such pseudopeptide analogues of the, natural amino acid sequence of the protein may very efficiently mimic the parent protein (Benkirane, J. Biol. Chem. 271 (1996), 33218-33224). For example, incorporation of easily available achiral Q-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769-777).

Superactive peptidomimetic analogues of small peptide hormones in other systems are described in the prior art (Zhang, Biochem. Biophys. Res. Commun. 224 (1996), 327-331). Appropriate peptidomimetics of the protein of the present invention can also be identified by the synthesis of peptidomimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

Furthermore, a three-dimensional and/or crystallographic structure of the protein of the invention can be used for the design of peptidomimetic inhibitors of the biological activity of the protein of the invention (Rose, Biochemistry 35 (1996), 12933-12944; Rutenber, Bioorg. Med. Chem. 4 (1996), 1545-1558).

In a further embodiment, the present invention relates to an antibody that binds specifically to the polypeptide of the present invention or parts, i.e. specific fragments or epitopes of such a protein.

The antibodies of the invention can be used to identify and isolate Rpi-blb2 and genes in any organism, preferably plants, prepared in plants described herein. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfr6, Meth. Enzymol. 73 (1981), 3, which comprise the fusion of mouse myeloma cells to spleen cells derived from immunized mammals.

Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97-105; Malmborg, J. Immunol. Methods 183 (1995), 7-13).

In many cases, the binding phenomena of antibodies to antigens is equivalent to other ligand/anti-ligand binding.

In one embodiment, the present invention relates to an antisense nucleic acid molecule comprising the complementary sequence of the polypeptide of the present invention.

Methods to modify the expression levels and/or the activity are known to persons skilled in the art and include for instance overexpression, co-suppression, the use of ribozymes, sense and anti-sense strategies, gene silencing approaches. "Sense strand" refers to the strand of a double-stranded DNA molecule that is homologous to a mRNA transcript thereof. The "anti-sense strand" contains an inverted sequence which is complementary to that of the "sense-strand".

An "antisense" nucleic acid molecule comprises a nucleotide sequence which is complementary to a "sense" nucleic acid molecule encoding a protein, e.g., complementary to the coding strand of a double-stranded cDNA molecule or complementary to an mRNA sequence. Accordingly, an antisense nucleic acid molecule can hydrogen bond to a sense nucleic acid molecule. The antisense nucleic acid molecule can be complementary to an entire Rpi-blb2 coding strand, or to only a portion thereof. Accordingly, an antisense nucleic acid molecule can be antisense to a "coding region" of the coding strand of a nucleotide sequence of a polynucleotide of the present invention. The term "coding region" refers to the region of the nucleotide sequence comprising codons which are translated into amino acid residues. Further, the antisense nucleic acid molecule is antisense to a "noncoding region" of the coding strand of a nucleotide sequence encoding Rpi-blb2. The term "noncoding region" refers to 5' and 3' sequences which flank the coding region that are not translated into a polypeptide, i.e., also referred to as 5' and 3' untranslated regions (5'-UTR or 3'-UTR).

Given the coding strand sequences encoding Rpi-blb2 disclosed herein, antisense nucleic acid molecules of the invention can be designed according to the rules of Watson and Crick base pairing. The antisense nucleic acid molecule can be complementary to the entire coding region of Rpi-blb2 mRNA, but can also be an oligonucleotide which is antisense to only a portion of the coding or noncoding region of Rpi-blb2 mRNA. For example, the antisense oligonucleotide can be complementary to the region surrounding the translation start site of Rpi-blb2 mRNA. An antisense oligonucleotide can be, for example, about 5, 10, 15, 20, 25, 30, 35, 40, 45, or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)racil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a polynucleotide has been subcloned in an antisense orientation (i.e., RNA transcribed from the inserted polynucleotide will be of an antisense orientation to a target polynucleotide of interest, described further in the following subsection).

The antisense nucleic acid molecules of the invention are typically administered to a cell or generated in situ such that they hybridise with or bind to cellular mRNA and/or genomic DNA encoding a Rpi-blb2 to thereby inhibit expression of the protein, e.g., by inhibiting transcription and/or translation. The hybridisation can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In a further embodiment, the antisense nucleic acid molecule of the invention can be an anomeric nucleic acid molecule. An α-anomeric nucleic acid molecule forms specific double-stranded hybrids with complementary RNA in which, contrary to the usual units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

Further the antisense nucleic acid molecule of the invention can be a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave Rpi-blb2 mRNA transcripts to thereby inhibit translation of mRNA. A ribozyme having specificity for a Rpi-blb2-encoding nucleic acid molecule can be designed based upon the nucleotide sequence of a Rpi-blb2 cDNA disclosed herein or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an encoding mRNA. See, e.g., Cech et al. U.S. Pat. No. 4,987,071 and Cech et al. U.S. Pat. No. 5,116,742. Alternatively, Rpi-blb2 mRNA can be used to select a catalytic RNA having a specific ribonuclease activity from a pool of RNA molecules. See, e.g., Bartel, D. and Szostak, J. W. (1993) Science 261:1411-1418.

The antisense molecule of the present invention comprises also a polynucleotide comprising a nucleotide sequences complementary to the regulatory region of a Rpi-blb2 nucleotide sequence, e.g., its promoter and/or enhancers, e.g. to form triple helical structures that prevent transcription of the gene in target cells. See generally, Helene, C. (1991) Anticancer Drug Des. 6(6):569-84; Helene, C. et al. (1992) Ann. N.Y. Acad. Sci. 660:27-36; and Maher, L. J. (1992) Bioassays 14(12):807-15.

In addition, in one embodiment, the present invention relates to a method for the production of transgenic plants, plant cells or plant tissue comprising the introduction of the polynucleotide or the vector of the present invention into the genome of said plant, plant tissue or plant cell. In a preferred embodiment, said vector or said polynucleotide and a vector or a polynucleotide for the expression of a further resistance gene, in particular for Rpi-blb, is also introduced into the genome of said plant, plant tissue or plant cell, before, after or together.

For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed and are described above in detail.

In general, such regulatory elements comprise a promoter active in plant cells. To obtain expression in all tissues of a transgenic plant, e.g. constitutive promoters are used, such as the 35 S promoter of CaMV (Odell, Nature 313 (1985), 810-812) or promoters of the polyubiquitin genes of maize (Christensen, Plant Mol. Biol. 18 (1982), 675-689). In order to achieve expression in specific tissues of a transgenic plant it is possible to use tissue specific promoters (see, e.g., Stockhaus, EMBO J. 8 (1989), 2245-2251). Known are also promoters which are specifically active in tubers of potatoes or in seeds of different plants species, such as maize, Vicia, wheat, barley etc. Inducible promoters may be used in order to be able to exactly control expression. Inducible promoters comprise also promoters, which are induced by infections of plants. Further embodiments are described above.

In one embodiment, the present invention relates to a method for producing a plant or a part thereof resistant to a pathogen of the phylum Oomycetes comprising the steps: expressing in the plant or a part thereof the polypeptide of the present invention and a further resistance protein.

Accordingly in one further embodiment, the present invention relates to transgenic plant or plant tissue of the invention or produced according to the method of the invention, which upon the presence of the polynucleotide or the vector is resistant to said pathogens.

The generation of a transformed organism (or of a transformed cell or tissue) requires introducing the DNA, RNA, or protein in question into the relevant host cell. A multiplicity of methods are available for this procedure, which is termed transformation (or transduction or transfection) (Keown et al. (1990) Methods in Enzymology 185:527-537). For example, the DNA or RNA can be introduced directly by microinjection or by bombardment with DNA-coated microparticles. Also, the cell can be permeabilized chemically, for example using polyethylene glycol, so that DNA can enter the cell by diffusion. The DNA can also be introduced by protoplast fusion with other DNA-containing units such as minicells, cells, lysosomes, or liposomes. Another suitable method of introducing DNA is electroporation, where the cells are permeabilized reversibly by an electrical pulse. Suitable methods have been described (for example by Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the above-described methods of transforming and regenerating plants from plant tissues or plant cells are exploited for transient or stable transformation. Suitable methods are especially protoplast transformation by polyethylene-glycol-induced DNA uptake, the ballistic method with the gene gun, what is known as the particle bombardment method, electroporation, incubation of dry embryos in DNA-containing solution, and microinjection.

In addition to these "direct" transformation techniques, transformation can also be effected by bacterial infection by means of Agrobacterium tumefaciens or Agrobacterium rhizogenes. The Agrobacterium-mediated transformation is best suited to dicotyledonous plant cells. The methods are described, for example, by Horsch R B et al. (1985) Science 225: 1229f.

When agrobacteria are used, the expression cassette must be integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the expression cassette to be introduced in the form of a flanking region.

Binary vectors are preferably used. Binary vectors are capable of replication both in E. coli and in Agrobacterium. As a rule, they comprise a selection marker gene and a linker or polylinker flanked by the right and left T-DNA border sequence. They can be transferred directly into Agrobacterium (Holsters et al. (1978) Mol Gen Genet 163:181-187). The selection marker gene permits the selection of transformed agrobacteria and is, for example, the nptII gene, which confers resistance to kanamycin. The Agrobacterium which acts as host organism in this case should already contain a plasmid with the vir region. The latter is required for transferring the T-DNA to the plant cell. An Agrobacterium transformed in this way can be used for transforming plant cells. The use of T-DNA for transforming plant cells has been studied and described intensively (EP 120 516; Hoekema, In: The Binary Plant Vector System, Offsetdrukkerij Kanters B. V., Alblasserdam, Chapter V; An et al. (1985) EMBO J 4:277-287). Various binary vectors are known, some of which are commercially available such as, for example, pBI101.2 or pBIN19 (Clontech Laboratories, Inc. USA).

Further promoters which are suitable for expression in plants have been described (Rogers et al. (1987) Meth in Enzymol 153:253-277; Schardl et al. (1987) Gene 61:1-11; Berger et al. (1989) Proc Natl Acad Sci USA 86:8402-8406).

Direct transformation techniques are suitable for any organism and cell type.

The plasmid used need not meet any particular requirements in the case of the injection or electroporation of DNA or RNA into plant cells. Simple plasmids such as those of the pUC series can be used. If complete plants are to be regenerated from the transformed cells, it is necessary for an additional selectable marker gene to be located on the plasmid.

Stably transformed cells, i.e. those which contain the introduced DNA integrated into the DNA of the host cell, can be selected from untransformed cells when a selectable marker is part of the DNA introduced. Examples of genes which can act as markers are all those which are capable of conferring resistance to antibiotics or herbicides (such as kanamycin, G 418, bleomycin, hygromycin or phosphinothricin) (see above). Transformed cells which express such marker genes are capable of surviving in the presence of concentrations of a corresponding antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide Glyphosate. The selection marker permits the selection of transformed cells from untransformed cells (McCormick et al. (1986) Plant Cell Reports 5:81-84). The resulting plants can be bred and hybridised in the customary fashion. Two or more generations should be grown in order to ensure that the genomic integration is stable and hereditary.

The abovementioned methods are described, for example, in Jenes B et al. (1993) Techniques for Gene Transfer, in: Transgenic Plants, Vol. 1, Engineering and Utilization, edited by S D Kung and R Wu, Academic Press, pp. 128-143 and in Potrykus (1991) Annu Rev Plant Physiol Plant Molec Biol 42:205-225). The construct to be expressed is preferably cloned into a vector which is suitable for the transformation of *Agrobacterium tumefaciens*, for example pBin19 (Bevan et al. (1984) Nucl Acids Res 12:8711f).

As soon as a transformed plant cell has been generated, a complete plant can be obtained using methods known to the skilled worker. For example, callus cultures are used as starting material. The development of shoot and root can be induced in this as yet undifferentiated cell biomass in a known fashion. The shoots obtained can be planted out and bred.

The skilled worker is familiar with such methods of regenerating intact plants from plant cells and plant parts. Methods to do so are described, for example, by Fennell et al. (1992) Plant Cell Rep. 11: 567-570; Stoeger et al (1995) Plant Cell Rep. 14:273-278; Jahne et al. (1994) Theor Appl Genet 89:525-533.

The method according to the invention can advantageously be combined with further methods which bring about pathogen resistance (for example to insects, fungi, bacteria, nematodes and the like), stress resistance or another improvement of the plant properties. Examples are mentioned, inter alia, by Dunwell J M, Transgenic approaches to crop improvement, J Exp Bot. 2000; 51 Spec No; pages 487-96.

Suitable strains of *Agrobacterium tumefaciens* and vectors as well as transformation of *Agrobacteria* and appropriate growth and selection media are well known to those skilled in the art and are described in the prior art (GV31 01 (pMK90RK), Koncz, Mol. Gen. Genet. 204 (1986), 383-396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467-8471; Koncz, Plant Mol. Biol. 20 (1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1-46; An, EMBO J. 4 (1985), 277-287).

Although the use of *Agrobacterium tumefaciens* is preferred in the method of the invention, other *Agrobacterium* strains, such as *Agrobacterium rhizogenes*, may be used, for example if a phenotype conferred by said strain is desired.

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc.

The term "transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid or as chimeric links, or alternatively, may be integrated into the host genome. The resulting transformed plant cell can then be used to regenerate a transformed plant in a manner known by a skilled person.

Accordingly, in one embodiment, the present invention relates to a plant cell comprising the polynucleotide the vector of the present invention or obtainable by the method of the present invention. Preferably, the cell comprises a further resistance conferring polynucleotide or vector, more preferred is a Rpi-blb encoding vector or polynucleotide.

Thus, the present invention relates also to transgenic plant cells which contain (preferably stably integrated into the genome) a polynucleotide according to the invention linked to regulatory elements which allow expression of the polynucleotide in plant cells and wherein the polynucleotide is foreign to the transgenic plant cell. For the meaning of foreign; see supra.

Thus, the present invention also relates to transgenic plants and plant tissue comprising transgenic plant cells according to the invention. Due to the (over)expression of a polypeptide of the invention, said plant or plant tissues are resistance to plant pathogens, in particular to Oomycetes. Preferably the plants are also resistance to other pathogen, e.g. to sucking plant pathogens. Further pathogens are described herein. Preferred is that said plants or plant tissue is resistant to *Phytophthora* species, most preferred to *P. infestans*.

For example, to obtain transgenic plants expressing the Rpi-blb2 gene, its coding region can be cloned, e.g., into the pBinAR vector (Höfgen und Willmitzer, Plant-Science, 66, 1990, 221-230). For example, following a polymerase chain reaction (PCR) technology the coding region of Rpi-blb2 can be amplified using Primers as shown in the examples and figures, e.g., in Table 3b in particular ARF1F and ARF1R. The obtained PCR fragment can be purified and subsequently the fragment can be cloned into a vector. The resulted vector can be transferred into *Agrobacterium tumefaciens*. This strain can be used to transform and transgenic plants can then be selected. In another embodiment, the present invention relates to a transgenic plant or plant tissue comprising the plant cell of the present invention.

"Transgenic", for example regarding a nucleic acid sequence, an expression cassette or a vector comprising said nucleic acid sequence or an organism transformed with said nucleic acid sequence, expression cassette or vector, refers to all those constructs originating by recombinant methods in which either a) the Rpi-blb2 nucleic acid sequence, or
b) a genetic control sequence linked operably to the Rpi-blb2 nucleic acid sequence, for example a promoter, or
c) (a) and (b)

are not located in their natural genetic environment or have been modified by recombinant methods, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1000 bp, very especially preferably at least 5000 bp, in length. A naturally occurring expression cassette—for example the naturally occurring combination of the Rpi-blb2 promoter with the corresponding Rpi-blb2 gene—becomes a transgenic expression cassette when it is modified by non-natural, synthetic "artificial" methods such as, for example, mutagenization. Such methods have been described (U.S. Pat. No. 5,565,350; WO 00/15815; also see above).

Further, the plant cell, plant tissue or plant can also be transformed such that further enzymes and proteins are (over) expressed which expression supports an increase of the plant's or the plant tissue's resistance, for example Rpi-blb (synonyms Rpi-blb1, RB or Sbu1), R1, Rpi-mcd, R-ber (synonym R12), Rpi1, Rpi-blb3, Rpi-ABPT1, R2, R3a or R3b, R4, R5, R6, R7, R8, R9, R10, R11, Ph-1, Ph-2 and/or Ph-3-proteins. Preferred is the coexpression of Rpi-blb and Rpi-blb2.

The present invention also relates to cultured plant tissues comprising transgenic plant cells as described above which show expression of a protein according to the invention.

Host or starting organisms which are preferred as transgenic organisms are mainly plants in accordance with the above definition. Included within the scope of the invention are all genera and species of higher and lower plants of the Plant Kingdom. Furthermore included are the mature plants, seed, shoots and seedlings, and parts, propagation material and cultures derived there from, for example cell cultures which have an increased Rpi-blb2 activity. Mature plants refers to plants at any developmental stage beyond that of the seedling. The term seedling refers to a young immature plant in an early developmental stage.

Any transformed plant obtained according to the invention can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention. As mentioned before, the present invention is in principle applicable to any plant and crop that can be transformed with any of the transformation method known to those skilled in the art.

In general, the plants which can be modified according to the invention and which either show overexpression of a protein according to the invention or a reduction of the synthesis of such a protein can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc. However, plants which can be infected by *Phytophthora* species are preferred.

Accordingly, in one embodiment the plant, plant cell or plant tissue of the invention or produced according to the method of the invention is selected from the group consisting of Menyanthaceae, Solanaceae, Sclerophylacaceae, Duckeodendraceae, Goetzeaceae, Convolvulaceae, Cuscutaceae, Polemoniaceae, and Hydrophyllaceae according to the Systema Naturae 2000, Brands, S. J., Amsterdam or has its origin thereof. Preferably said plant, plant cell or plant tissue of the invention or produced according to the method of the invention is a Solanaceae, preferably selected from the group of *Atropa, Browallia, Brunfelsia, Capsicum, Cestrum, Cyphomandra, Datura, Fabiana, Franciscea, Hyoscyamus, Lycium, Mandragora, Nicandra, Nicotiana, Petunia, Physalis, Schizanthus* and *Solanum* according to the Systema Naturae 2000, Brands, S. J., Amsterdam or has its origin thereof.

More preferred, the plant, plant cell or plant tissue of the invention or produced according to the method of the present invention is a *S. bulbocastanum, S. tuberosum* (potato), *S. lycopersicum* (tomato), *petunia, S. betaceum* (tree tomato), *S. muricatum* (pear melon) or *S. melongena* (eggplant). Even more preferred, the plant, plant tissue or plant cell is a *S. tuberosum* or *S. lycopersicum*. Most preferred is *S. tuberosum*. In other systems, the classification will be similar. The person skilled in the art knows the differences, e.g. more common, tomato is named systematically *Lycopersicon lycopersicum* (L.) Karsten ex Farwell.

In yet another aspect, the invention also relates to harvestable parts and to propagation material of the transgenic plants according to the invention which either contain transgenic plant cells expressing a nucleic acid molecule and/or the polypeptide according to the invention or which contains cells which show an increased level of the polypeptide of the invention.

Harvestable parts can be in principle any useful parts of a plant, for example, flowers, pollen, seedlings, tubers, leaves, stems, fruit, seeds, roots etc. Propagation material includes, for example, seeds, fruits, cuttings, seedlings, tubers, rootstocks etc. Preferred are potatoes, tomatoes, eggfruits or pear melons as harvestable or propagation material. In case, the plant of the invention is *petunia*, the present invention relates in one embodiment to the flowers of *petunia* as harvestable part.

The invention furthermore relates to the use of the transgenic organisms according to the invention and of the cells, cell cultures, parts—such as, for example, roots, leaves and the like in the case of transgenic plant organisms—derived from them, and to transgenic propagation material such as seeds or fruits, for the production of foodstuffs or feeding stuffs, pharmaceuticals or fine chemicals. In particular, potatoes can serve for the production of fine chemicals.

Accordingly in another embodiment, the present invention relates to the use of the polynucleotide, the plant, plant cell or plant tissue, the vector, or the polypeptide of the present invention for making fatty acids, carotenoids, isoprenoids, vitamins, lipids, wax esters, (poly)saccharides and/or polyhydroxyalkanoates, and/or its metabolism products, in particular, steroid hormones, cholesterol, prostaglandin, triacylglycerols, bile acids and/or ketone bodies producing cells, tissues and/or plants. There are a number of mechanisms by which the yield, production, and/or efficiency of production of fatty acids, carotenoids, isoprenoids, vitamins, wax esters, lipids, (poly)saccharides and/or polyhydroxyalkanoates, and/or its metabolism products, in particular, steroid hormones, cholesterol, triacylglycerols, prostaglandin, bile acids and/or ketone bodies or further of above defined fine chemicals incorporating such an altered protein can be affected. In the case of plants, by e.g. increasing the expression of acetyl-CoA which is the basis for many products, e.g., fatty acids, carotenoids, isoprenoids, vitamins, lipids, (poly)saccharides, wax esters, and/or polyhydroxyalkanoates, and/or its metabolism products, in particular, prostaglandin, steroid hormones, cholesterol, triacylglycerols, bile acids and/or ketone bodies in a cell, it may be possible to increase the amount of the produced said compounds thus permitting greater ease of harvesting and purification or in case of plants more efficient partitioning. Further, one or more of said metabolism products, increased amounts of the cofactors, precursor molecules, and intermediate compounds for the appropriate biosynthetic pathways maybe required. Therefore, by increasing the number and/or activity of transporter proteins involved in the import of nutrients, such as carbon sources (i.e., sugars), nitrogen sources (i.e., amino acids, ammonium salts), phosphate, and sulphur, it may be possible to improve the production of acetyl CoA and its metabolism products as mentioned above, due to the removal of any nutrient supply limitations on the biosynthetic process. In particular, it may be possible to increase the yield, production, and/or efficiency of production of said compounds, e.g. fatty acids, carotenoids, isoprenoids, vitamins, was esters, lipids, (poly)saccharides, and/or polyhydroxyalkanoates, and/or its metabolism products, in particular, steroid hormones, cholesterol, prostaglandin, triacylglycerols, bile acids and/or ketone bodies molecules etc. in plants.

Furthermore preferred is a method for the recombinant production of pharmaceuticals or fine chemicals in host organisms, wherein a host organism is transformed with one of the above-described expression cassettes and this expression cassette comprises one or more structural genes which encode the desired fine chemical or catalyse the biosynthesis of the desired fine chemical, the transformed host organism is cultured, and the desired fine chemical is isolated from the culture medium. This method can be applied widely to fine chemicals such as enzymes, vitamins, amino acids, sugars, fatty acids, and natural and synthetic flavorings, aroma substances and colorants. Especially preferred is the production of tocopherols and tocotrienols and carotenoids. The transformed host organisms are cultured and the products are isolated from the host organisms or the culture medium by methods known to the skilled worker. The production of pharmaceuticals such as, for example, antibodies or vaccines, is described by Hood E E, Jilka J M. Curr Opin Biotechnol. 1999 August; 10(4):382-6; Ma J K, Vine N D. Curr Top Microbiol Immunol. 1999; 236:275-92.

In one embodiment, the present invention also relates to the use of the polynucleotide, the vector, or the polypeptide of the present invention for producing a plant or a plant tissue, plant organ, or a plant cell or a part thereof resistant to said.

Furthermore, in one embodiment, the present invention relates to a method for the identification of a compound stimulating resistance to a said plant pathogen comprising:
a) contacting cells which express the polypeptide of the present invention or its mRNA with a candidate compound under cell cultivation conditions;
b) assaying an increase in expression of said polypeptide or said mRNA;
c) comparing the expression level to a standard response made in the absence of said candidate compound; whereby, an increased expression over the standard indicates that the compound is stimulating resistance.

Said compound may be chemically synthesized or microbiologically produced and/or comprised in, for example, samples, e.g., cell extracts from, e.g., plants, animals or microorganisms, e.g. pathogens. Furthermore, said compound(s) may be known in the art but hitherto not known to be capable of suppressing or activating Rpi-blb2. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994), in particular Chapter 17. The compounds may be, e.g., added to the reaction mixture, culture medium, injected into the cell or sprayed onto the plant.

If a sample containing a compound is identified in the method of the invention, then it is either possible to isolate the compound from the original sample identified as containing the compound capable of activating or increasing resistance to said pathogens, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. Preferably, the compound identified according to the above-described method or its derivative is further formulated in a form suitable for the application in plant breeding or plant cell and tissue culture.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Said compounds can also be functional derivatives or analogues of known inhibitors or activators. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art. Furthermore, peptidomimetics and/or computer aided design of appropriate derivatives and analogues can be used, for example, according to the methods described above. The cell or tissue that may be employed in the method of the invention preferably is a host cell, plant cell or plant tissue of the invention described in the embodiments hereinbefore.

Determining whether a compound is capable of suppressing or activating said resistance can be done, as described in the examples, in particular via sporulation index determination. The activator identified by the above-described method may prove useful as a fungicide or crop protectant. Thus, in a further embodiment the invention relates to a compound obtained or identified according to the method of the invention said compound being an agonist of Rpi-blb2.

Accordingly, in one embodiment, the present invention further relates to a compound identified by the method of the present invention.

Said compound is, for example, a homologue of Rpi-blb2. Homologues of the polypeptid of the present invention can be generated by mutagenesis, e.g., discrete point mutation or truncation of Rpi-blb2. As used herein, the term "homologue" refers to a variant form of the protein which acts as an agonist of the activity of the Rpi-blb2. An agonist of said protein can retain substantially the same, or a subset, of the biological activities of Rpi-blb2.

In one embodiment, the invention relates to an antibody specifically recognizing the compound of the present invention.

The invention also relates to a diagnostic composition comprising at least one of the aforementioned polynucleotides, nucleic acid molecules, vectors, proteins, antibodies or compounds of the invention and optionally suitable means for detection.

The diagnostic composition of the present invention is suitable for the isolation of mRNA from a cell and contacting the mRNA so obtained with a probe comprising a nucleic acid probe as described above under hybridising conditions, detecting the presence of mRNA hybridised to the probe, and thereby detecting the expression of the protein in the cell. Further methods of detecting the presence of a protein according to the present invention comprises immunotechniques well known in the art, for example enzyme linked immunosorbent assay. Furthermore, it is possible to use the nucleic acid molecules according to the invention in particular the markers described in the examples, e.g. in table 3a or 3b as molecular markers or primer in plant breeding.

Suitable means for detection are well known to a person skilled in the art, e.g. buffers and solutions for hybridisation assays, e.g. the aforementioned solutions and buffers, further and means for Southern-, Western-, Northern- etc. -blots, as e.g. described in Sambrook et al. are known.

In another embodiment, the present invention relates to a kit comprising the polynucleotide, the vector, the host cell, the polypeptide, the antisense nucleic acid, the antibody, plant cell, the plant or plant tissue, the harvestable part, the propagation material or the compound of the invention.

The compounds of the kit of the present invention may be packaged in containers such as vials, optionally with/in buffers and/or solution. If appropriate, one or more of said components may be packaged in one and the same container. Additionally or alternatively, one or more of said components may be adsorbed to a solid support as, e.g. a nitrocellulose filter, a glass plate, a chip, or a nylon membrane or to the well of a microtiterplate. The kit can be used for any of the herein described methods and embodiments, e.g. for the production of the host cells, transgenic plants, pharmaceutical compositions, detection of homologous sequences, identification of antagonists or agonists, etc.

Further, the kit can comprise instructions for the use of the kit for any of said embodiments, in particular for its use for increasing the resistance to one or more of said pathogens of a plant cell, plant tissue or plant.

In a preferred embodiment said kit comprises further a polynucleotide encoding one or more of the aforementioned resistance protein(s), preferably Rpi-blb, and/or an antibody, a vector, a host cell, an antisense nucleic acid, a plant cell or plant tissue and/or a plant related to said resistance protein(s), preferably to Rpi-blb.

In a further embodiment, the present invention relates a method for the production of a crop protectant providing the polynucleotide, the vector or the polypeptide of the invention or comprising the steps of the method of the invention; and formulating the polynucleotide, the vector or the polypeptide of the invention or the compound identified in step (c) of said method in a form applicable as plant agricultural composition.

In another embodiment, the present invention relates to a method for the production of a crop protectant composition comprising the steps of the method of the present invention; and (a) formulating the compound identified in step (c) in a form acceptable as agricultural composition.

Under "acceptable as agricultural composition" is understood, that such a composition is in agreement with the laws regulating the content of fungicides, plant nutrients, herbicides, etc. Preferably such a composition is without any harm for the protected plants and the animals (humans included) fed therewith.

The present invention also pertains to several embodiments relating to further uses and methods. The polynucleotide, polypeptide, protein homologues, fusion proteins, primers, vectors, host cells, described herein can be used in one or more of the following methods: identification of plants resistant to plant pathogens as mentioned and related organisms; mapping of genomes; identification and localization of sequences of interest; evolutionary studies; determination of regions required for function; modulation of an activity.

Accordingly, the polynucleotides of the present invention have a variety of uses. First, they may be used to identify an organism as being S. bulbocastanum or a close relative thereof. Also, they may be used to identify the presence of S. bulbocastanum or a relative thereof in a mixed population of plants. By probing the extracted genomic DNA of a culture of a unique or mixed population of plants under stringent conditions with a probe spanning a region of the gene of the present invention which is unique to this S. bulbocastanum, one can ascertain whether the present invention has been used or whether S. bulbocastanum or a relative, e.g. a close relative, is present.

Further, the polynucleotide of the invention may be sufficiently homologous to the sequences of related species such that these nucleic acid molecules may serve as markers for the construction of a genomic map in related organism.

The polynucleotides of the invention are also useful for evolutionary and protein structural studies. By comparing the sequences of the Rpi-blb2 of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. Further databases and addresses are known to the person skilled in the art and can also be obtained. An overview of patent information in biotechnology and a survey of relevant sources of patent information useful for retrospective searching and for current awareness is given in Berks, TIBTECH 12 (1994), 352-364.

Tables:

Table 1: Sequences:

TABLE 2

Segregation of resistance in 2851 progeny clones of BC4 mapping populations ARG 95-3 and ARP 96-11 in the field trial of 2000 at Marknesse, The Netherlands. Numbers of clones classified as having a resistant, susceptible or unknown phenotype is presented with percentages in parenthesis.

| Mapping population | No clones with susceptible phenotype | No clones with resistant phenotype | No clones with unknown phenotype | Totals |
|---|---|---|---|---|
| ARG 95-3 | 846 (37) | 886 (39) | 551 (24) | 2283 |
| ARP 96-11 | 256 (45) | 170 (30) | 142 (25) | 568 |
| Totals | 1102 (39) | 1056 (37) | 693 (24) | 2851 |

TABLE 3A

Overview of markers used for mapping Rpiblb2

| Marker | Ori[1] | Sequence | SEQ ID NO: | Annealing temp (° C.) | Restriction Enzyme[2] |
|---|---|---|---|---|---|
| E46M52 | F | TTGTGGTTATCGATGAGAAT | 11 | 56.5 | SCAR (b) |
|  | R | GAAACAACAGCAGGATAGTGAG | 12 |  |  |
| E46M52e | F | TTGTGGTTATCGATGAGAAT | 13 | 61 | SCAR (a, b); |
|  | R | GAAACAACAGCAGGATAGTGAG | 14 |  | MboI (c) |
| E40M58 | F | GAATTCAGCACAAATACCAA | 15 | 50 | DdeI (a) |
|  | R | TTAACGTTTACTATCACGAG | 16 |  |  |
| E40M58e | F | GTAGAAACAGCAGCCTCATAAGC | 17 | 55 | SCAR (a) |
|  | R | TTCTGCCTAATTGCCCTGTG | 18 |  |  |
| S1E00 | F | GGGGTTGGGAAGACAACGACAC | 19 | 50 | AFLP |
|  | R | AATTCCAAGATACAGTCAAATAC | 20 |  |  |
| 41L | F | AGGCAGGATTAACAGTAGAAG | 21 | 58 | TaqI (a) |
|  | R | CATGCTTTTAGGAAGAAGCTC | 22 |  |  |
| 36L | F | TTGAGACAAAGCAGCTCCAC | 23 | 59 | ApoI (a, b) |
|  | R | ACGTTTCTCACACCTACAGG | 24 |  |  |
| 69L | F | TGATGGCACGTTTGATCGTG | 25 | 61 | TaqI (a, b); |
|  | R | TAAGATCCAAACCAGCCACC | 26 |  | HpaII (c) |
| 69R | F | CCTTATCACACATGTGGCTAC | 27 | 58 | RsaI (a, b); |
|  | R | ATTGAAACGGAGGAAGTACAAC | 28 |  | ApoI (c) |
| 141R | F | TTCTTCATATGGCAGACCAAC | 29 | 60 | RsaI (a, b); |
|  | R | CTACTCTGCTGACATGCAGG | 30 |  | DdeI (c) |
| 24L | F | GAGATTCTCAAAGGTGTCTTCC | 31 | 60 | SCAR (a, b, c) |
|  | R | AACCTGTGCTTTCCCATTCG | 32 |  |  |
| 24R | F | CTTTCACAAGCGTCACTTTGG | 33 | 58 | SCAR (a, b) |
|  | R | TAAAAAGAATCAACAGGGCAAC | 34 |  |  |
| 14L | F | ACGACTGCTCAAAGTTGGCC | 35 | 58 | SCAR (a, b, c) |
|  | R | CCAAGAAGCCAGTTGAGAGC | 36 |  |  |
| 123L | F | GTAGATTACACTATGGATATGG | 37 | 60 | SCAR (a, b) |
|  | R | CAGTTAGCAGCAATGTCAGC | 38 |  |  |
| 123L2 | F | CATTCAACTAGGCCAAAAGTGG | 39 | 59 | SCAR (a, b); |
|  | R | CCAGGTAGGTGTTTTCTTCC | 40 |  | DraI (c) |
| 123R | F | GTTCTAAGTCAGATGCCACC | 41 | 62 | SCAR (a, b) |
|  | R | AAGTGCTCCAACACGAGCC | 42 |  |  |
| 133R | F | TGAGTTCTCTTACCCTGCG | 43 | 60 | SCAR (a, b) |
|  | R | GGATATCCAGCATCAATGCC | 44 |  |  |
| 133R2 | F | GGTGAGCCTCCTTGCATTCC | 45 | 60 | SCAR (a, b) |
|  | R | CCTGAGGGAAGATGTCACG | 46 |  |  |
| 99L | F | CCTAGTTTAGAGTGAGTAGAC | 47 | 58 | SCAR (a, b) |
|  | R | GTGATATATTGCTCAAGGATCC | 48 |  |  |
| 113R | F | GTTGCTGGCTGTCACTGATC | 49 | 59 | SCAR (a, b) |
|  | R | GTGATGTGCAGGGTTCAAGG | 50 |  |  |
| 67L | F | GATTAGTGTAGATCTTAGCTTG | 51 | 62 | MboI (a, b) |
|  | R | AAATCTCTCTCACAATTATCCC | 52 |  |  |
| 112L | F | CTATTGACTGAACCTGCTGAG | 53 | 56 | HaeIII (a); |
|  | R | TGAAGTCATTTAGTCCACAGC | 54 |  | HinfI (c) |
| CT216 (RFLP) | F | AGATCGGAGTGTGAACATGG | 55 | 56 |  |
|  | R | CTTCTACTTCTAGTCGACTGC | 56 |  |  |
| CT216 | F | CGTAGTCCATCTGAAGCTCC | 57 | 65 | SCAR (a, b) |
|  | R | TCTTCTTCTGCTAGTCGTCG | 58 |  |  |
| CT119 | F | ACTATTCTCACGTAAGGGACAC | 59 | 60 | HindIII (a, b) |
|  | R | GTGTACATGTATGAAACTCTAGC | 60 |  |  |
| CT119N | F | GTTCCTTTCAATCAGAAAGTAG | 61 | 55 | SCAR (a) |
|  | R | CTTTGGATGAGTCAAAAGGCT | 62 |  |  |
| 14L24L | F | univ14L |  | 60 | CfoI (c) |
|  | R | univ24L |  |  |  |
| SPB30L | F | CAAGTTACGGCAACCAAGAG | 63 | 57 | HpaII (c) |
|  | R | CTTTGACACAGTGTTAGAATGC | 64 |  |  |
| SPB39L | F | CGTGATCTAGGAGTTACGAC | 65 | 52 | SCAR (c) |
|  | R | CTTATTTTAAATACAAGACATCTGG | 66 |  |  |
| 24L9spec | F | univ. 14L |  | 56 | HhaI (c) |
|  | R | CAGAGGAAAGTCAACCAACG | 67 |  |  |
| 24Lspec | F | univ. 14L |  | 60 | CfoI (c) |
|  | R | CAGAGGAAAGTCAACCAACG | 68 |  |  |
| NptII | F | TCGGCTATGACTGGGCACAACAGA | 69 | 70 |  |
|  | R | AAGAAGGCGATAGAAGGCGATGCG | 70 |  |  |
| M13 | F | TGTAAAACGACGGCCAGT | 71 | 55 |  |
|  | R | GGAAACAGCTATGACCATG | 72 |  |  |

[1] Ori: Orientation of the primer; F: forward primer; R: reverse primers
[2] a: ARG95-3, b: ARP96-11, c: B6a

TABLE 3B

Overview of primers used for mapping Rpi-blb2

| primer | | OriSequence[1] | SEQ ID NO: |
|---|---|---|---|
| ARO 73 | F | TTCAGCACAAATACCAAT | 73 |
| ARO 74 | R | GATGTTCCCCTTCTTTTA | 74 |
| ARO 77 | R | TTGTGGTTATCGATGAGAAT | 75 |
| ARO 79 | R | ACCTGGCGTTCCTTATTTTT | 76 |
| ARO 94 | | NGTCASWGANAWGAA | 77 |
| ARO 128 | F | GATGGAGCGGAAAAGCCGGTG | 78 |
| ARO 129 | F | GGTGTTTTGTAGCATCTCCAG | 79 |
| ARO 295 | | CCATGATTACGCCAAGCTGG | 80 |
| ARO 296 | | GGTTTTCCCAGTCACGACGT | 81 |
| univ14L | F | AGAAAGCTCACCAGTGGACC | 82 |
| univ24L | R | ATTTATGGCTGCAGAGGACC | 83 |
| 123Mi | R | AAGTCCAATTGCTCATCCATC | 84 |
| 14L2 | R | TGCACCATGCACGAAGGTC | 85 |
| 24L2 | F | CAATWTTGGTTCCCGAAATTGG | 86 |
| ARF1F | F | ATGGAAAAACGAAAAGATAATGAAG | 87 |
| ARF1R | R | CTACTTAAATAACGGGATATCCTTC | 88 |
| ARO 602 | F | CCCATGACTCCTTGAGTTTG | 89 |
| S1 | | GGTGGGGTTGGGAAGACAACG | 90 |
| EcoR1 + 0 | | GTAGACTGCGTACCAATTC | 91 |
| MseI + 0 | | GATGAGTCCTGAGTAA | 92 |
| ARO 769 | | GTGCTTCATTCAAACTCAAGGAG | 95 |
| ARO 770 | | CTGAACTAGAAAAACTCACTGTAGA | 96 |
| ARO 771 | | GTTTGAAAAGATTGCAATTGCATG | 97 |
| ARO 772 | | CTCAGCCATCAGTTGAAACAGAGA | 98 |
| ARO 774 | | GAGAGAGATTCAAGAGGAGGAAGC | 99 |

[1] N = A + T + G + C, S = G + C, W = A + T

TABLE 5

Cycling conditions used for TAIL-PCR

| Reaction | cycle no. | Thermal condition |
|---|---|---|
| Primary | 1 | 92° C. (2 min), 95° C. (1 min) |
| | 5 | 94° C. (15 s), 63° C. (1 min), 72° C. (2 min) |
| | 1 | 94° C. (15 s), 30° C. (3 min), ramping to 72° C. over 3 min, 72° C. (2 min) |
| | 10 | 94° C. (5 s), 44° C. (1 min), 72° C. (2 min) |
| | 12[a] | 94° C. (5 s), 63° C. (1 min), 72° C. (2 min) |
| | | 94° C. (5 s), 63° C. (1 min), 72° C. (2 min) |
| | | 94° C. (5 s), 44° C. (1 min), 72° C. (2 min) |
| | 1 | 72° C. (5 min) |
| Secondary | 10[a] | 94° C. (5 s), 63° C. (1 min), 72° C. (2 min) |
| | | 94° C. (5 s), 63° C. (1 min), 72° C. (2 min) |
| | | 94° C. (5 s); 44° C. (1 min), 72° C. (2 min) |
| | 1 | 72° C. (5 min) |
| Tertiary | 20 | 94° C. (10 s), 44° C. (1 min), 72° C. (2 min) |
| | 1 | 72° C. (5 min) |

[a] these are nine-segment super cycles each consisting of two high-stringency and one reduced-stringency cycle

TABLE 4

Complementation of late blight susceptibility in potato

| BAC-library | Source BAC | Genotype[1] | cv Impala RGC-containing plants/ transformants | cv Impala R plants/ RGC-containing plants | cv Kondor RGC-containing plants/ transformants | cv Kondor R plants/ RGC-containing plants |
|---|---|---|---|---|---|---|
| ARD 1197-16 | 24 | $R_0$ (RGC1) | 12/15[a] | 0/12 | | |
| | | | 8/10[b] | 0/8 | | |
| | 24 | $R_0$ (RGC2) | 8/11[a] | 0/8 | | |
| | | | 5/6[b] | 0/5 | | |
| | 24 | $R_0$ (RGC3) | 11/13[a] | 0/11 | | |
| | | | 5/7[b] | 0/5 | | |
| | 211 | $R_0$ (RGC4) | 5/7[a] | 0/5 | 10/12[a] | 0/10 |
| | 242 | $R_0$ (RGC4) | 5/7[a] | 0/5 | 8/8[a] | 0/8 |
| | 211 | $R_0$ (RGC5) | 5/7[a] | 4/5 | 12/13[a] | 12/12 |
| | 211 | $R_0$ (RGC6) | — | — | — | — |
| | 211 | $R_0$ (RGC24L) | — | — | — | — |
| Blb 2002 | SPB39 | $R_0$ (RGC4) | 5/6[a] | 0/5 | 3/3[a] | 0/3 |
| | SPB39 | $R_0$ (RGC5) | 11/15[a] | 11/11 | 8/8[a] | 7/8 |
| | SPB39 | $R_0$ (RGC6) | 3/3[a] | 0/3 | 6/6[a] | 0/6 |
| | SPB30 | $R_0$ (RGC7) | 3/4[a] | 0/3 | 9/9[a] | 0/9 |
| | SPB30 | $R_0$ (RGC8) | 1/1[a] | 0/1 | — | — |
| | SPB39 | $R_0$ (24L) | — | — | — | — |
| | | $R_0$ (pBINPLUS) | 3/3 | 0/3 | 8/10 | 0/8 |

[1] $R_0$ genotypes are primary transformants obtained from transformation of the susceptible potato cultivars Impala or Kondor with T-DNA constructs containing the Rpi-blb2 gene candidates RGC1 to RGC8 and RGC24L or an empty pBINPLUS vector. *Agrobacterium tumefaciens* strains UIA143[a] or AGL0[b] were used for transformation of the *P. infestans* susceptible potato cultivars Impala and Kondor.

TABLE 6

Complementation of late blight susceptibility in tomato cultivar MoneyMaker by Rpi-blb2

| Bac-library | Source Bac | genotype | RGC-containing plants/ transformants | R plants/ RGC-containing plants |
|---|---|---|---|---|
| Blb 2002 | SPB39 | $R_0$ (RGC5) | 24/25 | 22/24 |

$R_0$ genotypes are primary transformants obtained from transformation of the susceptible tomato cultivar Moneymaker with the T-DNA construct containing the Rpi-blb2 gene RGC5. Agrobacterium tumefaciens strains UIA143[a] was used for transformation of the P. infestans susceptible tomato cultivar.

The figures show:

FIG. 1. Schematic representation of the development of the complex interspecific hybrid clones designated as 'ABPT' (1a) and the S. tuberosum mapping populations that were derived from two of these clones: ABPT clone 55 and ABPT clone 60 (1b to d). A; Solanum acaule, B; S. bulbocastanum, P; S. pureja, T; S. tubersosum, 2x; diploid (2n=2x=24), 3x; triploid, 4x; tetraploid, 6x; hexaploid, cv; cultivar. Codes in italics indicate mapping populations.

Figure 2:
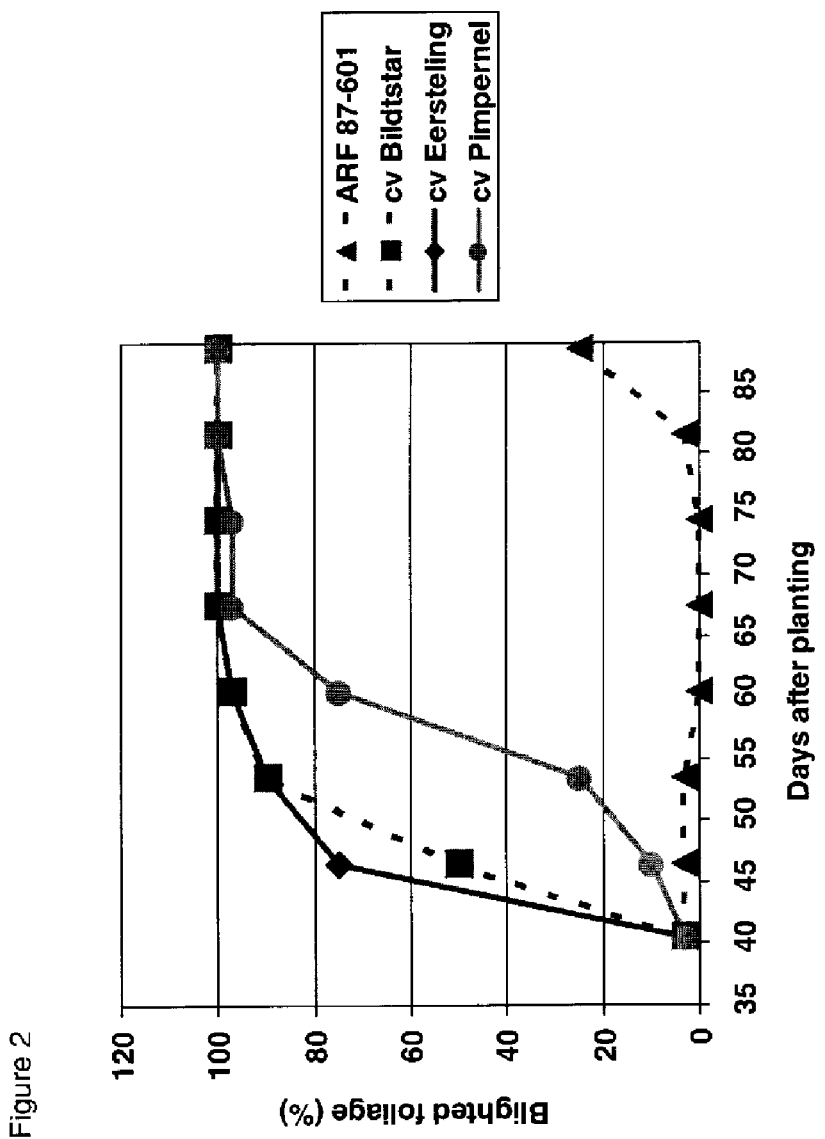
Figure 3:
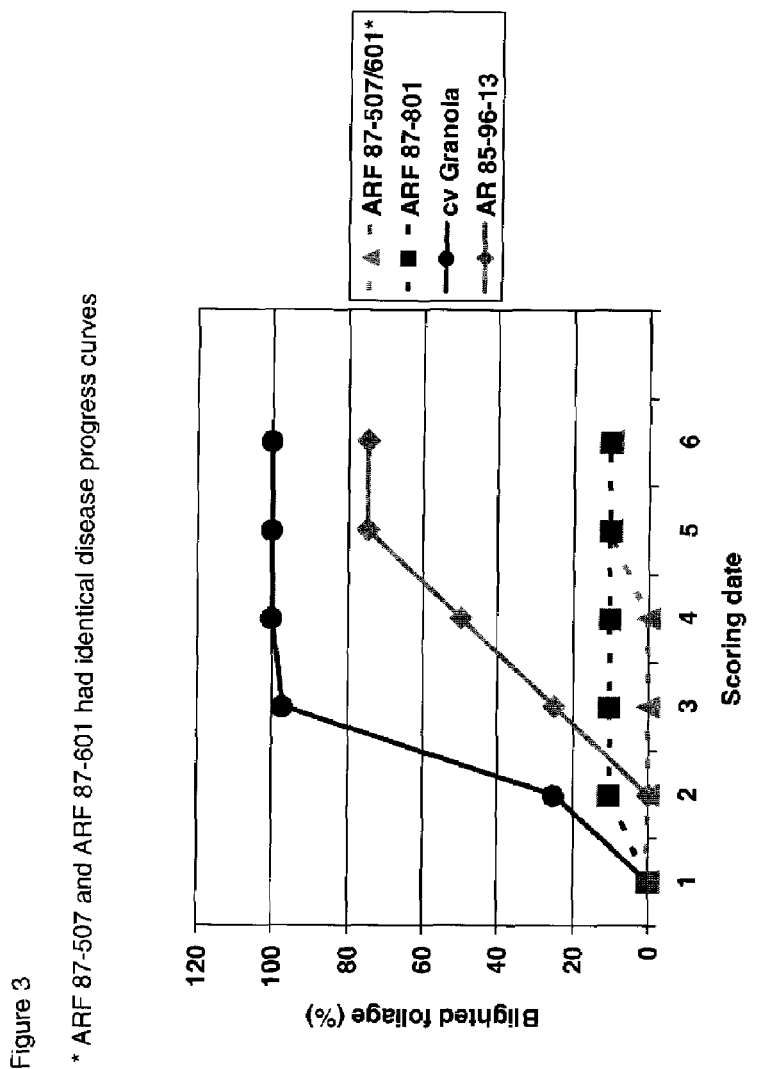

FIG. 2. Disease progress curves for clone ARF 87-601 and susceptible control cultivars (cv) Bildtstar, Eersteling and the partial resistant control cultivar Pimpernel in a field test for foliar resistance to late blight in Toluca Valley, Mexico in 1991. At eight time points after planting, the percentage-blighted foliage due to a natural late blight infection was scored on the 1 to 9 CIP scale (Estrada-Ramos, 1983).

FIG. 3. Disease progress curves for clone ARF 87-507, ARF 87-601, ARF 87-801, the susceptible control cultivar (cv) Granola and the partial resistant breeding clone AR 85-96-13 in a field test for foliar resistance to late blight in Benguet Province, Philippines in 1992. At six time points between August 25[th] to November 24[th], the percentage-blighted foliage due to a natural late blight infection was scored on the 1 to 9 CIP scale (Estrada-Ramos, 1983).

FIG. 4. Typical phenotypes in tetraploid resistant and susceptible parental clones and progeny clones segregating for Rpi-blb2 mediated resistance to late blight in the annual field trial at Marknesse, The Netherlands, approximately 6 weeks after inoculation with isolate IPO82001 of P. infestans. Six plant plots with a clone showing the resistant phenotype (within black solid line) that shows no or hardly any sporulating lesions and with a clone showing the susceptible phenotype (within white dotted line) that shows completely blighted foliage.

Figure 5:
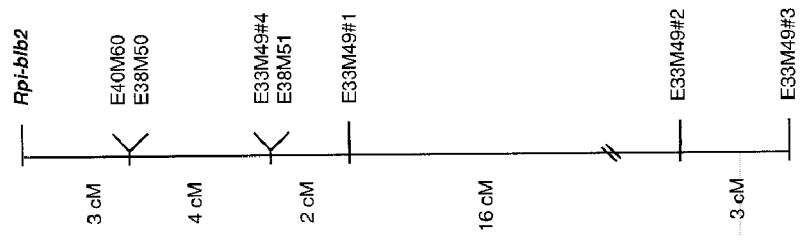

FIG. 5. Genetic map based on 109 progeny clones of S. tuberosum mapping population ARG 95-15 showing 7 AFLP markers that were found to cosegregate with the Rpi-blb2 locus. Numbers left to the vertical line indicate the genetic distance between flanking markers or the Rpi-blb2 locus in centimorgan (cM).

Figure 6:
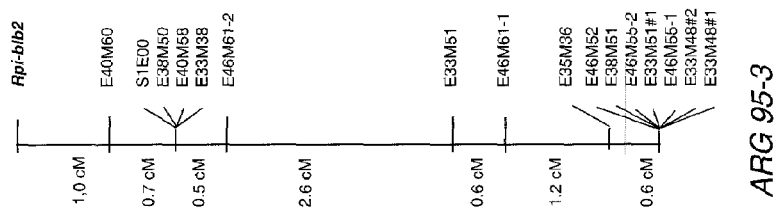

FIG. 6. Genetic map based on 137 progeny clones of S. tuberosum mapping population ARG 95-3 showing 15 AFLP markers and RGA marker S1E00 that were found to cosegregate with the Rpi-blb2 locus. Phenotypes of the progeny clones were obtained with detached leaf assays. Numbers left to the vertical line indicate the genetic distance between flanking markers or the Rpi-blb2 locus in centimorgan (cM).

Figure 7:
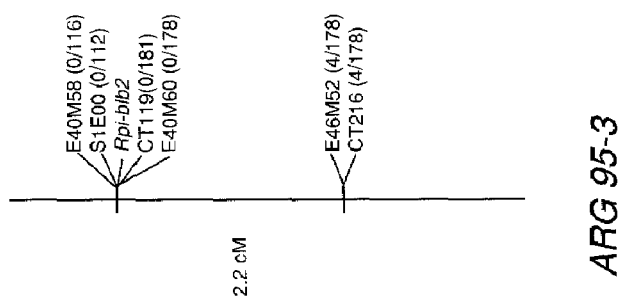

FIG. 7. Genetic map based on 178 progeny clones of S. tuberosum mapping population ARG 95-3 showing 5 markers that were found to cosegregate with the Rpi-blb2 locus on linkage group 6 of S. tuberosum. Phenotypes of the progeny clones were determined in the field trial at Marknesse, the Netherlands in 1998. Markers E40M58 and E46M52 were scored either as AFLP, CAPS, SCAR or extended (suffix: e) marker (table 3A). Partly, marker CT119 was scored as marker CT119N (table 3a). Marker CT216 was scored as SCAR marker. The number left to the vertical line indicates the genetic distance between flanking markers or the Rpi-blb2 locus in centimorgan (cM). For each marker, the number of recombinants between marker and phenotype and the total number of progeny clones scored is given in parenthesis.

Figure 8:
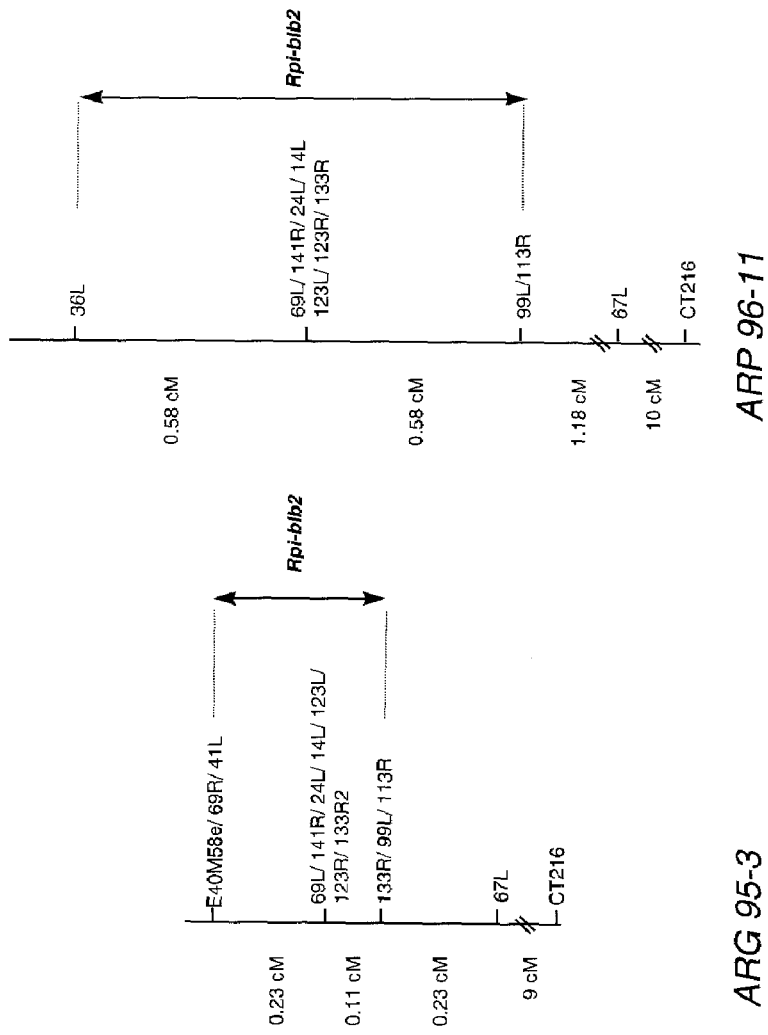

FIG. 8. Genetic maps based on 886 progeny clones of S. tuberosum mapping population ARG 95-3 and on 170 progeny clones of S. tuberosum mapping population ARP 96-11, showing markers that were found to cosegregate with the Rpi-blb2 locus on linkage group 6 of S. tuberosum. Phenotypes of the progeny clones were determined in the field trial at Marknesse, the Netherlands in 2000. The number left to the vertical line indicates the genetic distance between flanking markers in centimorgan (cM). The marker interval which delimitates the position of the Rpi-blb2 gene, based on detected recombination events in progeny clones, is indicated by double arrow headed lines.

Figure 9:
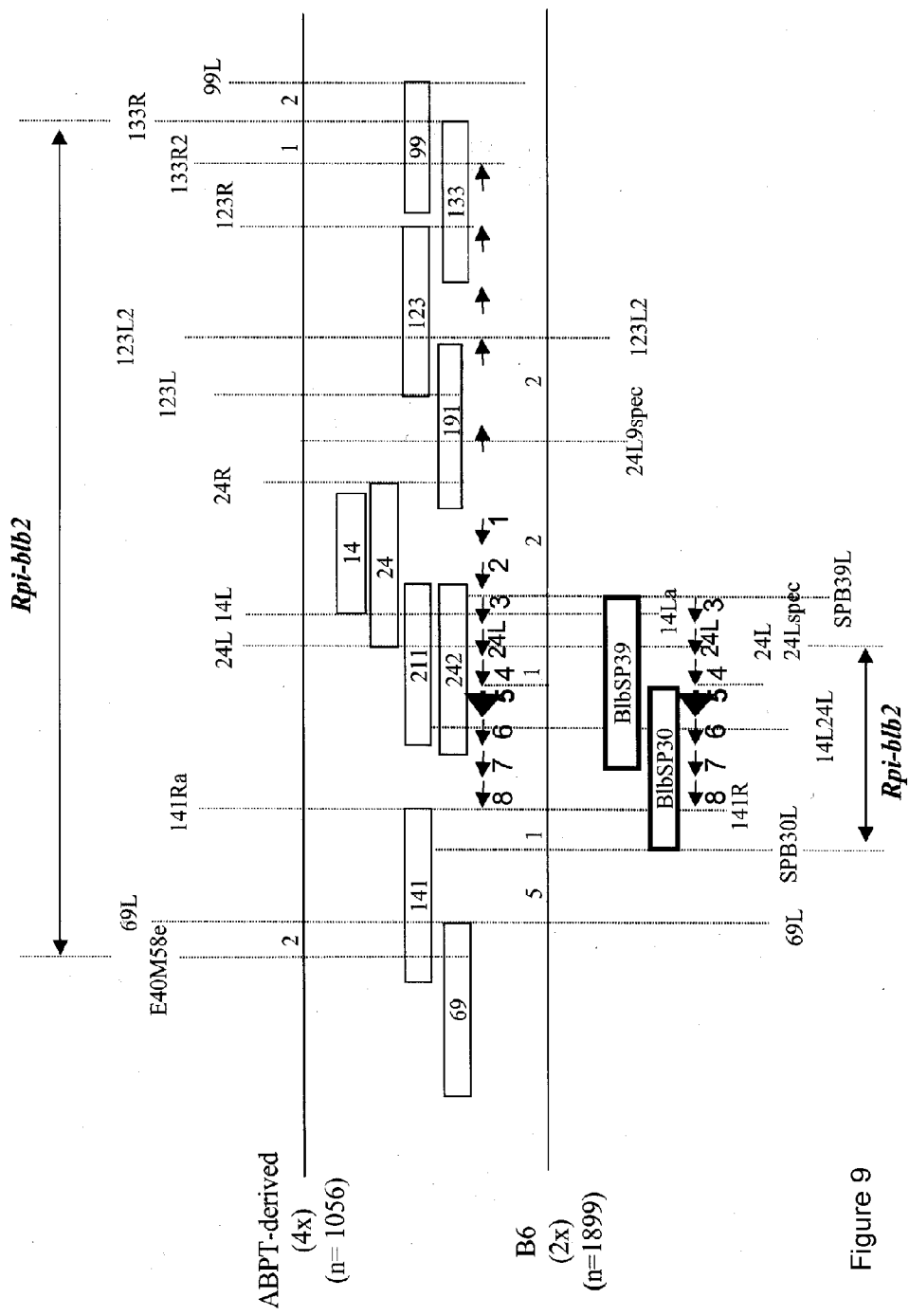

FIG. 9. Physical map of the genomic region containing Rpi-blb2 in S. tuberosum (upper horizontal line) and S. bulbocastanum (lower horizontal line). Vertical lines indicate the relative position of markers linked to resistance. Numbers above the horizontal lines are the number of recombinants identified between the flanking markers in 1056 and 1899 progeny plants of S. tuberosum, derived from complex species hybrids "ABPT" (FIG. 1), and S. bulbocastanum progeny plants respectively. ABPT-derived progeny comprises clones from both the mapping populations ARG 95-3 and ARP 96-11. Rectangles represent bacterial artificial chromosome (BAC) clones from the ARD 1197-16 BAC library except for BAC clones with prefix "Blb" which were from the S. bulbocastanum Blb 2002 BAC library. The marker interval which delimitates the position of the Rpi-blb2 gene, based on detected recombination events in progeny clones, is indicated by double arrow headed lines. Small arrows indicate positions of Resistance Gene Candidates (RGC's).

Figure 10:
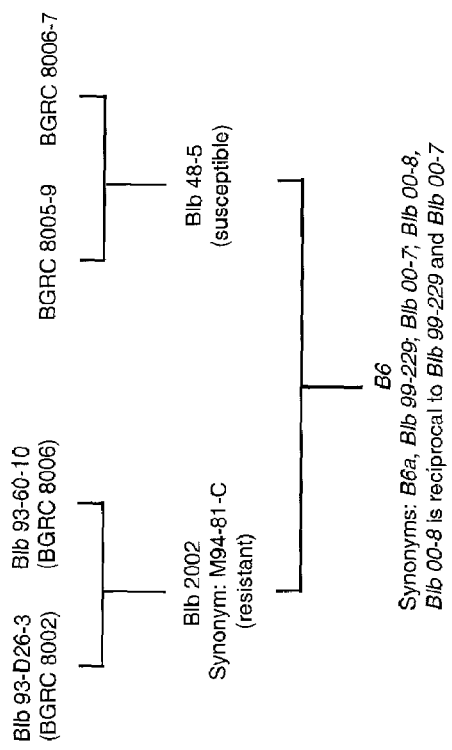

FIG. 10. Schematic representation of the development of the diploid, intraspecifc mapping population B6 of S. bulbocastanum. Codes in italics indicate mapping populations.

Figure 11:
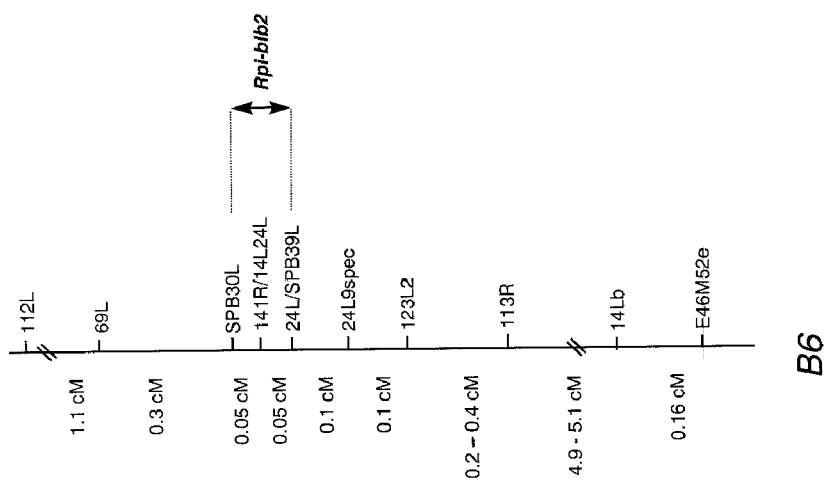

FIG. 11. Genetic map based on 1899 progeny clones of S. bulbocastanum mapping population B6, showing markers that were found to cosegregate with the Rpi-blb2 locus on chromosome 6 of S. bulbocastanum. Phenotypes of the progeny clones were determined by detached leaf assays. The number left to the vertical line indicates the genetic distance between flanking markers in centimorgan (cM). The marker interval which delimitates the position of the Rpi-blb2 gene, based on detected recombination events in progeny clones, is indicated by a double arrow headed line.

FIG. 12. Genetic complementation for late blight susceptibility. Typical disease phenotypes of potato (S. tuberosum) leaves, 6 days after inoculation with a sporangiospore suspensions of P. infestans isolate 655-2A. Leaf derived from kanamycin resistant cv Kondor plants transformed with pBINPLUS (control; A), leaves derived from cv Kondor plants harbouring BAC SPB39 derived (B) or BAC 211 derived RGC5 (C), leaf derived from kanamycin resistant cv Impala plants transformed with pBINPLUS (control; D), leaves derived from cv Impala plants harbouring BAC SPB39 derived (E) or BAC 211 derived RGC5 (F). Panels A and D depict typical susceptible responses with extensive sporulating lesions of P. infestans. Panels B, C, E and F depict typical resistance reactions observed at the sites of inoculation on transgenic potato plants harbouring Rpi-blb2.

FIG. 13. Nucleic acid sequences coding for the Rpi-blb2 gene. A. Coding nucleic acid sequence of the Rpi-blb2 gene (SEQ ID NO: 1). B. Coding nucleic acid sequence of the Rpi-blb2 gene including the intron sequence (position 43-128) (SEQ ID NO: 3). C. Sequence of the 7967 bp Sau3AI genomic DNA fragment of ARD 1197-16 BAC 211 present in p211F-C12 (SEQ ID NO: 5), one of the two genetic constructs used for genetic complementation for late blight resistance. The genomic fragment harbours the Rpi-blb2 gene including natural regulatory elements necessary for correct expression of the gene. The initiation codon (ATG position 1546-1548) and the termination codon (TAG position 5433-5435) are underlined. D. Sequence of the 9949 bp Sau3AI genomic DNA fragment of S. bulbocastanum 2002 BAC BlbSP39 present in pSP39-20 (SEQ ID NO: 6), one of the two genetic constructs used for genetic complementation for late blight resistance. The genomic fragment harbours the Rpi-blb2 gene including natural regulatory elements necessary for correct expression of the gene. The initiation codon (ATG position 1413-1415) and the termination codon (TAG position 5300-5303) are underlined.

FIG. 14. Putative Rpi-blb2 gene structure and deduced Rpi-blb2 protein sequence. A. Schematic representation of the Rpi-blb2 gene structure. Horizontal lines indicate exons. Open boxes represent coding sequence. Lines angled downwards indicate the positions of intron sequences. B. Deduced Rpi-blb2 protein sequence (SEQ ID NO: 4). The amino acid sequence deduced from the DNA sequence of Rpi-blb2 is divided into three domains (LZ, NBS and LRR). Hydrophobic residues in domain A that form the first residue of heptad repeats of the potential leucine zipper (LZ) domain are underlined. Conserved motifs in R proteins are written in lowercase and in italic in the NBS domain. Residues matching the consensus of the cytoplasmic LRR are indicated in bold in the LRR domain. Dots in the sequence have been introduced to align the sequence to the consensus LRR sequence of cytoplasmic LRRs.

FIG. 15. Alignment of the deduced protein products encoded by Rpi-blb2 (SEQ ID NO: 4), Mi-1.1 (SEQ ID NO: 8) and Mi-1.2 (SEQ ID NO: 10). The complete amino acid sequence of Rpi-blb2 is shown and amino acid residues from Mi-1.1 and Mi-1.2 that differ from the corresponding residue in Rpi-blb2. Dashes indicate gaps inserted to maintain optimal alignment. Amino acid residues that are specific for Rpi-blb2, when compared to those at corresponding positions in Mi-1.1 and Mi-1.2 are highlighted in bold and red. The regions of the LRRs that correspond to the β-strand/β-turn motif xxLxLxxxx are underlined. Conserved motifs in the NBS domain are indicated in lowercase. A vertical line indicates the division between CC-NBS and LRR region. The position of the VLDL motif which is conserved in the third LRR of many plant R proteins but not in Rpi-blb2 is indicated by a shaded rectangle.

FIG. 16. CLUSTAL W (1.82) Multiple Sequence Alignments of Mi1.1 (SEQ ID NO: 7), Mi1.2 (SEQ ID NO: 9) and Rpi-blb2 (SEQ ID NO: 1) nucleic acids.

FIG. 17. CLUSTAL W (1.82) Multiple Sequence Alignments of Mi1.1 (SEQ ID NO: 8), Mi1.2 (SEQ ID NO: 10) and Rpi-blb2 (SEQ ID NO: 2) proteins.

FIG. 18. Typical phenotypes of the resistance genes R2 (A) and Rpi-blb2 (B) compared to a susceptible phenotype of cv. Bintje (C). Panel A depicts a typical hypersensitive response reaction with very small necrotic spots, while panel B shows large necrotic regions that contain a low level of sporulation. Panel C depicts a typical susceptible reaction with clear sporulation.

This invention is further illustrated by the following examples which should not be construed as limiting.

EXAMPLES

Example 1

Evaluation of Resistance in ABPT Derived Back Cross Clones and Populations

BC2-clones ARF 87-507 and ARF 87-801 were selected from BC2-progeny obtained after two rounds of backcrossing on complex species hybrid ABPT-clone number 55 (FIG. 1a) with late blight (LB) susceptible S. tuberosum cultivar Oberambacher Frühe as first parent and S. tuberosum cultivars Arkula (FIG. 1b) and Blanka (FIG. 1c) respectively as second parents. Similarly, BC2-clone ARF 87-601 was obtained by successive crossing on ABPT-clone 60 with LB susceptible S. tuberosum cultivars Alcmaria and Blanka (FIG. 1d).

Clone ARF 87-601 was tested as part of a field test for screening of LB-resistance in the Toluca area in Mexico in 1991. A plot of clone ARF 87-601 with seven plants was evaluated in comparison to plots with nine plants each of the control cultivars Bildtstar, Eersteling and Pimpernel. According to the ratings for resistance to late blight in the Dutch National list of recommended potato cultivars of 1988, these control cultivars scored 3, 3 and 8 respectively on a scale from 3 to 8 of increasing resistance. Cultivar Pimpernel is considered as a source of partial resistance (Colon et al., 1985). About forty days after planting, natural infection by P. infestans established. The development of LB in the foliage then was monitored eight times during the period from July $16^{th}$ to September $2^{nd}$ (FIG. 2). There was a clear difference between the disease progress curves for ARF 87-601 in comparison to the control cultivars. At 74 days after planting, foliage of the control cultivars was completely or nearly completely blighted whereas clone ARF 87-601 showed no visible symptoms (FIG. 2). Clones ARF 87-507, ARF 87-801 and again clone ARF 87-601 showed comparable results in a field test for screening of LB-resistance in the Benguet Province of the Philippines in 1992 (FIG. 3). Ten plants each of the three BC2 clones, control cultivar Granola and the moderately LB resistant breeding clone AR 85-96-13, which was used as female parent to obtain AR 92-1197 (FIG. 1d), were planted on August $25^{th}$. The percentage of blighted foliage was scored six times after occurrence of natural infection by P. infestans. Disease progress curves of ABPT derived BC2-clones were markedly different when compared to cultivar Granola and clone AR 85-96-13 (FIG. 3). BC2-clones showed no or little LB symptoms and no clear disease progress during the scoring period whereas cultivar Granola had almost completely blighted foliage at the third scoring date.

Figure 1A:
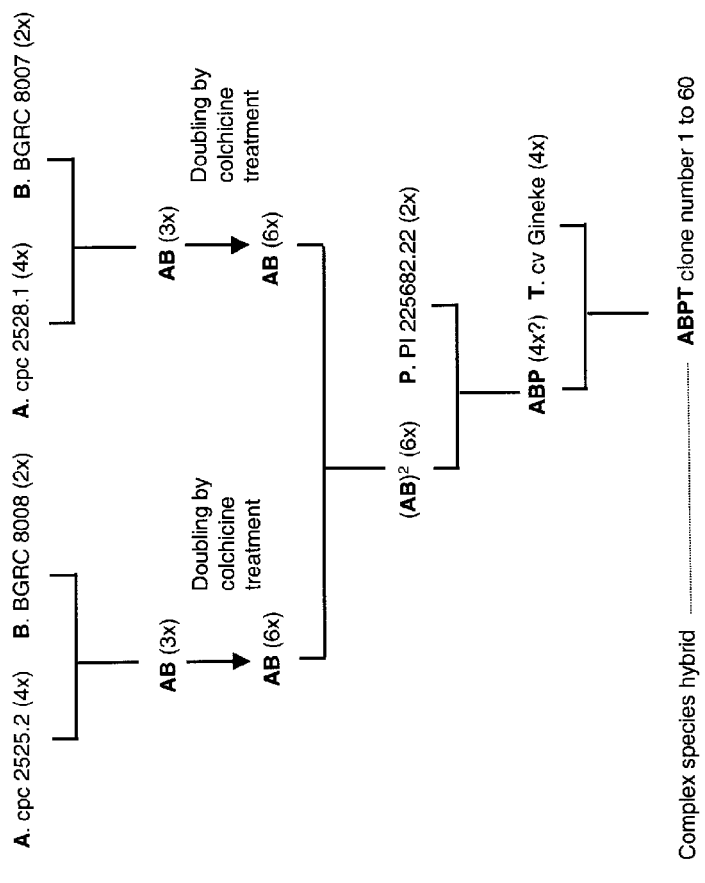
Figure 1B:
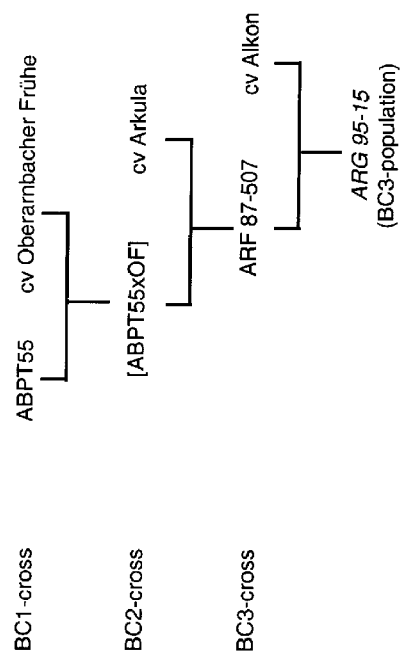
Figure 1C:
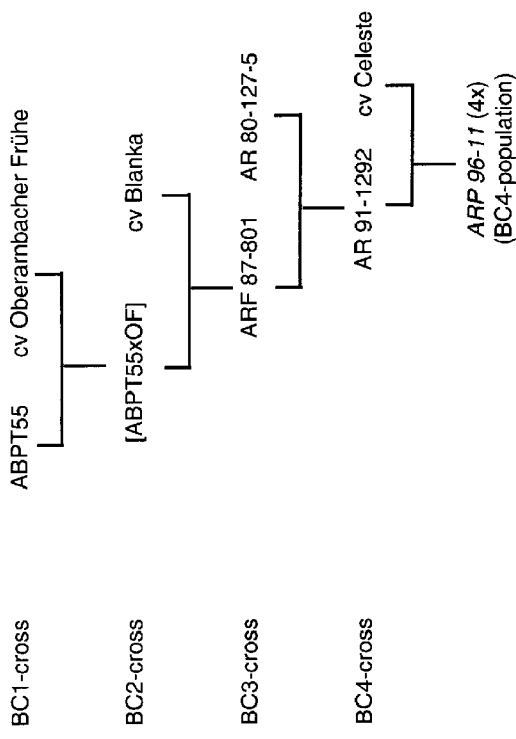
Figure 1D:
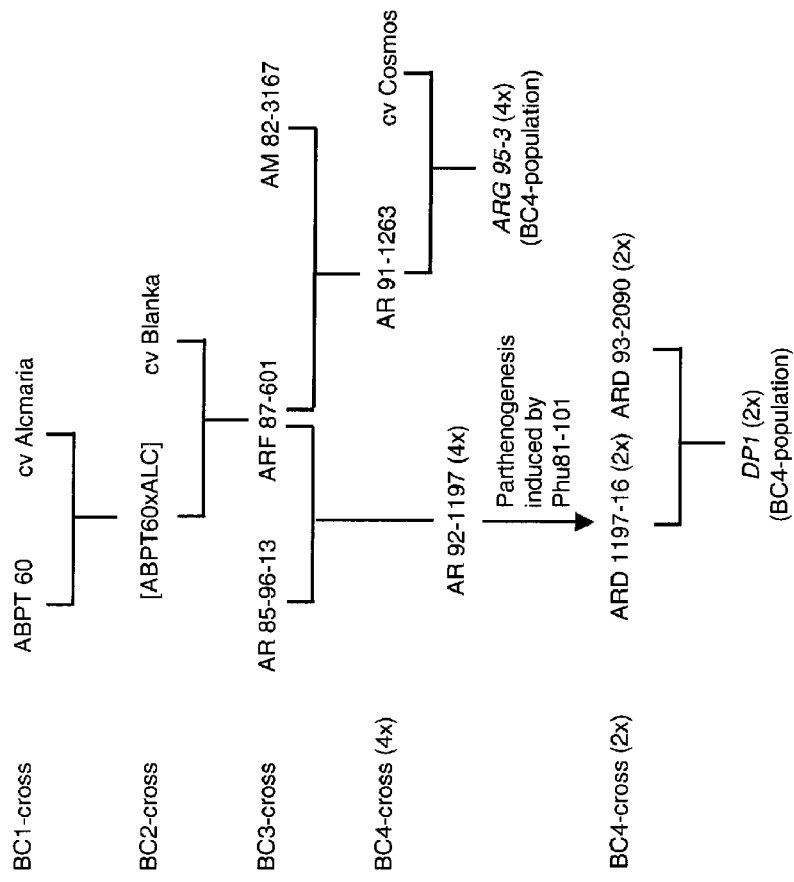

Clones ARF 87-601, ARF 87-507 and ARF 87-801 were used for further backcrossing with LB susceptible cultivars and breeding clones of S. tuberosum (FIG. 1b to 1d). This breeding work resulted in four different mapping populations, tetraploid BC3-population ARG 95-15, tetraploid BC4-populations ARG 95-3 and ARP 96-11 and diploid BC4-population DP1. During the successive steps of this breeding work resistant clones ARF 87-507, ARF 87-601, ARF 87-801, AR 91-1263, AR 91-1292 and AR 92-1197 were selected on the basis of agronomic performance in common practice breeding evaluations as well as by screening their parents and relevant progenies in a field trial at Marknesse, the Netherlands, that was inoculated with the complex isolate IPO82001 of P. infestans. The diploid (2n=2x=24)

clone ARD 1197-16 was selected among the progeny of cross AR 92-1197×Phu 81-101 (FIG. 1d), the latter parental clone being known for its capacity to induce parthenogenic seed set in the female parent (Hermsen and Verdenius, 1973). Initially, resistance to LB in ARD 1197-16 was found after repeated detached leaf assays using *P. infestans* isolates IPO82001, IPO655-2A and IPO428-2 and verified in a field trial in 1998 at Marknesse. The diploid status of clone ARD 1197-16 was confirmed by flow cytometry (Plant cytometry services, Schijndel, the Netherlands).

Clear segregation for the LB-resistance trait in ABPT-derived progeny and mapping populations was observed during successive years of field testing at the trial site of Marknesse, approximately 6 weeks after inoculation with isolate IPO82001 of *P. infestans*. Typically, resistant clones showed no or hardly any sporulating lesions whereas susceptible clones showed completely blighted foliage (FIG. 4) In 2000, a total of 2851 clones from the mapping populations ARG 95-3 and ARP 96-11 were screened as single plant plots. On average, 24 percent of the clones showed phenotypes that could not unambiguously be classified as resistant or susceptible. Clones that could be classified as such showed segregation ratio's of resistant to susceptible phenotypes of 1 to 1 and 1 to 1.5 for populations ARG 95-3 and ARP 96-11, respectively (Table 2).

Detached leaf assays with ABPT-derived progeny and mapping populations where found to be less accurate for phenotyping than screening under field conditions. Nevertheless, results of detached leaf assays were considered suitable for the initial determination of the phenotype of individual clones and thus, for construction of mapping populations.

Example 2

Genetic Mapping of the Rpi-blb2 Resistance Locus in ABPT Derived Back Cross Populations In all four mapping populations (FIG. 1), resistance segregated as expected for a monogenic trait, suggesting the presence of a dominant resistance allele at a single locus (Table 2). This locus was designated the Rpi-blb2 locus.

In order to identify markers linked to Rpi-blb2, an initial AFLP analysis with 14 primer combinations (pc) was carried out on DNA of 10 resistant and 10 susceptible ARG 95-15 progeny plants, based on detached leaf assay, including the parental clones. The testing of 21 potentially linked markers on an additional 89 plants identified several markers linked to resistance (FIG. 5). Subsequent bulked segregant analysis (BSA) with 160 pc's on 2 resistant and 2 susceptible DNA pools, each containing genomic DNA of 8 resistant or susceptible ARG 95-15 progeny plants, respectively, identified a total of 58 AFLP markers potentially linked to resistance (FIG. 5). When a number of these markers were tested on 137 progeny plants of ARG 95-3, they were also linked to resistance in this population, suggesting that the resistance in the two populations was determined by the same locus (FIG. 6). These cosegregating markers mapped 3 to 28 centimorgan (cM) and 1 to 7.2 cM to one side of the locus in ARG 95-15 and ARG 95-3 respectively, suggesting that Rpi-blb2 could be situated at a distal position on a chromosome.

To determine the position of the Rpi-blb2 on the genetic map of potato, the two cosegregating AFLP markers E40M58 and E46M52 (FIG. 6) were cloned into the pGEM-T vector (Promega, the Netherlands) and sequenced. Primers designed on the ends of the sequences of the cloned AFLP fragments (Table 3) were used to develop cleaved amplified polymorphic sequence (CAPS) marker E40M58 that was found to be cosegregating with the resistance trait in 25 resistant and 25 susceptible clones of ARG 95-3. CAPS marker E40M58 was subsequently tested on 46 progeny plants of the C×E mapping population (van Eck et al., 1995). These data were added to the existing marker scores of the C×E population. Joinmap (Stam, 1993) linkage analyses mapped E40M58 8 cM distal to GP79 (Gebhardt et al., 1991), positioning Rpi-blb2 on the short arm of chromosome 6. In 178 progeny plants of population ARG 95-3 no recombination between Rpi-blb2 and AFLP markers E40M58, E40M60 and CAPS marker CT119 was observed. AFLP marker E46M52 and sequence characterised amplified region (SCAR) marker CT216 mapped 2.2 cM proximal to the gene (FIG. 7).

Example 3

Identification of a RGA Marker Linked to Rpi-blb2

In an attempt to identify functionally relevant markers linked to resistance, primers designed on the conserved motifs of the NBS domain of plant R genes (Leister et al., 1996), were used in an adapted AFLP protocol (RGA-AFLP) to identify resistance gene analogue (RGA) specific markers.

Using the P-loop based primer S1 from Leister et al. (1996) in combination with the Eco00 AFLP primer, an RGA specific marker, S1E00 was developed which cosegregated with resistance and markers E40M58 and CT119 in the ARG 95-3 mapping population (FIGS. 6 and 7).

Example 4

Development of E40M58e and E46M52e SCAR Markers for Recombinant Screening

Using genomic DNA of AR 91-1263 as template, the cloned fragment of AFLP marker E46M52 was extended by TAIL-PCR. The primary TAIL-PCR was performed using primers ARO 77 (sp1) and ARO 94 (AD) Subsequently, the secondary PCR was performed using ARO 128 (sp2) and the tertiary PCR using ARO 129 (sp3) both in combination with primer AD. This resulted in an E46M52e fragment that was extended on the 5' end with approximately 500 bp. The E46M52e fragment was cloned in pGEM-T and sequenced. A new forward primer was designed on this sequence and PCR in combination with primer ARO 77 resulted in SCAR marker E46M52e that cosegregated with the resistant phenotype in the four *S. tuberosum* mapping populations and as CAPS marker also in population B6.

Using genomic DNA of ARD 1197-16 as template, the cloned fragment of AFLP marker E40M58 was also extended by TAIL-PCR. The primary TAIL-PCR was performed in both the 5' and 3' directions using sp1 primers ARO 73 (3') and 74 (5') in combination with primer AD. Subsequently, the secondary PCR was performed using as sp2 ARO 82 or 79, respectively. The fragments obtained from the secondary PCR, 750 bp from the 3' end and 400 bp from the 5' end were cloned in pGEM-T and sequenced. On the basis of both sequences, two new primers were designed resulting in a SCAR marker that cosegregated with resistance in mapping population ARG 95-3 and DP1 (Table 3). The fragment of SCAR marker E40M58e could be amplified in the resistant parents of mapping populations ARG 95-3 and DP1, which were both derived from ABPT clone 55 (FIG. 1), but PCR amplification in the parents or progeny clones of mapping populations ARP 96-11 and ARG 95-15, which were both derived from ABPT clone 60, did not give any detectable PCR product. It was assumed that this could have been caused by minor differences in the genomic sequence and therefore, the AFLP fragment was extended by TAIL-PCR using genomic DNA of clone AR 91-1292 as template. A fragment E40M58e2 of approximately 300 bp was obtained, cloned and sequenced. Comparison of the sequence with the original fragment of AFLP marker E40M58 showed that only the first 37 bp of the extended fragment were identical. PCR with primers designed on the sequence of E40M58e2 did not result in a polymorphic marker. Both of the extended markers E40M48e and E40M58e2 were tested on five resistant or susceptible clones of S. bulbocastanum (BGRC 8005 and 8006). Only the fragment of SCAR marker E40M58e could be amplified in four S. bulbocastanum clones, indicating that part of the sequence of E40M58e2 was not derived from S. bulbocastanum. This observation suggested that E40M58e was located on the border of the S. bulbocastanum introgression fragment in clone AR 91-1292 and that the position of the Rpi-blb2 locus was proximal to marker E40M58e.

Example 5

Mapping of Rpi-blb2 in a Diploid Mapping Population Derived from ABPT Material

A total of 149 progeny clones of diploid mapping population DP1 were screened with markers E40M58e and E46M52e. No recombination was found between these markers suggesting suppressed recombination in the genomic region studied when compared to the tetraploid mapping population ARG 95-3 (FIG. 7). A subset of 112 clones was screened for resistance to P. infestans isolates IPO82001, IPO655-2A and IPO428-2 in a partially repeated detached leaf assay. Eleven of the clones (11%) showed intermediate reactions and were classified as having unknown phenotypes. Another 51 and 50 clones were classified as resistant and susceptible respectively. Three progeny clones DP1-28, DP1-79 and DP1-81 were identified that were putatively recombined between the Rpi-blb2 locus and the markers E40M58e and E46M52e. In 2000, a subset of 50 out of the 112 phenotyped clones was tested for resistance to LB in the field at the trial site of Marknesse. Conclusive results on the phenotype for LB resistance were obtained for 33 out of the 50 clones. The phenotype of clones 28 and 81 as determined with the detached leaf assay appeared to be erroneous. Thus, it was concluded that these clones did not represent recombination events between Rpi-blb2 and the markers used. The phenotype of clone DP1-79 could not be verified conclusively under field conditions and this clone may represent the only recombination event between the Rpi-blb2 locus and the markers E40M58e and E46M52e in 101 progeny clones of DP1 (1 cM). Since it was shown that two markers, linked to the resistance trait in ARG 95-15, ARG 95-3 and ARP 96-11, cosegregated with the same locus for LB-resistance in DP1, it was concluded that the DP1 parental clone ARD 1197-16 was suitable as a source for Rpi-blb2 gene isolation in a map based cloning approach.

Example 6

Physical Mapping of the ABPT Derived Rpi-blb2 Locus

The resistant clone ARD 1197-16, heterozygous for the Rpi-blb2 locus, was used as source DNA for the construction of a BAC library (hereafter referred to as the ARD 1197-16 BAC library). High molecular weight DNA preparation and BAC library construction were carried out as described in Rouppe van der Voort et al. (1999). Initially, a total of 67968 clones with an average insert size of 100 kb, which corresponds to approximately 7 genome equivalents, were individually stored in 177 384-well microtiter plates at −80° C. Marker screening of the ARD 1197-16 BAC library was carried out as described in Rouppe van der Voort et al. (1999). Essentially, DNA pools generated for each 384-well plate were screened by PCR with SCAR or CAPS markers linked to the Rpi-blb2 locus in order to build a BAC contig across the Rpi-blb2 locus.

Screening of the ARD 1197-16 BAC library with markers E40M58e, S1E00 and CT119 identified several positive BAC clones, which served as seed BACs from which a chromosome walk across the Rpi-blb2 locus was initiated. Marker E40M58e was used to isolate the BAC clones 69 and 141 whereas BAC clones 14, 24, 123 and 133 were positive for marker S1E00. Marker CT119 was used to isolate BAC 67. After sequencing the left (L) and right (R) borders of these BAC clones, a new set of markers was developed; 14L, 24L, 24R, 69L, 69R, 141R, 123L, 123R, 133R and 67L. Screening of the isolated BAC clones with these markers showed that the following pairs of BAC clones shared overlap: the right side of 123 with the left side of 133, 14 completely with 24, and the left side of 69 with the right side of 141. BAC 67 did not share overlap with the other BAC clones. The finding that the S1E00 positive BAC clones 14, 24, 123, and 133 did not form a single contig indicated that S1E00 was a repetitive sequence. This, together with the finding that the right BAC-end sequences of BAC clones 24 and 123 showed high homology to different regions of the Mi1 resistance gene from tomato (Milligan et al., 1998, Simons et al., 1998), suggested that the Rpi-blb2 locus harboured more than one RGA. Screening of the initial ARD 1197-16 BAC library with markers 141R, 24L, 24R and 123L did not lead to contig extension. However, screening of the library with markers 123R and 133R resulted in the isolation of BAC clones 99 and 113, thereby extending the BAC 123/133 contig in one direction. BAC-end sequencing of these two BAC clones lead to the development of two new markers, 99L and 113R. Screening of the ARD 1197-16 BAC library with 69R lead to the extension of the 141/69 contig. Consecutive screening of the BAC library with markers derived from BAC clones that further extended this contig lead to the isolation of BAC clones 36, 41 and 112, and the development of markers 36L, 41 L and 112L.

In an attempt to complete the BAC contig across the Rpi-blb2 locus, the ARD 1197-16 BAC library was enlarged with an additional 38864 BAC clones of ~100 kb (384-well plate numbers 178-273). This second library was screened with markers 24L, 24R, 123L, and 141R, leading to the identification of BAC clones positive for both 24R and 123L (e.g. 191) and BAC clones positive for 24L (211, 242). In this way, the gap between BAC 24 and 123 was closed and the 24/14 contig was extended towards BAC clone 141. There were no new clones in the extended ARD 1197-16 library that were positive for marker 141R.

Example 7

Construction of Additional Markers in BAC 123/133 Region

In an attempt to develop additional polymorphic markers from BAC 123 and 133, a 10 kb sub-clone library was constructed of both BAC 123 and 133. BAC DNA was partially cleaved with Sau3AI and fragments of approximately 10 kbp were cloned in the BamHI site of vector pBINPLUS. In order to select clones containing the original BAC-end sequence, 288 subclones of BAC 123 and 192 of BAC 133 were screened with the BAC-end markers 123L or 133R. In total 14 subclones were positive for marker 123L and 11 for marker 133R. Subsequently, the orientation of the BAC-end positive clones was determined by several PCRs using either the forward or reverse primer of the relevant BAC-end marker in combination with primers M13F or M13R (Table 3). For marker 123L three sub-clones and two sub-clones for marker 133R were selected and the ends not containing the 123L or 133R marker were sequenced (approximately 500 bp). Based on the new sequence two new primers were designed for subclone 123 resulting in marker 123L2 and two new primers were designed for subclone 133 resulting in marker 123R2. SCAR marker 123L2, which was located 10 kbp proximal to marker 123L, appeared to be polymorphic in mapping populations ARG 95-3, ARP 96-11 and as CAPS in B6. SCAR marker 133R2, which was located 10 kbp distal to marker 133R, was only polymorphic in mapping populations ARG 95-3 and ARP 96-11.

Example 8

Fine Mapping of the Rpi-blb2 Locus in ABPT Derived Mapping Populations

In order to fine map the Rpi-blb2 locus in ABPT derived mapping populations a total of 2283 new progeny clones of mapping population ARG 95-3 and 598 clones of mapping population ARP 96-11 were tested for resistance to LB in the field at the trial site of Marknesse in 2000 (Table 2). In population ARG 95-3 846 clones (37%) were scored susceptible and 886 clones resistant (39%). The phenotypes of the remaining 551 clones were unclear. In population ARP 96-11 256 clones (45%) were scored susceptible and 170 clones (30%) resistant. The phenotypes of the remaining 142 (25%) were unclear (Table 2). The 846 and 170 resistant clones from mapping populations ARG 95-3 and ARP 96-11, were selected for recombinant screening with SCAR marker CT216 and CAPS marker 41L or 36L, respectively. In total 85 (9.6 cM) and 22 (12.9 cM) recombinants were obtained in mapping populations ARG 95-3 and ARP 96-11 respectively, that were subsequently screened with CAPS marker 67L, reducing the number of recombinants to 5 (0.56 cM) in the marker interval 67L-36L in case of mapping population ARG 95-3 and to 4 recombinants (2.35 cM) in the marker interval 67L-41L in case of the mapping population ARP 96-11 (FIG. 8). These remaining 9 recombinants were further analysed with SCAR and CAPS markers 113R, 99L, 133R, 133R2, 123R, 123L, 24R, 14L, 24L, 141R, 69L, E40M58e and 69R. The latter two markers were scored only in mapping population ARG 95-3.

In population ARG 95-3 two clones showed recombination between markers E40M58e and 69L, positioning the Rpi-blb2 gene 0.23 cM proximal to marker E40M58e. Two other clones were recombined between markers 113R and 67L and one was recombined between markers 133R2 and 133R, positioning the Rpi-blb2 gene 0.11 cM distal to marker 133R.

In population ARP 96-11, no recombination was detected between markers 41L and 69L, positioning the Rpi-blb2 gene 0.58 cM proximal to marker 36L. Two progeny clones were recombined between markers 113R and 67L, and one clone was recombined between markers 99L and 133R, positioning the Rpi-blb2 gene 0.58 cM distal to marker 99L (FIG. 8; FIG. 9).

Example 9

Evaluation and Genetic Mapping of Late Blight Resistance in a S. bulbocastanum Intraspecific Mapping Population In order to develop an intraspecific mapping population of S. bulbocastanum, a resistant clone Blb 2002 was obtained from an inter accession cross (FIG. 10). This clone was reciprocally crossed with a susceptible clone Blb 48-5 that was selected also in progeny from an inter accession cross (FIG. 10). The resulting population was designated B6 with synonyms B6a, Blb 99-229, Blb 00-7 and Blb 00-8.

Initially a small group of 47 progeny plants of the B6 population was screened for resistance to P. infestans in a partially repeated detached leaf assay using a sporangiospore solution of isolate IPO655-2A of P. infestans as inoculum. Plants with leaves that clearly showed sporulating lesions 6 to 9 days after inoculation were considered to have a susceptible phenotype whereas plants with leaves showing no visible symptoms or necrosis at the side of inoculation in the absence of clear sporulation were considered to be resistant. Of the 47 seedlings, 23 scored resistant and 24 susceptible. These data indicated that the progeny of mapping population B6 gave clear segregation of the resistance trait in the detached leaf assay and that resistance could be due to a single dominant gene or a tightly linked gene cluster. In order to determine the chromosome position of this locus, 46 seedlings were analysed with markers 112L and E46M52e. Marker 112L was found to be linked in repulsion with the resistant phenotype, as only two recombinants were obtained between this marker and the phenotype of the 46 seedlings (4 cM). Also, marker E46M52e was found to be linked in repulsion with the resistant phenotype. Here, five recombinants were obtained between marker E46M52e and the phenotype (11 cM). Furthermore, markers 69R, 69L and 141R were used for analysis of the seven recombinants between markers 112L and E40M58e with an additional group of 6, 15 and 14 non recombined seedlings respectively, and found to be completely linked in either coupling (marker 69R) or repulsion phase (markers 69L and 141R) to resistance, indicating that the resistance gene was located at the same locus, i.e. Rpi-blb2, as in the ABPT-derived mapping populations.

In order to determine the position of Rpi-blb2 more precisely relative to the available markers, another 849 seedlings of the B6 mapping population and 1054 seedlings from the reciprocal cross (FIG. 10) were grown and analysed for recombination between the markers E46M52e and 112L. Thus, in addition to the initial 47 seedlings, a total of 1903 individual offspring clones of the B6 population were screened. Recombination between markers E46M52e and 112L was detected in a total of 138 of these seedlings (7.25 cM). Fine mapping of the Rpi-blb2 locus was carried out in two steps. Firstly, the group of 138 recombinants was reduced to 19 by additional screening with markers 14Lb, 113R, 123L2, 24L, 141R and 69L (Table 3), derived from left (L) and right (R) border sequences of BAC clones isolated from the ARD 1197-16 BAC library and subsequent selection of all the seedlings that were recombined between markers 113R and 69L. Possibly due to double recombination, 4 recombinants gave patterns for the markers scored that deviated from scores expected in the case of single recombination events in the genetic interval studied and when assuming co-linearity of markers. These were withdrawn from further analyses. Secondly, the remaining 15 recombinants were analysed with markers from border sequences of BAC clones isolated from the Blb 2002 library, SPB39L and SPB30L, or with MiGA markers 24L9spec, 24Lspec and 14L24L (Table 3). Results of marker analyses of these remaining 15 recombinants, which gave clearly interpretable marker scores and phenotypes, positioned the Rpi-blb2 locus between markers 69L and 24L, on a 0.11 cM (n=1899) genetic interval (FIG. 11).

Example 10

MiGA Markers

Southern analysis of BAC clones 14, 24, 123 and 133 using markers 123R, 14L, or 24L as probes showed that these BAC clones contained several resistance gene analogs (RGAs). In view of the homology between the sequences of markers 14L, 24L and 123R with the Mi1 gene from tomato, RGAs within the Rpi-blb2 region are hereafter referred to as Mi gene analogs (MiGAs). In an attempt to develop additional polymorphic markers within the Rpi-blb2 interval, PCR fragments generated from BAC clones 24 and 123 with the primer combination 14LR and 24LF were cloned into the pGEM-T vector (Promega, the Netherlands) and partially sequenced. Based on the alignment of these partial sequences, a set of universal primers were designed, univ14L and univ24L (Table 3), with the aim to amplify the corresponding region of as many as possible MiGAs within the Rpi-blb2 interval. This universal primer set was subsequently used to develop MiGA specific SCAR/CAPS markers linked to Rpi-blb2 (e.g. markers 14L24L, 24Lspec, 24L9spec; FIG. 9).

Example 11

Physical Mapping of the S. bulbocastanum Derived Rpi-blb2 Locus

The resistant clone Blb 2002 heterozygous for the Rpi-blb2 locus, was used as source DNA for the construction of the S. bulbocastanum BAC library, hereafter referred to as the Blb 2002 BAC library. High molecular weight DNA preparation and BAC library construction were carried out as described previously. A total of approximately 100.000 clones were generated and stored as 50 bacterial pools containing approximately 2000 white colonies. These bacterial pools were generated by scraping the colonies from the agar plates into Luria Broth medium containing 18% glycerol and 12.5 μg/ml chloramphenicol using a sterile glass spreader. For the screening of the Blb 2002 BAC library, plasmid DNA was isolated from each pool of clones using the standard alkaline lysis protocol and PCR was carried out to identify positive pools. Bacteria corresponding to positive pools were diluted and plated on Luria Broth agar plates containing chloramphenicol (12.5 μg/ml). Individual white colonies were subsequently picked into 384-well microtiter plates and single positive BAC clones subsequently identified as described previously. Names of BAC clones isolated from the Blb 2002 BAC library carry the prefix BlbSP.

In order to build a Blb 2002 derived BAC contig across the Rpi-blb2 genetic marker interval (69L-24L) the Blb 2002 BAC library was screened with markers 141R and 24L. This lead to the isolation of BAC clones BlbSP39 and BlbSP30, which overlap with each other and span the 141R-24L marker interval. BAC end sequences of both BAC clones were used to develop the markers SPB30L and SPB39L (FIG. 9).

Example 12

Complementation Analyses

For complementation purposes, all Rpi-blb2 gene candidates, i.e. all MiGAs present on BAC clones BlbSP30, BlbSP39, 24, 242 and 211, were targeted for subcloning into the binary vector pBINPLUS (van Engelen et al., 1996). This was done as follows. Aliquots of approximately 1 μg BAC DNA were digested with 1 U, 0.1 U or 0.01 U of Sau3AI restriction enzyme for 30 min. The partially digested BAC DNA was subjected to contour-clamped homogeneous electric field (CHEF) electrophoresis at 4° C. in 0.5×TBE using a linear increasing pulse time of 1-10 sec and a field strength of 6 V/cm for 16 hr. After electrophoresis, the agarose gel was stained with ethidium bromide to locate the region of the gel containing DNA fragments of approximately 10 kbp in size. This region was excised from the gel and treated with GELASE (Epicentre Technologies, USA) according to the manufacturer. The size selected DNA was ligated to the BamHI-digested and dephosphorylated binary vector pBINPLUS (van Engelen et al., 1995) followed by transformation to ElectroMAX *E. coli* DH10B competent cells (Life Technologies, UK). Per BAC clone a total of 384 clones were PCR screened for the presence of MiGA sequences using the primers univ24L and univ14L (Table 3). Positive clones were selected for further characterisation. Based on the restriction pattern of the 14L24L fragments digested with the enzymes RsaI, TaqI, AluI, DpnII or MseI, the different groups of MiGAs were identified. The MiGA harbouring the marker 24L, which was completely present on BAC clones BlbSP39, 211 and 242 was not detected with the universal primers univ14L and univ24L.

The relative position of the MiGA sequences in the 10 kbp subclones was determined by PCR using internal primers 123Mi and 14L2 for the 5' end and univ14L and 24L2 for the 3' end in combination with primers derived from pBINPLUS vector sequences (ARO 295 and 296; Table 3). Two subclones per RGA of each BAC-library were selected for transformation.

For complementation analysis, the selected subclones were transferred to the susceptible potato cultivars Impala and Kondor through *Agrobacterium* mediated transformation using isolate UIA143 (Farrand et al., 1989) or AGLO (Lazo et al., 1991). Primary transformants harbouring the transgenes of interest were tested for resistance to *P. infestans* in detached leaf assays using isolate IPO655-2A and IPO82001 (Table 4). Only the genetic constructs harbouring RGC5, both derived from *S. tuberosum* and *S. bulbocastanum*, were able to complement the susceptible phenotype both in cultivar Impala and in Kondor; in total 18 out of 19 RGC5 containing primary transformants were resistant (Table 4, FIG. 12) whereas all RGC1, RGC2, RGC3, RGC4, RGC6 RGC7 or RGC8 genes containing primary transformants were susceptible to *P. infestans*. As the RGC5 transformants showed similar resistance phenotypes as the resistant *S. bulbocastanum* parent of mapping population B6, RGC5 was designated the Rpi-blb2 gene. The homologue RGC24L can also be transferred to the described susceptible potato cultivars and tested for resistance to *P. infestans* in a detached leaf assay.

A selection of primary transformants containing RGC5 was analysed for copy number by Southern analysis. EcoRI digested genomic DNA was hybridised with a nptII probe (Table 3). Based on the presence of the number of nptII hybridising fragments, the primary transformants contained at least 1 to 11 transgene inserts. In total, 4 single copy integrations in cultivar Impala and 6 in cultivar Kondor were observed of which one cultivar Kondor transformant appeared to have a *P. infestans* susceptible phenotype.

To investigate whether Rpi-blb2 can also complement the susceptible phenotype in tomato, primary transformants of cultivar Moneymaker harbouring the Rpi-blb2 gene construct were produced and tested with the potato derived isolates IPO82001 and IPO655-2A. The disease resistance assay revealed that RGC5 is also able to complement a susceptible tomato phenotype (Table 6).

Example 13

Rpi-blb2 Gene Structure and Putative Amino Acid Sequence

The inserts of the RGC5 containing binary subclones 211FIC12 and SP39-20 were sequenced by a primer walk strategy whereby consecutive rounds of sequencing were carried out using a set of nested primers which were designed as the contiguous sequence was extended. The first set of sequences was generated using the M13F and M13R primers. The complete sequences of the inserts of clones 211FIC12 and SP39 consisted of 7967 and 9949 nucleotides (nt), respectively (FIG. 13). The sequence of clone 211F/C12 was identical to the corresponding sequence within clone SP39-20. The position and putative structure of Rpi-blb2 was predicted using GEN-SCAN (Burge and Karlin, 1997), GeneMark (Lukashin and Borodovsky 1998) and through alignment to the gene sequences of Mi1.1 and Mi1.2.

The exact length and structure of the coding sequence was determined through 5' and 3' rapid amplification of cDNA ends (RACE) using the GeneRacer™ kit (Invitrogen™ Groningen, the Netherlands). RACE identified 5' and 3' Rpi-blb2 specific cDNA fragments comprising 5' and 3' untranslated regions (UTRs) of 767 and 201 nucleotides (nt), respectively. The Rpi-blb2 gene contains two introns. Intron 1 is 626 nt long and positioned within the 5' UTR ending 32 nucleotides upstream of the ATG start codon. Intron 2 is 86 nt long starting 43 nucleotides downstream of the ATG start codon of the gene. The coding sequence of the Rpi-blb2 transcript is 3804 nucleotides.

The deduced open reading frame of the Rpi-blb2 gene encodes a predicted polypeptide of 1267 amino acids with an estimated molecular weight of 146 kD (FIG. 14). Several functional motifs present in R genes of the NBS-LRR class of plant R genes are apparent in the encoded protein. As illustrated in FIG. 14, the Rpi-blb2 protein belongs to the leucine zipper (LZ) subset of NBS-LRR resistance proteins. The N-terminal half of the Rpi-blb2 protein contains a potential LZ region between amino acids 413 and 434 and six conserved motifs indicative of a nucleotide-binding site (van der Biezen and Jones, 1998). The C-terminal half of Rpi-blb comprises a series of 15 irregular LRRs that can be aligued according to the consensus sequence hxxhxxLxxLxLxxC/N/SxLxxLPxx (SEQ ID NO: 100) or hxxhxxLxxLxLxxC/N/SxxLxxLPxx (SEQ ID NO: 101) observed in other cytoplasmic R proteins, whereby h can be L, I, M, V or F, and x any amino acid residue (Jones and Jones, 1997).

Example 14

Homology to Known State of the Art R Gene Sequences

To identify in silico homologues of the Rpi-blb2 gene, BLAST searches (Altschul et al., 1990) were carried out with the coding sequence of the Rpi-blb2 gene. BLASTN searches identified a number of sequences with significant homology to the Rpi-blb2 gene. Using the alignment programme ClustalW (standard settings) in the DNAStar software package, we determined that the Rpi-blb2 coding sequence shares the highest homology to Mi-1.1 (89.8%) and Mi-1.2 (89.7%) (Genbank accession numbers AF039681 and AF039682, respectively). The latter sequence corresponds to the Mi gene from tomato that confers resistance to three of the most damaging species of the root knot nematodes (*Meloidogyne* spp.) (Milligan et al., 1998). In addition nucleotides 2410-3461 of the Rpi-blb2 coding sequence share 87.8% sequence homology to a partial NBS-LRR sequence from *Solanum nigrum* (Genbank accession number AY055116.1). At the amino acid level the putative Rpi-blb2 protein sequence shares the highest homology to Mi-1.1 (82% identity) and Mi-1.2 (81% identity) (Genbank accession numbers AF039681 and AF039682).

Through ClustalW alignment of the deduced amino acid sequences of Rpi-blb2, Mi-1.1 and Mi-1.2 we have identified 200 amino acid (aa) residues which are unique to Rpi-blb2 (FIG. 15). Of these, 31 are found at hypervariable positions, i.e. the residue at this position is different in all three sequences and 11 are encoded by small insertions (one 3 aa residue insertion and one 8 aa residue insertion). The rest are Rpi-blb2 specific in that the aa residues encountered at corresponding positions in Mi-1.1 and Mi-1.2 are different from the Rpi-blb2 residue but conserved in the two Mi protein sequences (FIG. 15). Interestingly, the VLDL motif that is conserved in the third LRR of many NBS-LRR proteins including Mi (Axtell et al., 2001; Banerjee et al., 2001), is not conserved in Rpi-blb2 (FIG. 15).

Example 15

Rpi-blb2 Allele Mining in Wild *Solanum* Species

Using primers ARF1F and ARF1R (Table 3B), designed around the start and stop codon of the Rpi-blb2 gene, it is possible to amplify by PCR, alleles of Rpi-blb2 from any *Solanum* species. The amplification products can be cloned between transcriptional regulatory sequences in a binary plasmid and transferred to *S. tuberosum* through *Agrobacterium* mediated transformation or any method known to those skilled in the art. The resulting primary transformants can subsequently be analysed for resistance to *P. infestans* or to any pathogen for which potato is a host plant.

Example 16

Material and Methods

Plant material and development of mapping populations in (1) *Solanum tuberosum*. Complex interspecifc hybrid clones, designated ABPT, were made by Hermsen and co-workers (Hermsen, 1966; Hermsen and Ramanna, 1969; Ramanna and Hermsen, 1971; Hermsen and Ramanna, 1973; Hermsen, 1983; Hermsen, 1994) (FIG. 1a). The chromosome doubling step with colchicines was described by Hermsen (1966) and Hermsen and De Boer (1971). The resistance in some of the ABPT clones to *P. infestans* is believed to be derived from either one or both of the accessions from *S. bulbocastanum* BGRC 8007 (CGN 21306; Pi 275196) and BGRC 8008 (CGN 17693; Pi 275198) that were used in the initial cross to produce hybrids between *S. acaule* and *S. bulbocastanum*, since all other parents that were used in the breeding scheme for ABPT-clones were susceptible or only partially resistant to *P. infestans* in detached leaf assays (Hermsen and Ramanna, 1973). Tubers from 19 clones of population [(ABPT clone number 55× cultivar (cv) Oberarnbacher Frühe)×cv Arkula], from 7 clones of population [(ABPT clone number 55×cv Oberarnbacher Frühe)×cv Blanka] and from 5 clones of population [(ABPT clone number 60×cv Alcmaria)×cv Blanka] were received in 1988 from the former Department of Plant Breeding of the Wageningen Agricultural University (Wageningen, the Netherlands). Clones ARF 87-507, ARF 87-801 and ARF 87-601 were selected from these populations respectively. They represented offspring from a second backcross (BC2) with the complex interspecific ABPT-clones and were used for further back crosses that resulted in one tetraploïd BC3 population, two tetraploid BC4 populations and one diploid BC4 population that were used for genetic mapping of the Rpi-blb2 gene (FIG. 1). The tetraploid *Solanum tuberosum* mapping population ARG 95-15 was produced by crossing *P. infestans* resistant clone ARF 87-507 with the susceptible cultivar Alkon. Tetraploid population ARG 95-3 was produced by crossing *P. infestans* resistant clone AR 91-1263 with the susceptible cultivar Cosmos. Tetraploid population ARP 96-11 was produced by crossing resistant clone AR 92-1292 with the susceptible cultivar Celeste. The diploid population DP1 was obtained by crossing the resistant clone ARD 1197-16 with the susceptible clone ARD 93-2090 (FIG. 1).

Plant Material and Development of Mapping Populations in (2) *Solanum bulbocastanum*.

The diploid *S. bulbocastanum* mapping population, designated B6 (synonym B6a, Blb 99-229, Blb 00-7 and Blb 00-8), was developed by crossing a *P. infestans* resistant clone Blb 2002 (synonym M94-81-C) with a susceptible clone Blb 48-5. Results from reciprocal crosses of population B6 were combined. The resistant parental clone of population B6 was obtained from a cross between *S. bulbocastanum* clone Blb 93-D26-3 (accession BGRC 8002; CGN 17690; Pi 275187) as female parent and *S. bulbocastanum* clone Blb 93-60-10 (accession BGRC 8006; Pi 275194) as male parent. The susceptible parental clone of population B6 was obtained from a cross between *S. bulbocastanum* clones from accessions BGRC 8005 (CGN 17692, PI 275193) and BGRC 8006 (FIG. 2).

Disease Assays; (1) *Phytophthora infestans* Isolates

Three different *P. infestans* isolates were obtained from Plant Research International B.V. (Wageningen, the Netherlands). Isolates had different race structures and mating types as follows: IPO82001: race structure 1.2.3.4.5.6.7.10.11, mating type A2; IPO655-2A: race structure 1.2.3.4.5.6.7.8.9.10.11, mating type A1; IPO428-2: race structure 1.2.3.4.5.6.7.8.9.10.11, mating type A2 (Flier et al., 2003).

Disease Assays; (2) Field Trials

Glasshouse grown seedling tubers or field grown seed potatoes were planted at trial sites in Marknesse, the Netherlands from 1985 tot 2002, in the Toluca area of Mexico in 1991 or at a site in the Benguet Province in the Philippines in 1992. For individual clones, plots were planted consisting of 1 to 10 tubers. Approximately 8 weeks after planting, the field at Marknesse was inoculated with a sporangiospore solution of *P. infestans* isolate IPO82001 and disease scores were collected 3 to 6 weeks after inoculation. Clones that were free or nearly free from late blight were classified as having a resistant phenotype whereas clones with a complete of nearly complete blighted foliage were classified as susceptible. Clones with intermediate reactions to late blight were classified as having an unknown phenotype. At the field trials in Mexico and the Philippines, natural infection had to occur. Once this natural infection by *P. infestans* established, the percentage of blighted foliage of plants on each plot was scored on 8 and 6 days respectively on a 1-9 scale were estimated percentages of blighted foliage from 1 tot 9 were: 0, 3, 10, 25, 50, 75, 90, 97 and 100 (Estrada-Ramos et al., 1983).

Disease Assays; (3) Detached Leaves

For the detached leaf assay, leaves from plants grown for 6 to 12 weeks in the greenhouse were placed in pieces of water-saturated florists foam, approximately 35×4×4 cm, and put in a tray (40 cm width, 60 cm length and 6 cm height) with a perforated bottom. Each leaf was inoculated with two droplets (25 µl each) of sporangiospore solution on the abaxial side. Subsequently, the tray was placed in a plastic bag on top of a tray, in which a water-saturated filter paper was placed, and incubated in a climate room at 17° C. and a 16 h/8 h day/night photoperiod with fluorescent light (Philips TLD50W/84HF and OSRAM L58W/21-840). After 6 to 9 days, the leaves were evaluated for the development of *P. infestans* disease symptoms.

Evaluation:

Plants with leaves that clearly showed sporulating lesions 6 to 9 days after inoculation were considered to have a susceptible phenotype, whereas plants with leaves showing no visible symptoms or necrosis at the side of inoculation in the absence of clear sporulation were considered to be resistant.

Plant DNA Marker Screening

Genomic DNA was extracted from young leaves according to Bendahmane et al. (1997). For PCR analysis, 15 µl reaction mixtures were prepared containing 0.5 µg DNA, 15 ng of each primer, 0.2 mM of each dNTP, 0.6 units Taq-polymerase (15 U/µl, SphaeroQ, Leiden, the Netherlands), 10 mM Tris-HCl pH 9, 1.5 mM $MgCl_2$, 50 mM KCl, 0.1% Triton X-100 and 0.01% (w/v) gelatine. The PCRs were performed using the following cycle profile: 25 seconds DNA denaturation at 94° C., 30 seconds annealing and 40 seconds elongation at 72° C. As a first step in PCR-amplification DNA was denatured for 5 min at 94° C. and finalised by an extra 5 min elongation step at 72° C. The amplification reactions were performed in a Biometra® T-Gradient or Biometra® Uno-II thermocycler (Westburg, Leusden, the Netherlands). Depending on the marker, the PCR product was digested with an appropriate restriction enzyme. An overview of the markers including primer sequences, annealing temperature and restriction enzymes if appropriate, is given in Table 3. Subsequently, the (cleaved) PCR products were analysed by electrophoresis in agarose or acrylamide gels. For acrylamide gel analysis, the CleanGel DNA Analysis Kit and DNA Silver Staining Kit (Amersham Pharmacia Biotech Benelux, Roosendaal, the Netherlands) were used.

Elongation of AFLP Fragments by Thermal Asymmetric Interfaced (TAIL)-PCR

Elongation of the sequence of an AFLP fragment was performed by TAIL-PCR according to Liu and Whittier (1995). Shortly, elongation of AFLP fragments was performed using 2 or 3 nested specific primers (sp) in combination with an arbitrary degenerate (AD) primer. The first PCR was performed with primers sp1 and AD, the second with sp2 and AD and the third with sp3 and AD according to the scheme described in Table 5. The PCR was performed in 25 µl reactions containing the standard PCR mix as described before, except that 30 ng of primer AD was used. The elongated fragments were cloned in pGEM-T (Promega, the Netherlands) and sequenced.

BAC Library Construction and Screening

The resistant clone ARD 1197-16, heterozygous for the Rpi-blb2 locus, was used as source DNA for the construction of the *S. tuberosum* BAC library. The resistant clone Blb 2002 heterozygous for the Rpi-blb2 locus, was used as source DNA for the construction of the *S. bulbocastanum* BAC library. High molecular weight DNA preparation and BAC library construction were carried out as described in Rouppe van der Voort et al. (1999). For the *S. tuberosum* BAC library, approximately 120.000 clones with an average insert size of 100 kb, which corresponds to 8 to 10 genome equivalents were finally obtained. A total of approximately 70.000 clones were individually stored in 177 384-well microtiter plates at −80° C. Another 50.000 clones were stored as 14 bacterial pools containing approximately 4000 white colonies. These were generated by scraping the colonies from the agar plates into Luria Broth medium containing 18% glycerol and 12.5 µg/ml chloramphenicol using a sterile glass spreader. These so-called super pools were also stored at −80° C. Finally, another 37.000 clones were added to the *S. tuberosum* BAC library. The *S. bulbocastanum* BAC library consisted of 48 super pools of approximately 2.000 colonies.

Marker screening of the BAC library harbouring the individually stored BAC clones was carried out as described in Rouppe van der Voort et al. (1999). For the screening of the BAC library stored as super pools, plasmid DNA was isolated from each pool of clones using the standard alkaline lysis protocol and PCR was carried out to identify positive pools. Bacteria corresponding to positive pools were diluted and plated on Luria Broth agar plates containing chloramphenicol (12.5 µg/ml) Individual white colonies were subsequently picked into 384-well microtiter plates and single positive BAC clones subsequently identified as described above. Names of BAC clones isolated from the super pools carry the prefix SP (e.g. SP39).

Subcloning of Candidate Genes

Candidate RGAs were subcloned from BAC clone 24, 211, 242, BLBSP39 and BLBSP30 as follows. Aliquots of approximately 1 µg BAC DNA were digested with 1 U, 0.1 U or 0.01 U of Sau3AI restriction enzyme for 30 min. The partially cleaved BAC DNA was subjected to CHEF electrophoresis at 4° C. in 0.5×TBE using a linear increasing pulse time of 1-10 sec and a field strength of 6 V/cm for 16 hr. After electrophoresis, the agarose gel was stained with ethidium bromide to locate the region of the gel containing DNA fragments of approximately 10 kbp in size. This region was excised from the gel and treated with GELASE (Epicentre Technologies, USA) according to the manufacturer. The size selected DNA was ligated to the BamHI-cleaved and dephosphorylated binary vector pBINPLUS (van Engelen et al., 1995) followed by transformation to ElectroMAX *E. coli* DH10B competent cells (Life Technologies, UK). A total of 192 clones were PCR screened for the presence of RGC sequences using the primers of marker 24L14L (Table 3). Positive clones were selected for further characterisation. Identification of clones harbouring RGC1, RGC2, RGC3, RG4, RGC5, RGC6, RGC7, RGC8 and RGC24L was carried out by sequencing 14L24L PCR fragments derived from positive clones. The relative position of the RGAs within a subclone was determined by PCR analysis using internal primers (24L2, 123Mi) in combination with pBINPLUS specific primers (Table 3).

*Agrobacterium tumefaciens* Mediated Transformation of Potato

Binary plasmids harbouring the candidate genes were transformed to *A. tumefaciens* strains AGL0 (Lazo et al., 1991) or UIA143 (Farrand et al., 1989), the latter containing the helper plasmid pCH32 (Hamilton et al., 1996). Overnight cultures of the transformed *A. tumefaciens* strains were used to transform potato tuber discs (cvs Impala and Kondor) according to standard protocols (Hoekema et al., 1989; Fillati et al., 1987). Shortly, certified seed potatoes of cultivars Impala and Kondor were peeled and surface sterilised for 30 min in a 1% sodium hypochlorate solution containing 0.1% Tween-20. Tubers were then washed thoroughly in large volumes of sterile distilled water (4 times, 10 min). Discs of approximately 2 mm thickness and 7 mm in diameter were sliced from cylinders of tuber tissue prepared with a corkbore. The tuber discs were transferred into liquid MS30 medium containing *A. tumefaciens* and incubated for 15 min. After removing the *A. tumefaciens* solution, the tuber discs were transferred to regeneration medium containing MS30, 0.9 mg/l IAA, 3.6 mg/l zeatine riboside and 8 g/l agar (Hoekema et al., 1989). The plates were incubated at 24° C., 16 hour day-length (Philips TLD50W/84HF). After 48 hours of co-cultivation, the tuber discs were rinsed for 5 min in liquid MS medium including antibiotics, 200 mg/l vancomycin, 250 mg/l cefotaxim and 75 mg/l kanamycin, and transferred to regeneration medium supplemented with the same antibiotics. The plates were incubated at 24° C., 16 hour day-length (Philips TLD50W/84HF). Every three weeks, the tuber discs were transferred to fresh medium. Regenerating shoots were transferred to MS30 medium containing 75 mg/l kanamycin. Rooting shoots were propagated in vitro and tested for absence of *A. tumefaciens* cells by incubating a piece of stem in 3 ml Luria Broth medium (3 weeks, 37° C., 400 rpm). One plant of each transformed regenerant was transferred to the greenhouse.

*Agrobacterium tumefaciens* Mediated Transformation of Tomato

Seeds of the susceptible tomato line Moneymaker were rinsed in 70% ethanol to dissolve the seed coat and washed with sterile water. Subsequently, the seeds were surface-sterilised in 1.5% sodium hypochlorite for 15 minutes, rinsed three times in sterile water and placed in containers containing 140 ml MS medium pH 6.0 (Murashige and Skoog, 1962) supplemented with 10 g/l sucrose (MS10) and 160 ml vermiculite. The seeds were left to germinate for 8 days at 25° C. and 0.5 W/M² light.

Eight day old cotyledon explants were pre-cultured for 24 hours in Petri dishes containing a two week old feeder layer of tobacco suspension cells plated on co-cultivation medium (MS30 pH 5.8 supplemented with Nitsch vitamines (Duchefa Biochemie B V, Haarlem, the Netherlands), 0.5 g/l MES buffer and 8 g/l Daichin agar).

Overnight cultures of *A. tumefaciens* were centrifuged and the pellet was resuspended in cell suspension medium (MS30 pH 5.8 supplemented with Nitsch vitamines, 0.5 g/l MES buffer, pH 5.8) containing 200 µM acetosyringone to a final $O.D._{600}$ of 0.25. The explants were then infected with the diluted overnight culture of *A. tumefaciens* UIA143 containing pBINRGC5 for 25 minutes, blotted dry on sterile filter paper and co-cultured for 48 hours on the original feeder layer plates. Culture conditions were as described above.

Following the co-cultivation, the cotyledons explants were transferred to Petri dishes with selective shoot inducing medium (MS pH 5.8 supplemented with 10 g/l glucose, including Nitsch vitamines, 0.5 g/l MES buffer, 5 g/l agargel, 2 mg/l zeatine riboside, 400 mg/l carbenicilline, 100 mg/l kanamicine, 0.1 mg/l IAA) and cultured at 25° C. with 3-5 W/m² light. The explants were sub-cultured every 3 weeks onto fresh medium. Emerging shoots were dissected from the underlying callus and transferred to containers with selective root inducing medium (MS10 pH 5.8 supplemented with Nitsch vitamines, 0.5 g/l MES buffer, 5 g/l agargel, 0.25 mg/l IBA, 200 mg/l carbenicillin and 100 mg/l kanamycine).

RNA Extraction

Total RNA was isolated using Trizol® according to the protocol supplied by the manufacturer (Invitrogen™, Groningen, the Netherlands) with minor modifications. Briefly, 0.5 g of young leaf tissue was ground in liquid nitrogen and the powder suspended in 5 ml Trizol®. After a 5 min incubation at room temperature (RT), 0.5 ml chloroform was added, the suspension was vortexed and incubated for 2 min. After centrifugation (15 min, 11404×g, 4° C.) the supernatant was transferred to a new tube and 2.5 ml isopropanol was added. After 10 min at RT, nucleic acids were precipitated (10 min, 11404×g, 4° C.). The pellet was washed with 5 ml 70% ethanol (5 min, RT) and after-centrifugation (5 min, 6415×g, 4° C.), the pellet was dried and resuspended in 100 µl sterile distilled water. PolyA+RNA was extracted from total RNA using the Oligotex™ mRNA midi kit (Qiagen, GmbH, Germany).

Rapid Amplification of cDNA Ends.

The 5' and 3' ends of the Rpi-blb2 cDNA and confirmation of putative intron positions was determined by rapid amplification of cDNA ends (RACE) using the GeneRacer™ kit (Invitrogen™, Groningen, the Netherlands). 5' RACE was carried out on cDNA synthesised with primer GSP4 (ARO 772). Subsequently, primer GSP6 (ARO 774) was used in combination with the GeneRacer™ 5' primer and the final amplification was carried out with GSP6 in combination with the GeneRacer™ 5' nested primer. 3' RACE was carried out with the nested primers GSP1 (ARO 769) and GSP2 (ARO 770) in combination with the GeneRacer 3' primer. The final amplification was carried out with GSP3 (ARO 771) in combination with GeneRacer nested 3' primer.

Both 3' and 5' RACE amplification steps were carried out using Accuprime (Invitrogen™, Groningen, the Netherlands) instead of the Taq polymerase supplied by the GeneRacer™ kit.

AFLP Fingerprinting and Cloning of AFLP Fragments

Template preparation and AFLP fingerprinting were essentially performed as described in Vos et al. (1995). In order to clone specific fragments $^{33}$P-labelled AFLP fragments were excised out of the acrylamide gel by overlaying the polyacrylamide gels, dried on Whatmann 3MM paper, with autoradiogram images. The pieces of gel/paper underneath the band of interest were cut out and transferred to 200 µl of TE and incubated for 1 h at room temperature. Five microlitres of supernatant was used to re-amplify the fragment, using a PCR in which the EcoRI+0 in combination with MseI+0 were used as primers. The re-amplified AFLP fragment was subsequently cloned into the pGEM-T cloning vector (Promega, the Netherlands) and the inserts of several clones sequenced.

The DNA sequence of the excised AFLP band was used to design locus-specific primers. The amplification product obtained with such primers was screened for internal polymorphisms with restriction enzymes. After restriction, the fragments were separated on a 2-3% agarose gel including ethidiumbromide.

RGA-AFLP Analysis

Template preparation was essentially performed as described in Vos et al. (1995). However, the second amplification step was carried out with the P-loop based primer S1 from Leister et al. (1996) in combination with the EcoRI+0 AFLP primer. A 10 µl reaction mixture [0.5 µl $^{33}$P-labelled S1 primer (10 ng/µl); 0.5 µl EcoRI+0 primer (10 ng/µl); 0.8 µl dNTPs (5 mM); 2 µl 10× Goldstar™ PCR buffer (Eurogenetc, Belgium); 1.2 µl MgCl$_2$ (25 mM); 0.06 µl Goldstar™ DNA polymerase (5 U/µl) (Eurogentec, Belgium); 14.94 µl MQ water] was added to 10 µl diluted template (20× diluted in MQ water) and a PCR reaction performed using the following cycle profile: 45 seconds DNA denaturation at 94° C., 45 seconds primer annealing at 49° C. and 2 min elongation step at 72° C. (35 cycles). Prior to the cycling the template DNA was denatured for 2 min at 94° C. and the PCR was finalised by a applying an extra 5 min elongation step at 72° C. The amplification reactions were performed in a Perkin Elmer 9600 thermocycler. The labelled PCR products fragments were separated on a 6% polyacrylamide gel and the individual bands visualized by autoradiography according to standard procedures.

Example 17

Phenotype of Rpi-blb2 Expression

Material & Methods

Four lesions (6 days after inoculation at standard conditions) of infected leaflets (IPO82001) were rinsed in 3 ml H$_2$O. The concentration was determined using a haemocytometer Fuchs-Rosenthal (W. Schreck Hofheim/Ts.)

Definition:

Sporulation index is the amount of sporangia per ml detected on lesions of infected leaflets.

TABLE 7

Sporulation index of different genotypes after infection with *P. infestans* in a detached leaf assay

| Genotype | Sporulation index sporangia/ml |
|---|---|
| cv. Bintje | 1.840.000 |
| ARD 92-1197-16 | 20.000 |
| R2-differential | 0 |

The difference between Rpi-blb2 and other *P. infestans* resistance genes is that Rpi-blb2 allows a low level of sporulation (FIG. 18). This is demonstrated by a detached leaf assay in which the lesions present on Rpi-blb2 genotype (ARD 92-1197-16) show a low level of sporangia in relation to complete absence of sporangia on a genotype containing the *S. demissum* gene R2. However, the sporulation index is only 1.1% of a susceptible phenotype (cv. Bintje) (Table 7 and FIG. 18.

Field experiments have also shown that Rpi-blb2 allows a low level of infection. Late blight symptoms developed at a low level during the growing season (FIG. 3, ARF87-801) or at the end of the growing season (FIG. 2, ARF87-601; FIG. 3, ARF87-507 and ARF87-601).

REFERENCES

Altschul, S. F., Gish, W., Miller, W., Myers, E. W., and Lipman, D. J. (1990) Basic local alignment search tool. Journal of Molecular Biology 215, 403-410.

Axtell, M. J., McNellis, T. W., Mudget, M. B., Hsu, C. S., and Staskawicz, B. J. (2001) Mutational analysis of the *Arabidopsis* RPS2 disease resistance gene and the corresponding *Pseudomonas syringae* avrRpt2 avirulence gene. Molecular Plant-Microbe interactions 14, 181-188.

Ballvora, A., Ercolano, M. R., Weis, J., Meksem, K., Bormann, C. A., Oberhagen, P., Salamini, F., and Gebhardt, C. (2002) The R1 gene for potato resistance to late blight (*Phytophthora infestans*) belongs to the leucine zipper/NBS/LRR class of plant resistance genes. Plant Journal 30, 361-371.

Banerjee, D., Zhang, X., and Bent, A. F. (2001) The leucine-rich repeat domain can determine effective interaction between RPS2 and other host factors in *Arabidopsis* RPS2-mediated disease resistance. Genetics 158, 439-450.

Bendahmane, A., Kanyuka, K., and Baulcombe, D. C. (1997) The High-resolution genetic and physical mapping of the Rx gene for extreme resistance to potato virus X in tetraploid potato. Theoretically Applied Genetics 95,153-162.

Burge, C. B. and Karlin, S. (1997) Prediction of complete gene structures in human genomic DNA. Journal of Molecular Biology 268, 78-94.

Colon, L. T., Turkensteen, L. J., Prummel, W., Budding, D. J. and Hoogendoom, J. (1985) Durable resistance to late blight (*Phytophthora infestans*) in old potato cultivars. European Journal of Plant Pathology 101, 387-397.

Dangl, J. L. and Jones, J. D. G. (2001) Plant pathogens and integrated defence responses to infection. Nature 411, 826-833.

Estrada-Ramos, N., Pérez-Alvarez, O., Henfling, J. and Malamud, O. (1983) In: W. J. Hooker (ed), Research for the potato in the year 2000. International Potato Center, Lima, Peru, pp 78-79.

Farrand, S. K., O'Morchoe, S. P., and McCutchan, J. (1989) Construction of an *Agrobacterium tumefaciens* C58 recA mutant. Journal of Bacteriology 171, 5314-5321.

Fillati, J. J., Kiser, J., Rose, R., and Comai, L. (1987) Efficient transfer of a glyphosphate tolerance gene into tomato using a binary *Agrobacterium tumefaciens* vector. Bio Technology 5, 726-730.

Flier, W. G. (2001) Variation in *Phytophthora infestans*, sources and implications. PhD thesis Wageningen University, Wageningen, the Netherlands, p. 93.

Flier, W. G., vandenBosch, G. B. M., and Turkensteen, L. J. (2003) Stability and partial resistance in potato cultivars exposed to aggressive strains of *Phytophthora infestans*. Plant Pathology 52 (3), 326-337.

Gebhardt, C, Ritter, E., Barone, A., Debener, T., Walkemeier, B., Schachtschabel, U., Kaufmann, H., Thompson, R. D., Bonierbale, M. W., Ganal, M. W., Tanksley, S. D., and Salamini, F. (1991) RFLP maps of potato and their alignment with the homologous tomato genome. Theoretically Applied Genetics 83, 49-57.

Hamilton, C. M., Frary, A., Lewis, C., and Tanksley, S. D. (1996) Stable transfer of intact high molecular weight DNA into plant chromosomes. Proceedings of National Academy of Science USA 93, 9975-9979.

Hermsen, J. G. Th. (1966) Crossability, fertility and cytogenetic studies in *Solanum acaule*×*Solanum bulbocastanum*. Euphytica 15, 149-155.

Hermsen, J. G. Th. and Ramanna, M. S. (1969) Meiosis in different F$_1$-hybrids of *Solanum acaule* Bitt.×*S. bulbocastanum* Dun. and it's bearing on genome relationship, fertility and breeding behaviour. Euphytica 18, 27-35.

Hermsen, J. G. Th., and De Boer, A. J. E. (1971) The effect of colchicines treatments on *Solanum acaule* and *S. bulbocastanum*; a complete analysis of ploidy chimeras in *S. bulbocastanum*. Euphytica 20, 171-180

Hermsen, J. G. Th. and Ramanna, M. S. (1973) Double-bridge hybrids of *Solanum bulbocastanum* and cultivars of *Solanum tuberosum*. Euphytica 22, 457-466

Hermsen, J. G. Th. and Verdenius, J. (1973) Selection from *Solanum tuberosum* group Phureja of genotypes combining high-frequency haploid induction with homozygosity for embryo-spot. Euphytica 22, 244-259.

Hermsen, J. G. Th. (1983) Utilization of wide crosses in potato breeding. In: Report of a planning conference on present and future strategies for potato breeding and improvement. International Potato Center, Lima, Peru, pp 115-132.

Hermsen, J. G. Th. (1994) Introgression of genes from wild species, including molecular and cellular approaches. In: J. E. Bradshaw and G. R. Mackay (eds), Potato Genetics, CAB International, Wallingford, UK. pp 515-538.

Hijmans, R. J., Forbes, G. A., and Walker, T. S. (2000) Estimating the global severity of potato late blight with GIS-linked disease forecast models. Plant Pathology 49, 697-705.

Hoekema, A., Hirsch, P. R., Hooykaas, P. J. J., and Schilperoort, R. A. (1983) A binary plant vector strategy based on separation of vir- and T-region of the *Agrobacterium tumefaciens* Ti-plasmid. Nature 303,179-180.

Hoekema, A., Huisman, M. J., Molendijk, L., van den Elzen, P. J. M., and Cornelissen, B. J. C. (1989) The genetic engineering of two commercial potato cultivars for resistance to potato virus X. Bio/Technology 7, 273-278.

Jones, D. A. and Jones, J. D. G. (1997) The role of leucine-rich repeat proteins in plant defences. Adv. Bot. Res. 24, 89-167.

Lazo, G. R., Stein, P. A. and Ludwig, R. A. (1991) A DNA transformation-competent *Arabidopsis* genomic library in *Agrobacterium*. Bio/Technology 9, 963-967.

Leach, J. E., Vera Cruz, C. M., Bai, J., and Leung, H. (2001) Pathogen fitness penalty as a predictor of durability of disease resistance genes. Annual Review Phytopathology 39,187-224.

Leister, D., Ballvora, A., Salamini, F., and Gebhardt, C. (1996) A PCR-based approach or isolating pathogen resistance genes from potato with potential for wide application in plants. Nature Genetics 14, 421-429.

Liu, Y-G., and Whittier, R. F. (1995) Thermal asymmetric interlaced PCR: Automatable amplification and sequencing of insert end fragments from P1 and YAC clones for chromosome walking. Genomics 25, 674-682.

Lukashin A. V. and M. Borodovsky (1998) GeneMark.hmm: new solutions for gene finding. Nucleic Acids Research 26, 1107-1115.

Milligan, S. B., Bodeau, J., Yaghoobi, J., Kaloshian, I., Zabel, P. and Williamson, V. M. (1998) The root-knot nematode resistance gene Mi from tomato is a member of the leucine zipper nucleotide binding leucine-rich repeat family of plant genes. Plant Cell 10, 1307-1319.

Nombela, G., Williamson, V. M., and Muniz, M. (2003) The root-knot nematode resistance gene Mi-1.2 of tomato is responsible for resistance against the whitefly *Bemisia tabaci*. Molecular Plant Microbe interactions 16 (7), 645-649.

Ramana, M. S. and Hermsen, J. G. Th. (1971) Somatic chromosome elimination and meiotic chromosome pairing in the triple hybrid 6x-(*Solanum acaule*×*S. bulbocastanum*)× 2x-*S. phureja*. Euphytica 20, 470-481

Rossi, M., Goggin, F. L., Milligan, S. B., Kaloshian, I., Ullman, D. E., Williamson, V. M. (1998) The nematode resistance gene Mi of tomato confers resistance against the potato aphid. Proceedings of the National Academy of Science USA 95, 9750-9754.

Rouppe van der Voort, J., Kanyuka, K., van der Vossen, E., Bendahmane, A., Mooijman, P., Klein-Lankhorst, R., Stiekema, W., Baulcombe, D. & Bakker, J. (1999) Tight physical linkage of the nematode resistance gene Gpa2 and the virus resistance gene Rx on a single segment introgressed from the wild species *Solanum tuberosum* subsp. *Andigena* CPC 1673 into cultivated potato. Molecular Plant Microbe Interactions 12, 197-206.

Schepers, H. and Wustman, R. (2003) *Phytophthora* 2003: middelen en aanpak. Inform a 6/juni 2003.

Simons, G., Groenendijk, J., Wijbrandi, J., Reijans, M., Groenen, J., Diergaarde, P., Van der Lee, T., Bleeker, M., Onstenk, J., de Both, M., Haring, M., Mes, J., Cornelissen, B., Zabeau, M and Vos, P. (1998) Dissection of the *Fusarium* 12 gene cluster in tomato reveals six homologues and one active gene copy. Plant Cell 10, 1055-1068.

Stam, P. (1993) Construction of integrated genetic linkage maps by means of a new computer package: Joinmap. Plant Journal 3, 739-744.

Song, J., Bradeen, J. M., Naess, S. K., Raasch, J. A., Wielgus, S. M., Haberlach, G. T., Liu, J., Kuang, H., Austin-Phillips, S., Buell, C. R., Helgeson, J. P. and Jiang, J. (2003) Gene RB cloned from *Solanum bulbocastanum* confers broad spectrum resistance to potato late blight. Proceedings of National Academy of Science USA 100, 9128-9133.

van der Biezen, E. A. and Jones, J. D. G. (1998) The NB-ARC domain: a novel signalling motif shared by plant resistance gene products and regulators of cell death in animals. Current Biology 8, 226-227.

van der Vossen, E., Sikkema, A., te Lintel Hekkert, B., Gros, J., Stevens, P., Muskens, M., Wouters, D., Pereira, A., Stiekema, W., and Allefs, J. (submitted) An ancient R gene from the wild potato species *Solanum bulbocastanum* confers broad-spectrum resistance to *Phytophthora infestans* in cultivated potato and tomato.

van Eck, H. J., Rouppe van der Voort, J. N. A. M., Draaistra, J., van Zandvoort, P., van Enckevort, E., Segers, B. Peleman, J., Jacobsen, E., Helder, J., and Bakker, J. (1995) The inheritance and chromosomal localization of AFLP markers in a non-inbred potato offspring. Molecular Breeding 1: 397-410.

van Engelen, F. A., Molthoff, J. W., Conner, A. J., Nap, J-P., Pereira, A. and Stiekema, W. J. (1995) pBINPLUS: an improved plant transformation vector based on pBIN19. Transgenic Research 4, 288-290.

Vos, P., Hogers, R., Bleeker, M., Rijans, M., Van der Lee, T., Homes, M., Frijters, A., Pot, J., Peleman, J., Kuiper, M. and Zabeau, M. (1995) AFLP: a new technique for DNA fingerprinting. Nucleic Acids Research, 23, 4407-4414.

Vos, P., Simons, G., Jesse, T., Wijbrandi, J., Heinen, L., Hogers, R., Frjters, A., Groenendijk, J., Diergaarde, P., Reijans, M., Fierens-Onstenk, J., de Both, M., Peleman, J., Liharska, T., Hontelez, J., and Zabeau, M. (1998) The tomato Mi-1 gene confers resistance to both root-knot nematodes and potato aphids. Nature Biotechnology 16 (13), 1365-1369.

```

The invention claimed is:

1. A method for generating or increasing the resistance of a plant to a plant pathogen of the phylum Oomyceta comprising increasing the activity of a Rpi-blb2 protein in the plant or a tissue, organ or cell of the plant or a part thereof by expressing a transgenic Rpi-blb2 protein encoding nucleic acid molecule, wherein the plant has increased resistance to the plant pathogen of the phylum Oomyceta, wherein said Rpi-blb2 protein encoding nucleic acid molecule is selected from the group consisting of:
   (a) a nucleic acid molecule encoding the polypeptide depicted in SEQ ID NO: 2 or 4;
   (b) a nucleic acid molecule comprising the coding sequence as depicted in SEQ ID NO: 3 or 5 or 6; and
   (c) a nucleic acid molecule encoding a polypeptide comprising a sequence having at least 95% identity to the amino acid sequence of the polypeptide encoded by the nucleic acid molecule of (a) or (b).

2. The method of claim 1 which results in reduction in sporulation index of at least 30% after infection with *P. infestans* compared to a wild type.

3. The method of claim 1, wherein the Rpi-blb2 protein comprises by a P-loop and a NBS domain.

4. The method of claim 1, wherein the Rpi-blb2 protein encoding nucleic acid molecule is a nucleic acid molecule encoding a polypeptide comprising a sequence having at least 95% identity to the amino acid sequence of SEQ ID NO: 2 or 4, wherein the polypeptide comprises a NBS domain and an LRR domain.

* * * * *

UNITED STATES PATENT AND TRADEMARK OFFICE
CERTIFICATE OF CORRECTION

PATENT NO. : 7,608,751 B2
APPLICATION NO. : 10/567980
DATED : October 27, 2009
INVENTOR(S) : Van Der Vossen et al.

It is certified that error appears in the above-identified patent and that said Letters Patent is hereby corrected as shown below:

On the Title Page:

Item (73), "Assignee: Kweek-En Researchbedruf Agrico B.V., Emmeloord (NL)"

should read -- Assignee: Kweek-En Researchbedrijf Agrico B.V., Emmeloord (NL) --.

In the Claims:

In Claim 3, in column 194, on line 23-24, "protein comprises by" should read -- protein comprises --.

Signed and Sealed this

Sixteenth Day of March, 2010

David J. Kappos
*Director of the United States Patent and Trademark Office*